US007060800B2

(12) United States Patent
Gorman

(10) Patent No.: US 7,060,800 B2
(45) Date of Patent: Jun. 13, 2006

(54) ANTIBODIES BINDING THE TNF RELATED PROTEIN, TNF-X

(75) Inventor: Daniel M. Gorman, Newark, CA (US)

(73) Assignee: Schering Corporation, Kenilworth, NJ (US)

(*) Notice: Subject to any disclaimer, the term of this patent is extended or adjusted under 35 U.S.C. 154(b) by 439 days.

(21) Appl. No.: 09/949,192

(22) Filed: Sep. 7, 2001

(65) Prior Publication Data

US 2002/0142292 A1 Oct. 3, 2002

Related U.S. Application Data

(60) Provisional application No. 60/231,267, filed on Sep. 8, 2000.

(51) Int. Cl.
*C07K 16/00* (2006.01)
*A61K 39/00* (2006.01)
*G01N 33/53* (2006.01)

(52) U.S. Cl. .............................. 530/387.9; 530/387.1; 530/387.7; 530/388.15; 530/391.1; 530/391.7; 530/388.1; 435/7.1; 435/335; 435/975; 424/184.1; 424/185.1

(58) Field of Classification Search ................ 530/350, 530/351, 387.1, 387.9, 388.2, 387.7, 388.15, 530/391.1, 391.3, 391.7; 435/7.1, 335, 975; 424/184.1, 185.1
See application file for complete search history.

(56) References Cited

U.S. PATENT DOCUMENTS 6,277,969 B1 * 8/2001 Le et al. .................... 536/23.1

FOREIGN PATENT DOCUMENTS

WO    WO 96/29411    9/1996

OTHER PUBLICATIONS

Locksley et al. 2001, The TNF and TNF Receptor Superfamilies: Integrating Mammalian Biology, Cell, vol. 104, pp487–501.*
Ngo et al., 1994, Computational Complexity, Protein Structure prediction, and the Levinthal Paradox, The Protein Folding Problem and Tertiary Structure Prediction, pp. 492–495.*
Wells, Aditivity of Mutational Effects in Proteins, 1990, Biochemistry, vol. 26, No:37, pp. 8509–8517.*
Alan Aderem & Richard J. Ulevitch, *Nature*, 406(6797):782–787, Aug. 17, 2000. "Toll–like receptors in the induction of the innate immune response".
James Melvin Anderson & Christina M. Van Itallie, *Current Biology*, 9(42):R922–4, Dec. 16, 1999. "Tight junctions: Closing in on the seal".
Kim E. Barrett, *Baillieres Clin Gastroenterol.*, 10(1):1–15, Mar. 1996. "Cytokines: sources, receptors and signalling".

Riccardo Bertini, et al., *J Exp Med.*, 189(11):1783–1789, Jun. 7, 1999. "Thioredoxin, a redox enzyme released in infection and inflammation, is a unique chemoattractant for neutrophils, monocytes, and T cells".
J. Briscoe, et al., *Philos Trans R Soc Lond B Biol Sci.* 351(1336):167–171, Feb. 29, 1996. "JAKs, STATs and signal transduction in response to the interferons and other cytokines".
Hee–Jeong Choi, et al., *Nat Struct Biol.*, 5(5):400–406, May 1998. "Crystal structure of a novel human peroxidase enzyme at 2.0 Å resolution".
Mikio Furuse, et al., *J Cell Biol.*, Nov. 15, 1999; 147(4):891–903, Nov. 15, 1999. "Manner of interaction of heterogeneous claudin species within and between tight junction strands".
Takashi Hirano, et al., *Genome Research*, 10(5):659–663, May 2000. "Null mutation of PCLN–1/Claudin–16 results in bovine chronic interstitial nephritis".
James N. Ihle, et al. *Stem Cells*, 15 (Suppl 1):105–111, 1997. "Jaks and Stats in cytokine signaling".
David E. Levy, *Cytokine Growth Factor Rev.*, 8(1):81–90, Mar. 1997. "The house that JAK/STAT built".
Michael J. Mendez, et al., *Nature Genetics*, 15(2):146–156, Feb. 1997. "Functional"transplant"of megabase human immunoglobulin loci recapitulates human antibody response in mice".
Kazumasa Morita, et al., *Proc Natl Acad Sci U S A*, 96(2):511–516, Jan. 19, 1999. "Claudin multigene family encoding four–transmembrane domain protein components of tight junction strands".
Henrik Nielsen, et al., *Protein Engineering*, 10(1):1–6, Jan. 1997. "Identification of prokaryotic and eukaryotic signal peptides and prediction of their cleavage sites".
David A. Schwarz, et al., *Immunity*, 9(5):657–668, Nov. 1998. "Schlafen, a new family of growth regulatory genes that affect thymocyte development".
Olli Silvennoinen, et al., *APMIS*, 105(7):497–509, Jul. 1997. "Cytokine receptor signal transduction through Jak tyrosine kinases and Stat transcription factors".
David B. Simon, et al., *Science*, 285(5424):103–106, Jul. 2, 1999. "Paracellin–1, a renal tight junction protein required for paracellular Mg2+ resorption".
Linda A. Winston & Tony Hunter, *Current Biology*, 6(6):668–671, Jun. 1, 1996. "Intracellular signalling: Putting JAKs on the kinase MAP".
J. Kawai, et al., *Database SWALL 'Online!'*, Accession Number Q9CQ18, Jun. 1, 2001. Definition: Functional annotation of a full–length mouse cDNA collection.

* cited by examiner

*Primary Examiner*—Janet Andres
*Assistant Examiner*—Jegatheesan Seharaseyon
(74) *Attorney, Agent, or Firm*—Laurie L. Hill; Edwin P. Ching

(57) ABSTRACT

Nucleic acids encoding mammalian, e.g., primate or rodent, genes, purified proteins and fragments thereof. Antibodies, both polyclonal and monoclonal, are also provided. Methods of using the compositions for both diagnostic and therapeutic utilities are provided.

20 Claims, 19 Drawing Sheets

```
TissueFactor   -METPAWPRVPRPETAVARTLLLGWVFAQVAGASGTTN-T
1274993R       ---------------MAGPERWGPLLLCLLQAAPGRPR-L
hIFNabR        MLLSQNAFIF--RSLNLVLMVYISLVFGISYDSPDYT---
CRF2-4         ---------------MAWSLGSWLGGCLLVSALGMV---
cytor x        --MMP-------KHCFLGFLISFFLTGVAGTQSTHES---
cytor7         -MRAPGRPAL--RPLPLPPLLLLLLAAPWGRAVPCVSGGL TissueFactor   VAAYNLTWKSTNFKTILEWEPK---PVN-QVYTVQISTKS
1274993aaR     APPQNVTLLSQNFSVYLTWLPGLGNPQD-VTYFVAYQSSP
hIFNabR        DESCTFKISLRNFRSILSWE-LKNHSIVPTHYTLLYTIMS
CRF2-4         PPPENVRMNSVNFKNILQWESPAFAKGN-LTFTAQYLSY-
cytor x        LKPQRVQFQSRNFHNILQWQPGRALTGNSSVYFVQYKIYG
cytor7         PKPANITFLSINMKNVLQWTPPEGLQGVKVTYTVQYFIYG TissueFactor   --GDWKSK--CFYTTDTECDLTDEIVKDVKQTYLARVFSY
1274993R       TRRRWREVEECAGTKELLCSMMCLKKQDLYNKFKGRVRTV
hIFNabR        KPEDKVVKNCANTTRSFCDLTDEW--RSTHEAYVTVLEG
CRF2-4         --RIFQDK--CMNTTLTECDFSSLS-KYGDHTL--RVRAE
cytor x        -QRQWKNKEDCWGTQELSCDLTSET-SDIQEPYYGRVRAA
cytor7         -QKKWLNKSECRNINRTYCDLSAET-SDYEHQYYAKVKAI TissueFactor   PAGNVESTGSAGEPLYENSPEFTPYLETNLGQPTIQSFEQ
1274993R       SPSSKS--------PWVESEYLDYLFEVEPAPP-VLVLTQ
hIFNabR        FSGNTT--------LFSCSHNFWLAIDMSFEPP-EFEIVG
CRF2-4         FADEHS--------DWVNIT-FCPVDDTIIGPP-GMQVEV
cytor x        SAGSYS--------EWSMTPRFTPWWETKIDPP-VMNITQ
cytor7         WGTKCS--------KWAESGRFYPFLETQIGPP-EVALTT TissueFactor   VGTKVNVTVEDERTLVR-RNNTFLSLRDVFGKDLIYTLYY
1274993R       T-EEILSANATYQLPP--------CMPPLD---LKYEVAF
hIFNabR        FTNHINVVVKFPSIVE---EELQFDLSLVIE-EQSEGIVK
CRF2-4         LADSLHMRFLAPKIEN---EYETWTMKNVYN-SWTYNVQY
cytor x        VNGSLLVILHAPNLPYRYQKEKNVSIEDYY--ELLYRVFI
cytor7         DEKSISVVLTAPEKWKRNPEDLPVSMQQIYS-NLKYNVSV
```

FIG.1A

```
TissueFactor  WKSSSSG-KKTAKTNTNEFLIDV--DKGENYCFSVQAVIP
1274993R      WKEGAGN------KVGSSFPAPR--LGPLLHPFLLRFFSP
hIFNabR       KHKPEIK---GNMSGNFTYIIDK-LIPNTNYCVSVYLEHS
CRF2-4        WKNGTDE--KFQITPQYDFEVLRNLEPWTTYCVQVRGFLP
cytor x       INNSLEKEQKVYEGAHRAVEIEA-LTPHSSYCVVAEIYQP
cytor7        LNTKSNR-TWSQCVTNHTLVLTW-LEPNTLYCVHVESFVP TissueFactor  SRTVNRKSTDS-PVECMGQEKGE---------FREIFYII
1274993R      -------SQPAPAPLLQEVFPVHS----------------
hIFNabR       D---EQAVIKS-PLKCTLLPPGQESESAESAKIGGIITVF
CRF2-4        DR--NKAGEWS-EPVCEQTTHDET------VPSWMVAVIL
cytor x       ML--DRRSQRS-EERCVEIP--------------------
cytor7        GP--PRRAQPS-EKQCARTLKDQSSEFKAKIIFWYVLPIS TissueFactor  GAVAFVVIILVIILAISLHKCRKAG---------------
1274993R      ----------------------------------------
hIFNabR       LIALVLTSTIVTLKWIGYICLRNSLPKVLNFHN---FLAW
CRF2-4        MASVFMVCLALLGCFSLLWCVYKKT-----------KY
cytor x       ----------------------------------------
cytor7        IT-VFLFSVMGYSIYRYIHVGKEKHPANLILIYGNEFDKR TissueFactor  ----------------------------------------
1274993R      ----------------------------------------
hIFNabR       PFPNLPPPLEAMDMVEVIYINRKKKVWDYNYDDES-DSDTE
CRF2-4        AFS-------------------------------------
cytor x       ----------------------------------------
cytor7        FFVPAEKIVINFITLNISDDSKISHQDMSLLGKSSDVSSL TissueFactor  ---------VGQSWK--------------------EN---
1274993R      ----------------------------------------
hIFNabR       AAPRTSGGGYTMHGLTVRPLGQASATSTESQLIDPESEEE
CRF2-4        --PR---NSLPQHLKEFLGHPHHNTLLFFSFPLSDEN---
cytor x       ----------------------------------------
cytor7        NDPQPSGNLRPPQEEEEVKHLGYASHLMEIFCDSEENTEG
```

FIG.1B

```
TissueFactor   ----------------------------------SP
1274993R       ------------------------------------
hIFNabR        PEEDYSSTEGSGGRITFNVDLNSVFLRVLDDEDSDDLEAP
CRF2-4         --------------------------------VFDK
cytor x        ------------------------------------
cytor7         SLQEEVSTQGTLLESQAALAVLGPQTLQYSYTPQLQDLDP TissueFactor   ----------------------------------------
1274993R       ----------------------------------------
hIFNabR        PDLPEVDVELPTMPKDSP-QQLELLSGPCERRKSPLQDPF
CRF2-4         ---------------D------------------------
cytor x        ----------------------------------------
cytor7         TSLTQQESLSRTIPPDKTVIEYEYDVRTTDICAGPEEQEL TissueFactor   LNVS------------------------------------
1274993R       ----------------------------------------
hIFNabR        LMLSSHLEEMVDPEDPDNVQSNHLLASGEG--------TQ
CRF2-4         LSVIAEDSESG-KQNP-----------G----------DS
cytor x        ----------------------------------------
cytor7         LAQEHTDSEEGPEEEPSTTLVDWDPQTGRLCIPSLSSFDQ TissueFactor   ----------------------------------------
1274993R       ----------------------------------------
hIFNabR        PTFPSPSSEG--------------LWSEDAPSDQSDTSES
CRF2-4         CSLGTPPGQG--------------PQS-------------
cytor x        ----------------------------------------
cytor7         DSEGCEPSEGDGLGEEGLLSRLXEEPAPDRPPGENETYLM TissueFactor   ---------------
1274993R       ---------------
hIFNabR        DVDLGDGYIMR---
CRF2-4 aa      ---------------
cytor x        ---------------
cytor7         QFMEEWGLYVQMEN
```

FIG.1C

```
pTNF-x    1                                             AGREGEE-    7
rTNF-x    1 MWAWGWAAAALLWLQTAGAGARQELKKSRQLFARVDSPNITTSNREGFPG  50
pTNF-y    1                                                     0 pTNF-x    8 ---PSQASGPEFSDAHMTWLNFVRRPDDGALRKRCGSRDKKPR---DLFG  51
rTNF-x   51 SVKPPEASGPELSDAHMTWLNFVRRPDDGSSRKRCRGRDKKSRGLSGLPG 100
pTNF-y    1                                                     0 pTNF-x   52 PPGPPG---------AEVTAETLLHEFQELLKEATERRFSGLLDPLLPQG  92
rTNF-x  101 PPGPPGPPGPPGSPGVGVTPEALLQEFQEILKEATELRFSGLPDTLLPQE 150
pTNF-y    1                                                     0 pTNF-x   93 RGLRLVGEAFHCRLQGPRRVDKRTLVELHGFQAPAAQGAFLRGSGLSLAS 142
rTNF-x  151 PSQRLVVEAFYCRLKGPVLVDKKTLVELQGFQAPTTQGAFLRGSGLSLSL 200
pTNF-y    1                          HELGVYYLPDAEGAFRRGPGLNLTS  25 pTNF-x  143 GRFTAPVSGIFQFSASLHVDHSELQGKARLRARDVVCVLICIESLCQRHT 192
rTNF-x  201 GRFTAPVSAIFQFSASLHVDHSELQGRGRLRTRDMVRVLICIESLCHRHT 250
pTNF-y   26 GQYRAPVAGFYALAATLHVALGEPPRRGPPRPRDHLRLLICIQSRCQRNT  75 pTNF-x  193 CLEAVSGLESNSRVFTLQVQGLLQLQAGQYASVFVDNGSGAVLTIQAGSS 242
rTNF-x  251 SLEAVSGLESNSRVFTVQVQGLLHLQSGQYVSVFVDNSSGAVLTIQNTSS 300
pTNF-y   76 SLEAIMGLESSSELFTISVNGVLYLQMGQWTSWACERPP-QALPLRGKWS 124 pTNF-x  243 FSGLLLGT    250
rTNF-x  301 FSGMLLGT    308
pTNF-y  125 TDLDNVWTVSE 135
```

FIG. 2

```
TLRL1_HU    ------------------------MLSG----VWFLSVLTVAGILQTES---------RKTAKDICKIRCLCEEKENVLNIN
TLRL2_HU    ------------------------MLQT----LAFAVTSLVLSCAET----------IDYYGEICDNACPCEEKDGILTVS
TLRL4_HU    ------------------------MFLW----LFLILSALISSTNAD---------SDISVEICN-VCSCVSVENVLYVN
TLRL3_HU    MKPSIAEMLHRGRMIWIILLSTIALGWTTPIPLIEDSEEIDEPCFDPCYCEVKESLFHIH
TLRL5_HU    ------------MKLWIHLFYSSLLACISLHSQTP--------VLSSRGSCDSLCNCEEKDGTMLIN
                                    *                  *        *    :: ::   :

TLRL1_HU    CENKGFTTVSLLQPPQYRIYQLFLNGNLLTRLYPNEFVNYSNAVTLHLGNNGLQEIRTGA
TLRL2_HU    CENRGIISLSEISPPRFPIYHLLLSGNLLNRLYPNEFVNYTGASILHLGSNVIQDIETGA
TLRL4_HU    CEKVSVYRPNQLKPPWSNFYHLNFQNNEFLNILYPNTFLNFSHAVSLHLGNNKLQNIEGGA
TLRL3_HU    CDSKGFTNISQITEFWSRPFKLYLQRNSMRKLYTNSFLHLNNAVSINLGNNALQDIQTGA
TLRL5_HU    CEAKGIKMVSEISVPPSRPFQLSLLNNGLTMLHTNDFSGLTNAISIHLGFNNIADIEIGA
            *:     .              .   ::*      . :  :   . *    *

TLRL1_HU    FSGLKTLKRLHLNNNKLEIILREDTFLGLESLEYLQADYNYISAIEAGAFSKLNKLKVLIL
TLRL2_HU    FHGLRGLRRLHLNNNKLELLRDDTFLGLENLEYLQVDYNYISVIEPNAFGKLHLLQVLIL
TLRL4_HU    FLGLSALKQLHLNNELKILRADTFLGIENLEYLQADYNLIKYIERGAFNKLHKLKVLIL
TLRL3_HU    ENGLKILKRLYLHENKLDVFRNDTFLGLESLEYLQADYNVIKRIESGAFRNLSKLRVLIL
TLRL5_HU    ENGLGLLKQLHINHNSLEILKEDTFHGLENLEFLQADNNFITVIEPSAFSKLNRLKVLIL
            . *: ::: : :.: : :: :. :** *::.**:****.  :  **. *::*.****
```

FIG. 3A

```
TLRL1_HU   NDNLLLSLPSNVFRFVLLTHLDLRGNRLKVMPEAGVLEHIGG-IMEIQLEENPWNCTCDL
TLRL2_HU   NDNLLSSLPNNLFRFVPLTHLDLRGNRLKLLPYVGLLQHMDK-VVELQLEENPWNCSCEL
TLRL4_HU   NDNLISFLPDNIFRFASLTHLDLRGNRIQKLPYIGVLEHIGR-VVELQLEDNPWNCSCDL
TLRL3_HU   NDNLIPMLPTNLFKAVSLTHLDLRGNRLKVLFYRGMLDHIGRSLMELQLEENPWNCTCEI
TLRL5_HU   NDNAIESLPPNIFRFVPLTHLDLRGNQLQTLPYVGFLEHIGR-ILDLQLEDNKWACNCDL
           ***  :**  *:* *:   ******:*:****  *  * .*:     ::::*****:* *   *:

TLRL1_HU   LPLKAWLDTIT--VFVGEIVCETPFRLHGKDVTQLTRQDLCPRKSASDSSQRGSHADTHV
TLRL2_HU   ISLKDWLDSISYSALVGDVVCETPFRLHGRDLDEVSKQELCKETNKQELCPMGTGSDFDVR-ILPPSQL
TLRL4_HU   LPLKAWLENMPYNIYIGEAICETPSDLYGRLLKETNKQELCPMGTGSDFDVR-ILPPSQL
TLRL3_HU   VQLKSWLERIPYTALVGDITCETPEHFHGKDLREIRKTELCPLLSDSEVEASLGIPHSSS
TLRL5_HU   LQLKTWLENMPPQSIIGDVVCNSPPEFFKGSILSRLKKESICPTPPVYEEHED----PSGS
           : ** :**. :      *:  *.:    .  *  :* ::*    .    :

TLRL1_HU   QRLSPT---MNPALN------------PTRAPKASRPP--KMRNRPTPR-VTVSKDRQSF
TLRL2_HU   GYLHTTPASVNSVATSSSA-------VYKPPLKPPKGTRQPNKPRVRPTSRQPSKDLGYSNY
TLRL4_HU   ENGYTTPNGHTTQTS----------LHRLVTKPPKTTNPS----KISGIVAGKALSNRNL
TLRL3_HU   SKENAWPTKPSSMLSSVHFTASSVEYKSSNKQPKPTKQP---RTPRPPSTSQALYPGPNQ
TLRL5_HU   LHLAATSSINDSRMS--------------------------------TKAPGL
              :   .:                                   .

FIG. 3B
```

```
TLRL1_HU      GPIMVYQTKSPVPLTCPSSCVCTSQSSDNGLNVNCQERKFTNISDLQPKPTSPKKLYLTG
TLRL2_HU      GPSIAYQTKSPVPLECPTACSNLQISDLGLNVNCQERKIESIAELQPKPYNPKKMYLTE
TLRL4_HU      SQIVSYQTRVPPLTPCPAPCFCKTHPSDLGLSVNCQEKNIQSMSELIPKPLNAKKLHVNG
TLRL3_HU      PPIAPYQTRPPIPIICPTGCTNLHINDLGLTVNCKERGFNNISELLPRPLNAKKLYLSS
TLRL5_HU      IPYITKPSTQLPGPYCPIPCNCKVLSPS-GLLIHCQERNIESLSDLRPPQNPRKLILAG
                **    .    *        .      ::.*.    * ..::*:  ..  : .

TLRL1_HU      NYLQTVYKNDLLEYSSLDLLHLGNNRIAVIQEGAFTNLTSLRRLYLNGNYLEVLYPSMFD
TLRL2_HU      NYLAVRRTDFLEATGLDLLHLGNNRISMIQDRAFGDLTNLRRLYLNGNRIERLSPELFY
TLRL4_HU      NSIKDVDVSDFTDFEGLDLLHLGSNQITVIKGDVFHNLTNLRRLYLNGNQIERLYPEIFS
TLRL3_HU      NLIQKIYRSDFWNFSSLDLLHLGNNRISYVQDGAFINLPNLKSLFLNGNDIEKLTPGMFR
TLRL5_HU      NIHSIMKSDLVEYFTLEMLHLGNNRIEVLEEGSFMNLTRLQKLYLNGNHLTKLSKGMFL
              *      .  . :    *:*** *: :  .. * .*  *::*:*** : .* . :

TLRL1_HU      GLQSLQYLYLEYNVIKEIKPLTFDALINLQLLFLNNNLLRSLPDNIFGGTALTRLNLRNN
TLRL2_HU      GLQSLQYLFLQYNLIREIQSGTFDPVPNLQLLFLNNNLLQAMPSGVFSGLTLLRLNLRSN
TLRL4_HU      GLHNLQYLYLEYNLIKEISAGTFDSMPNLQLLYLNNNLLKLFLNNNLLFLNNNLLRLNLRNN
TLRL3_HU      GLQSLHYLYFEFNVIREIQPAAFSIMPNLKLLFLNNNLLFLNNNLLRTLPTDAFAGTSLARLNLRKN
TLRL5_HU      GLHNLEYLYLEYNAIKEILPGTFNPMPKLKVLYLNNNLLQVLPPHIFSGVPLTKVNLKTN
              **:.*:** :::*  :**  .:* . :** :*:*****  .  .   *.  *. *: *

FIG. 3C
```

```
TLRL1_HU    HFSHLPVKGVLDQLPAFIQIDLQENPWDCTCDIMGLKDWTEHANSPVIINEVTCESPAKH
TLRL2_HU    HFTSLPVSGVLDQLKSLIQIDLHDNPWDCTCDIVGMKLWVEQLKVGVLVDEVICKAPKKF
TLRL4_HU    KFMYLPVSGVLDQLQSLTQIDLEGNPWDCTCDLVALKLWVEKLSDGIVVKELKCETPVQF
TLRL3_HU    YFLYLPVAGVLEHLNAIVQIDLNENPWDCTCDLVPFKQWIETISSVSVVGDVLCRSPENL
TLRL5_HU    QFTHLPVSNILDDLDLLTQIDLLTQIDLEDNPWDCSCDLVGLQQWIQKLSKNTVTDDILCTSPGHL
              *  *** .: *:: .   * .  ******.: ::  ::   *         :  .

TLRL1_HU    AGEILKFLGREAICPD--------SPNLSDGTVLSMNHNTDTPRSLSVS--PSSYPELH--
TLRL2_HU    AETDMRSIKSELLCPDYSDVVVSTPTPSSIQVPARTSAVTPAVRLNSTGAPASLGAGGGA
TLRL4_HU    ANIELKSLKNEILCPK---------LLNKPSAPFTSPAPAITFTTPLGPIRSPPGG---
TLRL3_HU    THRDVRTIELEVLCPE---------MLHVAPAGESPAQPGDSHLIGAPTSASPYEFSPPG--
TLRL5_HU    DKKELKALNSEILCPG---------LVNNPSMPTQTSYLMVTTPATTNTADTILRSLT
              : *   :  :* *              .

TLRL1_HU    TEVPLSVLILGLLVVFEILSVCFGAGLFVFVLKRR-KGVPSVPRNTNNLDVSSFQLQYGSY
TLRL2_HU    SSVPLSVLILSLLLVFIMSVFVAAGLFVLVMKRR-KKNQSDHTSTNNSDVSSFNMQYSVY
TLRL4_HU    -PVPLSILILSILVVLILTVFAFCLLVFVLRRN-KKPTVKHEGLNPDCGSMQLQRKH
TLRL3_HU    GPVPLSVLILSLLLVLFFSAVFVAAGLFAYVLRRKKLPFRSKRQEGVDLTGIQMCHRL
TLRL5_HU    DAVPLSVLILGLLIMFITIVFCAAGIVVLVLHRR-RRYKKKQVDEQMRDNSPVHLQYSMY
             ****:****:** :. :*:.: *   .          .                  *
```

FIG. 3D

```
TLRL1_HU    N-----------TETHDK--------------TDGHVYNYIPPPVGQMCQNPIYMQKEGDPVAYYR
TLRL2_HU    GGGGGTGGHPHAHVHHRGPALPKVKTPAGHVYEYIPHPLGHMCKNPIYRSREGNSVEDYK
TLRL4_HU    D-----------HKTNKK--------------DGLSTEAFIPQTIEQMSKSHTCGLKESETGFMFS
TLRL3_HU    FEDGGGGGGGSGGGGRPTLSSPEKAPPVGHVYEYIPHPVTQMCNNPIYKPREEEVAVSS
TLRL5_HU    G-----------HKTTHHTTE-----------RPSASLYEQHMVSPMVHVYRSPSFGPKHLEEEERN
                                            :  ::    :   .             : :

TLRL1_HU    NLQE--------------------FSYSN-----LEEKKEEP----------------
TLRL2_HU    DLHE--------------------LKVTYSSNHHLQQQQQPPPPQQPQQQ--------
TLRL4_HU    DPPG--------------------QKVVMRN---VADKEKDLLH--------------
TLRL3_HU    AQEAGSAERGGPGTQPPGMGEALLGSEQFAETPKENHSNYRTLLEKEKEWALAVSSSQLN
TLRL5_HU    EKEG--------------------SDAKHLQRSLLEQENHSP----------------
                                  :  :::   .   .

TLRL1_HU    --------------------ATPAYTISATELLEK-----QATP---REPELLYQNIA
TLRL2_HU    --PPPQLQLQPGEEERRESHHLRSPAYSVSTIEPRED----LLSPV--QDADRFYRGIL
TLRL4_HU    --------------------VDTRKRLSTIDELDE-----LFPS---RDSNVFIQNFL
TLRL3_HU    TIVTVNHHHPHHPAVGGVSGVVGGTGGDLAGFRHHEKNGGVLFPPGGCGSGSMLLDRE
TLRL5_HU    --------------------LTGSNMKYKTTNQSTE----FLS---FQDASSLYRNIL
                                 .                            .
```

FIG. 3E

```
TLRL1_HU    ERVKELPS---AG--LVHYN--FCTLPKRQFAPSYESRRQNQ------DRINKTVLYGT
TLRL2_HU    EPDKHCSTTPAGNSLPEYPKFPCSPAAYTFSPNYDLRRPHQYLHPGAGDSRLREPVLYSP
TLRL4_HU    ESKKEYNS-------------------IGVSGFEIRYPEKQPDK---------KSKKSLIGGN
TLRL3_HU    RPQPAPCTVGFVDCLYGTVPKLKELHVHPPGMQYPDLQQDA----------RLKETLLFSA
TLRL5_HU    EKERELQQLG-----ITEYLRKNIAQLQPDMEAHYPGAHEEL---------KLMETLMYSR
                                   *                                      ::    ::   .

TLRL1_HU    PRKCFVGQS-KPNHPLLQAKPQSEPDYLEVLEKQTAISQL
TLRL2_HU    PSAVFVEPN-RNEYLELKAKLNVEPDYLEVLEKQTTFSQF
TLRL4_HU    HSKIVVEQR-KSEYFELKAKLQSSPDYLQVLEEQTALNKI
TLRL3_HU    EKGFTDHQTQKSDYLELRAKLQTKPDYLEVLEKTTYRF--
TLRL5_HU    PRKVLVEQT-KNEYFELKANLHAEPDYLEVLEQQT-----
                 ::  ::     :    ::*:*:*:**:**::*:  *
```

FIG. 3F

```
r5685C6    MTSPSSFCLLLLQALGIVALGHFTKAQNN-TLIFTKGNTIRNCSCPVDIRDCDYSLANLI
p5685C6    MAPPSRHCLLLISTLGVFALNCFTKGQKNSTLIFTRENTIRNCSCSADIRDCDYSLANLM
           *:.**  .****:::.:.**.  ***.*:* ************..:************:

r5685C6    CSCKSILPSAMEQTSYHGHLTIWFTDISTLGHVLKFTLVQDLKLSLCGSSTFPTKYLAIC
p5685C6    CNCKTVLPLAVERTSYNGHLTIWFTDTSALGHLLNFTLVQDLKLSLCSTNTLPTEYLAIC
           *.*:*::**.*::* ****:::**:*:***********.::. *:.***** r5685C6    GLQRLRIHTKARHPSRGQSLLIHSRREGSS------LYKGWQTCMFISFLDVALFNGDSS
p5685C6    GLKRLRINMEAKHPFPEQSLLIHSGGDSDSREKPMWLHKGWQPCMYISFLDMALFNRDSA
           **:****:  *:** . *******  ..*      *:****. **:*****:****.*:

r5685C6    LKSYSIDNISSLASDFPDFSYFKTSPMPSNRSYVVTVIY
p5685C6    LKSYSIENVTSIANNFPDFSYFRTFPMPSNKSYVVTFIY
           *******:*::*:*::*****:*:******:*****:**
```

FIG. 4

```
D2    1  MASLGLQLVGYILGLLGLLGTLVAMLLPSWKTSSYVGASIVTAVGFSKGL       50
D8    1  MATHALEIAGLFLGGVGMVGTVAVTVMPQWRVSAFIENNIVVFENFWEGL       50
D17   1  MAFYPLQIAGLVLGFLGMVGTLATTLLPQWRVSAFVGSNIIVFERLWEGL       50
D7.2  1  MAVTACQGLGFVVSLIGIAGIIAATCMAQWSTQDLY-NNPVTAVENYQGL       49
          *  *            *      *     *   .         *  *

D2    51 WMECATHSTGITQCDIYSTLLGLPADIQGAQAMMVTSSAISSLACIISVV       100
D8    51 WMNCVRQANIRMQCKIYDSLLALSPDLQAARGLMCAASVMSELAFMAIL       100
D17   51 WMNCIRQARVRLQCKFYSSLLALPPALETARALMCVAVALSLIALLIGIC       100
D7.2  50 WRSCVRESSGFTECRGYFTLLGLPGKGQ---------VSGWLEGEI          86
          * *          *   *  *   .            *    .

D2    101 GMRCTVFCQES-RAKDRVAVAGGVFFILGGLLGFIPVAWNLHGILRDFYS     149
D8    101 GMKCTRCTGDNEKVKAHILLTAGINLLIITGMVGANPVNLVSNAIIRDFFT    150
D17   101 GMKQVQCTGSNERAKAYLLGTSGVLFLTGIFVLIPVSWTANIIIRDFYN     150
D7.2   87 GG-------GEE-----------------TAGSVWAPRQGLLGRE-----ELRFVFDRGN  117
          *                                              *
```

FIG. 5A

```
D2    150  PLVPDSMKFEIGEALYLGIISSLFSLIAGIILCFSCSSQRNRSNYYDAYQ  199
D8    151  PIVNVAQKRELGEALYLGWTTALVLIVGGALFCCVFCCNEKSSSYRYSIP  200
D17   151  PAIHIGQKRELGAALFLGWASAAVLFIGGGLLCGFCCCNRKKQGYRYPVP  200
D7.2  118  SHLHQGG-----------------------IGG----------RE----P  130
                                         *

D2    200  AQPLATRSSPRAGQPPPKVKSEFNSYSLTGYV  230
D8    201  SHRTTQKSYHTGK------KSPSVYSRSQYV   225
D17   201  GYRVPHTDKRRN-------TTMLSKTSTSYV   224
D7.2  131                                    130
```

FIG. 5B

```
B   1  MESLKTDTEMPYPEVIVDVGRVIFGEENRKKMTNSCLKRSENSRIIRA   48
C   1  MEANHCSLGVYPSYPDLVIDVGEVTLGEENRKKLQKTQRDQ-ERARVIRA  49
D   1     MNISVDLETNYAELVLDVGRVTLGENSRKKMKDCKLRKKQNERVSRA  47
E   1          MSLRIDVDTNFPECVVDAGKVTLGTQQRQEMDPRLREK-QNEIILRA  46
F   1  MEANQCPLVVEPSYPDLVINVGEVTLGEENRKKLQKIQRDQ-EKERVMRA  49
                    *   *       *         .         .     **

B  49  ICALLNSGGGVIKAEIDDKTYSYQCHGLGQDLETSFQKLLPS-GSQKYLD  97
C  50  ACALLNSGGGVIQMEMANR--DERPTEMGLDLEESLRKLIQYPYLQAFFE  97
D  48  MCALLNSGGGVIKAEIENEDYSYTKDGIGLDLENSFSNILLF-VP-EYLD  95
E  47  VCALLNSGGGIIKAEIE----------NKGYNYERHGVGLDVPPIFRSHLD 87
F  50  ACALLNSGGGVIRMAKK-----VEHPVEMGLDLEQSLRELIQSSDLQAFFE  95
        ********* .*.*              *       .      .

B  98  YMQQGHNLLIFVKSWSPD----VFSLPLRICSLRSNLYRRDVTSAINLSA 143
C  98  TKQHGRCFYIFVKSWSGDPFLKDGSFNSRICSLSSSLYCRSGTSVLHMNS 147
D  96  FMQNGNYELIFVKSWS------LNTSGLRITTLSSNLYKRDITSAKVMNA 139
E  88  KMQKENHFLIFVKSWNTEAGVP------LATLCSNLYHRERTSTDVMDS 130
F  96  TKQQGRCFYIFVKSWSSSGPFPEDRSVKPRLCSLSSSLYRRSETSVRSMDS 145
         *    . *****           *     * * **   .
```

FIG. 6A

B  144  SSALELLREKGFRAQRGRPRVKKLHPQQVLNRCIQEEEDMR------ILA  187
C  148  RQAFDFLKTKER-QSKYNLINEGSPPSKIMKAVYQNISESN------PA   189
D  140  TAALEFLKD--MKKTRGRLYLRPELLAKRPCVDIQEENNMK------ALA  181
E  131  QEALAFLKCRT--QTPTNINVSNSLGPQAAQGSVQYEGNIN------VSA  172
F  146  REAFCFLKTKR----KPKILEEG-PFHKIHKGVYQELPNSDPADPNSDPA  190
                *                                          *

B  188  SEFFKKDKIMYKEKLNFTESTHVEFKRFTTKKVIPRIKEMLPHYVSAFAN  237
C  190  YEVFQTDTIEYGEILSFPESPSIEFKQFSTKHIQQYVENIIPEYISAFAN  239
D  182  GVFFDRTELDRKEKLTFTESTHVEIKNFSTEKLLQRIKEILPQYVSAFAN  231
E  173  AALEDRKRLQYLEKLNLPESTHVEFVMFST-DVSHCVKDRLPKCVSAFAN  221
F  191  DLIFQKDYLEYGEILPFPESQLVEFKQFSTKHFQEYVKRTIPEYVPAFAN  240
           *           *  *  *  *          *        ****

B  238  TQGGYVLIGVDDKSKEVVGCKWEKVNPDLLKKEIENCIEKLPTFHFCCEK  287
C  240  TEGGYLFIGVDDKSRKVLGCAKEQVDPDSLKNVIARAISKLPIVHFCSSK  289
D  232  TDGGYLFIGLNED-KEIIGFKAEMSDLDDLEREIEKSIRKMPVHHFCMEK  280
E  222  TEGGYVFFGVHDETCQVIGCEKEKIDLTSLRASIDGCIKKLPVHHFCTQR  271
F  241  TGGGYLFXGVDDKSREVLGCAKENXDPDSLRXKIEXAIYKLPCXHFCQPQ  290
        * ***  *        *  *          *  *       *  **

FIG. 6B

```
B  288  PKVNFTTKILNVYQKDVLDGYVCVIQVEPFCCVVFEAEAPDSWIMKDNSVT      337
C  290  PRVEYSTKIVEVFCGKELYGYLCVIKVKAFCCVVFSEAPKSWMVREKYIR       339
D  281  KKINYSCKFLGVYDKGSLCGYVCALRVERFCCAVFAKEPDSWHVKDNRVM       330
E  272  PEIKYVLNFLEVHDKGALRGYVCAIKVEKFCCAVFEAKVPSSWQVKDNRVR      321
F  291  RPITFTLKIVDVLKRGELYGYACMIRVNPFCCAVFSEAPNSWIVEDKYVC       340
              *     *     .  *     *    **     * *.   *      .  . .

B  338  RLTAEQWVVMMLDTQ----------------------------------      352
C  340  PLTTEEWVEKMMDADPEFPPDEAEAFESQLSLSDSPSLCRPVYSKKGLEH      389
D  331  QLTRKEWIQFMVEAEPKFS--SSYEEVISQINTSLPAHSWPLL------EW    374
E  322  QLPTREWTAWMMEADPDLS--RCPEMVLQLSLSSATPRSKPVCIHKNSEC     369
F  341  SLTTEKWVGMMTDTDPDLL--QLSEDFECQLSLSSGPPLSRPVYSKKGLEH    389
              *     *     *  * . .  *   *   *

B  353  ---------SGKGK                                          357
C  390  KADLQQHLFPVPPGHLECTPESLWKELSLQHEGLKELIHKQMRPFSQGIV       439
D  375  QR---QRHHCPGLSGRITYTPENLCRKLFLQHEGLKQLICEEMDSVRKGSL      422
E  370  LKEQQKRYFPVESDRVVYTPESLYKELFSQHKGLRDLINTEMRPFSQGIL       419
F  390  KKELQQLLFSVPPGYLRYTPESLWRDLISEHRGLEELINKQMPFFRGIV        439
```

FIG. 6C

```
B  358                                                                              357
C  440  ILSRSWAVDLNLQEKPGVICDALLIAQNSTPILYTILREQDAEGQDYCTR                           489
D  423  IFSRSWSVDLGLQENHKVLCDALLISQDSPPVLYTFHMVQDEEFKGYSTQ                           472
E  420  IFSQSWAVDLGLQEKQGVICDALLISQNNTPILYTIFSKWDAGCKGYSMI                           469
F  440  ILSRSWAVDLNLQEKPGVICDALLIAQNSTPILYTILREQDAEGQDYCTR                           489

B  358                                                                              357
C  490  TAFTLKQKLVNMGGYTGKVCVRAKVLCLSPESSAEALEAAVSPMDYPASY                           539
D  473  TALTLKQKLAKIGGYTKKVCVMTKIFYLSPEG------                                       504
E  470  VAYSLKQKLVNKGGYTGRLCITPLVCVLNSDRKAQSVYSSY-LQIYPESY                           518
F  490  TAFTLKQKLVNMGGYTGKVCVRAKVLCLSPESSAEALEAAVSPMDYPASY                           539

B  358                                                                              357
C  540  SLAGTQHMEALLQSLVIVLLGFRSLLSDQLGCEVLNLLTAQQYEIFSRSL                           589
D  505  ------------MTSCQYDLRSQVI                                                    517
E  519  NFMTPQHMEALLQSLVIVLLGFKSFLSEELGSEVLNLLTNKQYELLSKNL                           568
F  540  SLAGTQHMEALLQSLVIVLLGFRSLLSDQLGCEVLNLLTAQQYEIFSRSL                           589
```

FIG. 6D

```
B  358                                                                              357
C  590  RKNRELFVHGLPGSGKTIMAMKIMEKIRNVFHCEAHRILYVCENQPLRNF              639
D  518  YPESYYFTRRKYLLKALFKALKRLKSLRDQFSFAENLYQIIG---------               559
E  569  RKTRELFVHGLPGSGKTILALRIMEKIRNVFHCEPANILYICENQPLKKL              618
F  590  RKNRELFVHGLPGSGKTIMAMKIMEKIRNVFHCEAHRILYVCENQPLRNF              639

B  358                                                                              357
C  640  ISD---RNICRAETRETFLREKFEHIQHIVIDEAQNFRTEDGDWYRKAKTI             687
D  560  -----------------------IDCFQKNDKKMFKSCRRL                       577
E  619  VSFSKKNICQPVTRKTFMKNNFEHIQHIIIDDAQNFRTEDGDWYGKAKFI             668
F  640  ISD---RNICRAETRKTFLRENFEHIQHIVIDEAQNFRTEDGDWYGKAKSI             687

B  358                                                                              357
C  688  TQREKDCPGVLWIFLDYFQTSHLGHSGLPPLSAQYPREELTRVVRNADEI             737
D  578  T                                                                578
E  669  TRQQRDGPGVLWIFLDYFQTYHLSCSGLPPPSDQYPREEINRVVRNAGPI             718
F  688  TRRAKGGILWIFLDYFQTSHLDCSGLPPLSDYPREELTRIVRNADPI                737
```

FIG. 6E

```
B  358                                                              357
C  738  AEYIQQEMQLIIENPPINIPHGYLAILSEAKWVPGVPGNTKIIKNFTLEQ           787
D  579                                                              578
E  719  ANYLQQVMQEARQNPPPNLPPGSLVMLYEPKWAQGVPGNLEIIEDLNLEE            768
F  738  AKYLQKENASN                                                  748

B  358                                                              357
C  788  IVTYVADTCRCFFERGYSPKDVAVLVSTVTEVEQYQSKLLKAMRKK----            833
D  579                                                              578
E  769  ILIYVANKCRFLLRNGYSPKDIAVLFTKASEVEKYKDRLLTAMRKRKLSQ            818
F  749                                                              748

B  358                                                              357
C  834  ------MVVQLSDACDMLGVHIVLDSVRRESGLERSIVFGIHPRTADPAI            877
D  579                                                              578
E  819  LHEESDLLLQIGDASDVLTDHIVLDSVCRFSGLERNIVFGINPGVAPPAG            868
F  749                                                              748

B  358                             357
C  878  LPNILICLASRAKQHLYIFL         897
D  579                             578
E  869  AYNLLLCLASRAKRHLYILKASV      891
F  749                             748
```

FIG. 6F

ANTIBODIES BINDING THE TNF RELATED PROTEIN, TNF-X

This application claims benefit of U.S. provisional patent application No. 60/231,267, filed Sep. 8, 2000.

FIELD OF THE INVENTION

The present invention relates to compositions and methods for affecting mammalian physiology, including morphogenesis or immune system function. In particular, it provides nucleic acids, proteins, and antibodies which regulate development and/or the immune system. Diagnostic and therapeutic uses of these materials are also disclosed.

BACKGROUND OF THE INVENTION

Recombinant DNA technology refers generally to techniques of integrating genetic information from a donor source into vectors for subsequent processing, such as through introduction into a host, whereby the transferred genetic information is copied and/or expressed in the new environment. Commonly, the genetic information exists in the form of complementary DNA (cDNA) derived from messenger RNA (mRNA) coding for a desired protein product. The carrier is frequently a plasmid having the capacity to incorporate cDNA for later replication in a host and, in some cases, actually to control expression of the cDNA and thereby direct synthesis of the encoded product in the host. See, e.g., Sambrook, et al. (1989) *Molecular Cloning: A Laboratory Manual,* (2d ed.), vols. 1–3, CSH Press, NY.

For some time, it has been known that the mammalian immune response is based on a series of complex cellular interactions, called the "immune network". Recent research has provided new insights into the inner workings of this network. While it remains clear that much of the immune response does, in fact, revolve around the network-like interactions of lymphocytes, macrophages, granulocytes, and other cells, immunologists now generally hold the opinion that soluble proteins, known as lymphokines, cytokines, or monokines, play critical roles in controlling these cellular interactions. The interferons are generally considered to be members of the cytokine family. Thus, there is considerable interest in the isolation, characterization, and mechanisms of action of cell modulatory factors, an understanding of which will lead to significant advancements in the diagnosis and therapy of numerous medical abnormalities, e.g., immune system disorders.

Lymphokines apparently mediate cellular activities in a variety of ways. See, e.g., Paul (ed. 1998) *Fundamental Immunology* 4th ed., Lippincott; and Thomson (ed. 1998) *The Cytokine Handbook* 3d ed., Academic Press, San Diego. They have been shown to support the proliferation, growth, and/or differentiation of pluripotential hematopoietic stem cells into vast numbers of progenitors comprising diverse cellular lineages which make up a complex immune system. Proper and balanced interactions between the cellular components are necessary for a healthy immune response. The different cellular lineages often respond in a different manner when lymphokines are administered in conjunction with other agents.

Cell lineages especially important to the immune response include two classes of lymphocytes: B-cells, which can produce and secrete immunoglobulins (proteins with the capability of recognizing and binding to foreign matter to effect its removal), and T-cells of various subsets that secrete lymphokines and induce or suppress the B-cells and various other cells (including other T-cells) making up the immune network. These lymphocytes interact with many other cell types.

One means to modulate the effect of a cytokine upon binding to its receptor, and therefore potentially useful in treating inappropriate immune responses, e.g., autoimmune, inflammation, sepsis, and cancer situations, is to inhibit the receptor signal transduction. In order to characterize the structural properties of a cytokine receptor in greater detail and to understand the mechanism of action at the molecular level, purified receptor will be very useful. The receptors provided herein, by comparison to other receptors or by combining structural components, will provide further understanding of signal transduction induced by ligand binding.

An isolated receptor gene should provide means to generate an economical source of the receptor, allow expression of more receptors on a cell leading to increased assay sensitivity, promote characterization of various receptor subtypes and variants, and allow correlation of activity with receptor structures. Moreover, fragments of the receptor may be useful as agonists or antagonists of ligand binding. See, e.g., Harada, et al. (1992) *J. Biol. Chem.* 267:22752–22758. Often, there are at least two critical subunits in the functional receptor. See, e.g., Gonda and D'Andrea (1997) *Blood* 89:355–369; Presky, et al. (1996) *Proc. Nat'l Acad. Sci. USA* 93:14002–14007; Drachman and Kaushansky (1995) *Curr. Opin. Hematol.* 2:22–28; Theze (1994) *Eur. Cytokine Netw.* 5:353–368; and Lemmon and Schlessinger (1994) *Trends Biochem. Sci.* 19:459–463. Other receptor types, e.g., TLR-like, will similarly be useful.

Likewise, identification of novel ligands will be useful. Members of the tumor necrosis factor (TNF) family and transforming growth factor (TGF) family of ligands have identified physiological effects.

Finally, genes which exhibit disease associated expression patterns will be useful in diagnostic or other uses. The molecular diagnostic utility may be applied to identify patients who will be responsive to particular therapies, or to predict responsiveness to treatment.

From the foregoing, it is evident that the discovery and development of new soluble proteins and their receptors, including ones similar to lymphokines, should contribute to new therapies for a wide range of degenerative or abnormal conditions which directly or indirectly involve development, differentiation, or function, e.g., of the immune system and/or hematopoietic cells. Moreover, novel markers will be useful in molecular diagnosis or therapeutic methods. In particular, the discovery and understanding of novel receptors or lymphokine-like molecules which enhance or potentiate the beneficial activities of other lymphokines would be highly advantageous. The present invention provides these and related compounds, and methods for their use.

BRIEF DESCRIPTION OF THE DRAWINGS

FIGS. 1A–1C show a sequence alignment of related IFN receptor family members. Tissue Factor is SEQ ID NO: 4; hIFNabR is SEQ ID NO: 5; CRF2-4 is SEQ ID NO: 6; cytor x is SEQ ID NO: 7; and cytor7 is SEQ ID NO: 8.

FIG. 2 shows an alignment of TNF-x and TNF-y polypeptides (SEQ ID NO:9, 11, and 13); p is primate, r is rodent.

FIGS. 3A–3F show an alignment of primate and rodent TLR-like protein sequences.

FIG. 4 shows an Alignment of primate and rodent 5685C6 polypeptide sequences.

FIG. 5 shows an alignment of Claudin homologs: D2 (SEQ ID NO:34); D8 (SEQ ID NO:37); D17 (SEQ ID NO:39); D7.2 (SEQ ID NO:41).

FIGS. 6A–6F show an aligment of Schlafen homologs: schlafen B (SEQ ID NO:43); schlafen C (SEQ ID NO:45); schlafen D (SEQ ID NO:47); schlafen E (SEQ ID NO:49); and schlafen F (SEQ ID NO:51).

SUMMARY OF THE INVENTION

The present invention is directed to novel genes, e.g., primate embodiments. These genes include receptors related to cytokine receptors, e.g., cytokine receptor like molecular structures, designated DNAX Interferon-like Receptor Subunit 4 (DIRS4); TNF related cytokines designated TNFx and TNFy; Toll-like receptor like molecules designated TLR-L1, TLR-L2, TLR-L3, TLR-L4, and TLR-L5; a TGF related molecule designated TGFx; a soluble Th2 cell produced entity designated 5685C6; a group of genes related to ones whose expression patterns correlate with medical conditions designated claudins, herein referred to as claudins D2, D8, D17, and D7.2; and a second group of genes related to ones whose expression patterns correlate with medical conditions designated schlafens, herein referred to as schlafens B, C, D, E, and F.

In particular, the present invention provides a composition of matter selected from: a substantially pure or recombinant polypeptide comprising at least three distinct nonoverlapping segments of at least four amino acids identical to segments of: SEQ ID NO: 2 (DIRS4); SEQ ID NO: 9, 11, 13, or 53 (TNFx or TNFy); SEQ ID NO: 15, 17, 19, 21, 23, 25, or 27 (TLR-L1 through TLR-L5); SEQ ID NO: 29 (TGFx): SEQ ID NO: 31 or 33 (5685C6); SEQ ID NO: 35, 37, 39, or 41 (claudins); SEQ ID NO: 43, 45, 47, 49, or 51 (schlafens). In preferred embodiments, the distinct nonoverlapping segments of identity: include one of at least eight amino acids; include one of at least four amino acids and a second of at least five amino acids; include at least three segments of at least four, five, and six amino acids; or include one of at least twelve amino acids. In certain embodiments, the polypeptide: is unglycosylated; is from a primate, such as a human; comprises at least contiguous seventeen amino acids of the SEQ ID NO; exhibits at least four nonoverlapping segments of at least seven amino acids of the SEQ ID NO; has a length at least about 30 amino acids; has a molecular weight of at least 30 kD with natural glycosylation; is a synthetic polypeptide; is attached to a solid substrate; is conjugated to another chemical moiety; or comprises a detection or purification tag, including a FLAG, His6, or Ig sequence. In other embodiments, the composition comprises: a substantially pure polypeptide; a sterile polypeptide; or the polypeptide and a carrier, wherein the carrier is: an aqueous compound, including water, saline, and/or buffer; and/or formulated for oral, rectal, nasal, topical, or parenteral administration.

Kit embodiments include those comprising such a polypeptide, and: a compartment comprising the polypeptide; or instructions for use or disposal of reagents in the kit.

Binding compound embodiments include those comprising an antigen binding site from an antibody, which specifically binds to a described polypeptide, wherein: the binding compound is in a container; the polypeptide is from a human; the binding compound is an Fv, Fab, or Fab2 fragment; the binding compound is conjugated to another chemical moiety; or the antibody: is raised to a recombinant polypeptide; is raised to a purified polypeptide; is immunoselected; is a polyclonal antibody; binds to a denatured antigen; exhibits a Kd to antigen of at least 30_M; is attached to a solid substrate, including a bead or plastic membrane; is in a sterile composition; or is detectably labeled, including a radioactive or fluorescent label.

Kit embodiments include those comprising such a binding compound, and: a compartment comprising the binding compound; or instructions for use or disposal of reagents in the kit.

Methods are provided, e.g., for producing an antigen:antibody complex, comprising contacting under appropriate conditions a primate polypeptide with such a described antibody, thereby allowing the complex to form. Also provided are methods of producing an antigen:antibody complex, comprising contacting under appropriate conditions a polypeptide with an antibody which binds thereto, thereby allowing the complex to form. And methods are provided to produce a binding compound comprising: immunizing an immune system with a polypeptide described; introducing a nucleic acid encoding the described polypeptide to a cell under conditions leading to an immune response, thereby producing said binding compound; or selecting for a phage display library for those phage which bind to the desired polypeptide.

Further compositions are provided, e.g., comprising: a sterile binding compound, or the binding compound and a carrier, wherein the carrier is: an aqueous compound, including water, saline, and/or buffer; and/or formulated for oral, rectal, nasal, topical, or parenteral administration.

Nucleic acid embodiments are provided, e.g., an isolated or recombinant nucleic acid encoding a polypeptide described, wherein the: polypeptide is from a primate; or the nucleic acid: encodes an antigenic polypeptide; encodes a plurality of antigenic polypeptide sequences of SEQ ID NO:2, 9, 11, 13, 15, 17, 19, 21, 23, 25, 27, 29, 31, 33, 35, 37, 39, 41, 43, 45, 47, 49, 51, or 53; exhibits identity over at least thirteen nucleotides to a natural cDNA encoding the segment; is an expression vector; further comprises an origin of replication; is from a natural source; comprises a detectable label; comprises synthetic nucleotide sequence; is less than 6 kb, preferably less than 3 kb; is a hybridization probe for a gene encoding the polypeptide; or is a PCR primer, PCR product, or mutagenesis primer.

Various embodiments also include cells comprising the recombinant nucleic acids, particularly wherein the cell is: a prokaryotic cell; a eukaryotic cell; a bacterial cell; a yeast cell; an insect cell; a mammalian cell; a mouse cell; a primate cell; or a human cell.

Kit embodiments include those comprising a described nucleic acid, and: a compartment comprising the nucleic acid; a compartment further comprising a primate polypeptide; or instructions for use or disposal of reagents in the kit.

Other nucleic acids are provided which: hybridize under wash conditions of 30 minutes at 37° C. and less than 2M salt to the coding portion of SEQ ID NO: 1, 8, 10, 12, 14, 16, 18, 20, 22, 24, 26, 28, 30, 32, 34, 36, 38, 40, 42, 44, 46, 48, 50 or 52; or exhibit identity over a stretch of at least about 30 nucleotides to a SEQ ID NO: 1, 8, 10, 12, 14, 16, 18, 20, 22, 24, 26, 28, 30, 32, 34, 36, 38, 40, 42, 44, 46, 48, 50, or 52. Preferably, the wash conditions are at 45° C. and/or 500 mM salt, or at 55° C. and/or 150 mM salt; or the stretch is at least 55 or 75 nucleotides.

Methods are provided, e.g., for making: a duplex nucleic acid comprising contacting: a described nucleic acid with a complementary nucleic acid, under appropriate conditions, thereby resulting in hybridization to form the complex; or a nucleic acid complementary to a described nucleic acid with its complementary nucleic acid, under appropriate conditions, thereby resulting in hybridization to form the complex; or a polypeptide comprising culturing a cell comprising a described nucleic acid under conditions resulting in expression of the nucleic acid.

And methods are provided to: modulate physiology or development of a cell comprising contacting the cell with a polypeptide comprising SEQ ID NO: 9, 11, 13, 29, 31, or 33; modulate physiology or development of a cell comprising contacting the cell with a binding compound which binds to SEQ ID NO: 9, 11, 13, 29, 31, 33 or 53, thereby blocking signaling mediated by a protein comprising the SEQ ID NO; label a cell comprising contacting the cell with a binding compound which binds to SEQ ID NO: 15, 17, 19, 21, 13, 15, or 37; or diagnose a medical condition comprising a step of evaluating expression of nucleic acid comprising SEQ ID NO: 34, 36, 38, 40, 42, 44, 46, 48, or 50.

DETAILED DESCRIPTION OF THE PREFERRED EMBODIMENTS

I. General

The present invention provides the amino acid sequences and nucleic acid sequences of mammalian, herein primate, genes. Among them is an interferon receptor-like subunit molecule, one designated DNAX Interferon Receptor family Subunit 4 (DIRS4), having particular defined properties, both structural and biological. Others include molecules designated TNFx and TNFy; Toll like receptor like molecules TLR-L1, TLR-L2, TLR-L3, TLR-L4, and TLR-L5; TGFx; 5685C6; claudins D2, D8, D17, and D7.2; and schlafens B, C, D, E, and F. Various cDNAs encoding these molecules were obtained from primate, e.g., human, cDNA sequence libraries. Other primate or other mammalian counterparts would also be desired. In certain cases, alternative splice variants should be available.

Some of the standard methods applicable are described or referenced, e.g., in Maniatis, et al. (1982) *Molecular Cloning. A Laboratory Manual,* Cold Spring Harbor Laboratory, Cold Spring Harbor Press; Sambrook, et al. (1989) *Molecular Cloning: A Laboratory Manual,* (2d ed.), vols. 1–3, CSH Press, NY; Ausubel, et al., *Biology,* Greene Publishing Associates, Brooklyn, N.Y.; or Ausubel, et al. (1987 and periodic supplements) *Current Protocols in Molecular Biology,* Greene/Wiley, New York; each of which is incorporated herein by reference.

A nucleotide and corresponding amino acid sequence for a primate, e.g., human DIRS4 coding segment is shown in SEQ ID NO: 1 and 2, respectively. The new DIRS4 lacks a transmembrane segment, which suggests that the subunit acts as a soluble subunit, and would thus be an alpha receptor subunit. Alternatively, or in addition, a splice variant would exist which contains a transmembrane segment. This is consistent with the observation that two transcripts are found in many cell types. Interferon receptor like subunits may be receptors for the IL-10 family of ligands, e.g., IL-10, AK155, IL-19, IL-20/mda-7, AK155, IL-D110, IL-D210, etc. See, e.g., Derwent patent sequence database.

Also provided are nucleotide (SEQ ID NO: 8, 10, 12, and 52) and corresponding amino acid sequences (SEQ ID NO: 9, 11, 13, and 53) for primate and rodent forms of TNFx and primate and rodent forms of TNFy. Features for primate TNFx include: cAMP PKsites about 38, 74, 79, 205; Cas Phos sites about 41, 61; Cyt_c-Mesite about 43; Histone-Me site about 35; Myristoly sites about 5, 57, 220, 232 N-GLYCOSYL site about 229; PHOS2 sites about 38–41, 79–82, 134–136; PKC ph sites about 77, 142. Also segments 119–250, and 209–221 are notable. For rodent TNFx, features include: A predicted signal 1–19; mature would begin at about 20. Other features: cAMP PK sites at about 34, 93, 132, 229, 248, 263; Cas Phos sites about 119, 232, 251; Cyt_c-Me sites about 26, 90, 172; Histone-Me site about 82; Myristoly sites around 278, 290, 303; N-GLYCOSYL: 3 sites about 39, 287, 297; PHOS2 sites about 26–29, 34–37, 90–92, 93–96, 138–140, 192–194, 248–251; and PKC ph sites about 43, 51, 80, 81, 152; TyKinsite about 154. Signal cleavage site predicted between pos. 19 and 20: AGA-GA. Other significant segments include from about 74–132, 94–118, 168–308, and 193–201.

Nucleotide and corresponding amino acid sequences for TLR-L1 through TLR-L5 are provided in SEQ ID NO:14–27. The EST distribution for TLR1 suggests mRNA expression is restricted to brain tissue; chromosome Xq27.1-28 coding region is on a single exon. Features for primate TLR1 (SEQ ID NO:15) include: Tyr Kin site about 704 (KEGDPVAY); Tyr Kin sites about 713 (RNLQEFSY), 825(KPQSEPDY); N-GLYCOSYL sites about 84 (NYS), 219 (NCT), 294 (NPT), 366 (NIS), 421 (NLT), 583 (NLS); likely a Type Ia membrane protein; a possible uncleavable N-term signal sequence; and a transmembrane prediction of about 618–634<612–646>. For rodent TLR-L1( SEQ ID NO:17), the features include: A predicted transmembrane segment from about residues 56–75; and predicted TyKin sites at about residues 136 and 145.

For primate TLR-L2 (SEQ ID NO:19) features include: N-glycosyl sites about 82 (NYT), 217 (NCS), 623 (NST), 674 (NQS); TyKin sites about 889 (RLREPVLY), 450 (RLSPELFY), 917 (KLNVEPDY); TyKin site about 889 (RLREPVLY), 917 (KLNVEPDY). Structurally this molecule has homology to type Ia membrane proteins.

Primate TLR-L3 (SEQ ID NO:23) has the following features: SIGNAL 1-26; TRANS 14-34; Pfam:LRRNT 43-73; Pfam:LRR 78-101; LRR_TYP 100-123; Pfam:LRR 102-125; LRR_TYP 124-147; Pfam:LRR 126-149, LRR_TYP 148-171; Pfam:LRR 150-173; LRR_TYP 172-195; LRR_PS 172-194; Pfam:LRR 174-197; LRR_TYP 196-219; LRRCT 232-282; Pfam:LRRCT 232-282 with SEG 331-349 or SEG 365-379; Pfam:LRRNT 372-405; LRRNT 372-410; Pfam:LRR 409-432; LRR_TYP 431-454; Pfam:LRR 433-456; LRR_PS 455-477; LRR_TYP 455-478; Pfam:LRR 457-480; LRR_TYP 479-502; Pfam:LRR 481-504 with SEG 502-519; LRR_TYP 503-526; LRR_PS 503-525; Pfam:LRR 505-528; Pfam:LRRCT 562-612; LRRCT 562-612; TRANS 653-673; SEG 653-676; SEG 712-723; SEG 760-776; SEG 831-855. Structurally this molecule has homology to type Ia membrane proteins.

Primate TLR-L4 (SEQ ID NO:25) EST distributions suggest mRNA expression is restricted to brain tissue; human chromosome Xq26.3-28; predicted features at about, e.g., SIGNAL 1-18; SEG 22-38; Pfam:LRR 60-83; LRR_TYP 82-105; Pfam:LRR 84-107; LRR_PS 106-128; LRR_TYP 106-129; Pfam:LRR 108-131; LRR_TYP 130-153; Pfam:LRR 132-155; LRR_SD22 154-174; LRR_PS 154-176; LRR_TYP 154-177; Pfam:LRR 156-178; LRR_SD22 177-198; LRR_PS 177-198; LRR_TYP 178-201; Pfam:LRR 179-200; Pfam:LRRCT 213-263; LRRCT 213-263; LRRNT 341-379; Pfam:LRRNT 341-374; Pfam:LRR 378-401; LRR_TYP 400-423; LRR_SD22 400-421; Pfam:LRR 402-425; LRR_TYP 424-447; LRR_SD22 424-450; LRR_PS 424-447; Pfam:LRR 426-449; LRR_TYP 448-471; LRR_PS 448-470; Pfam:LRR450-473; LRR_TYP 472-495; LRR_PS 472-494; Pfam:LRR 474-497; SEG 474-488; LRRCT 531-581; Pfam:LRRCT 531-581; SEG 617-643; TRANS 623-643; N-GLYCOSYL sites about 81 (NFS), 216 (NCS), 308 (NPS), 325 (NLS), 423 (NLT);

chromosome Xq26.3-28; coding region is on a single exon. Stucturally this molecule appears to be a Type Ia membrane protein.

For primate TLR-L5 (SEQ ID NO:27) the entire coding region lies on a single exon on human chromosome 13; predicted features at about, e.g., SIGNAL 1-20; Pfam:LRR 65-88; LRR_TYP 87-110; Pfam:LRR 89-112; LRR_TYP 111-134; Pfam:LRR 113-136; LRR_PS 135-157; LRR_ SD22 135-156; LRR_TYP 135-158; Pfam:LRR 137-160; LRR_TYP 159-182; LRR_SD22 159-177; LRR_PS 159-181; Pfam:LRR 161-184; LRR_SD22 182-203; LRR_TYP 185-206; Pfam:LRR 185-205; LRRCT 218-268; Pfam:LR-RCT 218-268; Hybrid:LRRNT 328-364; Pfam:LRRNT 328-360; LRR_SD22 386-407; Pfam:LRR 388-411; LRR_TYP 389-409; LRR_PS 410-432; LRR_TYP 410-433; LRR_ SD22 410-428; Pfam:LRR412-435; LRR_SD22 434-453; LRR_PS 434-457; LRR_TYP 434-457; Pfam:LRR 436-459; SEG 436-445; LRR_PS 458-480; LRR_SD22 458-484; LRR_TYP 458-481; SEG 459-476; Pfam:LRR 460-483; SEG 503-516; LRRCT 517-567; Pfam:LRRCT 517-567; SEG 585-596; TRANS 607-627; SEG 701-710; N-GLYCOSYL 3 sites about 292 (NDS), 409 (NLT), 572 (NPS); TyKin site about 798 (KLMETLMY).

Nucleotide and corresponding amino acid sequences for a primate, e.g., human, TGFx coding segment, are represented by SEQ ID NO:28 and 29, respectively. Human TGFx maps to chromosome 5 (clone CITB-H1_2319M24). Predicted features (SEQ ID NO: 29) include: TGFB domain 115-212; Pfam:TGF-beta 115-167; Pfam:TGF-beta 205-212; TGF-beta like conserved Cys residues at positions 115, 144, 148, 177, 209, 211.

Nucleotide and corresponding amino acid sequences for 5685C6 coding segments are presented in SEQ ID NO:30-33. The primate clone maps to chromosome 21q22.1. Features of primate 5685C6 (SEQ ID NO:31) include: N-GLYCOSYL sites about 10 (NST), 23 (NCS), 76 (NFT), 169 (NVT), 191 (NKS); most likely cleavage site predicted between pos. 19 and 20: VFA-LN. The secreted protein produced by Th2 cells. The corresponding rodent polypeptide (SEQ ID NO:33) has the following features Predicted features: N-GLYCOSYL sites about 6 (NNT), 19 (NCS), 159 (NRS); most likely cleavage site between pos. 26 and 27: TKA-QN. 5685C6 molecules appear to be soluble entities which are expressed in Th2 clones. The entities are useful markers of Th2 cells, and will be useful in characterizing such cell types.

Nucleotide and corresponding amino acid sequences for claudins D2, D8, D17, and D7.2 are SEQ ID NO:34-41 (See, e.g., Simon, et al. (1999) Science 285:103-106).

Nucleotide and corresponding amino acid sequences for schlafens B, C, D, E, and F (see, e.g., see Schwarz, et al. (1998) Immunity 9:657-668) are SEQ ID NO:42-51.

As used herein, the term DIRS4 shall be used to describe a protein comprising a protein or peptide segment having or sharing the amino acid sequence shown in the SEQ ID NOs noted above, or a substantial fragment thereof. The invention also includes a protein variation of the respective DIRS4 allele whose sequence is provided, e.g., a mutein or soluble extracellular construct. Typically, such agonists or antagonists will exhibit less than about 10% sequence differences, and thus will often have between 1- and 11-fold substitutions, e.g., 2-, 3-, 5-, 7-fold, and others. It also encompasses allelic and other variants, e.g., natural polymorphic, of the protein described. Typically, it will bind to its corresponding biological ligand, perhaps in a dimerized state with a second receptor subunit, with high affinity, e.g., at least about 100 nM, usually better than about 30 nM, preferably better than about 10 nM, and more preferably at better than about 3 nM. The term shall also be used herein to refer to related naturally occurring forms, e.g., alleles, polymorphic variants, and metabolic variants of the mammalian protein.

Likewise, reference to the other genes described herein will be made. General descriptions directed to the methods of making or structural features will often be applicable to the other entities provided herein, e.g., the TNFx, TNFy, TLR-L1, TLR-L2, TLR-L3, TLR-L4, TLR-L5, TGFx, 5685C6, claudins D2, D8, D17, D7.2, and schlafens B, C, D, E, and F. Antibodies thereto, nucleic acids encoding them, etc., will be similarly applicable to the different entities.

This invention also encompasses proteins or peptides having substantial amino acid sequence identity with the amino acid sequences. It will include sequence variants with relatively few substitutions, e.g., preferably less than about 3-5.

A substantial polypeptide "fragment", or "segment", is a stretch of amino acid residues of at least about 8 amino acids, generally at least 10 amino acids, more generally at least 12 amino acids, often at least 14 amino acids, more often at least 16 amino acids, typically at least 18 amino acids, more typically at least 20 amino acids, usually at least 22 amino acids, more usually at least 24 amino acids, preferably at least 26 amino acids, more preferably at least 28 amino acids, and, in particularly preferred embodiments, at least about 30 or more amino acids. Sequences of segments of different proteins can be compared to one another over appropriate length stretches.

Fragments may have ends which begin and/or end at virtually all positions, e.g., beginning at residues 1, 2, 3, etc., and ending at, e.g., the carboxy-terminus (N), N-1, N-2, etc., in all practical combinations of different lengths. Particularly interesting polypeptides have one or both ends corresponding to structural domain or motif boundaries, as described, or of the designated lengths with one end adjacent one of the described boundaries. In nucleic acid embodiments, often segments which encode such polypeptides would be of particular interest.

Amino acid sequence homology, or sequence identity, is determined by optimizing residue matches. In some comparisons, gaps may be introduces, as required. See, e.g., Needleham, et al. (1970) *J. Mol. Biol.* 48:443-453; Sankoff, et al. (1983) chapter one in *Time Warps, String Edits, and Macromolecules: The Theory and Practice of Sequence Comparison,* Addison-Wesley, Reading, Mass.; and software packages from IntelliGenetics, Mountain View, Calif.; and the University of Wisconsin Genetics Computer Group (GCG), Madison, Wis.; each of which is incorporated herein by reference. This analysis is especially important when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Homologous amino acid sequences are intended to include natural allelic and interspecies variations in the cytokine sequence. Typical homologous proteins or peptides will have from 50-100% homology (if gaps can be introduced), to 60-100% homology (if conservative substitutions are included) with an amino acid sequence segment of the appropriate SEQ ID NOs noted above. Homology measures will be at least about 70%, generally at least 76%, more generally at least 81%, often at least 85%, more often at least 88%, typically at least 90%, more typically at least 92%, usually at least 94%, more usually at least 95%, preferably at least 96%, and more preferably at least 97%, and in particularly preferred embodiments, at least 98% or more. The degree of homology will vary with the length of the compared segments. Homologous proteins or peptides, such as the allelic variants, will share most biological activities with the embodiments described individually, e.g., in the various tables.

As used herein, the term "biological activity" is used to describe, without limitation, effects on inflammatory responses, innate immunity, and/or morphogenic development by cytokine-like ligands. For example, the receptors typically should mediate phosphatase or phosphorylase activities, which activities are easily measured by standard procedures. See, e.g., Hardie, et al. (eds. 1995) *The Protein Kinase FactBook* vols. I and II, Academic Press, San Diego, Calif.; Hanks, et al. (1991) *Meth. Enzymol.* 200:38–62; Hunter, et al. (1992) *Cell* 70:375–388; Lewin (1990) *Cell* 61:743–752; Pines, et al. (1991) *Cold Spring Harbor Symp. Quant. Biol.* 56:449–463; and Parker, et al. (1993) *Nature* 363:736–738. The receptors, or portions thereof, may be useful as phosphate labeling enzymes to label general or specific substrates.

The terms ligand, agonist, antagonist, and analog of, e.g., a DIRS4_include molecules that modulate the characteristic cellular responses to cytokine ligand proteins, as well as molecules possessing the more standard structural binding competition features of ligand-receptor interactions, e.g., where the receptor is a natural receptor or an antibody. The cellular responses likely are typically mediated through receptor tyrosine kinase pathways.

Also, a ligand is a molecule which serves either as a natural ligand to which said receptor, or an analog thereof, binds, or a molecule which is a functional analog of the natural ligand. The functional analog may be a ligand with structural modifications, or may be a wholly unrelated molecule which has a molecular shape which interacts with the appropriate ligand binding determinants. The ligands may serve as agonists or antagonists, see, e.g., Goodman, et al. (eds. 1990) *Goodman & Gilman's: The Pharmacological Bases of Therapeutics,* Pergamon Press, New York.

Rational drug design may also be based upon structural studies of the molecular shapes of a receptor or antibody and other effectors or ligands. See, e.g., Herz, et al. (1997) *J. Recept. Signal Transduct. Res.* 17:671–776; and Chaiken, et al. (1996) *Trends Biotechnol.* 14:369–375. Effectors may be other proteins which mediate other functions in response to ligand binding, or other proteins which normally interact with the receptor. One means for determining which sites interact with specific other proteins is a physical structure determination, e.g., x-ray crystallography or 2 dimensional NMR techniques. These will provide guidance as to which amino acid residues form molecular contact regions. For a detailed description of protein structural determination, see, e.g., Blundell and Johnson (1976) *Protein Crystallography,* Academic Press, New York, which is hereby incorporated herein by reference.

II. Activities

The cytokine receptor-like proteins will have a number of different biological activities, e.g., modulating cell proliferation, or in phosphate metabolism, being added to or removed from specific substrates, typically proteins. Such will generally result in modulation of an inflammatory function, other innate immunity response, or a morphological effect. The subunit will probably have a specific low affinity binding to the ligand.

Different receptors may mediate different signals. The TLR-L receptors may signal similar biology to the TLRs, which mediate fundamental innate immune or developmental responses. See, e.g., Aderem adn Ulevitch (2000) *Nature* 406:782–787. The TNFs and TGF are likely to signal as cytokines, as may the 5685C6, which seemingly is expressed by Th2 cells. The 5685C6 genes appear to be secreted proteins, which exhibit a cleavable signal sequence.

The claudins appear to be membrane proteins exhibiting 4 transmembrane segments, and seem to be associated with tight junctions and/or paracellular transport. They may also affect epithelial permeability or conductances, e.g., ion, across membranes. The claudin-D2 member of the claudin family is found to have regulated expression correlating with Crohn's disease. The other family members exhibit differential regulation in disease states, e.g., in Crohn's disease, ulcerative colitis, and various interstitial lung diseases. This is consistent with an important role in these disease processes. A functional role in the tight junctions/paracellular transport is consistent with problems in intestinal physiology.

Claudins define a structurally related multi-gene family of 4 TM proteins with distinct tissue distribution patterns. The claudins are major structural proteins of tight junctions (TJs) and can promote their formation. Their expression is necessary but not sufficient for tight junction formation. When expressed in fibroblasts, claudin-1 is capable of inducing a continuous association of adjacent cells, resulting in a cobblestone like pattern. However, this continuous barrier is not a tight junction. Claudins can be found outside of tight junction in certain cells. Claudin-3 and claudin-4 are receptors for *Clostridium perfringens* enterotoxin, a causative agent of fluid accumulation in the intestinal tract, causing diarrhea. Claudin-5 is deleted in Velo-cardio-facial syndrome (VCFS). Claudin-5 is only expressed in endothelial cells, and in some tissues it is even further restricted to arterials.

Mutations in Paracellin-1, claudin family member and a major renal tight junction protein, cause renal magnesium wasting with nephrocalcinosis. Thus, claudins may play important roles in selective paracellular conductance by determining the permeability of different epithelia.

The schlafens are members of a family of proteins of whose members are growth regulatory genes. See, e.g., Schwarz, et al. (1998) *Immunity* 9:657–668. These novel human sequences are related to the mouse Schlafen2 gene. It was observed to be differentially regulated in mouse IBD: Rag Hh+ (IL-10 treated) colon expression was higher than Rag Hh+ alone and mimicked the expression of Rag Hh−.

The DIRS4 has the characteristic extracellular motifs of a receptor signaling through the JAK pathway. See, e.g., Ihle, et al. (1997) *Stem Cells* 15(suppl. 1):105–111; Silvennoinen, et al. (1997) *APMIS* 105:497–509; Levy (1997) *Cytokine Growth Factor Review* 8:81–90; Winston and Hunter (1996) *Current Biol.* 6:668–671; Barrett (1996) *Baillieres Clin. Gastroenterol.* 10:1–15; and Briscoe, et al. (1996) *Philos. Trans. R. Soc. Lond. B. Biol. Sci.* 351:167–171.

The biological activities of the cytokine or other receptor subunits will be related to addition or removal of phosphate moieties to substrates, typically in a specific manner, but occasionally in a non specific manner. Substrates may be identified, or conditions for enzymatic activity may be assayed by standard methods, e.g., as described in Hardie, et al. (eds. 1995) *The Protein Kinase FactBook* vols. I and II, Academic Press, San Diego, Calif.; Hanks, et al. (1991) *Meth. Enzymol.* 200:38–62; Hunter, et al. (1992) *Cell* 70:375–388; Lewin (1990) *Cell* 61:743–752; Pines, et al. (1991) *Cold Spring Harbor Symp. Quant. Biol.* 56:449–463; and Parker, et al. (1993) *Nature* 363:736–738.

III. Nucleic Acids

This invention contemplates use of isolated nucleic acid or fragments, e.g., which encode these or closely related proteins, or fragments thereof, e.g., to encode a corresponding polypeptide, preferably one which is biologically active. In addition, this invention covers isolated or recombinant DNAs which encode such proteins or polypeptides having characteristic sequences of the DIRS4 or the other genes. Typically, the nucleic acid is capable of hybridizing, under appropriate conditions, with a nucleic acid sequence segment shown in the appropriate SEQ ID NOs noted above, but preferably not with other genes. Said biologically active protein or polypeptide can be a full length protein, or fragment, and will typically have a segment of amino acid sequence highly homologous, e.g., exhibiting significant stretches of identity, to ones described. Further, this invention covers the use of isolated or recombinant nucleic acid, or fragments thereof, which encode proteins having fragments which are equivalent to the described proteins. The isolated nucleic acids can have the respective regulatory sequences in the 5' and 3' flanks, e.g., promoters, enhancers, poly-A addition signals, and others from the natural gene.

An "isolated" nucleic acid is a nucleic acid, e.g., an RNA, DNA, or a mixed polymer, which is substantially pure, e.g., separated from other components which naturally accompany a native sequence, such as ribosomes, polymerases, and flanking genomic sequences from the originating species. The term embraces a nucleic acid sequence which has been removed from its naturally occurring environment, and includes recombinant or cloned DNA isolates, which are thereby distinguishable from naturally occurring compositions, and chemically synthesized analogs or analogs biologically synthesized by heterologous systems. A substantially pure molecule includes isolated forms of the molecule, either completely or substantially pure.

An isolated nucleic acid will generally be a homogeneous composition of molecules, but will, in some embodiments, contain heterogeneity, preferably minor. This heterogeneity is typically found at the polymer ends or portions not critical to a desired biological function or activity.

A "recombinant" nucleic acid is typically defined either by its method of production or its structure. In reference to its method of production, e.g., a product made by a process, the process is use of recombinant nucleic acid techniques, e.g., involving human intervention in the nucleotide sequence. Typically this intervention involves in vitro manipulation, although under certain circumstances it may involve more classical animal breeding techniques. Alternatively, it can be a nucleic acid made by generating a sequence comprising fusion of two fragments which are not naturally contiguous to each other, but is meant to exclude products of nature, e.g., naturally occurring mutants as found in their natural state. Thus, for example, products made by transforming cells with an unnaturally occurring vector is encompassed, as are nucleic acids comprising sequence derived using any synthetic oligonucleotide process. Such a process is often done to replace a codon with a redundant codon encoding the same or a conservative amino acid, while typically introducing or removing a restriction enzyme sequence recognition site. Alternatively, the process is performed to join together nucleic acid segments of desired functions to generate a single genetic entity comprising a desired combination of functions not found in the commonly available natural forms, e.g., encoding a fusion protein. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. This will include a dimeric repeat. Specifically included are synthetic nucleic acids which, by genetic code redundancy, encode equivalent polypeptides to fragments of the described sequences and fusions of sequences from various different related molecules, e.g., other cytokine receptor family members.

A "fragment" in a nucleic acid context is a contiguous segment of at least about 17 nucleotides, generally at least 21 nucleotides, more generally at least 25 nucleotides, ordinarily at least 30 nucleotides, more ordinarily at least 35 nucleotides, often at least 39 nucleotides, more often at least 45 nucleotides, typically at least 50 nucleotides, more typically at least 55 nucleotides, usually at least 60 nucleotides, more usually at least 66 nucleotides, preferably at least 72 nucleotides, more preferably at least 79 nucleotides, and in particularly preferred embodiments will be at least 85 or more nucleotides. Typically, fragments of different genetic sequences can be compared to one another over appropriate length stretches, particularly defined segments such as the domains described below.

A nucleic acid which codes for, e.g., a DIRS4, will be particularly useful to identify genes, mRNA, and cDNA species which code for itself or closely related proteins, as well as DNAs which code for polymorphic, allelic, or other genetic variants, e.g., from different individuals or related species. Other genes will be useful as markers for particular cell types, or diagnostic of various physiological conditions. Preferred probes for such screens may, in certain circumstances, be those regions of the gene which are conserved between different polymorphic variants or which contain nucleotides which lack specificity, and will preferably be full length or nearly so. In other situations, polymorphic variant specific sequences will be more useful.

This invention further covers recombinant nucleic acid molecules and fragments having a nucleic acid sequence identical to or highly homologous to the isolated DNA set forth herein. In particular, the sequences will often be operably linked to DNA segments which control transcription, translation, and DNA replication. Alternatively, recombinant clones derived from the genomic sequences, e.g., containing introns, will be useful for transgenic studies, including, e.g., transgenic cells and organisms, and for gene therapy. See, e.g., Goodnow (1992) "Transgenic Animals" in Roitt (ed.) *Encyclopedia of Immunology* Academic Press, San Diego, pp. 1502–1504; Travis (1992) *Science* 256:1392–1394; Kuhn, et al. (1991) *Science* 254:707–710; Capecchi (1989) *Science* 244:1288; Robertson (1987)(ed.) *Teratocarcinomas and Embryonic Stem Cells: A Practical Approach* IRL Press, Oxford; and Rosenberg (1992) *J. Clinical Oncology* 10:180–199. Operable association of heterologous promoters with natural gene sequences is also provided, as are vectors encoding, e.g., the DIRS4 with a receptor partner. See, e.g., Treco, et al. WO96/29411 or U.S. Ser. No. 08/406,030.

Homologous, or highly identical, nucleic acid sequences, when compared to one another, e.g., DIRS4 sequences, exhibit significant similarity The standards for homology in nucleic acids are either measures for homology generally used in the art by sequence comparison or based upon hybridization conditions. Comparative hybridization conditions are described in greater detail below.

Substantial identity in the nucleic acid sequence comparison context means either that the segments, or their complementary strands, when compared, are identical when optimally aligned, with appropriate nucleotide insertions or deletions, in at least about 60% of the nucleotides, generally at least 66%, ordinarily at least 71%, often at least 76%, more often at least 80%, usually at least 84%, more usually at least 88%, typically at least 91%, more typically at least about 93%, preferably at least about 95%, more preferably at least about 96 to 98% or more, and in particular embodiments, as high at about 99% or more of the nucleotides, including, e.g., segments encoding structural domains such as the segments described below. Alternatively, substantial identity will exist when the segments will hybridize under selective hybridization conditions, to a strand or its complement, typically using a described sequence. Typically, selective hybridization will occur when there is at least about 55% homology over a stretch of at least about 14 nucleotides, more typically at least about 65%, preferably at least about 75%, and more preferably at least about 90%. See, Kanehisa (1984) *Nucl. Acids Res.* 12:203–213, which is incorporated herein by reference. The length of homology comparison, as described, may be over longer stretches, and in certain embodiments will be over a stretch of at least about 17 nucleotides, generally at least about 20 nucleotides, ordinarily at least about 24 nucleotides, usually at least about 28 nucleotides, typically at least about 32 nucleotides, more typically at least about 40 nucleotides, preferably at least about 50 nucleotides, and more preferably at least about 75 to 100 or more nucleotides. This includes, e.g., 125, 150, 175, 200, 225, 250, 275, 300, 400, 500, 700, 900, and other lengths.

Stringent conditions, in referring to homology in the hybridization context, will be stringent combined conditions of salt, temperature, organic solvents, and other parameters typically controlled in hybridization reactions. Stringent temperature conditions will usually include temperatures in excess of about 30° C., more usually in excess of about 37° C., typically in excess of about 45° C., more typically in excess of about 55° C., preferably in excess of about 65° C., and more preferably in excess of about 70° C. Stringent salt conditions will ordinarily be less than about 500 mM, usually less than about 400 mM, more usually less than about 300 mM, typically less than about 200 mM, preferably less than about 100 mM, and more preferably less than about 80 mM, even down to less than about 20 mM. However, the combination of parameters is much more important than the measure of any single parameter. See, e.g., Wetmur and Davidson (1968) *J. Mol. Biol.* 31:349–370, which is hereby incorporated herein by reference.

The isolated DNA can be readily modified by nucleotide substitutions, nucleotide deletions, nucleotide insertions, and inversions of nucleotide stretches. These modifications result in novel DNA sequences which encode this protein or its derivatives. These modified sequences can be used to produce mutant proteins (muteins) or to enhance the expression of variant species. Enhanced expression may involve gene amplification, increased transcription, increased translation, and other mechanisms. Such mutant derivatives include predetermined or site-specific mutations of the protein or its fragments, including silent mutations using genetic code degeneracy. "Mutant DIRS4" as used herein encompasses a polypeptide otherwise falling within the homology definition of the DIRS4 as set forth above, but having an amino acid sequence which differs from that of other cytokine receptor-like proteins as found in nature, whether by way of deletion, substitution, or insertion. In particular, "site specific mutant DIRS4" encompasses a protein having substantial sequence identity with a protein of SEQ ID NO:2, and typically shares most of the biological activities or effects of the forms disclosed herein.

Although site specific mutation sites are predetermined, mutants need not be site specific. Mammalian DIRS4 mutagenesis can be achieved by making amino acid insertions or deletions in the gene, coupled with expression. Substitutions, deletions, insertions, or many combinations may be generated to arrive at a final construct. Insertions include amino- or carboxy- terminal fusions. Random mutagenesis can be conducted at a target codon and the expressed mammalian DIRS4 mutants can then be screened for the desired activity, providing some aspect of a structure-activity relationship. Methods for making substitution mutations at predetermined sites in DNA having a known sequence are well known in the art, e.g., by M13 primer mutagenesis. See also Sambrook, et al. (1989) and Ausubel, et al. (1987 and periodic Supplements).

The mutations in the DNA normally should not place coding sequences out of reading frames and preferably will not create complementary regions that could hybridize to produce secondary mRNA structure such as loops or hairpins.

The phosphoramidite method described by Beaucage and Carruthers (1981) *Tetra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence.

Polymerase chain reaction (PCR) techniques can often be applied in mutagenesis. Alternatively, mutagenesis primers are commonly used methods for generating defined mutations at predetermined sites. See, e.g., Innis, et al. (eds. 1990) *PCR Protocols: A Guide to Methods and Applications* Academic Press, San Diego, Calif.; and Dieffenbach and Dveksler (1995; eds.) *PCR Primer: A Laboratory Manual* Cold Spring Harbor Press, CSH, NY.

Antisense and other technologies for blocking expression of these genes are also available. See, e.g., Misquitta and Paterson (1999) *Proc. Nat'l Acad. Sci. USA* 96:1451–1456.

IV. Proteins, Peptides

As described above, the present invention encompasses primate DIRS4, e.g., whose sequences are disclosed in SEQ ID NO:2, and described above. Allelic and other variants are also contemplated, including, e.g., fusion proteins combining portions of such sequences with others, including epitope tags and functional domains. Analogous methods and applications exist directed to the other genes described herein.

The present invention also provides recombinant proteins, e.g., heterologous fusion proteins using segments from these proteins. A heterologous fusion protein is a fusion of proteins or segments which are naturally not normally fused in the same manner. Thus, e.g., the fusion product of a DIRS4 with another cytokine receptor is a continuous protein molecule having sequences fused in a typical peptide linkage, typically made as a single translation product and exhibiting properties, e.g., sequence or antigenicity, derived from each source peptide. A similar concept applies to heterologous nucleic acid sequences.

In addition, new constructs may be made from combining similar functional or structural domains from other related proteins, e.g., cytokine receptors or Toll-like receptor like genes, including species variants. For example, ligand-binding or other segments may be "swapped" between different new fusion polypeptides or fragments. See, e.g., Cunningham, et al. (1989) *Science* 243:1330–1336; and O'Dowd, et al. (1988) *J. Biol. Chem.* 263:15985–15992, each of which is incorporated herein by reference. Thus, new chimeric polypeptides exhibiting new combinations of specificities will result from the functional linkage of receptor-binding specificities. For example, the ligand binding domains from other related receptor molecules may be added or substituted for other domains of this or related proteins. The resulting protein will often have hybrid function and properties. For example, a fusion protein may include a targeting domain which may serve to provide sequestering of the fusion protein to a particular subcellular organelle.

Candidate fusion partners and sequences can be selected from various sequence data bases, e.g., GenBank, c/o IntelliGenetics, Mountain View, Calif.; and BCG, University of Wisconsin Biotechnology Computing Group, Madison, Wis., which are each incorporated herein by reference.

The present invention particularly provides muteins which bind cytokine-like ligands, and/or which are affected in signal transduction. Structural alignment of human DIRS4 with other members of the cytokine receptor family show conserved features/residues. Alignment of the human DIRS4 sequence with other members of the cytokine receptor family indicates various structural and functionally shared features. See also, Bazan, et al. (1996) *Nature* 379:591; Lodi, et al. (1994) *Science* 263:1762–1766; Sayle and Milner-White (1995) *TIBS* 20:374–376; and Gronenberg, et al. (1991) *Protein Engineering* 4:263–269. Similarly, the other genes have related family members.

Substitutions with either mouse sequences or human sequences are particularly preferred. Conversely, conservative substitutions away from the ligand binding interaction regions will probably preserve most signaling activities; and conservative substitutions away from the intracellular domains will probably preserve most ligand binding properties.

"Derivatives" of the various proteins include amino acid sequence mutants, glycosylation variants, metabolic derivatives, and covalent or aggregative conjugates with other chemical moieties. Covalent derivatives can be prepared by linkage of functionalities to groups which are found in amino acid side chains or at the N- or C- termini, e.g., by means which are well known in the art. These derivatives can include, without limitation, aliphatic esters or amides of the carboxyl termninus, or of residues containing carboxyl side chains, O-acyl derivatives of hydroxyl group-containing residues, and N-acyl derivatives of the amino terminal amino acid or amino-group containing residues, e.g., lysine or arginine. Acyl groups are selected from the group of alkyl-moieties, including C3 to C18 normal alkyl, thereby forming alkanoyl aroyl species.

In particular, glycosylation alterations are included, e.g., made by modifying the glycosylation patterns of a polypeptide during its synthesis and processing, or in further processing steps. Particularly preferred means for accomplishing this are by exposing the polypeptide to glycosylating enzymes derived from cells which normally provide such processing, e.g., mammalian glycosylation enzymes. Deglycosylation enzymes are also contemplated. Also embraced are versions of the same primary amino acid sequence which have other minor modifications, including phosphorylated amino acid residues, e.g., phosphotyrosine, phosphoserine, or phosphothreonine.

A major group of derivatives are covalent conjugates of the proteins or fragments thereof with other proteins of polypeptides. These derivatives can be synthesized in recombinant culture such as N- or C-terminal fusions or by the use of agents known in the art for their usefulness in cross-linking proteins through reactive side groups. Preferred derivatization sites with cross-linking agents are at free amino groups, carbohydrate moieties, and cysteine residues.

Fusion polypeptides between the proteins and other homologous or heterologous proteins are also provided. Homologous polypeptides may be fusions between different proteins, resulting in, for instance, a hybrid protein exhibiting binding specificity for multiple different cytokine ligands, or a receptor which may have broadened or weakened specificity of substrate effect. Likewise, heterologous fusions may be constructed which would exhibit a combination of properties or activities of the derivative proteins. Typical examples are fusions of a reporter polypeptide, e.g., luciferase, with a segment or domain of a receptor, e.g., a ligand-binding segment, so that the presence or location of a desired ligand may be easily determined. See, e.g., Dull, et al., U.S. Pat. No. 4,859,609, which is hereby incorporated herein by reference. Other gene fusion partners include glutathione-S-transferase (GST), bacterial β-galactosidase, trpE, Protein A, β-lactamase, alpha amylase, alcohol dehydrogenase, and yeast alpha mating factor. See, e.g., Godowski, et al. (1988) *Science* 241:812–816.

The phosphoramidite method described by Beaucage and Carruthers (1981) *Tetra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence.

Such polypeptides may also have amino acid residues which have been chemically modified by phosphorylation, sulfonation, biotinylation, or the addition or removal of other moieties, particularly those which have molecular shapes similar to phosphate groups. In some embodiments, the modifications will be useful labeling reagents, or serve as purification targets, e.g., affinity ligands.

Fusion proteins will typically be made by either recombinant nucleic acid methods or by synthetic polypeptide methods. Techniques for nucleic acid manipulation and expression are described generally, for example, in Sambrook, et al. (1989) *Molecular Cloning: A Laboratory Manual* (2d ed.), Vols. 1–3, Cold Spring Harbor Laboratory, and Ausubel, et al. (eds. 1987 and periodic supplements) *Current Protocols in Molecular Biology*, Greene/Wiley, New York, which are each incorporated herein by reference. Techniques for synthesis of polypeptides are described, for example, in Merrifield (1963) *J. Amer. Chem. Soc.* 85:2149–2156; Merrifield (1986) *Science* 232: 341–347; and Atherton, et al. (1989) *Solid Phase Peptide Synthesis: A Practical Approach*, IRL Press, Oxford; each of which is incorporated herein by reference. See also Dawson, et al. (1994) *Science* 266:776–779 for methods to make larger polypeptides.

This invention also contemplates the use of derivatives of these proteins other than variations in amino acid sequence or glycosylation. Such derivatives may involve covalent or aggregative association with chemical moieties. These derivatives generally fall into three classes: (1) salts, (2) side chain and terminal residue covalent modifications, and (3) adsorption complexes, for example with cell membranes. Such covalent or aggregative derivatives are useful as immunogens, as reagents in immunoassays, or in purification methods such as for affinity purification of a receptor or other binding molecule, e.g., an antibody. For example, a cytokine ligand can be immobilized by covalent bonding to a solid support such as cyanogen bromide-activated Sepharose, by methods which are well known in the art, or adsorbed onto polyolefin surfaces, with or without glutaraldehyde cross-linking, for use in the assay or purification of an cytokine receptor, antibodies, or other similar molecules. The ligand can also be labeled with a detectable group, for example radioiodinated by the chloramine T procedure, covalently bound to rare earth chelates, or conjugated to another fluorescent moiety for use in diagnostic assays.

A polypeptide of this invention can be used as an immunogen for the production of antisera or antibodies. These may be specific, e.g., capable of detecting or distinguishing between other related family members or various fragments thereof. The purified proteins can be used to screen monoclonal antibodies or antigen-binding fragments prepared by immunization with various forms of impure preparations containing the protein. In particular, the term "antibodies" also encompasses antigen binding fragments of natural antibodies, e.g., Fab, Fab2, Fv, etc. The purified proteins can also be used as a reagent to detect antibodies generated in response to the presence of elevated levels of expression, or immunological disorders which lead to antibody production to the endogenous receptor. Additionally, fragments may also serve as immunogens to produce the antibodies of the present invention. For example, this invention contemplates antibodies having binding affinity to or being raised against the amino acid sequences provided, fragments thereof, or various homologous peptides. In particular, this invention contemplates antibodies having binding affinity to, or having been raised against, specific fragments which are predicted to be, or actually are, exposed at the exterior protein surfaces.

The blocking of physiological response to the receptor ligands may result from the inhibition of binding of the ligand to the receptor, likely through competitive inhibition. Antibodies to ligands may be antagonists. Thus, in vitro assays of the present invention will often use antibodies or antigen binding segments of these antibodies, or fragments attached to solid phase substrates. Assays will also allow for the diagnostic determination of the effects of mutations and modifications, e.g., which affect signaling or enzymatic function.

This invention also contemplates the use of competitive drug screening assays, e.g., where neutralizing antibodies to the receptor or fragments compete with a test compound for binding to a ligand or other antibody. In this manner, the neutralizing antibodies or fragments can be used to detect the presence of a polypeptide which shares one or more binding sites to a receptor and can also be used to occupy binding sites on a receptor that might otherwise bind a ligand.

V. Making Nucleic Acids and Protein

DNA which encodes the protein or fragments thereof can be obtained by chemical synthesis, screening cDNA libraries, or by screening genomic libraries prepared from a wide variety of cell lines or tissue samples. Natural sequences can be isolated using standard methods and the sequences provided herein. Other species counterparts can be identified by hybridization techniques, or by various PCR techniques, or combined with or by searching in sequence databases, e.g., GenBank.

This DNA can be expressed in a wide variety of host cells which can, in turn, e.g., be used to generate polyclonal or monoclonal antibodies; for binding studies; for construction and expression of modified constructs; and for structure/function studies. Variants or fragments can be expressed in host cells that are transformed or transfected with appropriate expression vectors. These molecules can be substantially free of protein or cellular contaminants, other than those derived from the recombinant host, and therefore are particularly useful in pharmaceutical compositions when combined with a pharmaceutically acceptable carrier and/or diluent. The protein, or portions thereof, may be expressed as fusions with other proteins.

Expression vectors are typically self-replicating DNA or RNA constructs containing the desired receptor gene or its fragments, usually operably linked to suitable genetic control elements that are recognized in a suitable host cell. These control elements are capable of effecting expression within a suitable host. The specific type of control elements necessary to effect expression will depend upon the eventual host cell used. Generally, the genetic control elements can include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also usually contain an origin of replication that allows the vector to replicate independently of the host cell.

The vectors of this invention include those which contain DNA which encodes a protein, as described, or a fragment thereof encoding a biologically active equivalent polypeptide. The DNA can be under the control of a viral promoter and can encode a selection marker. This invention further contemplates use of such expression vectors which are capable of expressing eukaryotic cDNA coding for such a protein in a prokaryotic or eukaryotic host, where the vector is compatible with the host and where the eukaryotic cDNA coding for the receptor is inserted into the vector such that growth of the host containing the vector expresses the cDNA in question. Usually, expression vectors are designed for stable replication in their host cells or for amplification to greatly increase the total number of copies of the desirable gene per cell. It is not always necessary to require that an expression vector replicate in a host cell, e.g., it is possible to effect transient expression of the protein or its fragments in various hosts using vectors that do not contain a replication origin that is recognized by the host cell. It is also possible to use vectors that cause integration of the protein encoding portion or its fragments into the host DNA by recombination.

Vectors, as used herein, comprise plasmids, viruses, bacteriophage, integratable DNA fragments, and other vehicles which enable the integration of DNA fragments into the genome of the host. Expression vectors are specialized vectors which contain genetic control elements that effect expression of operably linked genes. Plasmids are the most commonly used form of vector but all other forms of vectors which serve an equivalent function and which are, or become, known in the art are suitable for use herein. See, e.g., Pouwels, et al. (1985 and Supplements) *Cloning Vectors: A Laboratory Manual,* Elsevier, N.Y., and Rodriguez, et al. (eds. 1988) *Vectors: A Survey of Molecular Cloning Vectors and Their Uses,* Buttersworth, Boston, which are incorporated herein by reference.

Transformed cells are cells, preferably mammalian, that have been transformed or transfected with receptor vectors constructed using recombinant DNA techniques. Transformed host cells usually express the desired protein or its fragments, but for purposes of cloning, amplifying, and manipulating its DNA, do not need to express the subject protein. This invention further contemplates culturing transformed cells in a nutrient medium, thus permitting the receptor to accumulate in the cell membrane. The protein can be recovered, either from the culture or, in certain instances, from the culture medium.

For purposes of this invention, nucleic sequences are operably linked when they are functionally related to each other. For example, DNA for a presequence or secretory leader is operably linked to a polypeptide if it is expressed as a preprotein or participates in directing the polypeptide to the cell membrane or in secretion of the polypeptide. A promoter is operably linked to a coding sequence if it controls the transcription of the polypeptide; a ribosome binding site is operably linked to a coding sequence if it is positioned to permit translation. Usually, operably linked means contiguous and in reading frame, however, certain genetic elements such as repressor genes are not contiguously linked but still bind to operator sequences that in turn control expression.

Suitable host cells include prokaryotes, lower eukaryotes, and higher eukaryotes. Prokaryotes include both gram negative and gram positive organisms, e.g., *E. coli* and *B. subtilis*. Lower eukaryotes include yeasts, e.g., *S. cerevisiae* and *Pichia*, and species of the genus *Dictyostelium*. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or many of its derivatives. Vectors that can be used to express the receptor or its fragments include, but are not limited to, such vectors as those containing the lac promoter (pUC-series); trp promoter (pBR322-trp); Ipp promoter (the pIN-series); lambda-pP or pR promoters (pOTS); or hybrid promoters such as ptac (pDR540). See Brosius, et al. (1988) "Expression Vectors Employing Lambda-, trp-, lac-, and Ipp-derived Promoters", in *Vectors: A Survey of Molecular Cloning Vectors and Their Uses*, (eds. Rodriguez and Denhardt), Buttersworth, Boston, Chapter 10, pp. 205–236, which is incorporated herein by reference.

Lower eukaryotes, e.g., yeasts and *Dictyostelium*, may be transformed with DIRS4 sequence containing vectors. For purposes of this invention, the most common lower eukaryotic host is the baker's yeast, *Saccharomyces cerevisiae*. It will be used to generically represent lower eukaryotes although a number of other strains and species are also available. Yeast vectors typically consist of a replication origin (unless of the integrating type), a selection gene, a promoter, DNA encoding the receptor or its fragments, and sequences for translation termination, polyadenylation, and transcription termination. Suitable expression vectors for yeast include such constitutive promoters as 3-phosphoglycerate kinase and various other glycolytic enzyme gene promoters or such inducible promoters as the alcohol dehydrogenase 2 promoter or metallothionine promoter. Suitable vectors include derivatives of the following types: self-replicating low copy number (such as the YRp-series), self-replicating high copy number (such as the YEp-series); integrating types (such as the YIp-series), or mini-chromosomes (such as the YCp-series).

Higher eukaryotic tissue culture cells are normally preferred host cells for expression of the functionally active interleukin protein. In principle, many higher eukaryotic tissue culture cell lines are workable, e.g., insect baculovirus expression systems, whether from an invertebrate or vertebrate source. However, mammalian cells are preferred. Transformation or transfection and propagation of such cells has become a routine procedure. Examples of useful cell lines include HeLa cells, Chinese hamster ovary (CHO) cell lines, baby rat kidney (BRK) cell lines, insect cell lines, bird cell lines, and monkey (COS) cell lines. Expression vectors for such cell lines usually include an origin of replication, a promoter, a translation initiation site, RNA splice sites (if genomic DNA is used), a polyadenylation site, and a transcription termination site. These vectors also usually contain a selection gene or amplification gene. Suitable expression vectors may be plasmids, viruses, or retroviruses carrying promoters derived, e.g., from such sources as from adenovirus, SV40, parvoviruses, vaccinia virus, or cytomegalovirus. Representative examples of suitable expression vectors include pCDNA1; pCD, see Okayama, et al. (1985) *Mol. Cell Biol.* 5:1136–1142; pMClneo PolyA, see Thomas, et al. (1987) *Cell* 51:503–512; and a baculovirus vector such as pAC 373 or pAC 610.

For secreted proteins, an open reading frame usually encodes a polypeptide that consists of a mature or secreted product covalently linked at its N-terminus to a signal peptide. The signal peptide is cleaved prior to secretion of the mature, or active, polypeptide. The cleavage site can be predicted with a high degree of accuracy from empirical rules, e.g., von-Heijne (1986) *Nucleic Acids Research* 14:4683–4690 and Nielsen, et al. (1997) *Protein Eng.* 10:1–12, and the precise amino acid composition of the signal peptide often does not appear to be critical to its function, e.g., Randall, et al. (1989) *Science* 243:1156–1159; Kaiser et al. (1987) *Science* 235:312–317.

It will often be desired to express these polypeptides in a system which provides a specific or defined glycosylation pattern. In this case, the usual pattern will be that provided naturally by the expression system. However, the pattern will be modifiable by exposing the polypeptide, e.g., an unglycosylated form, to appropriate glycosylating proteins introduced into a heterologous expression system. For example, the gene may be co-transformed with one or more genes encoding mammalian or other glycosylating enzymes. Using this approach, certain mammalian glycosylation patterns will be achievable in prokaryote or other cells.

The source of protein can be a eukaryotic or prokaryotic host expressing recombinant gene, such as is described above. The source can also be a cell line such as mouse Swiss 3T3 fibroblasts, but other mammalian cell lines are also contemplated by this invention, with the preferred cell line being from the human species.

Now that the sequences are known, the primate protein, fragments, or derivatives thereof can be prepared by conventional processes for synthesizing peptides. These include processes such as are described in Stewart and Young (1984) *Solid Phase Peptide Synthesis*, Pierce Chemical Co., Rockford, Ill.; Bodanszky and Bodanszky (1984) *The Practice of Peptide Synthesis,* Springer-Verlag, New York; and Bodanszky (1984) *The Principles of Peptide Synthesis,* Springer-Verlag, New York; all of each which are incorporated herein by reference. For example, an azide process, an acid chloride process, an acid anhydride process, a mixed anhydride process, an active ester process (for example, p-nitrophenyl ester, N-hydroxysuccinimide ester, or cyanomethyl ester), a carbodiimidazole process, an oxidative-reductive process, or a dicyclohexylcarbodiimide (DCCD)/additive process can be used. Solid phase and solution phase syntheses are both applicable to the foregoing processes. Similar techniques can be used with partial polypeptide sequences.

The various proteins, fragments, or derivatives are suitably prepared in accordance with the above processes as typically employed in peptide synthesis, generally either by a so-called stepwise process which comprises condensing an amino acid to the terminal amino acid, one by one in sequence, or by coupling peptide fragments to the terminal amino acid. Amino groups that are not being used in the coupling reaction typically must be protected to prevent coupling at an incorrect location.

If a solid phase synthesis is adopted, the C-terminal amino acid is bound to an insoluble carrier or support through its carboxyl group. The insoluble carrier is not particularly limited as long as it has a binding capability to a reactive carboxyl group. Examples of such insoluble carriers include halomethyl resins, such as chloromethyl resin or bromomethyl resin, hydroxymethyl resins, phenol resins, tert-alkyloxycarbonylhydrazidated resins, and the like.

An amino group-protected amino acid is bound in sequence through condensation of its activated carboxyl group and the reactive amino group of the previously formed peptide or chain, to synthesize the peptide step by step. After synthesizing the complete sequence, the peptide is split off from the insoluble carrier to produce the peptide. This solid-phase approach is generally described by Merrifield, et al. (1963) in *J. Am. Chem. Soc.* 85:2149–2156, which is incorporated herein by reference.

The prepared protein and fragments thereof can be isolated and purified from the reaction mixture by means of peptide separation, e.g., by extraction, precipitation, electrophoresis, various forms of chromatography, and the like. The proteins of this invention can be obtained in varying degrees of purity depending upon desired uses. Purification can be accomplished by use of the protein purification techniques disclosed herein, see below, or by the use of the antibodies herein described in methods of immunoabsorbant affinity chromatography. This immunoabsorbant affinity chromatography is carried out by first linking the antibodies to a solid support and then contacting the linked antibodies with solubilized lysates of appropriate cells, lysates of other cells expressing the receptor, or lysates or supernatants of cells producing the protein as a result of DNA techniques, see below.

Generally, the purified protein will be at least about 40% pure, ordinarily at least about 50% pure, usually at least about 60% pure, typically at least about 70% pure, more typically at least about 80% pure, preferable at least about 90% pure and more preferably at least about 95% pure, and in particular embodiments, 97%–99% or more. Purity will usually be on a weight basis, but can also be on a molar basis. Different assays will be applied as appropriate.

VI. Antibodies

Antibodies can be raised to the various mammalian, e.g., primate DIRS4, proteins and fragments thereof, both in naturally occurring native forms and in their recombinant forms, the difference being that antibodies to the active receptor are more likely to recognize epitopes which are only present in the native conformations. Denatured antigen detection can also be useful in, e.g., Western analysis. Anti-idiotypic antibodies are also contemplated, which would be useful as agonists or antagonists of a natural receptor or an antibody.

Antibodies, including binding fragments and single chain versions, against predetermined fragments of the protein can be raised by immunization of animals with conjugates of the fragments with immunogenic proteins. Monoclonal antibodies are prepared from cells secreting the desired antibody. These antibodies can be screened for binding to normal or defective protein, or screened for agonistic or antagonistic activity. These monoclonal antibodies will usually bind with at least a $K_D$ of about 1 mM, more usually at least about 300 µM, typically at least about 100 µM, more typically at least about 30 µM, preferably at least about 10 µM, and more preferably at least about 3 µM or better.

The antibodies, including antigen binding fragments, of this invention can have significant diagnostic or therapeutic value. They can be potent agonists or antagonists, e.g., that bind to the receptor and inhibit or simulate binding to ligand, or inhibit the ability of the receptor to elicit a biological response, e.g., act on its substrate. They also can be useful as non-neutralizing antibodies or for use as markers for detection or diagnosis, and can be coupled to toxins or radionuclides to bind producing cells. Further, these antibodies can be conjugated to drugs or other therapeutic agents, either directly or indirectly by means of a linker.

The antibodies of this invention can also be useful in diagnostic applications. As capture or non-neutralizing antibodies, they might bind to the antigen without inhibiting, e.g., ligand or substrate binding. As neutralizing antibodies, they can be useful in competitive binding assays. They will also be useful in detecting or quantifying antigen. They may be used as reagents for Western blot analysis, or for immunoprecipitation or immunopurification of the respective protein.

Protein fragments may be joined to other materials, particularly polypeptides, as fused or covalently joined polypeptides to be used as immunogens. Mammalian cytokine receptors, cytokines, enzymes, marker proteins, and fragments may be fused or covalently linked to a variety of immunogens, such as keyhole limpet hemocyanin, bovine serum albumin, tetanus toxoid, etc. See *Microbiology,* Hoeber Medical Division, Harper and Row, 1969; Landsteiner (1962) *Specificity of Serological Reactions,* Dover Publications, New York; and Williams, et al. (1967) *Methods in Immunology and Immunochemistry,* Vol. 1, Academic Press, New York; each of which are incorporated herein by reference, for descriptions of methods of preparing polyclonal antisera. A typical method involves hyperimmunization of an animal with an antigen. The blood of the animal is then collected shortly after the repeated immunizations and the gamma globulin is isolated.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) *Basic and Clinical Immunology* (4th ed.), Lange Medical Publications, Los Altos, Calif., and references cited therein; Harlow and Lane (1988) *Antibodies: A Laboratory Manual,* CSH Press; Goding (1986) *Monoclonal Antibodies: Principles and Practice* (2d ed.) Academic Press, New York; and particularly in Kohler and Milstein (1975) in *Nature* 256: 495–497, which discusses one method of generating monoclonal antibodies. Summarized briefly, this method involves injecting an animal with an immunogen. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve in vitro exposure of lymphocytes to the antigenic polypeptides or alternatively to selection of libraries of antibodies in phage or similar vectors. See, Huse, et al. (1989) "Generation of a Large Combinatorial Library of the Immunoglobulin Repertoire in Phage Lambda," *Science* 246:1275–1281; and Ward, et al. (1989) *Nature* 341:544–546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant or chimeric immunoglobulins may be produced, see Cabilly, U.S. Pat. No. 4,816,567; or made in transgenic mice, see Mendez, et al. (1997) *Nature Genetics* 15:146–156.

The antibodies of this invention can also be used for affinity chromatography in isolating the proteins or peptides. Columns can be prepared where the antibodies are linked to a solid support, e.g., particles, such as agarose, Sephadex, or the like, where a cell lysate may be passed through the column, the column washed, followed by increasing concentrations of a mild denaturant, whereby the purified protein will be released. Conversely, the protein may be used to purify antibody by immunoselection.

The antibodies may also be used to screen expression libraries for particular expression products. Usually the antibodies used in such a procedure will be labeled with a moiety allowing easy detection of presence of antigen by antibody binding.

Antibodies raised against a protein will also be used to raise anti-idiotypic antibodies. These will be useful in detecting or diagnosing various immunological conditions related to expression of the protein or cells which express the protein. They also will be useful as agonists or antagonists of a ligand, which may be competitive inhibitors or substitutes for naturally occurring ligands.

A target protein that specifically binds to or that is specifically immunoreactive with an antibody generated against it, such as an immunogen consisting of a described amino acid sequence, is typically determined in an immunoassay. The immunoassay typically uses a polyclonal antiserum which was raised, e.g., to a protein of SEQ ID NO: 2. This antiserum is selected to have low crossreactivity against other cytokine receptor family members, e.g., IFN receptor subunits, preferably from the same species, and any such crossreactivity is removed by immunoabsorption prior to use in the immunoassay.

In order to produce antisera for use in an immunoassay, the protein, e.g., of SEQ ID NO: 2, is isolated as described herein. For example, recombinant protein may be produced in a mammalian cell line. An appropriate host, e.g., an inbred strain of mice such as Balb/c, is immunized with the selected protein, typically using a standard adjuvant, such as Freund's adjuvant, and a standard mouse immunization protocol (see Harlow and Lane, supra). Alternatively, a synthetic peptide derived from the sequences disclosed herein and conjugated to a carrier protein can be used an immunogen.

Polyclonal sera are collected and titered against the immunogen protein in an immunoassay, e.g., a solid phase immunoassay with the immunogen immobilized on a solid support. Polyclonal antisera with a titer of $10^4$ or greater are selected and tested for their cross reactivity against other cytokine receptor family members, e.g., receptors aligned in FIG. 1, using a competitive binding immunoassay such as the one described in Harlow and Lane, supra, at pages 570–573. Preferably at least two cytokine receptor family members are used in this determination. These cytokine receptor family members can be produced as recombinant proteins and isolated using standard molecular biology and protein chemistry techniques as described herein.

Immunoassays in the competitive binding format can be used for the crossreactivity determinations. For example, the protein of SEQ ID NO: 2 can be immobilized to a solid support. Proteins added to the assay compete with the binding of the antisera to the immobilized antigen. The ability of the above proteins to compete with the binding of the antisera to the immobilized protein is compared to selected other receptor subunits. The percent crossreactivity for the above proteins is calculated, using standard calculations. Those antisera with less than 10% crossreactivity with each of the proteins listed above are selected and pooled. The cross-reacting antibodies are then removed from the pooled antisera by immunoabsorption with the above-listed proteins.

The immunoabsorbed and pooled antisera are then used in a competitive binding inmmunoassay as described above to compare a second protein to the immunogen protein. In order to make this comparison, the two proteins are each assayed at a wide range of concentrations and the amount of each protein required to inhibit 50% of the binding of the antisera to the immobilized protein is determined. If the amount of the second protein required is less than twice the amount of the protein of the selected protein or proteins that is required, then the second protein is said to specifically bind to an antibody generated to the immunogen.

It is understood that these proteins are members of families of homologous proteins. For a particular gene product, such as the DIRS4, the term refers not only to the amino acid sequences disclosed herein, but also to other proteins that are allelic, non-allelic, or species variants. It is also understood that the terms include nonnatural mutations introduced by deliberate mutation using conventional recombinant technology such as single site mutation, or by excising short sections of DNA encoding the respective proteins, or by substituting new amino acids, or adding new amino acids. Such minor alterations typically will substantially maintain the immunoidentity of the original molecule and/or its biological activity. Thus, these alterations include proteins that are specifically immunoreactive with a designated naturally occurring DIRS4 protein. The biological properties of the altered proteins can be determined by expressing the protein in an appropriate cell line and measuring the appropriate effect, e.g., upon transfected lymphocytes. Particular protein modifications considered minor would include conservative substitution of amino acids with similar chemical properties, as described above for the cytokine receptor family as a whole. By aligning a protein optimally with the protein of the cytokine receptors and by using the conventional inmnunoassays described herein to determine immunoidentity, one can determine the protein compositions of the invention.

VII. Kits and Quantitation

Both naturally occurring and recombinant forms of the molecules of this invention are particularly useful in kits and assay methods. For example, these methods would also be applied to screening for binding activity, e.g., ligands or receptors for these proteins. Several methods of automating assays have been developed in recent years so as to permit screening of tens of thousands of compounds per year. See, e.g., a BIOMEK automated workstation, Beckman Instruments, Palo Alto, Calif., and Fodor, et al. (1991) *Science* 251:767–773, which is incorporated herein by reference. The latter describes means for testing binding by a plurality of defined polymers synthesized on a solid substrate. The development of suitable assays to screen for a ligand or agonist/antagonist homologous proteins can be greatly facilitated by the availability of large amounts of purified, soluble cytokine receptors in an active state such as is provided by this invention. Alternatively, production of large amounts of ligand will be useful in screening for receptor. Markers will also be available in large amounts to generate specific reagents.

Purified protein, e.g., DIRS4, can be coated directly onto plates or otherwise presented for use in the ligand or antibody screening techniques. However, non-neutralizing antibodies to these proteins can be used as capture antibodies to immobilize the respective receptor on the solid phase, useful, e.g., in diagnostic uses.

This invention also contemplates use of, e.g., DIRS4, fragments thereof, peptides, and their fusion products in a variety of diagnostic kits and methods for detecting the presence of the protein or its ligand. Alternatively, or additionally, antibodies against the molecules may be incorporated into the kits and methods. Typically the kit will have a compartment containing either a peptide or gene segment or a reagent which recognizes one or the other. Typically, recognition reagents, in the case of peptide, would be a receptor or antibody, or in the case of a gene segment, would usually be a hybridization probe. Diagnostic applications will be useful for the markers, as described.

A preferred kit for determining the concentration of, e.g., DIRS4, in a sample would typically comprise a labeled compound, e.g., ligand or antibody, having known binding affinity for DIRS4, a source of DIRS4 (naturally occurring or recombinant) as a positive control, and a means for separating the bound from free labeled compound, for example a solid phase for immobilizing the DIRS4 in the test sample. Compartments containing reagents, and instructions, will normally be provided.

Antibodies, including antigen binding fragments, specific for mammalian claudins or schlafens or a peptide fragment, or receptor fragments are useful in diagnostic applications to detect the presence of elevated levels of protein and/or its fragments. Diagnostic assays may be homogeneous (without a separation step between free reagent and antibody-antigen complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA) and the like. For example, unlabeled antibodies can be employed by using a second antibody which is labeled and which recognizes the antibody to a cytokine receptor or to a particular fragment thereof. These assays have also been extensively discussed in the literature. See, e.g., Harlow and Lane (1988) *Antibodies: A Laboratory Manual,* CSH., and Coligan (ed. 1991 and periodic supplements) *Current Protocols In Immunology* Greene/Wiley, New York.

Anti-idiotypic antibodies may have similar use to serve as agonists or antagonists of cytokine receptors or ligands. These should be useful as therapeutic reagents under appropriate circumstances.

Frequently, the reagents for diagnostic assays are supplied in kits, so as to optimize the sensitivity of the assay. For the subject invention, depending upon the nature of the assay, the protocol, and the label, either labeled or unlabeled antibody, or labeled ligand is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent, and will contain instructions for proper use and disposal of reagents. Desirably, the reagents are provided as a dry lyophilized powder, where the reagents may be reconstituted in an aqueous medium having appropriate concentrations for performing the assay.

The aforementioned constituents of the diagnostic assays may be used without modification or may be modified in a variety of ways. For example, labeling may be achieved by covalently or non-covalently joining a moiety which directly or indirectly provides a detectable signal. In many of these assays, a test compound, cytokine receptor, ligand, or antibodies thereto can be labeled either directly or indirectly. Possibilities for direct labeling include label groups: radio-labels such as $^{125}I$, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Both of the patents are incorporated herein by reference. Possibilities for indirect labeling include biotinylation of one constituent followed by binding to avidin coupled to one of the above label groups.

There are also numerous methods of separating the bound from the free ligand, or alternatively the bound from the free test compound. The cytokine receptor can be immobilized on various matrixes followed by washing. Suitable matrices include plastic such as an ELISA plate, filters, and beads. Methods of immobilizing the receptor to a matrix include, without limitation, direct adhesion to plastic, use of a capture antibody, chemical coupling, and biotin-avidin. The last step in this approach involves the precipitation of antibody/antigen complex by any of several methods including those utilizing, e.g., an organic solvent such as polyethylene glycol or a salt such as ammonium sulfate. Other suitable separation techniques include, without limitation, the fluorescein antibody magnetizable particle method described in Rattle, et al. (1984) *Clin. Chem.* 30(9):1457–1461, and the double antibody magnetic particle separation as described in U.S. Pat. No. 4,659,678, each of which is incorporated herein by reference.

Methods for linking protein or fragments to various labels are well reported in the literature. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequences provided. These sequences can be used as probes for detecting levels of the respective genes or transcripts in patients suspected of having an immunological or other medical disorder. The preparation of both RNA and DNA nucleotide sequences, the labeling of the sequences, and the preferred size of the sequences has received ample description and discussion in the literature. Normally an oligonucleotide probe should have at least about 14 nucleotides, usually at least about 18 nucleotides, and the polynucleotide probes may be up to several kilobases. Various labels may be employed, most commonly radionuclides, particularly $^{32}$P. However, other techniques may also be employed, such as using biotin modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed which can recognize specific duplexes, including DNA duplexes, RNA duplexes, DNA-RNA hybrid duplexes, or DNA-protein duplexes. The antibodies in turn may be labeled and the assay carried out where the duplex is bound to a surface, so that upon the formation of duplex on the surface, the presence of antibody bound to the duplex can be detected. The use of probes to the novel anti-sense RNA may be carried out in conventional techniques such as nucleic acid hybridization, plus and minus screening, recombinational probing, hybrid released translation (HRT), and hybrid arrested translation (HART). This also includes amplification techniques such as polymerase chain reaction (PCR).

Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet, et al. (1989) *Progress in Growth Factor Res.* 1:89–97.

VIII. Therapeutic Utility

This invention provides reagents with significant therapeutic value. See, e.g., Levitzki (1996) *Curr. Opin. Cell Biol.* 8:239–244. The cytokine receptors (naturally occurring or recombinant), fragments thereof, mutein receptors, and antibodies, along with compounds identified as having binding affinity to the receptors or antibodies, should be useful in the treatment of conditions exhibiting abnormal expression of the receptors of their ligands. Such abnormality will typically be manifested by immunological or other disorders. Additionally, this invention should provide therapeutic value in various diseases or disorders associated with abnormal expression or abnormal triggering of response to the ligand. The biology of interferons, IL-10, TNFs, and TGFs are well described. Conversely, the TLRs have also been the subject of much interest, and the described homologs described herein will also be of similar interest. Associations with significant medical conditions for the claudins and schlafens is described below.

Recombinant proteins, muteins, agonist or antagonist antibodies thereto, or antibodies can be purified and then administered to a patient. These reagents can be combined for therapeutic use with additional active ingredients, e.g., in conventional pharmaceutically acceptable carriers or diluents, along with physiologically innocuous stabilizers and excipients. These combinations can be sterile, e.g., filtered, and placed into dosage forms as by lyophilization in dosage vials or storage in stabilized aqueous preparations. This invention also contemplates use of antibodies or binding fragments thereof which are not complement binding.

Ligand screening using receptor or fragments thereof can be performed to identify molecules having binding affinity to the receptors. Subsequent biological assays can then be utilized to determine if a putative ligand can provide competitive binding, which can block intrinsic stimulating activity. Receptor fragments can be used as a blocker or antagonist in that it blocks the activity of ligand. Likewise, a compound having intrinsic stimulating activity can activate the receptor and is thus an agonist in that it simulates the activity of ligand, e.g., inducing signaling. This invention further contemplates the therapeutic use of antibodies to cytokine receptors as antagonists.

Conversely, receptor screening for receptors for ligands can be performed. However, ligands can also be screened for function using biological assays, which are typically simple due to the soluble nature of the ligands.

The quantities of reagents necessary for effective therapy will depend upon many different factors, including means of administration, target site, reagent physiological life, pharmacological life, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds. 1990) *Goodman and Gilman's: The Pharmacological Bases of Therapeutics,* 8th Ed., Pergamop, Press; and *Remington's Pharmaceutical Sciences,* 17th ed. (1990), Mack Publishing Co., Easton, Pa.; each of which is hereby incorporated herein by reference. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index,* Merck & Co., Rahway, N.J. Dosage ranges would ordinarily be expected to be in amounts lower than 1 mM concentrations, typically less than about 10 μM concentrations, usually less than about 100 nM, preferably less than about 10 pM (picomolar), and most preferably less than about 1 fM (femtomolar), with an appropriate carrier. Slow release formulations, or slow release apparatus will often be utilized for continuous administration.

Cytokines, receptors, fragments thereof, and antibodies or its fragments, antagonists, and agonists, may be administered directly to the host to be treated or, depending on the size of the compounds, it may be desirable to conjugate them to carrier proteins such as ovalbumin or serum albumin prior to their administration. Therapeutic formulations may be administered in many conventional dosage formulations. While it is possible for the active ingredient to be administered alone, it is preferable to present it as a pharmaceutical formulation. Formulations comprise at least one active ingredient, as defined above, together with one or more acceptable carriers thereof. Each carrier must be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by methods well known in the art of pharmacy. See, e.g., Gilman, et al. (eds. 1990) *Goodman and Gilman's: The Pharmacological Bases of Therapeutics,* 8th Ed., Pergamon Press; and *Remington's Pharmaceutical Sciences,* 17th ed. (1990), Mack Publishing Co., Easton, Pa.; Avis, et al. (eds. 1993) *Pharmaceutical Dosage Forms: Parenteral Medications* Dekker, N.Y.; Lieberman, et al. (eds. 1990) *Pharmaceutical Dosage Forms: Tablets* Dekker, N.Y.; and Lieberman, et al. (eds. 1990) *Pharmaceutical Dosage Forms: Disperse Systems* Dekker, N.Y. The therapy of this invention may be combined with or used in association with other therapeutic agents, e.g., agonists or antagonists of other cytokine receptor family members.

IX. Screening

Drug screening using DIRS4, TLR-L receptors, or fragments thereof can be performed to identify compounds having binding affinity to the receptor subunits, including isolation of associated components. See, e.g., Emory and Schlegel (1996) *Cost-Effective Strategies for Automated and Accelerated High-Throughput Screening* IBC, Inc., Southborough, Mass. Subsequent biological assays can then be utilized to determine if the compound has intrinsic stimulating activity and is therefore a blocker or antagonist in that it blocks the activity of the ligand. Likewise, a compound having intrinsic stimulating activity can activate the receptor and is thus an agonist in that it simulates the activity of a cytokine ligand. This invention further contemplates the therapeutic use of antibodies to the receptor as cytokine agonists or antagonists.

Conversely, for ligands, receptors may be screened. Orphan receptor subunits, or testing of known receptor subunits in known or novel pairings may be performed.

One method of drug screening utilizes eukaryotic or prokaryotic host cells which are stably transformed with recombinant DNA molecules expressing the DIRS4 or TLR-L receptors. Cells may be isolated which express a receptor in isolation from other functional receptors, or in combination with other specific subunits. Such cells, either in viable or fixed form, can be used for standard ligand/receptor binding assays. See also, Parce, et al. (1989) *Science* 246:243–247; and Owicki, et al. (1990) *Proc. Nat'l Acad. Sci. USA* 87:4007–4011, which describe sensitive methods to detect cellular responses. Competitive assays are particularly useful, where the cells (source of putative ligand) are contacted and incubated with a labeled receptor or antibody having known binding affinity to the ligand, such as $^{125}$I-antibody, and a test sample whose binding affinity to the binding composition is being measured. The bound and free labeled binding compositions are then separated to assess the degree of ligand binding. The amount of test compound bound is inversely proportional to the amount of labeled receptor binding to the known source. Any one of numerous techniques can be used to separate bound from free ligand to assess the degree of ligand binding. This separation step could typically involve a procedure such as adhesion to filters followed by washing, adhesion to plastic followed by washing, or centrifugation of the cell membranes. Viable cells could also be used to screen for the effects of drugs on cytokine mediated functions, e.g., second messenger levels, i.e., $Ca^{++}$; cell proliferation; inositol phosphate pool changes; and others. Some detection methods allow for elimination of a separation step, e.g., a proximity sensitive detection system. Calcium sensitive dyes will be useful for detecting $Ca^{++}$ levels, with a fluorimeter or a fluorescence cell sorting apparatus.

X. Ligands

The descriptions of the DIRS4 and TLR-L receptors herein provide means to identify ligands, as described above. Such ligand should bind specifically to the respective receptor with reasonably high affinity. Various constructs are made available which allow either labeling of the receptor to detect its ligand. For example, directly labeling cytokine receptor, fusing onto it markers for secondary labeling, e.g., FLAG or other epitope tags, etc., will allow detection of receptor. This can be histological, as an affinity method for biochemical purification, or labeling or selection in an expression cloning approach. A two-hybrid selection system may also be applied making appropriate constructs with the available cytokine receptor sequences. See, e.g., Fields and Song (1989) *Nature* 340:245–246.

Generally, descriptions of cytokine receptors will be analogously applicable to individual specific embodiments directed to DIRS4 or TLR-L reagents and compositions. Conversely, soluble ligands, e.g., TNFs and TGFs, will be characterized for biological activity.

The broad scope of this invention is best understood with reference to the following examples, which are not intended to limit the inventions to the specific embodiments.

EXAMPLES

I. General Methods

Some of the standard methods are described or referenced, e.g., in Maniatis, et al. (1982) *Molecular Cloning, A Laboratory Manual*, Cold Spring Harbor Laboratory, Cold Spring Harbor Press; Sambrook, et al. (1989) *Molecular Cloning: A Laboratory Manual*, (2d ed.), vols. 1–3, CSH Press, NY; Ausubel, et al., *Biology*, Greene Publishing Associates, Brooklyn, N.Y.; or Ausubel, et al. (1987 and Supplements) *Current Protocols in Molecular Biology*, Greene/Wiley, New York. Methods for protein purification include such methods as ammonium sulfate precipitation, column chromatography, electrophoresis, centrifugation, crystallization, and others. See, e.g., Ausubel, et al. (1987 and periodic supplements); Coligan, et al. (ed. 1996) and periodic supplements, *Current Protocols In Protein Science* Greene/Wiley, New York; Deutscher (1990) "Guide to Protein Purification" in *Methods in Enzymology*, vol. 182, and other volumes in this series; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See, e.g., Hochuli (1989) *Chemische Industrie* 12:69–70; Hochuli (1990) "Purification of Recombinant Proteins with Metal Chelate Absorbent" in Setlow (ed.) *Genetic Engineering, Principle and Methods* 12:87–98, Plenum Press, N.Y.; and Crowe, et al. (1992) *QIAexpress: The High Level Expression & Protein Purification System* QUIAGEN, Inc., Chatsworth, Calif.

Computer sequence analysis is performed, e.g., using available software programs, including those from the GCG (U. Wisconsin) and GenBank sources. Public sequence databases were also used, e.g., from GenBank and others.

Many techniques applicable to IL-10 or IL-12 receptors may be applied to the DIRS4 or other receptor subunits, as described, e.g., in U.S. Ser. No. 08/110,683 (IL-10 receptor), which is incorporated herein by reference.

II. Computational Analysis

Human sequences were identified from genomic sequence database using, e.g., the BLAST server (Altschul, et al. (1994) *Nature Genet.* 6:119–129). Standard analysis programs may be used to evaluate structure, e.g., PHD (Rost and Sander (1994) *Proteins* 19:55–72) and DSC (King and Stemberg (1996) *Protein Sci.* 5:2298–2310). Standard comparison software includes, e.g., Altschul, et al. (1990) *J. Mol. Biol.* 215:403–10; Waterman (1995) *Introduction to Computational Biology: Maps, Sequences, and Genomes* Chapman & Hall; Lander and Waterman (eds. 1995) *Calculating the Secrets of Life: Applications of the Mathematical Sciences in Molecular Biology* National Academy Press; and Speed and Waterman (eds. 1996) *Genetic Mapping and DNA Sequencing* (Ima Volumes in Mathematics and Its Applications, Vol 81) Springer Verlag.

III. Cloning of full-length cDNAs; Chromosomal localization

PCR primers derived from the sequences are used to probe a human cDNA library. Full length cDNAs for primate, rodent, or other species DIRS4 are cloned, e.g., by DNA hybridization screening of_gt10 phage. PCR reactions are conducted using T. aquaticus Taqplus DNA polymerase (Stratagene) under appropriate conditions.

Chromosome spreads are prepared. In situ hybridization is performed on chromosome preparations obtained from phytohemagglutinin-stimulated human lymphocytes cultured for 72 h. 5-bromodeoxyuridine was added for the final seven hours of culture (60_g/ml of medium), to ensure a posthybridization chromosomal banding of good quality.

A PCR fragment, amplified with the help of primers, is cloned into an appropriate vector. The vector is labeled by nick-translation with $^3$H. The radiolabeled probe is hybridized to metaphase spreads at final concentration of 200 ng/ml of hybridization solution as described in Mattei, et al. (1985) Hum. Genet. 69:327–331.

After coating with nuclear track emulsion (KODAK NTB$_2$), slides are exposed. To avoid any slipping of silver grains during the banding procedure, chromosome spreads are first stained with buffered Giemsa solution and metaphase photographed. R-banding is then performed by the fluorochrome-photolysis-Giemsa (FPG) method and metaphases rephotographed before analysis. Alternatively, mapped sequence tags may be searched in a database.

Similar appropriate methods are used for other species.

IV. Localization of mRNA

Human multiple tissue (Cat # 1, 2) and cancer cell line blots (Cat # 7757-1), containing approximately 2 μg of poly(A)$^+$ RNA per lane, are purchased from Clontech (Palo Alto, Calif.). Probes are radiolabeled with[α-$^{32}$P] dATP, e.g., using the Amersham Rediprime random primer labeling kit (RPN1633). Prehybridization and hybridizations are performed at 65° C. in 0.5 M Na$_2$HPO$_4$, 7% SDS, 0.5 M EDTA (pH 8.0). High stringency washes are conducted, e.g., at 65° C. with two initial washes in 2×SSC, 0.1% SDS for 40 min followed by a subsequent wash in 0.1×SSC, 0.1% SDS for 20 min. Membranes are then exposed at −70° C. to X-Ray film (Kodak) in the presence of intensifying screens. More detailed studies by cDNA library Southerns are performed with selected human DIRS4 clones to examine their expression in hemopoietic or other cell subsets.

Alternatively, two appropriate primers are selected, e.g., from the tables. RT-PCR is used on an appropriate mRNA sample selected for the presence of message to produce a cDNA, e.g., a sample which expresses the gene.

Full length clones may be isolated by hybridization of cDNA libraries from appropriate tissues pre-selected by PCR signal. Northern blots can be performed.

Message for genes encoding each gene will be assayed by appropriate technology, e.g., PCR, immunoassay, hybridization, or otherwise. Tissue and organ cDNA preparations are available, e.g., from Clontech, Mountain View, Calif. Identification of sources of natural expression are useful, as described. And the identification of functional receptor subunit pairings will allow for prediction of what cells express the combination of receptor subunits which will result in a physiological responsiveness to each of the cytokine ligands.

For mouse distribution, e.g., Southern Analysis can be performed: DNA (5 μg) from a primary amplified cDNA library was digested with appropriate restriction enzymes to release the inserts, run on a 1% agarose gel and transferred to a nylon membrane (Schleicher and Schuell, Keene, N.H.).

Samples for mouse mRNA isolation may include: resting mouse fibroblastic L cell line (C200); Braf:BR (Braf fusion to estrogen receptor) transfected cells, control (C201); T cells, TH1 polarized (Mel14 bright, CD4+ cells from spleen, polarized for 7 days with IFN-γ and anti IL-4; T200); T cells, TH2 polarized (Mel14 bright, CD4+ cells from spleen, polarized for 7 days with IL-4 and anti-IFN-γ; T201); T cells, highly TH1 polarized (see Openshaw, et al. (1995) J. Exp. Med. 182:1357–1367; activated with anti-CD3 for 2, 6, 16 h pooled; T202); T cells, highly TH2 polarized (see Openshaw, et al. (1995) J. Exp. Med. 182:1357–1367; activated with anti-CD3 for 2, 6, 16 h pooled; T203); CD44− CD25+ pre T cells, sorted from thymus (T204); TH1 T cell clone D1.1, resting for 3 weeks after last stimulation with antigen (T205); TH1 T cell clone D1.1, 10 μg/ml ConA stimulated 15 h (T206); TH2 T cell clone CDC35, resting for 3 weeks after last stimulation with antigen (T207); TH2 T cell clone CDC35, 10 μg/ml ConA stimulated 15 h (T208); Mel14+ naive T cells from spleen, resting (T209); Mel14+ T cells, polarized to Th1 with IFN-γ/IL-12/anti-IL-4 for 6, 12, 24 h pooled (T210); Mel14+ T cells, polarized to Th2 with IL-4/anti-IFN-γ for 6, 13, 24 h pooled (T211); unstimulated mature B cell leukemia cell line A20 (B200); unstimulated B cell line CH12 (B201); unstimulated large B cells from spleen (B202); B cells from total spleen, LPS activated (B203); metrizamide enriched dendritic cells from spleen, resting (D200); dendritic cells from bone marrow, resting (D201); monocyte cell line RAW 264.7 activated with LPS 4 h (M200); bone-marrow macrophages derived with GM and M-CSF (M201); macrophage cell line J774, resting (M202); macrophage cell line J774+LPS+anti-IL-10 at 0.5, 1, 3, 6, 12 h pooled (M203); macrophage cell line J774+LPS+IL-10 at 0.5, 1, 3, 5, 12 h pooled(M204); aerosol challenged mouse lung tissue, Th2 primers, aerosol OVA challenge 7, 14, 23 h pooled (see Garlisi, et al. (1995) Clinical Immunology and Immunopathology 75:75–83; X206); Nippostrongulus-infected lung tissue (see Coffmnan, et al. (1989) Science 245:308–310; X200); total adult lung, normal (O200); total lung, rag-1 (see Schwarz, et al. (1993) Immunodeficiency 4:249–252; O205); IL-10 K. O. spleen (see Kuhn, et al. (1991) Cell 75:263–274; X201); total adult spleen, normal (O201); total spleen, rag-1 (O207); IL-10 K.O. Peyer's patches (O202); total Peyer's patches, normal (O210); IL-10 K.O. mesenteric lymph nodes (X203); total mesenteric lymph nodes, normal (O211); IL-10 K.O. colon (X203); total colon, normal (O212); NOD mouse pancreas (see Makino, et al. (1980) Jikken Dobutsu 29:1–13; X205); total thymus, rag-1 (O208); total kidney, rag-1 (O209); total heart, rag-1 (O202); total brain, rag-1 (O203); total testes, rag-1 (O204); total liver, rag-1 (O206); rat normal joint tissue (O300); and rat arthritic joint tissue (X300).

Samples for human mRNA isolation may include: peripheral blood mononuclear cells (monocytes, T cells, NK cells, granulocytes, B cells), resting (T100); peripheral blood mononuclear cells, activated with anti-CD3 for 2, 6, 12 h pooled (T101); T cell, TH0 clone Mot 72, resting (T102); T cell, TH0 clone Mot 72, activated with anti-CD28 and anti-CD3 for 3, 6, 12 h pooled (T103); T cell, TH0 clone Mot 72, anergic treated with specific peptide for 2, 7, 12 h pooled (T104); T cell, TH1 clone HY06, resting (T107); T cell, TH1 clone HY06, activated with anti-CD28 and anti-CD3 for 3, 6, 12 h pooled (T108); T cell, TH1 clone HY06, anergic treated with specific peptide for 2, 6, 12 h pooled (T109); T cell, TH2 clone HY935, resting (T110); T cell, TH2 clone HY935, activated with anti-CD28 and anti-CD3 for 2, 7, 12 h pooled (T111); T cells CD4+CD45RO- T cells polarized 27 days in anti-CD28, IL-4, and anti IFN-γ, TH2 polarized, activated with anti-CD3 and anti-CD28 4 h (T116); T cell tumor lines Jurkat and Hut78, resting (T117); T cell clones, pooled AD130.2, Tc783.12, Tc783.13, Tc783.58, Tc782.69, resting (T118); T cell random γδ T cell clones, resting (T119); Splenocytes, resting (B100); Splenocytes, activated with anti-CD40 and IL-4 (B101); B cell EBV lines pooled WT49, RSB, JY, CVIR, 721.221, RM3, HSY, resting (B102); B cell line JY, activated with PMA and ionomycin for 1, 6 h pooled (B103); NK 20 clones pooled, resting (K100); NK 20 clones pooled, activated with PMA and ionomycin for 6 h (K101); NKL clone, derived from peripheral blood of LGL leukemia patient, IL-2 treated (K106); NK cytotoxic clone 640-A30-1, resting (K107); hematopoietic precursor line TF1, activated with PMA and ionomycin for 1, 6 h pooled (C100); U937 premonocytic line, resting (M100); U937 premonocytic line, activated with PMA and ionomycin for 1, 6 h pooled (M101); elutriated monocytes, activated with LPS, IFNγ, anti-IL-10 for 1, 2, 6, 12, 24 h pooled (M102); elutriated monocytes, activated with LPS, IFNγ, IL-10 for 1, 2, 6, 12, 24 h pooled (M103); elutriated monocytes, activated with LPS, IFNγ, anti-IL-10 for 4, 16 h pooled (M106); elutriated monocytes, activated with LPS, IFNγ, IL-10 for 4, 16 h pooled (M107); elutriated monocytes, activated LPS for 1 h (M108); elutriated monocytes, activated LPS for 6 h (M109); DC 70% CD1a+, from CD34+ GM-CSF, TNFα 12 days, resting (D101); DC 70% CD1a+, from CD34+ GM-CSF, TNFα 12 days, activated with PMA and ionomycin for 1 hr (D102); DC 70% CD1a+, from CD34+ GM-CSF, TNFα 12 days, activated with PMA and ionomycin for 6 hr (D103); DC 95% CD1a+, from CD34+ GM-CSF, TNF_12 days FACS sorted, activated with PMA and ionomycin for 1, 6 h pooled (D104); DC 95% CD14+, ex CD34+ GM-CSF, TNFα 12 days FACS sorted, activated with PMA and ionomycin 1, 6 hr pooled (D105); DC CD1a+ CD86+, from CD34+ GM-CSF, TNFα 12 days FACS sorted, activated with PMA and ionomycin for 1, 6 h pooled (D106); DC from monocytes GM-CSF, IL-4 5 days, resting (D107); DC from monocytes GM-CSF, IL-4 5 days, resting (D108); DC from monocytes GM-CSF, IL-4 5 days, activated LPS 4, 16 h pooled (D109); DC from monocytes GM-CSF, IL-4 5 days, activated TNFα, monocyte supe for 4, 16 h pooled (D110); leiomyoma L11 benign tumor (X101); normal myometrium M5 (O115); malignant leiomyosarcoma GS1 (X103); lung fibroblast sarcoma line MRC5, activated with PMA and ionomycin for 1, 6 h pooled (C101); kidney epithelial carcinoma cell line CHA, activated with PMA and ionomycin for 1, 6 h pooled (C102); kidney fetal 28 wk male (O100); lung fetal 28 wk male (O101); liver fetal 28 wk male (O102); heart fetal 28 wk male (O103); brain fetal 28 wk male (O104); gallbladder fetal 28 wk male (O106); small intestine fetal 28 wk male (O107); adipose tissue fetal 28 wk male (O108); ovary fetal 25 wk female (O109); uterus fetal 25 wk female (O110); testes fetal 28 wk male (O111); spleen fetal 28 wk male (O112); adult placenta 28 wk (O113); and tonsil inflamed, from 12 year old (X100).

For the DIRS4, southern blot analysis revealed expression in several cDNA libraries, including resting MOT72 (Th0 clone); resting, activated, and anti-peptide HY06 (Th1 clone); activated T cells CD4+, Th2 polarized; resting pooled T cell clones; resting and activated splenocytes; resting EBV B cells; activated JY (B cell line); cytotoxic NK cells; TF1 cells; resting and activated U937 cells; monocytes treated with anti-IL-10; monocytes (anti-IL-10 and IL-10 stimulated); activated monocytes; dendritic cells (activated and resting); MRC5 (lung fibroblast sarcoma line); CHA (kidney epithelial carcinoma line); normal and asthmatic monkey lung; normal and smoker lung; normal colon; fetal lung; liver; gall bladder; and small intestine. There were two transcript sizes, about 500 bp and about 1.8 kb bands, suggesting two different transcripts, possibly soluble and membrane spanning forms.

The primate, e.g., human, TNFx expression, by PCR, is high in allergic lung and normal lung; much lower in adult placenta, fetal spleen, and normal skin. Essentially no expression in gut samples and fetal organs. In cells, high expression was detected in resting HY06 cells and TF-1; lower in activated HY06 cell and JY cells, and no significant expression in the other human samples tested, e.g., most in the list above. Table 1 shows additional TaqMan expression data for human TNFx.

TABLE 1

| LIBRARY | Ct_gene | LIBRARY | Ct_gene |
|---|---|---|---|
| PBMC resting | 44.64 | mono + anti-IL-10 | 22.47 |
| PBMC activated | 40.48 | mono + IL-10 | 21.04 |
| Mot 72 resting | 26.29 | M1 | 40.52 |
| Mot 72 activated | 24.51 | M6 | 21.75 |
| Mot 72 anti-peptide | 20.72 | 70% DC resting | 26.27 |
| HY06 resting | 15.86 | D1 | 37.94 |
| HY06 activated | 18.3 | D6 | 25.05 |
| HY06 anti-peptide | 24.27 | CD1a+ 95% | 26.87 |
| HY935 resting | 25.97 | CD14+ 95% | 35.17 |
| HY935 activated | 25.03 | CD1a+ CD86+ | 27.48 |
| B21 resting | 26.3 | DC/GM/IL-4 | 32.33 |
| B21 activated | 24.53 | DC LPS | 27.81 |
| Tc gamma delta | 45 | DC mix | 27.32 |
| Jurkat resting pSPORT | 45 | fetal kidney | 26.41 |
| Jurkat activated pSPORT | 28.09 | fetal lung | 31.16 |
| Splenocytes resting | 23.51 | fetal liver | 26.28 |
| Splenocytes activated | 26.19 | fetal heart | 34.28 |
| Bc | 23.88 | fetal brain | 25.02 |
| JY | 19.29 | fetal small intestine | 37.89 |
| NK pool | 38.21 | fetal adipose tissue | 26.41 |
| NK pool activated | 37.54 | fetal ovary | 37.49 |
| NKA6 pSPORT | 34.39 | fetal uterus | 26.03 |
| NKL/IL-2 | 25.71 | fetal testes | 36.65 |
| NK cytotox. | 23.28 | fetal spleen | 23.2 |
| NK non cytotox. | 26.35 | adult placenta | 24.06 |
| U937/CD004 resting | 28.18 | inflammed tonsil | 26.21 |
| U937 activated | 26.21 | TF1 | 23.48 |
| C− | 27 | MRC5 | 33.99 |
| C+ | 23.13 | CHA | 28.27 |
| mast cell pME | 28.65 | Taq_control | 50 |
| TC1080 CD28− pMET7 | 38.1 | Crohns colon 403242A | 28.32 |
| RV-C30 TR1 pMET7 | 24.97 | lung 080698-2 | 27.42 |
| DC resting mono-derived | 28.12 | 18 hr. Ascaris lung | 28.06 |
| DC CD40L activ. mono-deriv. | 27.07 | hi dose IL-4 lung | 34.01 |
| DC resting CD34-derived | 28.9 | normal colon #22 | 44.6 |
| DC TNF/TGFb act CD34-der. | 36.74 | ulcerative colitis colon #26 | 38.12 |
| allergic lung #19 | 20.21 | normal thyroid | 28.14 |
| Pneumocystis carnii lung #20 | 36.33 | Hashimotos thyroiditis | 36.88 |
| RA synovium pool | 28 | normal skin | 24.12 |
| Psoriasis skin | 32.37 | Crohns colon 4003197A | 30.31 |
| normal lung | 35.68 | lung 121897-1 | 36.25 |
| 4 hr. Ascaris lung | 31.45 | Crohns colon 9609C144 | 27.49 |
| 24 hr. Ascaris lung | 26.34 | A549 unstim. | 28.03 |
| normal lung pool | 22.21 | A549 activated | 24.1 |
| Taq_control_genomic_1 genomic_1 | 50 | Taq_control_water | 50 |

The rodent, e.g., mouse, TNFx is highly expressed in 5 month ApoE KO mouse aorta; C57B6 3 wk polarized Th1 cells; and C57B6 3 wk polarized Th2 cells. It is less highly expressed in Balb/c 3 wk polarized Th2 cells, LPS treated spleen, and various other Th2 polarized populations. In tissues, by PCR, it is expressed highly in TNK KO spleen, NZB/W spleen, NZB/W kidney, NZB/W spleen, GF ears/skin; rag-1 testis, w.t. C57B6 spleen, w.t. C57B6 pancreas, and 2 mo. lung. It is expressed at lower levels in influenza lung, rag-1 lung, rag-1 spleen, spinal cord samples, lung samples, stomach, and lymph nodes. Table 2 shows additional TaqMan expression data for mouse TNFx.

TABLE 2

| LIBRARY | Ct_gene | LIBRARY | Ct_gene |
|---|---|---|---|
| L cell | 26 | rag-1 brain | 24.47 |
| TH1 7day | 26.63 | rag-1 testes | 38.4 |
| TH2 7day | 24.56 | rag-1 lung | 22.81 |
| TH1 3 week Balb/C | 39.09 | rag-1 liver | 36.69 |
| TH2 3 week Balb/C | 24.48 | rag-1 spleen | 24.23 |
| preT | 36.92 | rag-1 thymus | 23.91 |
| D1.1 resting | 32.74 | rag-1 kidney | 22.32 |
| D1.1 con A stim. | 37.76 | w.t. Peyers patches | 25.48 |
| CDC35 resting | 30.8 | w.t. mesenteric lymph nodes | 25.59 |
| CDC35 con A stim. | 41.92 | w.t. colon | 28.7 |
| Mel 14+ naive T | 28.16 | Braf:ER (−) oligo dT | 38.53 |
| Mel14+ TH1 | 29.2 | TH1 3 week C57 Bl/6 | 23.12 |
| Mel 14+ TH2 | 25.02 | TH2 3 week C57 Bl/6 | 22.54 |
| A20 | 37.61 | TH1 3 week Balb/C fresh | 28.02 |
| CH12 | 25.29 | TH2 3 week Balb/C fresh | 37.73 |
| lg. B cell | 30.34 | b.m. DC (YJL) resting | 27.99 |
| LPS spleen | 24.04 | b.m. DC (YJL) aCD40 stim. | 40.47 |
| macrophage | 28.6 | b.m. mf + LPS + aIL-10R | 29.74 |
| J774 resting | 39.73 | b.m. mf + LPS + IL-10 | 27.67 |
| J774 +LPS + anti-IL-10 | 36.51 | peritoneal mf | 37.02 |
| J774 +LPS + IL-10 | 40.53 | MC-9/MCP-12 pMET7 | 39.68 |
| Nippo-infected lung | 25.87 | EC | 40.13 |
| IL-10 K.O. spleen | 24.18 | EC + TNFa | 40.54 |
| IL-10 K.O. colon | 36.97 | bEnd3 + TNFa | 41.26 |
| asthmatic lung | 26.61 | bEnd3 + TNFa + IL-10 | 38.35 |
| w.t. lung | 24.06 | ApoE aorta 5 month | 21.03 |
| w.t. spleen | 28.87 | ApoE aorta 12 month | 34.28 |
| rag-1 heart | 26.48 | NZ B/W kidney | 21.02 |
| Nippo IL-4 K.O. lung | 28.59 | NZ B/W spleen | 21.2 |
| Nippo anti IL-5 lung | 25.73 | tolerized & challenged lung | 27.17 |
| Influenza lung | 23.93 | Aspergillus lung | 23.32 |
| b common lung 2 month | 24.53 | Taq_control_water | 50 |
| IL-10 K.O. stomach | 29.87 | Taq_control_genomic_1 | 50 |
| IL-10 K.O. MLN aIL-12 | 26.58 | Tac_control_genomic_2 | 50 |
| IL-10 K.O. MLN + IL-10 | 25.89 | w.t. d17 spinal cord EAE model | 22.87 |
| Rag-2 Hh−colon | 29.2 | TNF K.O. d17 spinal cord EAE model | 22.84 |
| Rag-2 Hh+colon | 27.1 | TNF K.O. spinal cord | 23.27 |
| IL-7 K.O./Rag-2 Hh− colon | 40 | TNF K.O. spleen | 20.78 |
| IL-7 K.O./Rag-2 Hh+ colon | 40 | G.F. ears (skin) | 20.7 |
| transfer model IBD | 28.1 | w.t. spinal cord | 22.74 |
| w.t. C57 Bl/6 aorta | 39.38 | w.t. C57 Bl/6 spleen | 22.15 |
| w.t. thymus | 27.05 | w.t. C57 Bl/6 pancreas | 24.75 |
| w.t. stomach | 26.49 | MM2/MM3 activated. pME | 37.67 |
| MM2/MM3 resting pME | 37.62 | | |

TABLE 3

| LIBRARY | Ct_gene | LIBRARY | Ct_gene |
|---|---|---|---|
| PBMC resting | 45 | mono + IL-10 | 42.96 |
| PBMC activated | 44.16 | M1 | 41.25 |
| Mot 72 resting | 42.47 | M6 | 45 |
| Mot 72 activated | 28.59 | 70% DC resting | 40.37 |
| Mot 72 anti-peptide | 42.47 | D1 | 28.94 |
| HY06 resting | 43.19 | D6 | 28.38 |
| HY06 activated | 41.48 | CD1a+ 95% | 25.63 |
| HY06 anti-peptide | 43.28 | CD14+ 95% | 28.36 |
| HY935 resting | 45 | CD1a+ CD86+ | 28.67 |
| HY935 activated | 43.62 | DC/GM/IL-4 | 45 |
| B21 resting | 41.73 | DC LPS | 38.8 |
| B21 activated | 44.35 | DC mix | 26.53 |
| Tc gamma delta | 43.21 | fetal kidney | 27.98 |
| Jurkat resting pSPORT | 23.44 | fetal lung | 30.57 |
| Jurkat activated pSPORT | 25.19 | fetal liver | 43.92 |
| Splenocytes resting | 38.72 | fetal heart | 40.84 |
| Splenocytes activated | 44.09 | fetal brain | 26.02 |
| Bc | 44.83 | fetal small intestine | 40.05 |
| JY | 43.05 | fetal adipose tissue | 23.63 |
| NK pool | 39.09 | fetal ovary | 25.85 |
| NK pool activated | 44.32 | fetal uterus | 27.57 |
| NKA6 pSPORT | 42.8 | fetal testes | 45 |
| NKL/IL-2 | 45 | fetal spleen | 39.08 |
| NK cytotox. | 44.79 | adult placenta | 28.05 |
| NK non cytotox. | 45 | inflammed tonsil | 45 |
| U937/CD004 resting | 24.17 | TF1 | 22.09 |
| U937 activated | 24.41 | MRC5 | 26.18 |
| C− | 40.38 | CHA | 19.22 |
| C+ | 41.17 | mastcell pME | 43.93 |
| mono + anti-IL-10 | 45 | TC1080 CD28− pMET7 | 41.62 |
| DC resting mono-derived | 45 | RV-C30 TR1 pMET7 | 42.76 |
| DC CD40L activ. mono-deriv. | 45 | 4 hr. Ascaris lung | 45 |
| DC resting CD34-derived | 45 | 24 hr. Ascaris lung | 45 |
| DC TNF/TGFb act CD34-der. | 39.71 | normal lung pool | 45 |
| allergic lung #19 | 43.22 | normal skin | 42.69 |
| Pneumocystis carnii lung #20 | 43.81 | Crohns colon 4003197A | 29.82 |
| normal colon #22 | 43.66 | lung 121897-1 | 45 |
| ulcerative colitis colon #26 | 45 | Crohns colon 9609C144 | 41.86 |
| normal thyroid | 27.71 | A549 unstim. | 27.09 |
| Hashimotos thyroiditis | 27.4 | A549 activated | 29.01 |
| RA synovium pool | 28 | Taq_control_water | 50 |
| Psoriasis skin | 31.49 | Tac_control_genomic_1 | 50 |
| normal lung | 45 | Taq_control_genomic_2 | 50 |
| Crohns colon 403242A | 33.18 | 18 hr. Ascaris lung | 44.16 |
| lung 080698-2 | 30.01 | hi dose IL-4 lung | 43.59 |

Table 4 provides TaqMan expression data for rodent, e.g., moust TNFy.

The primate, e.g., human, TNFy is expressed in fetal adipose tissue and fetal ovary. It is expressed at a lower level in fetal brain, Hashimoto's thyroiditis, RA synovium pool, adult placenta, and fetal uterus. It is expressed at lower levels in fetal kidney, normal thyroid, and detectable in Crohn's colon, psoriasis skin, and fetal lung. It is essentially undetectable in other organs evaluated, including various Ascaris challenged lung samples. In cell libraries, it is expressed in TF-1 cells, and much lower in CHA cells, and was not significantly expressed in other cell lines tested. Table 3 provides additional TaqMan expression data for human TNFy.

| LIBRARY | Ct_gene | LIBRARY | Ct_gene |
|---|---|---|---|
| L cell | 40 | rag-1 lung | 40 |
| TH1 7 day | 40 | rag-1 liver | 40 |
| TH2 7 day | 27.11 | rag-1 spleen | 23.97 |
| TH1 3 week Balb/C | 40 | rag-1 thymus | 26.29 |
| TH2 3 week Balb/C | 26.95 | rag-1 kidney | 40 |
| preT | 40 | w.t. Peyers patches | 27.04 |
| D1.1 resting | 40 | w.t. mesenteric lymph nodes | 40 |
| D1.1 con A stim. | 40 | w.t. colon | 26.63 |
| CDC35 resting | 40 | Braf:ER (-) oligo dT | 40 |
| CDC35 con A stim. | 39.83 | TH1 3 week C57 Bl/6 | 26.78 |
| Mel 14+ naive T | 40 | TH2 3 week C57 Bl/6 | 40 |
| Mel14+ TH1 | 40 | TH1 3 week Balb/C fresh | 40 |

-continued

| LIBRARY | Ct_gene | LIBRARY | Ct_gene |
|---|---|---|---|
| Mel 14+ TH2 | 31.22 | TH2 3 week Balb/C fresh | 40 |
| A20 | 27.39 | b.m. DC (YJL) resting | 40 |
| CH12 | 28.18 | b.m. DC (YJL) aCD40 stim. | 40 |
| lg. B cell | 26.35 | b.m. mf + LPS + aIL-10R | 40 |
| LPS spleen | 21.58 | b.m. mf + LPS + IL-10 | 40 |
| macrophage | 40 | peritoneal mf | 40 |
| J774 resting | 24.99 | MC-9/MCP-12 pMET7 | 40 |
| J774 +LPS + anti-IL-10 | 28.41 | EC | 40 |
| J774 +LPS + IL-10 | 27.57 | EC + TNFa | 40 |
| Nippo-infected lung | 26.98 | bEnd3 + TNFa | 40 |
| IL-10 K.O. spleen | 25.43 | bEnd3 + TNFa + IL-10 | 40 |
| IL-10 K.O. colon | 23.68 | ApoE aorta 5 month | 35.16 |
| asthmatic lung | 37.45 | ApoE aorta 12 month | 35.47 |
| w.t. lung | 40 | NZ B/W kidney | 37.17 |
| w.t. spleen | 39.95 | NZ B/W spleen | 25.25 |
| rag-1 heart | 40 | tolerized & challenged lung | 40 |
| rag-1 brain | 40 | Aspergillus lung | 39.26 |
| rag-1 testes | 40 | Nippo IL-4 K.O. lung | 26.13 |
| Influenza lung | 37.13 | Nippo anti IL-5 lung | 34.73 |
| b common lung 2 month | 39.33 | w.t. thymus | 40 |
| IL-10 K.O. stomach | 27.3 | w.t. stomach | 30.14 |
| IL-10 K.O. MLN aIL-12 | 40 | MM2/MM3 resting pME | 40 |
| IL-10 K.O. MLN + IL-10 | 37.97 | MM2/MM3 activated. pME | 40 |
| Rag-2 Hh− colon | 26.95 | Taq_control_water | 50 |
| Rag-2 Hh+ colon | 22.94 | Taq_control_genomic_1 | 50 |
| IL-7 K.O./Rag-2 Hh− colon | 26.77 | Taq_control_genomic_2 | 50 |
| IL-7 K.O./Rag-2 Hh+ colon | 24.24 | w.t. d17 spinal cord EAE model | 40 |
| transfer model IBD | 23.01 | TNF K.O. d17 spinal cord EAE model | 40 |
| w.t. C57 Bl/6 aorta | 40 | TNF K.O. spinal cord | 27.99 |
| w.t. spinal cord | 38.8 | TNF K.O. spleen | 24.93 |
| w.t. C57 Bl/6 spleen | 26.38 | G.F. ears (skin) | 40 |
| w.t. C57 Bl/6 pancreas | 40 | | |

The primate, e.g., human, TLR-L1 is expressed in TF-1 cells, D6 cells, and barely detectable in resting U937 cells, resting Jurkat cells, and pooled NK cells. In tissues, it is found in fetal uterus, fetal ovary, allergic lung, and fetal testis. Lower levels are found in fetal kidney, fetal small intestine, fetal brain, fetal adipose tissue, normal lung pool, and fetal lung.

The primate, e.g., human, TLR-L2, TLR-L3, and TLR-L4 seem to be expressed in brain tissue.

The primate, e.g., human, TLR-L5 seems to be expressed in unstimulated A549, activated A549, MRC5, and Bc cell lines. Among tissues, it is most highly expressed in fetal uterus, fetal small intestine, and lesser in fetal lung, fetal kidney, fetal liver, and fetal ovary. It is just detectable in fetal brain, fetal adipose, fetal testes, psoriasis skin, and various intestinal samples.

The 5685C6 probes show positive hybridization to subtraction libraries of Th2 minus Th1 polarized cells, and absence of hybridization to libraries of Th1 minus Th2 polarized cells. This suggests that the probe is present selectively in Th2 polarized cells, and can serve as a marker for such cell type. PCR techniques should confirm the expression profile.

Structurally, this protein exhibits similarities to other proteins possessing a thioredoxin fold, including a peroxidase protein, e.g., glutathione peroxidase. See Choi, et al. (1998) Nature Structural Biol. 5:400–406. Thioredoxin has been reported to exhibit certain chemoattractant activities. See Bertini, et al. (1999) J. Expt'l Med. 189:1783–1789.

TaqMan primers were designed for all four novel claudin transcripts. These primer sets were used to screen a panel of human libraries representing different cell types, tissues, and disease states, and two extended cDNA panels. The cDNA panels were composed of samples derived from either normal or diseased human lung or intestine. The claudin genes are some of the most highly regulated genes detected. Moreover, claudin D8 shows the greatest reciprocal regulation between Crohn's and Ulcerative colitis samples, making it a good candidate in future diagnostic panels for these diseases.

claudin-D2: In library southerns, expression is highest in one Crohn's colon, the fetal intestine, and two epithelial cell lines, lower level expression in fetal lung, kidney, ovary and testes. In human cDNA panels, this is highly up-regulated in 8/9 Crohn's disease, both with and without steroid treatment (mean induction=53x, n=9). In addition, claudin-D2 is also induced in 9/12 ulcerative colitis samples (mean induction= 8.2x), but this induction is significantly less than that observed in the Crohn's disease samples. Also up-regulated (mean induction=29 x) in 12/13 interstitial lung disease samples (idiopathic pulmonary fibrosis, hypersensitive pneumonitis, and eosinophilic granuloma).

claudin-D8: In library southerns, expression is highest in fetal kidney and normal colon. Also, expressed in ulcerative colitis colon, thyroid, and fetal lung. No expression is observed in the cells on the panel. In human cDNA panels, high level expression in the gut. Little to no expression in all Crohnds disease samples mean reduction 130 x, n=9). Some ulcerative colitis samples also have reduced claudin-D8 expression, but the pattern is heterogeneous. In contrast, claudin-D8 is up-regulated in several interstitial lung disease samples (12/15, mean induction=9x), but the level of expression in these samples is on the order of ten fold lower than in normal colon. It is also induced in primary human bronchial epithelial cells by I-309.

claudin-D17: In library southerns, overall the expression level measured is low relative to the other claudins described here, on the order of 100 fold lower. It is unclear whether the expression level is actually lower or whether the primers for this gene are insensitive (non-optimal). Expression is highest in one of the asthma lungs and in psoriatic skin. No expression is observed in the cell lines on the panel. In human cDNA panels, the expression is increased in 8/11 ulcerative colitis samples (mean induction=13x), while the expression is unchanged in Crohn's disease samples. Expressed at low level in primary bronchial epithelial cell lines, induced by I-309. Otherwise, level is too low to detect except in sporadic samples.

claudin-D7.2: In library southerns, expressed at highest level in human fetal and adult lung, monkey lungs, and in one Crohn's colon sample. Lower level expression in the two epithelial (A549 and CHA) and one fibroblast (MRC5) cell lines on the panel. In human cDNA panels, expressed at a high level in the gut and an even higher level in the lung. Up-regulated in Crohn's disease samples from patients which have not been treated with steroids (mean induction= 3.7x, n=4). No consistent modulation of this gene in any of the lung diseases examined on this panel.

Claudin family structure: If the genomic structural organization of Claudin family members is based upon that of Paracellin-1, then the proteins would all be encoded by 5 exons. The putative splice sites and exon numbers are predictable, corresponding to the residues of D2 about: 2 codons upstream from M1; A43, A75, G129, and C182; and transmembrane segments corresponding to about G17-V36, M83-C104, V117-H141, and L164-Q188. Paracellin has an extra 60 amino acids at its N-terminus, which is located on the cytoplasmic side of the membrane.

Disease Associations: Claudin-D2 is up-regulated in 8/9 Crohn's disease relative to the control samples, while claudin-D8 is down-regulated. All claudins, described in this invention disclosure, show disease association as described above.

The claudins may form part of a diagnostic panel of genes that could distinguish Crohn's disease from ulcerative colitis, or assist in the determination of disease severity in either or both diseases. For example, claudin-D2 is expressed at higher levels in Crohn's disease than in ulcerative colitis. In contrast, the claudin-D8, cluster 1645577, is expressed at very low levels in Crohn's disease samples, and is less dramatically reduced in most ulcerative colitis samples. See, e.g., Simon, et al. (1999) *Science* 285:103–106; Hirano, et al. (19xx) *Genome Research* 10:659–663; Morita, et al. (1999) *Proc. Nat'l Acad. Sci. USA* 96:511–516; Anderson and Van Itallie (1999) *Current Biology* 9:R922–R924; and Furuse, et al. (1999) *J. Cell Biol.* 147:891–903.

Introduction of an adenovirus or another expression vector expressing the claudin-D8 ortholog into the intestines of patients with inflammatory bowel disease may improve intestinal barrier function and ameliorate disease.

In contrast, antibodies to one of the claudins described here may be able to: induce an intracellular signal that could promote tight junction formation and lead to improved intestinal barrier function; block entry of pathogenic agents, which may play a causative role in initiation or maintenance of either Crohn's disease or ulcerative colitis; promote migration of myeloid cells across tight junctions and allow clearance of pathogenic agents prior to infection of the epithelium.

Expression of schlafen family members in fibroblasts/thymoma cells retards or arrests cell growth. They guide cell growth and T-cell development, and are an integral component of the machinery that maintains T-cell quiescence. They may have important roles in the development or maintenance of autoimmune disorders. The mouse schlafens participate in the regulation of the cell cycle. This family is characterized by two splice variants: a short and a long form.

Schlafen B: 748 aa; ORF. Quantitative PCR analysis reveals in T cells, resting DC, M1 macrophage cell panel. Induced in Hashimoto's thyroiditis, fetal kidney, fetal uterus, and fetal spleen. Slightly induced in Crohn's colon.

Schlafen C: 891 aa, full ORF. Quantitative PCR data revealed this to be significantly up-regulated in all Crohn's samples, asthmatic lung, Ascaris lung, Hashimoto's thyroiditis, and fetal tissues compared to control.

Schlafen D: 578 aa, full ORF. The quantitative PCR data for human schlafen D revealed that it is significantly differentially regulated in Crohn's disease and Ulcerative Colitis compared to normal colon. Also it appears to be highly expressed in many developing tissues (fetal) and disease states (allergic, Ascaris and pneumocystis carnii lungs, Crohn's colon, ulcerative colitis, and Psoriasis skin) compared to cell lines.

Schlafen E: 897 aa, full ORF. Quantitative PCR analysis reveals expression in the colon, fetal liver, fetal lung, fetal ovary, and fetal uterus, and significantly upregulated in one Crohn's sample and highly induced in Hashimoto's thyroiditis.

Schlafen F: 358 aa; full ORF. Distribution analysis is not complete.

Similar samples may isolated in other species for evaluation.

V. Cloning of Species Counterparts

Various strategies are used to obtain species counterparts of, e.g., the DIRS4, preferably from other primates or rodents. One method is by cross hybridization using closely related species DNA probes. It may be useful to go into evolutionarily similar species as intermediate steps. Another method is by using specific PCR primers based on the identification of blocks of similarity of difference between genes, e.g., areas of highly conserved or nonconserved polypeptide or nucleotide sequence.

VI. Production of Mammalian Protein

An appropriate, e.g., GST, fusion construct is engineered for expression, e.g., in *E. coli*. For example, a mouse IGIF pGex plasmid is constructed and transformed into *E. coli*. Freshly transformed cells are grown, e.g., in LB medium containing 50 μg/ml ampicillin and induced with IPTG (Sigma, St. Louis, Mo.). After overnight induction, the bacteria are harvested and the pellets containing, e.g., the DIRS4 protein, are isolated. The pellets are homogenized, e.g., in TE buffer (50 mM Tris-base pH 8.0, 10 mM EDTA and 2 mM pefabloc) in 2 liters. This material is passed through a microfluidizer (Microfluidics, Newton, Mass.) three times. The fluidized supernatant is spun down on a Sorvall GS-3 rotor for 1 h at 13,000 rpm. The resulting supernatant containing the cytokine receptor protein is filtered and passed over a glutathione-SEPHAROSE column equilibrated in 50 mM Tris-base pH 8.0. The fractions containing the DIRS4-GST fusion protein are pooled and cleaved, e.g., with thrombin (Enzyme Research Laboratories, Inc., South Bend, Ind.). The cleaved pool is then passed over a Q-SEPHAROSE column equilibrated in 50 mM Tris-base. Fractions containing DIRS4 are pooled and diluted in cold distilled $H_2O$, to lower the conductivity, and passed back over a fresh Q-Sepharose column, alone or in succession with an immunoaffinity antibody column. Fractions containing the DIRS4 protein are pooled, aliquoted, and stored in the −70° C. freezer.

Comparison of the CD spectrum with cytokine receptor protein may suggest that the protein is correctly folded. See Hazuda, et al. (1969) *J. Biol. Chem.* 264:1689–1693.

For other genes, e.g., membrane proteins, the protein may be best expressed on cell surfaces. Those may be in prokaryote expression systems, or eukaryotes. Surface expressed forms will most likely have conformations consistent with the natural interaction with lipid.

VII. Determining Physiological Forms of Receptors

The cellular forms of receptors for ligands can be tested with the various ligands and receptor subunits provided, e.g., IL-10 related sequences. In particular, multiple cytokine receptor like ligands have been identified, see, e.g., U.S. Ser. Nos. 60/027,368, 08/934,959, and 08/842,659, which are incorporated herein by reference.

Cotransformation of the DIRS4 with putative other receptor subunits may be performed. Such cells may be used to screen putative cytokine ligands, such as the AK155, for signaling. A cell proliferation assay may be used.

In addition, it has been known that many cytokine receptors function as heterodimers, e.g., a soluble alpha subunit, and transmembrane beta subunit. Subunit combinations can be tested now with the provided reagents. In particular, appropriate constructs can be made for transformation or transfection of subunits into cells. Combinatorial transfections of transformations can make cells expressing defined subunits, which can be tested for response to the predicted ligands. Appropriate cell types can be used, e.g., 293 T cells, with, e.g., an NFκb reporter construct.

Biological assays for receptors will generally be directed to the ligand binding feature of the protein or to the kinase/phosphatase activity of the receptor. The activity will typically be reversible, as are many other enzyme reactions, and may mediate phosphatase or phosphorylase activities, which activities are easily measured by standard procedures.

See, e.g., Hardie, et al. (eds. 1995) *The Protein Kinase FactBook* vols. I and II, Academic Press, San Diego, Calif.; Hanks, et al. (1991) *Meth. Enzymol.* 200:38–62; Hunter, et al. (1992) *Cell* 70:375–388; Lewin (1990) *Cell* 61:743–752; Pines, et al. (1991) *Cold Spring Harbor Symp. Quant. Biol.* 56:449–463; and Parker, et al. (1993) *Nature* 363:736–738.

The family of cytokines contains molecules which are important mediators of hematopoiesis or inflammatory disease. See, e.g., Nelson and Martin (eds. 2000) *Cytokines in Pulmonary Disease* Dekker, N.Y.; Ganser and Hoelzer (eds. 1999) *Cytokines in the Treatment of Hematopoietic Failure* Dekker, N.Y.: Remick and Friedland (eds. 1997) *Cytokines in Health and Disease* Dekker, N.Y.; Dinarello (1996) *Blood* 87:2095–2147; and Thomson (ed. 1994) *The Cytokine Handbook* Academic Press, San Diego. Ligand and receptors are very important in the signaling process.

VIII. Antibodies Specific for Proteins

Inbred Balb/c mice are immunized intraperitoneally with recombinant forms of the protein, e.g., purified DIRS4 or stable transfected NIH-3T3 cells. Animals are boosted at appropriate time points with protein, with or without additional adjuvant, to further stimulate antibody production. Serum is collected, or hybridomas produced with harvested spleens.

Alternatively, Balb/c mice are immunized with cells transformed with the gene or fragments thereof, either endogenous or exogenous cells, or with isolated membranes enriched for expression of the antigen. Serum is collected at the appropriate time, typically after numerous further administrations. Various gene therapy techniques may be useful, e.g., in producing protein in situ, for generating an immune response. Serum may be immunoselected to prepare substantially purified antibodies of defined specificity and high affinity.

Monoclonal antibodies may be made. For example, splenocytes are fused with an appropriate fusion partner and hybridomas are selected in growth medium by standard procedures. Hybridoma supernatants are screened for the presence of antibodies which bind to the DIRS4, e.g., by ELISA or other assay. Antibodies which specifically recognize specific DIRS4 embodiments may also be selected or prepared.

In another method, synthetic peptides or purified protein are presented to an immune system to generate monoclonal or polyclonal antibodies. See, e.g., Coligan (ed. 1991) *Current Protocols in Immunology* Wiley/Greene; and Harlow and Lane (1989) *Antibodies: A Laboratory Manual* Cold Spring Harbor Press. In appropriate situations, the binding reagent is either labeled as described above, e.g., fluorescence or otherwise, or immobilized to a substrate for panning methods. Nucleic acids may also be introduced into cells in an animal to produce the antigen, which serves to elicit an immune response. See, e.g., Wang, et al. (1993) *Proc. Nat'l. Acad. Sci.* 90:4156–4160; Barry, et al. (1994) *BioTechniques* 16:616–619; and Xiang, et al. (1995) *Immunity* 2: 129–135.

Moreover, antibodies which may be useful to determine the combination of the DIRS4 with a functional alpha subunit may be generated. Thus, e.g., epitopes characteristic of a particular functional alpha/beta combination may be identified with appropriate antibodies.

IX. Production of Fusion Proteins

Various fusion constructs are made, e.g., with DIRS4. A portion of the appropriate gene is fused to an epitope tag, e.g., a FLAG tag, or to a two hybrid system construct. See, e.g., Fields and Song (1989) *Nature* 340:245–246.

The epitope tag may be used in an expression cloning procedure with detection with anti-FLAG antibodies to detect a binding partner, e.g., ligand for the respective cytokine receptor. The two hybrid system may also be used to isolate proteins which specifically bind to DIRS4.

X. Structure Activity Relationship

Information on the criticality of particular residues is determined using standard procedures and analysis. Standard mutagenesis analysis is performed, e.g., by generating many different variants at determined positions, e.g., at the positions identified above, and evaluating biological activities of the variants. This may be performed to the extent of determining positions which modify activity, or to focus on specific positions to determine the residues which can be substituted to either retain, block, or modulate biological activity.

Alternatively, analysis of natural variants can indicate what positions tolerate natural mutations. This may result from populational analysis of variation among individuals, or across strains or species. Samples from selected individuals are analyzed, e.g., by PCR analysis and sequencing. This allows evaluation of population polymorphisms.

XI. Isolation of a Ligand for Receptor

A cytokine receptor can be used as a specific binding reagent to identify its binding partner, by taking advantage of its specificity of binding, much like an antibody would be used. Typically, the binding receptor is a heterodimer of receptor subunits. A binding reagent is either labeled as described above, e.g., fluorescence or otherwise, or immobilized to a substrate for panning methods.

The binding composition is used to screen an expression library made from a cell line which expresses a binding partner, i.e., ligand, preferably membrane associated. Standard staining techniques are used to detect or sort surface expressed ligand, or surface expressing transformed cells are screened by panning. Screening of intracellular expression is performed by various staining or immunofluorescence procedures. See also McMahan, et al. (1991) *EMBO J.* 10:2821–2832.

For example, on day 0, precoat 2-chamber permanox slides with 1 ml per chamber of fibronectin, 10 ng/ml in PBS, for 30 min at room temperature. Rinse once with PBS. Then plate COS cells at $2–3\times10^5$ cells per chamber in 1.5 ml of growth media. Incubate overnight at 37° C.

On day 1 for each sample, prepare 0.5 ml of a solution of 66 µg/ml DEAE-dextran, 66 µM chloroquine, and 4 µg DNA in serum free DME. For each set, a positive control is prepared, e.g., of DIRS4-FLAG cDNA at 1 and 1/200 dilution, and a negative mock. Rinse cells with serum free DME. Add the DNA solution and incubate 5 hr at 37° C. Remove the medium and add 0.5 ml 10% DMSO in DME for 2.5 min. Remove and wash once with DME. Add 1.5 ml growth medium and incubate overnight.

On day 2, change the medium. On days 3 or 4, the cells are fixed and stained. Rinse the cells twice with Hank's Buffered Saline Solution (HBSS) and fix in 4% paraformaldehyde (PFA)/glucose for 5 min. Wash 3× with HBSS. The slides may be stored at −80° C. after all liquid is removed. For each chamber, 0.5 ml incubations are performed as follows. Add HBSS/saponin (0.1%) with 32 µl/ml of 1 M $NaN_3$ for 20 min. Cells are then washed with HBSS/saponin 1×. Add appropriate DIRS4 or DIRS4/antibody complex to cells and incubate for 30 min. Wash cells twice with HBSS/saponin. If appropriate, add first antibody for 30 min. Add second antibody, e.g., Vector anti-mouse antibody, at 1/200 dilution, and incubate for 30 min. Prepare ELISA solution, e.g., Vector Elite ABC horseradish peroxidase solution, and preincubate for 30 min. Use, e.g., 1 drop of solution A (avidin) and 1 drop solution B (biotin) per 2.5 ml HBSS/ saponin. Wash cells twice with HBSS/saponin. Add ABC HRP solution and incubate for 30 min. Wash cells twice with HBSS, second wash for 2 min, which closes cells. Then add Vector diaminobenzoic acid (DAB) for 5 to 10 min. Use 2 drops of buffer plus 4 drops DAB plus 2 drops of $H_2O_2$ per 5 ml of glass distilled water. Carefully remove chamber and rinse slide in water. Air dry for a few minutes, then add 1 drop of Crystal Mount and a cover slip. Bake for 5 min at 85–90° C.

Evaluate positive staining of pools and progressively subclone to isolation of single genes responsible for the binding.

Alternatively, receptor reagents are used to affinity purify or sort out cells expressing a putative ligand. See, e.g., Sambrook, et al. or Ausubel, et al.

Another strategy is to screen for a membrane bound receptor by panning. The receptor cDNA is constructed as described above. The ligand can be immobilized and used to immobilize expressing cells. Immobilization may be achieved by use of appropriate antibodies which recognize, e.g., a FLAG sequence of a DIRS4 fusion construct, or by use of antibodies raised against the first antibodies. Recursive cycles of selection and amplification lead to enrichment of appropriate clones and eventual isolation of receptor expressing clones.

Phage expression libraries can be screened by mammalian DIRS4. Appropriate label techniques, e.g., anti-FLAG antibodies, will allow specific labeling of appropriate clones.

All citations herein are incorporated herein by reference to the same extent as if each individual publication or patent application was specifically and individually indicated to be incorporated by reference.

Many modifications and variations of this invention can be made without departing from its spirit and scope, as will be apparent to those skilled in the art. The specific embodiments described herein are offered by way of example only, and the invention is to be limited by the terms of the appended claims, along with the full scope of equivalents to which such claims are entitled; and the invention is not to be limited by the specific embodiments that have been presented herein by way of example.

What is claimed is:

1. An isolated antibody or antigen binding fragment thereof, which specifically binds to a polypeptide of SEQ ID NO: 9.

2. The isolated antibody or antigen binding fragment thereof of claim 1, wherein said antibody or antigen binding fragment thereof, is in a container.

3. The isolated antibody or antigen binding fragment thereof of claim 1, wherein said antibody or antigen binding fragment thereof, is from a human.

4. The isolated antibody or antigen binding fragment thereof of claim 1, wherein said antibody or antigen binding fragment thereof, is a Fv, Fab, or Fab$_2$ fragment.

5. The isolated antibody or antigen binding fragment thereof of claim 1, wherein said antibody or antigen binding fragment thereof, is conjugated to another chemical moiety.

6. The isolated antibody or antigen binding fragment thereof of claim 1, wherein said antibody or antigen binding fragment thereof, is generated using a recombinant polypeptide of SEQ ID NO:9.

7. The isolated antibody or antigen binding fragment thereof of claim 1, wherein said antibody or antigen binding fragment thereof, is generated using a purified polypeptide of SEQ ID NO:9.

8. The isolated antibody or antigen binding fragment thereof of claim 1, wherein said antibody or antigen binding fragment thereof, is:
   a) is a polyclonal antibody;
   b) a monoclonal antibody;
   c) a humanized antibody; or
   d) a chimeric antibody.

9. The isolated antibody or antigen binding fragment thereof of claim 1, wherein said antibody or antigen binding fragment thereof, binds to a denatured polypeptide of SEQ ID NO:9.

10. The isolated antibody or antigen binding fragment thereof of claim 1, wherein said antibody or antigen binding fragment thereof, exhibits a $K_d$ to a polypeptide of SEQ ID NO: 9 of at least 30 µM.

11. The isolated antibody or antigen binding fragment thereof of claim 1, wherein said antibody or antigen binding fragment thereof, is attached to a solid substrate.

12. The isolated antibody or antigen binding fragment thereof of claim 1, wherein said substrate is a bead or plastic membrane.

13. The isolated antibody or antigen binding fragment thereof of claim 1, wherein said antibody or antigen binding fragment thereof, is detectably labeled.

14. A kit comprising said isolated antibody or antigen binding fragment thereof, of claim 1, and:
   a) a compartment comprising said antibody or antigen binding fragment thereof; or
   b) instructions for use or disposal reagents in said kit.

15. A method of producing the isolated antibody or antigen binding compound thereof of claim 1, comprising:
   a) immunizing a mammalian host with said polypeptide; or
   b) selecting for a phage display library for those phage which bind to said polypeptide.

16. The isolated antibody or antigen binding fragment thereof of claim 1, wherein said antibody or antigen binding fragment thereof, is in a sterile composition.

17. The isolated antibody or antigen binding fragment thereof of claim 16, wherein said label is a radioactive or fluorescent label.

18. A composition comprising:
   a) said isolated antibody or antigen binding fragment thereof of claim 1, wherein said antibody or antigen binding fragment thereof, is sterile; or
   b) said antibody or antigen binding fragment thereof, of claim 1, and a carrier.

19. The composition of claim 18, wherein said carrier is an aqueous compound is water, saline, or buffer.

20. The composition of claim 18, wherein said carrier is formulated for oral, rectal, nasal, topical, or parenteral administration.

* * * * *

SEQUENCE LISTING

<160> NUMBER OF SEQ ID NOS: 53

<210> SEQ ID NO 1
<211> LENGTH: 704
<212> TYPE: DNA
<213> ORGANISM: Homo sapiens

<400> SEQUENCE: 1

```
atggcgggc  ccgagcgctg  gggcccctg  ctcctgtgcc  tgctgcaggc  cgctccaggg      60
aggccccgtc  tggcccctcc  ccagaatgtg  acgctgctct  cccagaactt  cagcgtgtac     120
ctgacatggc  tcccagggct  tggcaacccc  caggatgtga  cctattttgt  ggcctatcag     180
agctctccca  cccgtagacg  gtggcgcgaa  gtggaagagt  gtgcgggaac  caaggagctg     240
ctatgttcta  tgatgtgcct  gaagaaacag  gacctgtaca  acaagttcaa  gggacgcgtg     300
cggacggttt  ctcccagctc  caagtccccc  tgggtggagt  ccgaataccc  ggattacctt     360
tttgaagtgg  agccggcccc  acctgtcctg  gtgctcaccc  agacggagga  gatcctgagt     420
gccaatgcca  cgtaccagct  gccccctgc  atgcccac  tggatctgaa  gtatgaggtg     480
gcattctgga  aggagggggc  cggaaacaag  gtgggaagct  cctttcctgc  ccccaggcta     540
ggcccgctcc  tccacccctt  cttactcagg  ttcttctcac  cctcccagcc  tgctcctgca     600 ccctcctcc   aggaagtctt  ccctgtacac  tcctgaactt  ctggcagtca  gccctaataa     660
aatctgatca  aagtaaaaaa  aaaaaaaaag  ggcggccgcc  gact                      704
```

<210> SEQ ID NO 2
<211> LENGTH: 211
<212> TYPE: PRT
<213> ORGANISM: Homo sapiens

<400> SEQUENCE: 2

```
Met Ala Gly Pro Glu Arg Trp Gly Pro Leu Leu Leu Cys Leu Leu Gln
 1               5                  10                  15

Ala Ala Pro Gly Arg Pro Arg Leu Ala Pro Pro Gln Asn Val Thr Leu
            20                  25                  30

Leu Ser Gln Asn Phe Ser Val Tyr Leu Thr Trp Leu Pro Gly Leu Gly
        35                  40                  45
```

```
Asn Pro Gln Asp Val Thr Tyr Phe Val Ala Tyr Gln Ser Ser Pro Thr
    50                  55                  60

Arg Arg Arg Trp Arg Glu Val Glu Glu Cys Ala Gly Thr Lys Glu Leu
 65                  70                  75                  80

Leu Cys Ser Met Met Cys Leu Lys Lys Gln Asp Leu Tyr Asn Lys Phe
                 85                  90                  95

Lys Gly Arg Val Arg Thr Val Ser Pro Ser Ser Lys Ser Pro Trp Val
            100                 105                 110

Glu Ser Glu Tyr Leu Asp Tyr Leu Phe Glu Val Glu Pro Ala Pro Pro
            115                 120                 125

Val Leu Val Leu Thr Gln Thr Glu Glu Ile Leu Ser Ala Asn Ala Thr
            130                 135                 140

Tyr Gln Leu Pro Pro Cys Met Pro Pro Leu Asp Leu Lys Tyr Glu Val
145                 150                 155                 160

Ala Phe Trp Lys Glu Gly Ala Gly Asn Lys Val Gly Ser Ser Phe Pro
                165                 170                 175

Ala Pro Arg Leu Gly Pro Leu Leu His Pro Phe Leu Leu Arg Phe Phe
            180                 185                 190

Ser Pro Ser Gln Pro Ala Pro Ala Pro Leu Leu Gln Glu Val Phe Pro
            195                 200                 205

Val His Ser
        210

<210> SEQ ID NO 3
<211> LENGTH: 295
<212> TYPE: PRT
<213> ORGANISM: Homo sapiens

<400> SEQUENCE: 3

Met Glu Thr Pro Ala Trp Pro Arg Val Pro Arg Pro Glu Thr Ala Val
 1               5                  10                  15

Ala Arg Thr Leu Leu Leu Gly Trp Val Phe Ala Gln Val Ala Gly Ala
                20                  25                  30

Ser Gly Thr Thr Asn Thr Val Ala Ala Tyr Asn Leu Thr Trp Lys Ser
            35                  40                  45

Thr Asn Phe Lys Thr Ile Leu Glu Trp Glu Pro Lys Pro Val Asn Gln
 50                  55                  60

Val Tyr Thr Val Gln Ile Ser Thr Lys Ser Gly Asp Trp Lys Ser Lys
 65                  70                  75                  80

Cys Phe Tyr Thr Thr Asp Thr Glu Cys Asp Leu Thr Asp Glu Ile Val
                 85                  90                  95

Lys Asp Val Lys Gln Thr Tyr Leu Ala Arg Val Phe Ser Tyr Pro Ala
            100                 105                 110

Gly Asn Val Glu Ser Thr Gly Ser Ala Gly Glu Pro Leu Tyr Glu Asn
            115                 120                 125

Ser Pro Glu Phe Thr Pro Tyr Leu Glu Thr Asn Leu Gly Gln Pro Thr
            130                 135                 140

Ile Gln Ser Phe Glu Gln Val Gly Thr Lys Val Asn Val Thr Val Glu
145                 150                 155                 160

Asp Glu Arg Thr Leu Val Arg Arg Asn Asn Thr Phe Leu Ser Leu Arg
                165                 170                 175

Asp Val Phe Gly Lys Asp Leu Ile Tyr Thr Leu Tyr Tyr Trp Lys Ser
            180                 185                 190

Ser Ser Ser Gly Lys Lys Thr Ala Lys Thr Asn Thr Asn Glu Phe Leu
```

-continued

```
                195                 200                 205
Ile Asp Val Asp Lys Gly Glu Asn Tyr Cys Phe Ser Val Gln Ala Val
    210                 215                 220

Ile Pro Ser Arg Thr Val Asn Arg Lys Ser Thr Asp Ser Pro Val Glu
225                 230                 235                 240

Cys Met Gly Gln Glu Lys Gly Glu Phe Arg Glu Ile Phe Tyr Ile Ile
                245                 250                 255

Gly Ala Val Ala Phe Val Val Ile Ile Leu Val Ile Ile Leu Ala Ile
                260                 265                 270

Ser Leu His Lys Cys Arg Lys Ala Gly Val Gly Gln Ser Trp Lys Glu
                275                 280                 285

Asn Ser Pro Leu Asn Val Ser
290                 295

<210> SEQ ID NO 4
<211> LENGTH: 515
<212> TYPE: PRT
<213> ORGANISM: Homo sapiens

<400> SEQUENCE: 4

Met Leu Leu Ser Gln Asn Ala Phe Ile Phe Arg Ser Leu Asn Leu Val
1               5                   10                  15

Leu Met Val Tyr Ile Ser Leu Val Phe Gly Ile Ser Tyr Asp Ser Pro
                20                  25                  30

Asp Tyr Thr Asp Glu Ser Cys Thr Phe Lys Ile Ser Leu Arg Asn Phe
            35                  40                  45

Arg Ser Ile Leu Ser Trp Glu Leu Lys Asn His Ser Ile Val Pro Thr
    50                  55                  60

His Tyr Thr Leu Leu Tyr Thr Ile Met Ser Lys Pro Glu Asp Leu Lys
65                  70                  75                  80

Val Val Lys Asn Cys Ala Asn Thr Thr Arg Ser Phe Cys Asp Leu Thr
                85                  90                  95

Asp Glu Trp Arg Ser Thr His Glu Ala Tyr Val Thr Val Leu Glu Gly
            100                 105                 110

Phe Ser Gly Asn Thr Thr Leu Phe Ser Cys Ser His Asn Phe Trp Leu
        115                 120                 125

Ala Ile Asp Met Ser Phe Glu Pro Pro Glu Phe Glu Ile Val Gly Phe
    130                 135                 140

Thr Asn His Ile Asn Val Val Val Lys Phe Pro Ser Ile Val Glu Glu
145                 150                 155                 160

Glu Leu Gln Phe Asp Leu Ser Leu Val Ile Glu Glu Gln Ser Glu Gly
                165                 170                 175

Ile Val Lys Lys His Lys Pro Glu Ile Lys Gly Asn Met Ser Gly Asn
                180                 185                 190

Phe Thr Tyr Ile Ile Asp Lys Leu Ile Pro Asn Thr Asn Tyr Cys Val
            195                 200                 205

Ser Val Tyr Leu Glu His Ser Asp Glu Gln Ala Val Ile Lys Ser Pro
    210                 215                 220

Leu Lys Cys Thr Leu Leu Pro Pro Gly Gln Glu Ser Glu Ser Ala Glu
225                 230                 235                 240

Ser Ala Lys Ile Gly Gly Ile Ile Thr Val Phe Leu Ile Ala Leu Val
                245                 250                 255

Leu Thr Ser Thr Ile Val Thr Leu Lys Trp Ile Gly Tyr Ile Cys Leu
                260                 265                 270
```

```
Arg Asn Ser Leu Pro Lys Val Leu Asn Phe His Asn Phe Leu Ala Trp
        275                 280                 285

Pro Phe Pro Asn Leu Pro Pro Leu Glu Ala Met Asp Met Val Glu Val
    290                 295                 300

Ile Tyr Ile Asn Arg Lys Lys Val Trp Asp Tyr Asn Tyr Asp Asp
305                 310                 315                 320

Glu Ser Asp Ser Asp Thr Glu Ala Ala Pro Arg Thr Ser Gly Gly Gly
                325                 330                 335

Tyr Thr Met His Gly Leu Thr Val Arg Pro Leu Gly Gln Ala Ser Ala
                340                 345                 350

Thr Ser Thr Glu Ser Gln Leu Ile Asp Pro Glu Ser Glu Glu Pro
        355                 360                 365

Asp Leu Pro Glu Val Asp Val Glu Leu Pro Thr Met Pro Lys Asp Ser
    370                 375                 380

Pro Gln Gln Leu Glu Leu Leu Ser Gly Pro Cys Glu Arg Arg Lys Ser
385                 390                 395                 400

Pro Leu Gln Asp Pro Phe Pro Glu Glu Asp Tyr Ser Ser Thr Glu Gly
                405                 410                 415

Ser Gly Gly Arg Ile Thr Phe Asn Val Asp Leu Asn Ser Val Phe Leu
                420                 425                 430

Arg Val Leu Asp Asp Glu Asp Ser Asp Asp Leu Glu Ala Pro Leu Met
                435                 440                 445

Leu Ser Ser His Leu Glu Glu Met Val Asp Pro Glu Asp Pro Asp Asn
        450                 455                 460

Val Gln Ser Asn His Leu Leu Ala Ser Gly Glu Gly Thr Gln Pro Thr
465                 470                 475                 480

Phe Pro Ser Pro Ser Ser Glu Gly Leu Trp Ser Glu Asp Ala Pro Ser
                485                 490                 495

Asp Gln Ser Asp Thr Ser Glu Ser Asp Val Asp Leu Gly Asp Gly Tyr
                500                 505                 510

Ile Met Arg
        515

<210> SEQ ID NO 5
<211> LENGTH: 325
<212> TYPE: PRT
<213> ORGANISM: Homo sapiens

<400> SEQUENCE: 5

Met Ala Trp Ser Leu Gly Ser Trp Leu Gly Gly Cys Leu Leu Val Ser
1               5                   10                  15

Ala Leu Gly Met Val Pro Pro Glu Asn Val Arg Met Asn Ser Val
            20                  25                  30

Asn Phe Lys Asn Ile Leu Gln Trp Glu Ser Pro Ala Phe Ala Lys Gly
            35                  40                  45

Asn Leu Thr Phe Thr Ala Gln Tyr Leu Ser Tyr Arg Ile Phe Gln Asp
        50                  55                  60

Lys Cys Met Asn Thr Thr Leu Thr Glu Cys Asp Phe Ser Ser Leu Ser
65                  70                  75                  80

Lys Tyr Gly Asp His Thr Leu Arg Val Arg Ala Glu Phe Ala Asp Glu
                85                  90                  95

His Ser Asp Trp Val Asn Ile Thr Phe Cys Pro Val Asp Asp Thr Ile
            100                 105                 110

Ile Gly Pro Pro Gly Met Gln Val Glu Val Leu Ala Asp Ser Leu His
        115                 120                 125
```

```
Met Arg Phe Leu Ala Pro Lys Ile Glu Asn Glu Tyr Glu Thr Trp Thr
130                 135                 140

Met Lys Asn Val Tyr Asn Ser Trp Thr Tyr Asn Val Gln Tyr Trp Lys
145                 150                 155                 160

Asn Gly Thr Asp Glu Lys Phe Gln Ile Thr Pro Gln Tyr Asp Phe Glu
                165                 170                 175

Val Leu Arg Asn Leu Glu Pro Trp Thr Thr Tyr Cys Val Gln Val Arg
            180                 185                 190

Gly Phe Leu Pro Asp Arg Asn Lys Ala Gly Glu Trp Ser Glu Pro Val
        195                 200                 205

Cys Glu Gln Thr Thr His Asp Glu Thr Val Pro Ser Trp Met Val Ala
    210                 215                 220

Val Ile Leu Met Ala Ser Val Phe Met Val Cys Leu Ala Leu Leu Gly
225                 230                 235                 240

Cys Phe Ser Leu Leu Trp Cys Val Tyr Lys Lys Thr Lys Tyr Ala Phe
                245                 250                 255

Ser Pro Arg Asn Ser Leu Pro Gln His Leu Lys Glu Phe Leu Gly His
                260                 265                 270

Pro His His Asn Thr Leu Leu Phe Phe Ser Phe Pro Leu Ser Asp Glu
            275                 280                 285

Asn Asp Val Phe Asp Lys Leu Ser Val Ile Ala Glu Asp Ser Glu Ser
        290                 295                 300

Gly Lys Gln Asn Pro Gly Asp Ser Cys Ser Leu Gly Thr Pro Pro Gly
305                 310                 315                 320

Gln Gly Pro Gln Ser
                325

<210> SEQ ID NO 6
<211> LENGTH: 231
<212> TYPE: PRT
<213> ORGANISM: Homo sapiens

<400> SEQUENCE: 6

Met Met Pro Lys His Cys Phe Leu Gly Phe Leu Ile Ser Phe Phe Leu
1               5                   10                  15

Thr Gly Val Ala Gly Thr Gln Ser Thr His Glu Ser Leu Lys Pro Gln
                20                  25                  30

Arg Val Gln Phe Gln Ser Arg Asn Phe His Asn Ile Leu Gln Trp Gln
            35                  40                  45

Pro Gly Arg Ala Leu Thr Gly Asn Ser Ser Val Tyr Phe Val Gln Tyr
        50                  55                  60

Lys Ile Tyr Gly Gln Arg Gln Trp Lys Asn Lys Glu Asp Cys Trp Gly
65                  70                  75                  80

Thr Gln Glu Leu Ser Cys Asp Leu Thr Ser Glu Thr Ser Asp Ile Gln
                85                  90                  95

Glu Pro Tyr Tyr Gly Arg Val Arg Ala Ala Ser Ala Gly Ser Tyr Ser
                100                 105                 110

Glu Trp Ser Met Thr Pro Arg Phe Thr Pro Trp Trp Glu Thr Lys Ile
            115                 120                 125

Asp Pro Pro Val Met Asn Ile Thr Gln Val Asn Gly Ser Leu Leu Val
        130                 135                 140

Ile Leu His Ala Pro Asn Leu Pro Tyr Arg Tyr Gln Lys Glu Lys Asn
145                 150                 155                 160

Val Ser Ile Glu Asp Tyr Tyr Glu Leu Leu Tyr Arg Val Phe Ile Ile
```

-continued

```
                165                 170                 175
Asn Asn Ser Leu Glu Lys Glu Gln Lys Val Tyr Glu Gly Ala His Arg
            180                 185                 190
Ala Val Glu Ile Glu Ala Leu Thr Pro His Ser Ser Tyr Cys Val Val
        195                 200                 205
Ala Glu Ile Tyr Gln Pro Met Leu Asp Arg Arg Ser Gln Arg Ser Glu
    210                 215                 220
Glu Arg Cys Val Glu Ile Pro
225                 230
```

<210> SEQ ID NO 7
<211> LENGTH: 553
<212> TYPE: PRT
<213> ORGANISM: Homo sapiens
<220> FEATURE:
<221> NAME/KEY: MISC_FEATURE
<222> LOCATION: (522)..(522)
<223> OTHER INFORMATION: unknown amino

<400> SEQUENCE: 7

```
Met Arg Ala Pro Gly Arg Pro Ala Leu Arg Pro Leu Pro Leu Pro Pro
1               5                   10                  15
Leu Leu Leu Leu Leu Ala Ala Pro Trp Gly Arg Ala Val Pro Cys
            20                  25                  30
Val Ser Gly Gly Leu Pro Lys Pro Ala Asn Ile Thr Phe Leu Ser Ile
        35                  40                  45
Asn Met Lys Asn Val Leu Gln Trp Thr Pro Pro Glu Gly Leu Gln Gly
    50                  55                  60
Val Lys Val Thr Tyr Thr Val Gln Tyr Phe Ile Tyr Gly Gln Lys Lys
65                  70                  75                  80
Trp Leu Asn Lys Ser Glu Cys Arg Asn Ile Asn Arg Thr Tyr Cys Asp
                85                  90                  95
Leu Ser Ala Glu Thr Ser Asp Tyr Glu His Gln Tyr Tyr Ala Lys Val
            100                 105                 110
Lys Ala Ile Trp Gly Thr Lys Cys Ser Lys Trp Ala Glu Ser Gly Arg
        115                 120                 125
Phe Tyr Pro Phe Leu Glu Thr Gln Ile Gly Pro Pro Glu Val Ala Leu
    130                 135                 140
Thr Thr Asp Glu Lys Ser Ile Ser Val Val Leu Thr Ala Pro Glu Lys
145                 150                 155                 160
Trp Lys Arg Asn Pro Glu Asp Leu Pro Val Ser Met Gln Gln Ile Tyr
                165                 170                 175
Ser Asn Leu Lys Tyr Asn Val Ser Val Leu Asn Thr Lys Ser Asn Arg
            180                 185                 190
Thr Trp Ser Gln Cys Val Thr Asn His Thr Leu Val Leu Thr Trp Leu
        195                 200                 205
Glu Pro Asn Thr Leu Tyr Cys Val His Val Glu Ser Phe Val Pro Gly
    210                 215                 220
Pro Pro Arg Arg Ala Gln Pro Ser Glu Lys Gln Cys Ala Arg Thr Leu
225                 230                 235                 240
Lys Asp Gln Ser Ser Glu Phe Lys Ala Lys Ile Ile Phe Trp Tyr Val
                245                 250                 255
Leu Pro Ile Ser Ile Thr Val Phe Leu Phe Ser Val Met Gly Tyr Ser
            260                 265                 270
Ile Tyr Arg Tyr Ile His Val Gly Lys Glu Lys His Pro Ala Asn Leu
        275                 280                 285
```

```
Ile Leu Ile Tyr Gly Asn Glu Phe Asp Lys Arg Phe Val Pro Ala
    290                 295                 300

Glu Lys Ile Val Ile Asn Phe Ile Thr Leu Asn Ile Ser Asp Asp Ser
305                 310                 315                 320

Lys Ile Ser His Gln Asp Met Ser Leu Leu Gly Lys Ser Ser Asp Val
                325                 330                 335

Ser Ser Leu Asn Asp Pro Gln Pro Ser Gly Asn Leu Arg Pro Pro Gln
            340                 345                 350

Glu Glu Glu Glu Val Lys His Leu Gly Tyr Ala Ser His Leu Met Glu
        355                 360                 365

Ile Phe Cys Asp Ser Glu Glu Asn Thr Glu Gly Thr Ser Leu Thr Gln
    370                 375                 380

Gln Glu Ser Leu Ser Arg Thr Ile Pro Pro Asp Lys Thr Val Ile Glu
385                 390                 395                 400

Tyr Glu Tyr Asp Val Arg Thr Thr Asp Ile Cys Ala Gly Pro Glu Glu
                405                 410                 415

Gln Glu Leu Ser Leu Gln Glu Val Ser Thr Gln Gly Thr Leu Leu
            420                 425                 430

Glu Ser Gln Ala Ala Leu Ala Val Leu Gly Pro Gln Thr Leu Gln Tyr
        435                 440                 445

Ser Tyr Thr Pro Gln Leu Gln Asp Leu Asp Pro Leu Ala Gln Glu His
    450                 455                 460

Thr Asp Ser Glu Glu Gly Pro Glu Glu Pro Ser Thr Thr Leu Val
465                 470                 475                 480

Asp Trp Asp Pro Gln Thr Gly Arg Leu Cys Ile Pro Ser Leu Ser Ser
                485                 490                 495

Phe Asp Gln Asp Ser Glu Gly Cys Glu Pro Ser Glu Gly Asp Gly Leu
            500                 505                 510

Gly Glu Glu Gly Leu Leu Ser Arg Leu Xaa Glu Glu Pro Ala Pro Asp
        515                 520                 525

Arg Pro Pro Gly Glu Asn Glu Thr Tyr Leu Met Gln Phe Met Glu Glu
    530                 535                 540

Trp Gly Leu Tyr Val Gln Met Glu Asn
545                 550

<210> SEQ ID NO 8
<211> LENGTH: 687
<212> TYPE: DNA
<213> ORGANISM: Homo sapiens
<220> FEATURE:
<221> NAME/KEY: CDS
<222> LOCATION: (1)..(684)
<223> OTHER INFORMATION:

<400> SEQUENCE: 8 atg gct gaa ctt tgt ccg gcg gcc gga cga cgg cgc ctt aag gaa gcg    48
Met Ala Glu Leu Cys Pro Ala Ala Gly Arg Arg Arg Leu Lys Glu Ala
1               5                   10                  15 gtg cgg aag cag gga caa gaa gcc gcg gga tct ctt cgg tcc ccc agg    96
Val Arg Lys Gln Gly Gln Glu Ala Ala Gly Ser Leu Arg Ser Pro Arg
            20                  25                  30 acc tcc agg tgc aga agt gac cgc gga gac tct gct tca cga gtt tca   144
Thr Ser Arg Cys Arg Ser Asp Arg Gly Asp Ser Ala Ser Arg Val Ser
        35                  40                  45 gga gct gct gaa aga ggc cac gga gcg ccg gtt ctc agg gct tct gga   192
Gly Ala Ala Glu Arg Gly His Gly Ala Pro Val Leu Arg Ala Ser Gly
    50                  55                  60
```

```
ccc gct gct gcc cca ggg gcg ggc ctg cgg ctg gtg ggc gag gcc ttt    240
Pro Ala Ala Ala Pro Gly Ala Gly Leu Arg Leu Val Gly Glu Ala Phe
 65                  70                  75                  80 cac tgc cgg ctg cag ggt ccc cgc cgg gtg gac aag cgg acg ctg gtg    288
His Cys Arg Leu Gln Gly Pro Arg Arg Val Asp Lys Arg Thr Leu Val
                 85                  90                  95 gag ctg cat ggt ttc cag gct cct gct gcc caa ggt gcc ttc ctg cga    336
Glu Leu His Gly Phe Gln Ala Pro Ala Ala Gln Gly Ala Phe Leu Arg
            100                 105                 110 ggc tcc ggt ctg agc ctg gcc tcg ggt cgg ttc acg gcc ccc gtg tcc    384
Gly Ser Gly Leu Ser Leu Ala Ser Gly Arg Phe Thr Ala Pro Val Ser
        115                 120                 125 ggc atc ttc cag ttc tct gcc agt ctg cac gtg gac cac agt gag ctg    432
Gly Ile Phe Gln Phe Ser Ala Ser Leu His Val Asp His Ser Glu Leu
    130                 135                 140 cag ggc aag gcc cgg ctg cgg gcc cgg gac gtg gtg tgt gtt ctc atc    480
Gln Gly Lys Ala Arg Leu Arg Ala Arg Asp Val Val Cys Val Leu Ile
145                 150                 155                 160 tgt att gag tcc ctg tgc cag cgc cac acg tgc ctg gag gcc gtc tca    528
Cys Ile Glu Ser Leu Cys Gln Arg His Thr Cys Leu Glu Ala Val Ser
                165                 170                 175 ggc ctg gag agc aac agc agg gtc ttc acg cta cag gtg cag ggg ctg    576
Gly Leu Glu Ser Asn Ser Arg Val Phe Thr Leu Gln Val Gln Gly Leu
            180                 185                 190 ctg cag ctg cag gct gga cag tac gct tct gtg ttt gtg gac aat ggc    624
Leu Gln Leu Gln Ala Gly Gln Tyr Ala Ser Val Phe Val Asp Asn Gly
        195                 200                 205 tcc ggg gcc gtc ctc acc atc cag gcg ggc tcc agc ttc tcc ggg ctg    672
Ser Gly Ala Val Leu Thr Ile Gln Ala Gly Ser Ser Phe Ser Gly Leu
    210                 215                 220 ctc ctg ggc acg tga                                                687
Leu Leu Gly Thr
225

<210> SEQ ID NO 9
<211> LENGTH: 228
<212> TYPE: PRT
<213> ORGANISM: Homo sapiens

<400> SEQUENCE: 9

Met Ala Glu Leu Cys Pro Ala Ala Gly Arg Arg Leu Lys Glu Ala
 1               5                  10                  15

Val Arg Lys Gln Gly Gln Glu Ala Ala Gly Ser Leu Arg Ser Pro Arg
             20                  25                  30

Thr Ser Arg Cys Arg Ser Asp Arg Gly Asp Ser Ala Ser Arg Val Ser
         35                  40                  45

Gly Ala Ala Glu Arg Gly His Gly Ala Pro Val Leu Arg Ala Ser Gly
     50                  55                  60

Pro Ala Ala Pro Gly Ala Gly Leu Arg Leu Val Gly Glu Ala Phe
 65                  70                  75                  80

His Cys Arg Leu Gln Gly Pro Arg Arg Val Asp Lys Arg Thr Leu Val
                 85                  90                  95

Glu Leu His Gly Phe Gln Ala Pro Ala Ala Gln Gly Ala Phe Leu Arg
            100                 105                 110

Gly Ser Gly Leu Ser Leu Ala Ser Gly Arg Phe Thr Ala Pro Val Ser
        115                 120                 125

Gly Ile Phe Gln Phe Ser Ala Ser Leu His Val Asp His Ser Glu Leu
    130                 135                 140
```

```
Gln Gly Lys Ala Arg Leu Arg Ala Arg Asp Val Val Cys Val Leu Ile
145                 150                 155                 160

Cys Ile Glu Ser Leu Cys Gln Arg His Thr Cys Leu Glu Ala Val Ser
                165                 170                 175

Gly Leu Glu Ser Asn Ser Arg Val Phe Thr Leu Gln Val Gln Gly Leu
            180                 185                 190

Leu Gln Leu Gln Ala Gly Gln Tyr Ala Ser Val Phe Val Asp Asn Gly
        195                 200                 205

Ser Gly Ala Val Leu Thr Ile Gln Ala Gly Ser Ser Phe Ser Gly Leu
    210                 215                 220

Leu Leu Gly Thr
225

<210> SEQ ID NO 10
<211> LENGTH: 1232
<212> TYPE: DNA
<213> ORGANISM: Mus musculus
<220> FEATURE:
<221> NAME/KEY: CDS
<222> LOCATION: (241)..(1104)
<223> OTHER INFORMATION:

<400> SEQUENCE: 10
gggaggccta gggagaaagt agttctcttt cggtggcagg gttgctgtcg agggcaccga      60
gcaggagata ggtcgacaga acgaggagt tctggctcct cctgcagaca tgcaccagcg     120
gctgctgggc tcgtccctgg gcctcgcccc cgcgcggggg ctctgaatgc ctgccgccgc     180
ccccatgaga gcaccggcct gggctcccgc ccctaagcct ctgctcgcgg agactgagcc     240 atg tgg gcc tgg ggc tgg gcc gct gca gcg ctc ctc tgg cta cag act       288
Met Trp Ala Trp Gly Trp Ala Ala Ala Ala Leu Leu Trp Leu Gln Thr
1               5                   10                  15 gca gga gcc ggg gcc cgg cag gag ctc aag aag tct cgg cag ctg ttt       336
Ala Gly Ala Gly Ala Arg Gln Glu Leu Lys Lys Ser Arg Gln Leu Phe
            20                  25                  30 gcg cgt gtg gat tcc ccc aat att acc acg tcc aac cgt gag gga ttc       384
Ala Arg Val Asp Ser Pro Asn Ile Thr Thr Ser Asn Arg Glu Gly Phe
        35                  40                  45 cca ggc tcc gtc aag ccc ccg gaa gcc tct gga cct gag ctc tca gat       432
Pro Gly Ser Val Lys Pro Pro Glu Ala Ser Gly Pro Glu Leu Ser Asp
    50                  55                  60 gcc cac atg acg tgg ttg aac ttt gtc cga cgg cca gat gat ggg tcc       480
Ala His Met Thr Trp Leu Asn Phe Val Arg Arg Pro Asp Asp Gly Ser
65                  70                  75                  80 ccc cca gga cct cct ggc cct cct ggt ccc cct ggc tcc cct ggt gtg       528
Pro Pro Gly Pro Pro Gly Pro Pro Gly Pro Pro Gly Ser Pro Gly Val
                85                  90                  95 ggc gtt acc cca gag gcc tta ctg cag gaa ttt cag gag ata ctg aaa       576
Gly Val Thr Pro Glu Ala Leu Leu Gln Glu Phe Gln Glu Ile Leu Lys
            100                 105                 110 gag gcc aca gaa ctt cga ttc tca ggg cta cca gac aca ttg tta ccc       624
Glu Ala Thr Glu Leu Arg Phe Ser Gly Leu Pro Asp Thr Leu Leu Pro
        115                 120                 125 cag gaa ccc agc caa cgg ctg gtg gtt gag gcc ttc tac tgc cgt ttg       672
Gln Glu Pro Ser Gln Arg Leu Val Val Glu Ala Phe Tyr Cys Arg Leu
    130                 135                 140 aaa ggc cct gtg ctg gtg gac aag aag act ctg gtg gaa ctg caa gga       720
Lys Gly Pro Val Leu Val Asp Lys Lys Thr Leu Val Glu Leu Gln Gly
145                 150                 155                 160
```

```
ttc caa gct cct act act cag ggc gcc ttc ctg cgg gga tct ggc ctg      768
Phe Gln Ala Pro Thr Thr Gln Gly Ala Phe Leu Arg Gly Ser Gly Leu
                165                 170                 175 agc ctg tcc ttg ggc cga ttc aca gcc cca gtc tct gcc atc ttc cag      816
Ser Leu Ser Leu Gly Arg Phe Thr Ala Pro Val Ser Ala Ile Phe Gln
            180                 185                 190 ttt tct gcc agc ctg cac gtg gac cac agt gaa ctg cag ggc aga ggc      864
Phe Ser Ala Ser Leu His Val Asp His Ser Glu Leu Gln Gly Arg Gly
        195                 200                 205 cgg ttg cgt acc cgg gat atg gtc cgt gtt ctc atc tgt att gag tcc      912
Arg Leu Arg Thr Arg Asp Met Val Arg Val Leu Ile Cys Ile Glu Ser
    210                 215                 220 ttg tgt cat cgt cat acg tcc ctg gag gct gta tca ggt ctg gag agc      960
Leu Cys His Arg His Thr Ser Leu Glu Ala Val Ser Gly Leu Glu Ser
225                 230                 235                 240 aac agc agg gtc ttc aca gtg cag gtt cag ggg ctg ctg cat cta cag     1008
Asn Ser Arg Val Phe Thr Val Gln Val Gln Gly Leu Leu His Leu Gln
                245                 250                 255 tct gga cag tat gtc tct gtg ttc gtg gac aac agt tct ggg gca gtc     1056
Ser Gly Gln Tyr Val Ser Val Phe Val Asp Asn Ser Ser Gly Ala Val
            260                 265                 270 ctc acc atc cag aac act tcc agc ttc tcg gga atg ctt ttg ggt acc     1104
Leu Thr Ile Gln Asn Thr Ser Ser Phe Ser Gly Met Leu Leu Gly Thr
        275                 280                 285 tagcggagct gaagaaacga ttgtggattg aggaaccaac accttgcttc ttagaggagc   1164
tgaaaaggac tactcactcc ccttttaata gttttcatag caataaagaa ctccaaactt   1224
cttcatct                                                            1232

<210> SEQ ID NO 11
<211> LENGTH: 288
<212> TYPE: PRT
<213> ORGANISM: Mus musculus

<400> SEQUENCE: 11

Met Trp Ala Trp Gly Trp Ala Ala Ala Ala Leu Leu Trp Leu Gln Thr
1               5                   10                  15

Ala Gly Ala Gly Ala Arg Gln Glu Leu Lys Lys Ser Arg Gln Leu Phe
            20                  25                  30

Ala Arg Val Asp Ser Pro Asn Ile Thr Thr Ser Asn Arg Glu Gly Phe
        35                  40                  45

Pro Gly Ser Val Lys Pro Pro Glu Ala Ser Gly Pro Glu Leu Ser Asp
    50                  55                  60

Ala His Met Thr Trp Leu Asn Phe Val Arg Arg Pro Asp Asp Gly Ser
65                  70                  75                  80

Pro Pro Gly Pro Pro Gly Pro Gly Pro Gly Ser Pro Gly Val
                85                  90                  95

Gly Val Thr Pro Glu Ala Leu Leu Gln Glu Phe Gln Glu Ile Leu Lys
                100                 105                 110

Glu Ala Thr Glu Leu Arg Phe Ser Gly Leu Pro Asp Thr Leu Leu Pro
            115                 120                 125

Gln Glu Pro Ser Gln Arg Leu Val Val Glu Ala Phe Tyr Cys Arg Leu
        130                 135                 140

Lys Gly Pro Val Leu Val Asp Lys Lys Thr Leu Val Glu Leu Gln Gly
145                 150                 155                 160

Phe Gln Ala Pro Thr Thr Gln Gly Ala Phe Leu Arg Gly Ser Gly Leu
                165                 170                 175
```

```
Ser Leu Ser Leu Gly Arg Phe Thr Ala Pro Val Ser Ala Ile Phe Gln
            180                 185                 190

Phe Ser Ala Ser Leu His Val Asp His Ser Glu Leu Gln Gly Arg Gly
        195                 200                 205

Arg Leu Arg Thr Arg Asp Met Val Arg Val Leu Ile Cys Ile Glu Ser
    210                 215                 220

Leu Cys His Arg His Thr Ser Leu Glu Ala Val Ser Gly Leu Glu Ser
225                 230                 235                 240

Asn Ser Arg Val Phe Thr Val Gln Val Gln Gly Leu Leu His Leu Gln
                245                 250                 255

Ser Gly Gln Tyr Val Ser Val Phe Val Asp Asn Ser Ser Gly Ala Val
            260                 265                 270

Leu Thr Ile Gln Asn Thr Ser Ser Phe Ser Gly Met Leu Leu Gly Thr
        275                 280                 285

<210> SEQ ID NO 12
<211> LENGTH: 477
<212> TYPE: DNA
<213> ORGANISM: Homo sapiens
<220> FEATURE:
<221> NAME/KEY: CDS
<222> LOCATION: (1)..(474)
<223> OTHER INFORMATION:

<400> SEQUENCE: 12 gcg ccg cgc gtg gag gcc gct ttc ctc tgc cgc ctg cgc cgg gac gcg      48
Ala Pro Arg Val Glu Ala Ala Phe Leu Cys Arg Leu Arg Arg Asp Ala
1               5                   10                  15 ttg gtg gag cgg cgc gcg ctg cac gag ctt ggc gtc tac tac ctg ccc      96
Leu Val Glu Arg Arg Ala Leu His Glu Leu Gly Val Tyr Tyr Leu Pro
            20                  25                  30 gac gcc gag ggt gcc ttc cgc cgc ggc ccg ggc ctg aac ttg acc agc     144
Asp Ala Glu Gly Ala Phe Arg Arg Gly Pro Gly Leu Asn Leu Thr Ser
        35                  40                  45 ggc cag tac agg gcg ccc gtg gct ggc ttc tac gct ctc gcc gcc acg     192
Gly Gln Tyr Arg Ala Pro Val Ala Gly Phe Tyr Ala Leu Ala Ala Thr
    50                  55                  60 ctg cac gtg gcg ctc ggg gag ccg ccg agg agg ggg ccg ccg cgc ccc     240
Leu His Val Ala Leu Gly Glu Pro Pro Arg Arg Gly Pro Pro Arg Pro
65                  70                  75                  80 cgg gac cac ctg cgc ctg ctc atc tgc atc cag tcc cgg tgc cag cgc     288
Arg Asp His Leu Arg Leu Leu Ile Cys Ile Gln Ser Arg Cys Gln Arg
                85                  90                  95 aac acg tcc ctg gag gcc atc atg ggc ctg gag agc agc agt gag ctc     336
Asn Thr Ser Leu Glu Ala Ile Met Gly Leu Glu Ser Ser Ser Glu Leu
            100                 105                 110 ttc acc atc tct gtg aat ggc gtc ctg tac ctg cag atg ggg cag tgg     384
Phe Thr Ile Ser Val Asn Gly Val Leu Tyr Leu Gln Met Gly Gln Trp
        115                 120                 125 acc tcc tgg gcg tgt gag cgg cca cca cag gcc ctt cct ctc agg ggc     432
Thr Ser Trp Ala Cys Glu Arg Pro Pro Gln Ala Leu Pro Leu Arg Gly
    130                 135                 140 aaa tgg agc aca gat cta gac aat gtg tgg aca gtg tca gag tag         477
Lys Trp Ser Thr Asp Leu Asp Asn Val Trp Thr Val Ser Glu
145                 150                 155

<210> SEQ ID NO 13
<211> LENGTH: 158
<212> TYPE: PRT
<213> ORGANISM: Homo sapiens
```

```
<400> SEQUENCE: 13

Ala Pro Arg Val Glu Ala Phe Leu Cys Arg Leu Arg Arg Asp Ala
1               5                   10                  15

Leu Val Glu Arg Arg Ala Leu His Glu Leu Gly Val Tyr Tyr Leu Pro
            20                  25                  30

Asp Ala Glu Gly Ala Phe Arg Arg Gly Pro Gly Leu Asn Leu Thr Ser
        35                  40                  45

Gly Gln Tyr Arg Ala Pro Val Ala Gly Phe Tyr Ala Leu Ala Ala Thr
    50                  55                  60

Leu His Val Ala Leu Gly Glu Pro Arg Arg Gly Pro Pro Arg Pro
65                  70                  75                  80

Arg Asp His Leu Arg Leu Leu Ile Cys Ile Gln Ser Arg Cys Gln Arg
                85                  90                  95

Asn Thr Ser Leu Glu Ala Ile Met Gly Leu Glu Ser Ser Ser Glu Leu
            100                 105                 110

Phe Thr Ile Ser Val Asn Gly Val Leu Tyr Leu Gln Met Gly Gln Trp
        115                 120                 125

Thr Ser Trp Ala Cys Glu Arg Pro Pro Gln Ala Leu Pro Leu Arg Gly
    130                 135                 140

Lys Trp Ser Thr Asp Leu Asp Asn Val Trp Thr Val Ser Glu
145                 150                 155

<210> SEQ ID NO 14
<211> LENGTH: 3180
<212> TYPE: DNA
<213> ORGANISM: Homo sapiens
<220> FEATURE:
<221> NAME/KEY: CDS
<222> LOCATION: (143)..(2677)
<223> OTHER INFORMATION:

<400> SEQUENCE: 14
gctggaagca gcgtcttatt ttaccttgtt ctcccacttc ctgaagatgc taaactcctg      60
gtggactgca gaggagaggg attcagtctt ctcctgatgt gtttgcctgt aggtacctga    120
gttgacaccg aagctcctaa ag atg ctg agc ggc gtt tgg ttc ctc agt gtg    172
                          Met Leu Ser Gly Val Trp Phe Leu Ser Val
                          1               5                   10 tta acc gtg gcc ggg atc tta cag aca gag agt cgc aaa act gcc aaa    220
Leu Thr Val Ala Gly Ile Leu Gln Thr Glu Ser Arg Lys Thr Ala Lys
            15                  20                  25 gac att tgc aag atc cgc tgt ctg tgt gaa gaa aag gaa aac gta ctg    268
Asp Ile Cys Lys Ile Arg Cys Leu Cys Glu Glu Lys Glu Asn Val Leu
        30                  35                  40 aat atc aac tgt gag aac aaa gga ttt aca aca gtt agc ctg ctc cag    316
Asn Ile Asn Cys Glu Asn Lys Gly Phe Thr Thr Val Ser Leu Leu Gln
    45                  50                  55 ccc ccc cag tat cga atc tat cag ctt ttt ctc aat gga aac ctc ttg    364
Pro Pro Gln Tyr Arg Ile Tyr Gln Leu Phe Leu Asn Gly Asn Leu Leu
60                  65                  70 aca aga ctg tat cca aac gaa ttt gtc aat tac tcc aac gcg gtg act    412
Thr Arg Leu Tyr Pro Asn Glu Phe Val Asn Tyr Ser Asn Ala Val Thr
75                  80                  85                  90 ctt cac cta ggt aac aac ggg tta cag gag atc cga acg ggg gca ttc    460
Leu His Leu Gly Asn Asn Gly Leu Gln Glu Ile Arg Thr Gly Ala Phe
            95                  100                 105 agt ggc ctg aaa act ctc aaa aga ctg cat ctc aac aac aac aag ctt    508
Ser Gly Leu Lys Thr Leu Lys Arg Leu His Leu Asn Asn Asn Lys Leu
        110                 115                 120
```

```
gag ata ttg agg gag gac acc ttc cta ggc ctg gag agc ctg gag tat    556
Glu Ile Leu Arg Glu Asp Thr Phe Leu Gly Leu Glu Ser Leu Glu Tyr
        125                 130                 135 ctc cag gcc gac tac aat tac atc agt gcc atc gag gct ggg gca ttc    604
Leu Gln Ala Asp Tyr Asn Tyr Ile Ser Ala Ile Glu Ala Gly Ala Phe
    140                 145                 150 agc aaa ctt aac aag ctc aaa gtg ctc atc ctg aat gac aac ctt ctg    652
Ser Lys Leu Asn Lys Leu Lys Val Leu Ile Leu Asn Asp Asn Leu Leu
155                 160                 165                 170 ctt tca ctg ccc agc aat gtg ttc cgc ttt gtc ctg ctg acc cac tta    700
Leu Ser Leu Pro Ser Asn Val Phe Arg Phe Val Leu Leu Thr His Leu
                175                 180                 185 gac ctc agg ggg aat agg cta aaa gta atg cct ttt gct ggc gtc ctt    748
Asp Leu Arg Gly Asn Arg Leu Lys Val Met Pro Phe Ala Gly Val Leu
        190                 195                 200 gaa cat att gga ggg atc atg gag att cag ctg gag gaa aat cca tgg    796
Glu His Ile Gly Gly Ile Met Glu Ile Gln Leu Glu Glu Asn Pro Trp
    205                 210                 215 aat tgc act tgt gac tta ctt cct ctc aag gcc tgg cta gac acc ata    844
Asn Cys Thr Cys Asp Leu Leu Pro Leu Lys Ala Trp Leu Asp Thr Ile
220                 225                 230 act gtt ttt gtg gga gag att gtc tgt gag act ccc ttt agg ttg cat    892
Thr Val Phe Val Gly Glu Ile Val Cys Glu Thr Pro Phe Arg Leu His
235                 240                 245                 250 ggg aaa gac gtg acc cag ctg acc agg caa gac ctc tgt ccc aga aaa    940
Gly Lys Asp Val Thr Gln Leu Thr Arg Gln Asp Leu Cys Pro Arg Lys
        255                 260                 265 agt gcc agt gat tcc agt cag agg ggc agc cat gct gac acc cac gtc    988
Ser Ala Ser Asp Ser Ser Gln Arg Gly Ser His Ala Asp Thr His Val
    270                 275                 280 caa agg ctg tca cct aca atg aat cct gct ctc aac cca acc agg gct   1036
Gln Arg Leu Ser Pro Thr Met Asn Pro Ala Leu Asn Pro Thr Arg Ala
285                 290                 295 ccg aaa gcc agc cgg ccg ccc aaa atg aga aat cgt cca act ccc cga   1084
Pro Lys Ala Ser Arg Pro Pro Lys Met Arg Asn Arg Pro Thr Pro Arg
        300                 305                 310 gtg act gtg tca aag gac agg caa agt ttt gga ccc atc atg gtg tac   1132
Val Thr Val Ser Lys Asp Arg Gln Ser Phe Gly Pro Ile Met Val Tyr
315                 320                 325                 330 cag acc aag tct cct gtg cct ctc acc tgt ccc agc agc tgt gtc tgc   1180
Gln Thr Lys Ser Pro Val Pro Leu Thr Cys Pro Ser Ser Cys Val Cys
                335                 340                 345 acc tct cag agc tca gac aat ggt ctg aat gta aac tgc caa gaa agg   1228
Thr Ser Gln Ser Ser Asp Asn Gly Leu Asn Val Asn Cys Gln Glu Arg
        350                 355                 360 aag ttc act aat atc tct gac ctg cag ccc aaa ccg acc agt cca aag   1276
Lys Phe Thr Asn Ile Ser Asp Leu Gln Pro Lys Pro Thr Ser Pro Lys
    365                 370                 375 aaa ctc tac cta aca ggg aac tat ctt caa act gtc tat aag aat gac   1324
Lys Leu Tyr Leu Thr Gly Asn Tyr Leu Gln Thr Val Tyr Lys Asn Asp
380                 385                 390 ctc tta gaa tac agt tct ttg gac tta ctg cac tta gga aac aac agg   1372
Leu Leu Glu Tyr Ser Ser Leu Asp Leu Leu His Leu Gly Asn Asn Arg
395                 400                 405                 410 att gca gtc att cag gaa ggt gcc ttt aca aac ctg acc agt tta cgc   1420
Ile Ala Val Ile Gln Glu Gly Ala Phe Thr Asn Leu Thr Ser Leu Arg
        415                 420                 425 aga ctt tat ctg aat ggc aat tac ctt gaa gtg ctg tac cct tct atg   1468
Arg Leu Tyr Leu Asn Gly Asn Tyr Leu Glu Val Leu Tyr Pro Ser Met
```

-continued

|  |  |  |  |  |  |  |  |  |  |  |  |  |  |  |  |
|---|---|---|---|---|---|---|---|---|---|---|---|---|---|---|---|
|  | | 430 | | | | | 435 | | | | | 440 | | | |
| ttt | gat | gga | ctg | cag | agc | ttg | caa | tat | ctc | tat | tta | gag | tat | aat | gtc | 1516
| Phe | Asp | Gly | Leu | Gln | Ser | Leu | Gln | Tyr | Leu | Tyr | Leu | Glu | Tyr | Asn | Val |
|  |  |  | 445 |  |  |  |  | 450 |  |  |  |  | 455 |  |  |
| att | aag | gaa | att | aag | cct | ctg | acc | ttt | gat | gct | ttg | att | aac | cta | cag | 1564
| Ile | Lys | Glu | Ile | Lys | Pro | Leu | Thr | Phe | Asp | Ala | Leu | Ile | Asn | Leu | Gln |
|  | 460 |  |  |  |  | 465 |  |  |  |  | 470 |  |  |  |  |
| cta | ctg | ttt | ctg | aac | aac | aac | ctt | ctt | cgg | tcc | tta | cct | gat | aat | ata | 1612
| Leu | Leu | Phe | Leu | Asn | Asn | Asn | Leu | Leu | Arg | Ser | Leu | Pro | Asp | Asn | Ile |
| 475 |  |  |  |  | 480 |  |  |  |  | 485 |  |  |  |  | 490 |
| ttt | ggg | ggg | acg | gcc | cta | acc | agg | ctg | aat | ctg | aga | aac | aac | cat | ttt | 1660
| Phe | Gly | Gly | Thr | Ala | Leu | Thr | Arg | Leu | Asn | Leu | Arg | Asn | Asn | His | Phe |
|  |  |  |  | 495 |  |  |  |  | 500 |  |  |  |  | 505 |  |
| tct | cac | ctg | ccc | gtg | aaa | ggg | gtt | ctg | gat | cag | ctc | ccg | gct | ttc | atc | 1708
| Ser | His | Leu | Pro | Val | Lys | Gly | Val | Leu | Asp | Gln | Leu | Pro | Ala | Phe | Ile |
|  |  |  | 510 |  |  |  |  | 515 |  |  |  |  | 520 |  |  |
| cag | ata | gat | ctg | cag | gag | aac | ccc | tgg | gac | tgt | acc | tgt | gac | atc | atg | 1756
| Gln | Ile | Asp | Leu | Gln | Glu | Asn | Pro | Trp | Asp | Cys | Thr | Cys | Asp | Ile | Met |
|  |  | 525 |  |  |  |  | 530 |  |  |  |  | 535 |  |  |  |
| ggg | ctg | aaa | gac | tgg | aca | gaa | cat | gcc | aat | tcc | cct | gtc | atc | att | aat | 1804
| Gly | Leu | Lys | Asp | Trp | Thr | Glu | His | Ala | Asn | Ser | Pro | Val | Ile | Ile | Asn |
|  | 540 |  |  |  |  | 545 |  |  |  |  | 550 |  |  |  |  |
| gag | gtg | act | tgc | gaa | tct | cct | gct | aag | cat | gca | ggg | gag | ata | cta | aaa | 1852
| Glu | Val | Thr | Cys | Glu | Ser | Pro | Ala | Lys | His | Ala | Gly | Glu | Ile | Leu | Lys |
| 555 |  |  |  |  | 560 |  |  |  |  | 565 |  |  |  |  | 570 |
| ttt | ctg | ggg | agg | gag | gct | atc | tgt | cca | gac | agc | cca | aac | ttg | tca | gat | 1900
| Phe | Leu | Gly | Arg | Glu | Ala | Ile | Cys | Pro | Asp | Ser | Pro | Asn | Leu | Ser | Asp |
|  |  |  |  | 575 |  |  |  |  | 580 |  |  |  |  | 585 |  |
| gga | acc | gtc | ttg | tca | atg | aat | cac | aat | aca | gac | aca | cct | cgg | tcg | ctt | 1948
| Gly | Thr | Val | Leu | Ser | Met | Asn | His | Asn | Thr | Asp | Thr | Pro | Arg | Ser | Leu |
|  |  |  | 590 |  |  |  |  | 595 |  |  |  |  | 600 |  |  |
| agt | gtg | tct | cct | agt | tcc | tat | cct | gaa | cta | cac | act | gaa | gtt | cca | ctg | 1996
| Ser | Val | Ser | Pro | Ser | Ser | Tyr | Pro | Glu | Leu | His | Thr | Glu | Val | Pro | Leu |
|  |  | 605 |  |  |  |  | 610 |  |  |  |  | 615 |  |  |  |
| tct | gtc | tta | att | ctg | gga | ttg | ctt | gtt | gtt | ttc | atc | tta | tct | gtc | tgt | 2044
| Ser | Val | Leu | Ile | Leu | Gly | Leu | Leu | Val | Val | Phe | Ile | Leu | Ser | Val | Cys |
|  | 620 |  |  |  |  | 625 |  |  |  |  | 630 |  |  |  |  |
| ttt | ggg | gct | ggt | tta | ttc | gtc | ttt | gtc | ttg | aaa | cgc | cga | aag | gga | gtg | 2092
| Phe | Gly | Ala | Gly | Leu | Phe | Val | Phe | Val | Leu | Lys | Arg | Arg | Lys | Gly | Val |
| 635 |  |  |  |  | 640 |  |  |  |  | 645 |  |  |  |  | 650 |
| ccg | agc | gtt | ccc | agg | aat | acc | aac | aac | tta | gac | gta | agc | tcc | ttt | caa | 2140
| Pro | Ser | Val | Pro | Arg | Asn | Thr | Asn | Asn | Leu | Asp | Val | Ser | Ser | Phe | Gln |
|  |  |  |  | 655 |  |  |  |  | 660 |  |  |  |  | 665 |  |
| tta | cag | tat | ggg | tct | tac | aac | act | gag | act | cac | gat | aaa | aca | gac | ggc | 2188
| Leu | Gln | Tyr | Gly | Ser | Tyr | Asn | Thr | Glu | Thr | His | Asp | Lys | Thr | Asp | Gly |
|  |  |  | 670 |  |  |  |  | 675 |  |  |  |  | 680 |  |  |
| cat | gtc | tac | aac | tat | atc | ccc | cca | cct | gtg | ggt | cag | atg | tgc | caa | aac | 2236
| His | Val | Tyr | Asn | Tyr | Ile | Pro | Pro | Pro | Val | Gly | Gln | Met | Cys | Gln | Asn |
|  |  | 685 |  |  |  |  | 690 |  |  |  |  | 695 |  |  |  |
| ccc | atc | tac | atg | cag | aag | gaa | gga | gac | cca | gta | gcc | tat | tac | cga | aac | 2284
| Pro | Ile | Tyr | Met | Gln | Lys | Glu | Gly | Asp | Pro | Val | Ala | Tyr | Tyr | Arg | Asn |
|  | 700 |  |  |  |  | 705 |  |  |  |  | 710 |  |  |  |  |
| ctg | caa | gag | ttc | agc | tat | agc | aac | ctg | gag | gag | aaa | aaa | gaa | gag | cca | 2332
| Leu | Gln | Glu | Phe | Ser | Tyr | Ser | Asn | Leu | Glu | Glu | Lys | Lys | Glu | Glu | Pro |
| 715 |  |  |  |  | 720 |  |  |  |  | 725 |  |  |  |  | 730 |
| gcc | aca | cct | gct | tac | aca | ata | agt | gcc | act | gag | ctg | cta | gaa | aag | cag | 2380
| Ala | Thr | Pro | Ala | Tyr | Thr | Ile | Ser | Ala | Thr | Glu | Leu | Leu | Glu | Lys | Gln |
|  |  |  |  | 735 |  |  |  |  | 740 |  |  |  |  | 745 |  |
| gcc | aca | cca | aga | gag | cct | gag | ctg | ctg | tat | caa | aat | att | gct | gag | cga | 2428

```
                                                       Ala Thr Pro Arg Glu Pro Glu Leu Leu Tyr Gln Asn Ile Ala Glu Arg
                                                                       750                 755                 760 gtc aag gaa ctt ccc agc gca ggc cta gtc cac tat aac ttt tgt acc        2476
Val Lys Glu Leu Pro Ser Ala Gly Leu Val His Tyr Asn Phe Cys Thr
        765                 770                 775 tta cct aaa agg cag ttt gcc cct tcc tat gaa tct cga cgc caa aac        2524
Leu Pro Lys Arg Gln Phe Ala Pro Ser Tyr Glu Ser Arg Arg Gln Asn
    780                 785                 790 caa gac aga atc aat aaa acc gtt tta tat gga act ccc agg aaa tgc        2572
Gln Asp Arg Ile Asn Lys Thr Val Leu Tyr Gly Thr Pro Arg Lys Cys
795                 800                 805                 810 ttt gtg ggg cag tca aaa ccc aac cac cct tta ctg caa gct aag ccg        2620
Phe Val Gly Gln Ser Lys Pro Asn His Pro Leu Leu Gln Ala Lys Pro
                815                 820                 825 caa tca gaa ccg gac tac ctc gaa gtt ctg gaa aaa caa act gca atc        2668
Gln Ser Glu Pro Asp Tyr Leu Glu Val Leu Glu Lys Gln Thr Ala Ile
            830                 835                 840 agt cag ctg tgaagggaaa tcatttacaa ccctaaggca tcagaggatg                2717
Ser Gln Leu
        845 ctgctccgaa ctgttggaaa caaggacatt agcttttgtg tttgtttttg ttctcccttt      2777 cccagtgtta atgggggact ttgaaaatgt ttgggagata ggatgaagtc atgattttgc      2837 ttttgcaagt tttcctttaa attatttctc tctcgctctc ctcccctcct ttttttttt      2897 tttttttttt tcttttttccc ttctcttctt aggaaccatc agtggacatg aatgtttcta    2957 caatgcattt cttcatagat tttgtttatg gttttgtttc ttttttcttc tttgtttttc     3017 agtgtgggag tgggaagagg agattatagt gactgaagaa agaataggca aacttttcaa     3077 atgaaaatgg atatttagtg tattttgtag aagatctcca aagatctttt gtgactacaa     3137 cttcttttgt aaataatgat atatggtatt tccatcgtca gtt                       3180

<210> SEQ ID NO 15
<211> LENGTH: 845
<212> TYPE: PRT
<213> ORGANISM: Homo sapiens

<400> SEQUENCE: 15

Met Leu Ser Gly Val Trp Phe Leu Ser Val Leu Thr Val Ala Gly Ile
1               5                   10                  15

Leu Gln Thr Glu Ser Arg Lys Thr Ala Lys Asp Ile Cys Lys Ile Arg
            20                  25                  30

Cys Leu Cys Glu Glu Lys Glu Asn Val Leu Asn Ile Asn Cys Glu Asn
        35                  40                  45

Lys Gly Phe Thr Thr Val Ser Leu Leu Gln Pro Gln Tyr Arg Ile
    50                  55                  60

Tyr Gln Leu Phe Leu Asn Gly Asn Leu Leu Thr Arg Leu Tyr Pro Asn
65                  70                  75                  80

Glu Phe Val Asn Tyr Ser Asn Ala Val Thr Leu His Leu Gly Asn Asn
                85                  90                  95

Gly Leu Gln Glu Ile Arg Thr Gly Ala Phe Ser Gly Leu Lys Thr Leu
            100                 105                 110

Lys Arg Leu His Leu Asn Asn Asn Lys Leu Glu Ile Leu Arg Glu Asp
        115                 120                 125

Thr Phe Leu Gly Leu Glu Ser Leu Glu Tyr Leu Gln Ala Asp Tyr Asn
    130                 135                 140

Tyr Ile Ser Ala Ile Glu Ala Gly Ala Phe Ser Lys Leu Asn Lys Leu
```

-continued

```
        145                 150                 155                 160
Lys Val Leu Ile Leu Asn Asp Asn Leu Leu Ser Leu Pro Ser Asn
                165                 170                 175
Val Phe Arg Phe Val Leu Thr His Leu Asp Leu Arg Gly Asn Arg
                180                 185                 190
Leu Lys Val Met Pro Phe Ala Gly Val Leu Glu His Ile Gly Gly Ile
                195                 200                 205
Met Glu Ile Gln Leu Glu Glu Asn Pro Trp Asn Cys Thr Cys Asp Leu
                210                 215                 220
Leu Pro Leu Lys Ala Trp Leu Asp Thr Ile Thr Val Phe Val Gly Glu
225                 230                 235                 240
Ile Val Cys Glu Thr Pro Phe Arg Leu His Gly Lys Asp Val Thr Gln
                245                 250                 255
Leu Thr Arg Gln Asp Leu Cys Pro Arg Lys Ser Ala Ser Asp Ser Ser
                260                 265                 270
Gln Arg Gly Ser His Ala Asp Thr His Val Gln Arg Leu Ser Pro Thr
                275                 280                 285
Met Asn Pro Ala Leu Asn Pro Thr Arg Ala Pro Lys Ala Ser Arg Pro
                290                 295                 300
Pro Lys Met Arg Asn Arg Pro Thr Pro Arg Val Thr Val Ser Lys Asp
305                 310                 315                 320
Arg Gln Ser Phe Gly Pro Ile Met Val Tyr Gln Thr Lys Ser Pro Val
                325                 330                 335
Pro Leu Thr Cys Pro Ser Ser Cys Val Cys Thr Ser Gln Ser Ser Asp
                340                 345                 350
Asn Gly Leu Asn Val Asn Cys Gln Glu Arg Lys Phe Thr Asn Ile Ser
                355                 360                 365
Asp Leu Gln Pro Lys Pro Thr Ser Pro Lys Lys Leu Tyr Leu Thr Gly
                370                 375                 380
Asn Tyr Leu Gln Thr Val Tyr Lys Asn Asp Leu Leu Glu Tyr Ser Ser
385                 390                 395                 400
Leu Asp Leu Leu His Leu Gly Asn Asn Arg Ile Ala Val Ile Gln Glu
                405                 410                 415
Gly Ala Phe Thr Asn Leu Thr Ser Leu Arg Arg Leu Tyr Leu Asn Gly
                420                 425                 430
Asn Tyr Leu Glu Val Leu Tyr Pro Ser Met Phe Asp Gly Leu Gln Ser
                435                 440                 445
Leu Gln Tyr Leu Tyr Leu Glu Tyr Asn Val Ile Lys Glu Ile Lys Pro
                450                 455                 460
Leu Thr Phe Asp Ala Leu Ile Asn Leu Gln Leu Leu Phe Leu Asn Asn
465                 470                 475                 480
Asn Leu Leu Arg Ser Leu Pro Asp Asn Ile Phe Gly Gly Thr Ala Leu
                485                 490                 495
Thr Arg Leu Asn Leu Arg Asn Asn His Phe Ser His Leu Pro Val Lys
                500                 505                 510
Gly Val Leu Asp Gln Leu Pro Ala Phe Ile Gln Ile Asp Leu Gln Glu
                515                 520                 525
Asn Pro Trp Asp Cys Thr Cys Asp Ile Met Gly Leu Lys Asp Trp Thr
                530                 535                 540
Glu His Ala Asn Ser Pro Val Ile Ile Asn Glu Val Thr Cys Glu Ser
545                 550                 555                 560
Pro Ala Lys His Ala Gly Glu Ile Leu Lys Phe Leu Gly Arg Glu Ala
                565                 570                 575
```

```
Ile Cys Pro Asp Ser Pro Asn Leu Ser Asp Gly Thr Val Leu Ser Met
            580                 585                 590

Asn His Asn Thr Asp Thr Pro Arg Ser Leu Ser Val Ser Pro Ser Ser
            595                 600                 605

Tyr Pro Glu Leu His Thr Glu Val Pro Leu Ser Val Leu Ile Leu Gly
            610                 615                 620

Leu Leu Val Val Phe Ile Leu Ser Val Cys Phe Gly Ala Gly Leu Phe
625                 630                 635                 640

Val Phe Val Leu Lys Arg Arg Lys Gly Val Pro Ser Val Pro Arg Asn
                645                 650                 655

Thr Asn Asn Leu Asp Val Ser Ser Phe Gln Leu Gln Tyr Gly Ser Tyr
            660                 665                 670

Asn Thr Glu Thr His Asp Lys Thr Asp Gly His Val Tyr Asn Tyr Ile
            675                 680                 685

Pro Pro Pro Val Gly Gln Met Cys Gln Asn Pro Ile Tyr Met Gln Lys
            690                 695                 700

Glu Gly Asp Pro Val Ala Tyr Tyr Arg Asn Leu Gln Glu Phe Ser Tyr
705                 710                 715                 720

Ser Asn Leu Glu Glu Lys Lys Glu Glu Pro Ala Thr Pro Ala Tyr Thr
                725                 730                 735

Ile Ser Ala Thr Glu Leu Leu Glu Lys Gln Ala Thr Pro Arg Glu Pro
            740                 745                 750

Glu Leu Leu Tyr Gln Asn Ile Ala Glu Arg Val Lys Glu Leu Pro Ser
            755                 760                 765

Ala Gly Leu Val His Tyr Asn Phe Cys Thr Leu Pro Lys Arg Gln Phe
770                 775                 780

Ala Pro Ser Tyr Glu Ser Arg Arg Gln Asn Gln Asp Arg Ile Asn Lys
785                 790                 795                 800

Thr Val Leu Tyr Gly Thr Pro Arg Lys Cys Phe Val Gly Gln Ser Lys
                805                 810                 815

Pro Asn His Pro Leu Leu Gln Ala Lys Pro Gln Ser Glu Pro Asp Tyr
            820                 825                 830

Leu Glu Val Leu Glu Lys Gln Thr Ala Ile Ser Gln Leu
            835                 840                 845

<210> SEQ ID NO 16
<211> LENGTH: 469
<212> TYPE: DNA
<213> ORGANISM: Mus musculus

<400> SEQUENCE: 16
ctgaaattcc tgggaaggga ggctatttgt ccagaaaatc ctaacctgtc agatgggact      60
attttgtcaa tgaatcacaa cacagacaca cctagatcac ttagtgtgtc tcctagttct     120
taccccgaac tacacactga agttccactc tccgttttaa ttttaggatt gcttgtggtt     180
tttatcctgt ctgtctgttt tggggcgggg ttgttcgtct tgttctgaa gcgtcgaaag      240 ggagtgccaa atgttcccag gaatgccacc aacttagatg taagttcctt ccagttacaa     300
tatgggtctt acaacaccga gactaatgat aaagctgatg ccacgtcta taactacatt      360 cctccacctg tgggtcagat gtgccaaaac cccatctaca tgcagaagga aggagaccca     420
gtggcctatt accgaaatct gcaggacttc agctatggca acctggagg                469

<210> SEQ ID NO 17
<211> LENGTH: 156
```

```
<212> TYPE: PRT
<213> ORGANISM: Mus musculus

<400> SEQUENCE: 17

Leu Lys Phe Leu Gly Arg Glu Ala Ile Cys Pro Glu Asn Pro Asn Leu
1               5                   10                  15

Ser Asp Gly Thr Ile Leu Ser Met Asn His Asn Thr Asp Thr Pro Arg
            20                  25                  30

Ser Leu Ser Val Ser Pro Ser Tyr Pro Glu Leu His Thr Glu Val
        35                  40                  45

Pro Leu Ser Val Leu Ile Leu Gly Leu Val Val Phe Ile Leu Ser
50                  55                  60

Val Cys Phe Gly Ala Gly Leu Phe Val Phe Val Leu Lys Arg Arg Lys
65                  70                  75                  80

Gly Val Pro Asn Val Pro Arg Asn Ala Thr Asn Leu Asp Val Ser Ser
                85                  90                  95

Phe Gln Leu Gln Tyr Gly Ser Tyr Asn Thr Glu Thr Asn Asp Lys Ala
            100                 105                 110

Asp Gly His Val Tyr Asn Tyr Ile Pro Pro Val Gly Gln Met Cys
        115                 120                 125

Gln Asn Pro Ile Tyr Met Gln Lys Glu Gly Asp Pro Val Ala Tyr Tyr
    130                 135                 140

Arg Asn Leu Gln Asp Phe Ser Tyr Gly Asn Leu Glu
145                 150                 155

<210> SEQ ID NO 18
<211> LENGTH: 3402
<212> TYPE: DNA
<213> ORGANISM: Homo sapiens
<220> FEATURE:
<221> NAME/KEY: CDS
<222> LOCATION: (89)..(2899)
<223> OTHER INFORMATION:

<400> SEQUENCE: 18
tagacgcgga gcccaaggag gtaaaatgca cacttgctgc cccccagtaa ctttggaaca      60
ggaccttcac agaaaaatgc atagctgg atg ctg cag act cta gcg ttt gct       112
                              Met Leu Gln Thr Leu Ala Phe Ala
                              1               5 gta aca tct ctc gtc ctt tcg tgt gca gaa acc atc gat tat tac ggg      160
Val Thr Ser Leu Val Leu Ser Cys Ala Glu Thr Ile Asp Tyr Tyr Gly
        10                  15                  20 gaa atc tgt gac aat gca tgt cct tgt gag gaa aag gac ggc att tta      208
Glu Ile Cys Asp Asn Ala Cys Pro Cys Glu Glu Lys Asp Gly Ile Leu
25                  30                  35                  40 act gtg agc tgt gaa aac cgg ggg atc atc agt ctc tct gaa att agc      256
Thr Val Ser Cys Glu Asn Arg Gly Ile Ile Ser Leu Ser Glu Ile Ser
                45                  50                  55 cct ccc cgt ttc cca atc tac cac ctc ttg ttg tcc gga aac ctt ttg      304
Pro Pro Arg Phe Pro Ile Tyr His Leu Leu Leu Ser Gly Asn Leu Leu
            60                  65                  70 aac cgt ctc tat ccc aat gag ttt gtc aat tac act ggg gct tca att      352
Asn Arg Leu Tyr Pro Asn Glu Phe Val Asn Tyr Thr Gly Ala Ser Ile
        75                  80                  85 ttg cat cta ggt agc aat gtt atc cag gac att gag acc ggg gct ttc      400
Leu His Leu Gly Ser Asn Val Ile Gln Asp Ile Glu Thr Gly Ala Phe
    90                  95                  100 cat ggg cta cgg ggt ttg agg aga ttg cat cta aac aat aat aaa ctg      448
His Gly Leu Arg Gly Leu Arg Arg Leu His Leu Asn Asn Asn Lys Leu
```

-continued

```
            105                 110                 115                 120
gaa ctt ctg cga gat gat acc ttc ctt ggc ttg gag aac ctg gag tac         496
Glu Leu Leu Arg Asp Asp Thr Phe Leu Gly Leu Glu Asn Leu Glu Tyr
                    125                 130                 135 cta cag gtc gat tac aac tac atc agc gtc att gaa ccc aat gct ttt         544
Leu Gln Val Asp Tyr Asn Tyr Ile Ser Val Ile Glu Pro Asn Ala Phe
                140                 145                 150 ggg aaa ctg cat ttg ttg cag gtg ctt atc ctc aat gac aat ctt ttg         592
Gly Lys Leu His Leu Leu Gln Val Leu Ile Leu Asn Asp Asn Leu Leu
            155                 160                 165 tcc agt tta ccc aac aat ctt ttc cgt ttt gtg ccc tta acg cac ttg         640
Ser Ser Leu Pro Asn Asn Leu Phe Arg Phe Val Pro Leu Thr His Leu
        170                 175                 180 gac ctc cgg ggg aac cgg ctg aaa ctt ctg ccc tac gtg ggc ctc ttg         688
Asp Leu Arg Gly Asn Arg Leu Lys Leu Leu Pro Tyr Val Gly Leu Leu
185                 190                 195                 200 cag cac atg gat aaa gtt gtg gag cta cag ctg gag gaa aac cct tgg         736
Gln His Met Asp Lys Val Val Glu Leu Gln Leu Glu Glu Asn Pro Trp
                    205                 210                 215 aat tgt tct tgt gag ctg atc tct cta aag gat tgg ttg gac agc atc         784
Asn Cys Ser Cys Glu Leu Ile Ser Leu Lys Asp Trp Leu Asp Ser Ile
                220                 225                 230 tcc tat tca gcc ctg gtg ggg gat gta gtt tgt gag acc ccc ttc cgc         832
Ser Tyr Ser Ala Leu Val Gly Asp Val Val Cys Glu Thr Pro Phe Arg
            235                 240                 245 tta cac gga agg gac ttg gac gag gta tcc aag cag gaa ctt tgc cca         880
Leu His Gly Arg Asp Leu Asp Glu Val Ser Lys Gln Glu Leu Cys Pro
        250                 255                 260 agg aga ctt att tct gac tac gag atg agg ccg cag acg cct ttg agc         928
Arg Arg Leu Ile Ser Asp Tyr Glu Met Arg Pro Gln Thr Pro Leu Ser
265                 270                 275                 280 acc acg ggg tat tta cac acc acc ccg gcg tca gtg aat tct gtg gcc         976
Thr Thr Gly Tyr Leu His Thr Thr Pro Ala Ser Val Asn Ser Val Ala
                    285                 290                 295 act tct tcc tct gct gtt tac aaa ccc cct ttg aag ccc cct aag ggg        1024
Thr Ser Ser Ser Ala Val Tyr Lys Pro Pro Leu Lys Pro Pro Lys Gly
                300                 305                 310 act cgc caa ccc aac aag ccc agg gtg cgc ccc acc tct cgg cag ccc        1072
Thr Arg Gln Pro Asn Lys Pro Arg Val Arg Pro Thr Ser Arg Gln Pro
            315                 320                 325 tct aag gac ttg ggc tac agc aac tat ggc ccc agc atc gcc tat cag        1120
Ser Lys Asp Leu Gly Tyr Ser Asn Tyr Gly Pro Ser Ile Ala Tyr Gln
        330                 335                 340 acc aaa tcc ccg gtg cct ttg gag tgt ccc acc gcg tgc tct tgc aac        1168
Thr Lys Ser Pro Val Pro Leu Glu Cys Pro Thr Ala Cys Ser Cys Asn
345                 350                 355                 360 ctg cag atc tct gat ctg ggc ctc aac gta aac tgc cag gag cga aag        1216
Leu Gln Ile Ser Asp Leu Gly Leu Asn Val Asn Cys Gln Glu Arg Lys
                    365                 370                 375 atc gag agc atc gct gaa ctg cag ccc aag ccc tac aat ccc aag aaa        1264
Ile Glu Ser Ile Ala Glu Leu Gln Pro Lys Pro Tyr Asn Pro Lys Lys
                380                 385                 390 atg tat ctg aca gag aac tac atc gct gtc gtg cgc agg aca gac ttc        1312
Met Tyr Leu Thr Glu Asn Tyr Ile Ala Val Val Arg Arg Thr Asp Phe
            395                 400                 405 ctg gag gcc acg ggg ctg gac ctc ctg cac ctg ggg aat aac cgc atc        1360
Leu Glu Ala Thr Gly Leu Asp Leu Leu His Leu Gly Asn Asn Arg Ile
        410                 415                 420 tcg atg atc cag gac cgc gct ttc ggg gat ctc acc aac ctg agg cgc        1408
```

```
Ser Met Ile Gln Asp Arg Ala Phe Gly Asp Leu Thr Asn Leu Arg Arg
425                 430                 435                 440 ctc tac ctg aat ggc aac agg atc gag agg ctg agc ccg gag tta ttc    1456
Leu Tyr Leu Asn Gly Asn Arg Ile Glu Arg Leu Ser Pro Glu Leu Phe
                445                 450                 455 tat ggc ctg cag agc ctg cag tat ctc ttc ctc cag tac aat ctc atc    1504
Tyr Gly Leu Gln Ser Leu Gln Tyr Leu Phe Leu Gln Tyr Asn Leu Ile
            460                 465                 470 cgc gag att cag tct gga act ttt gac ccg gtc cca aac ctc cag ctg    1552
Arg Glu Ile Gln Ser Gly Thr Phe Asp Pro Val Pro Asn Leu Gln Leu
        475                 480                 485 cta ttc ttg aat aac aac ctc ctg cag gcc atg ccc tca ggc gtc ttc    1600
Leu Phe Leu Asn Asn Asn Leu Leu Gln Ala Met Pro Ser Gly Val Phe
    490                 495                 500 tct ggc ttg acc ctc ctc agg cta aac ctg agg agt aac cac ttc acc    1648
Ser Gly Leu Thr Leu Leu Arg Leu Asn Leu Arg Ser Asn His Phe Thr
505                 510                 515                 520 tcc ttg cca gtg agt gga gtt ttg gac cag ctg aag tca ctc atc caa    1696
Ser Leu Pro Val Ser Gly Val Leu Asp Gln Leu Lys Ser Leu Ile Gln
                525                 530                 535 atc gac ctg cat gac aat cct tgg gat tgt acc tgt gac att gtg ggc    1744
Ile Asp Leu His Asp Asn Pro Trp Asp Cys Thr Cys Asp Ile Val Gly
            540                 545                 550 atg aag ctg tgg gtg gag cag ctc aaa gtg ggc gtc cta gtg gac gag    1792
Met Lys Leu Trp Val Glu Gln Leu Lys Val Gly Val Leu Val Asp Glu
        555                 560                 565 gtg atc tgt aag gcg ccc aaa aaa ttc gct gag acc gac atg cgc tcc    1840
Val Ile Cys Lys Ala Pro Lys Lys Phe Ala Glu Thr Asp Met Arg Ser
    570                 575                 580 att aag tcg gag ctg ctg tgc cct gac tat tca gat gta gta gtt tcc    1888
Ile Lys Ser Glu Leu Leu Cys Pro Asp Tyr Ser Asp Val Val Val Ser
585                 590                 595                 600 acg ccc aca ccc tcc tct atc cag gtc cct gcg agg acc agc gcc gtg    1936
Thr Pro Thr Pro Ser Ser Ile Gln Val Pro Ala Arg Thr Ser Ala Val
                605                 610                 615 act cct gcg gtc cgg ttg aat agc acc ggg gcc ccc gcg agc ttg ggc    1984
Thr Pro Ala Val Arg Leu Asn Ser Thr Gly Ala Pro Ala Ser Leu Gly
            620                 625                 630 gca ggc gga ggg gcg tcg tcg gtg ccc ttg tct gtg tta att ctc agc    2032
Ala Gly Gly Gly Ala Ser Ser Val Pro Leu Ser Val Leu Ile Leu Ser
        635                 640                 645 ctc ctg ctg gtt ttc atc atg tcc gtc ttc gtg gcc gcc ggg ctc ttc    2080
Leu Leu Leu Val Phe Ile Met Ser Val Phe Val Ala Ala Gly Leu Phe
    650                 655                 660 gtg ctg gtc atg aag cgc agg aag aag aac cag agc gac cac acc agc    2128
Val Leu Val Met Lys Arg Arg Lys Lys Asn Gln Ser Asp His Thr Ser
665                 670                 675                 680 acc aac aac tcc gac gtg agc tcc ttt aac atg cag tac agc gtg tac    2176
Thr Asn Asn Ser Asp Val Ser Ser Phe Asn Met Gln Tyr Ser Val Tyr
                685                 690                 695 ggc ggc ggc ggc ggc acg ggc ggc cac cca cac gcg cac gtg cat cac    2224
Gly Gly Gly Gly Gly Thr Gly Gly His Pro His Ala His Val His His
            700                 705                 710 cgc ggg ccc gcg ctg ccc aag gtg aag acg ccc gcg ggc cac gtg tat    2272
Arg Gly Pro Ala Leu Pro Lys Val Lys Thr Pro Ala Gly His Val Tyr
        715                 720                 725 gaa tac atc ccc cac cca ctg ggc cac atg tgc aaa aac ccc atc tac    2320
Glu Tyr Ile Pro His Pro Leu Gly His Met Cys Lys Asn Pro Ile Tyr
730                 735                 740
```

| | | |
|---|---|---|
| cgc tcc cga gag ggc aac tcc gta gag gat tac aaa gac ctg cac gag<br>Arg Ser Arg Glu Gly Asn Ser Val Glu Asp Tyr Lys Asp Leu His Glu<br>745                              750                               755                           760 | 2368 |

```
cgc tcc cga gag ggc aac tcc gta gag gat tac aaa gac ctg cac gag      2368
Arg Ser Arg Glu Gly Asn Ser Val Glu Asp Tyr Lys Asp Leu His Glu
745                 750                 755                 760 ctc aag gtc acc tac agc agc aac cac cac ctg cag cag cag cag cag      2416
Leu Lys Val Thr Tyr Ser Ser Asn His His Leu Gln Gln Gln Gln Gln
                765                 770                 775 ccg ccg ccg cca ccg cag cag cca cag cag cag ccc ccg ccg cag ctg      2464
Pro Pro Pro Pro Pro Gln Gln Pro Gln Gln Gln Pro Pro Pro Gln Leu
            780                 785                 790 cag ctg cag cct ggg gag gag gag agg cgg gaa agc cac cac ttg cgg      2512
Gln Leu Gln Pro Gly Glu Glu Glu Arg Arg Glu Ser His His Leu Arg
        795                 800                 805 agc ccc gcc tac agc gtc agc acc atc gag ccc cgg gag gac ctg ctg      2560
Ser Pro Ala Tyr Ser Val Ser Thr Ile Glu Pro Arg Glu Asp Leu Leu
    810                 815                 820 tcg ccg gtg cag gac gcc gac cgc ttt tac agg ggc att tta gaa cca      2608
Ser Pro Val Gln Asp Ala Asp Arg Phe Tyr Arg Gly Ile Leu Glu Pro
825                 830                 835                 840 gac aaa cac tgc tcc acc acc ccc gcc ggc aat agc ctc ccg gaa tat      2656
Asp Lys His Cys Ser Thr Thr Pro Ala Gly Asn Ser Leu Pro Glu Tyr
                845                 850                 855 ccc aaa ttc ccg tgc agc ccc gct gct tac act ttc tcc ccc aac tat      2704
Pro Lys Phe Pro Cys Ser Pro Ala Ala Tyr Thr Phe Ser Pro Asn Tyr
            860                 865                 870 gac ctg aga cgc ccc cat cag tat ttg cac ccg ggg gca ggg gac agc      2752
Asp Leu Arg Arg Pro His Gln Tyr Leu His Pro Gly Ala Gly Asp Ser
        875                 880                 885 agg cta cgg gaa ccg gtg ctc tac agc ccc ccg agt gct gtc ttt gta      2800
Arg Leu Arg Glu Pro Val Leu Tyr Ser Pro Pro Ser Ala Val Phe Val
    890                 895                 900 gaa ccc aac cgg aac gaa tat ctg gag tta aaa gca aaa cta aac gtt      2848
Glu Pro Asn Arg Asn Glu Tyr Leu Glu Leu Lys Ala Lys Leu Asn Val
905                 910                 915                 920 gag ccg gac tac ctc gaa gtg ctg gaa aaa cag acc acg ttt agc cag      2896
Glu Pro Asp Tyr Leu Glu Val Leu Glu Lys Gln Thr Thr Phe Ser Gln
                925                 930                 935 ttc taaaagcaaa gaaactctct tggagctttt gcatttaaaa caaacaagca           2949
Phe agcagacaca cacagtgaac acatttgatt aattgtgttg tttcaacgtt tagggtgaag    3009
tgccttggca cgggatttct cagcttcggt ggaagatacg aaaagggtgt gcaatttcct    3069
ttaaaattta cacgtgggaa acatttgtgt aaactgggca catcactttc tcttcttgcg    3129 tgtgggcag gtgtggagaa gggctttaag gaggccaatt tgctgcgcgg gtgacctgtg     3189
aaaggtcaca gtcattttg tagtggttgg aagtgctaag aatggtggat gatggcagag     3249
catagattct actcttcctc ttttgcttcc tccccctccc ccgccctgc cccacctctc     3309 tttctcccct tttaagccat gggtgggtct aactggcttt tgtggagaaa ttagcacacc    3369
ccaactttaa taggaaattt gttctctttt tcc                                 3402
```

<210> SEQ ID NO 19
<211> LENGTH: 937
<212> TYPE: PRT
<213> ORGANISM: Homo sapiens

<400> SEQUENCE: 19

Met Leu Gln Thr Leu Ala Phe Ala Val Thr Ser Leu Val Leu Ser Cys
1               5                   10                 15

Ala Glu Thr Ile Asp Tyr Tyr Gly Glu Ile Cys Asp Asn Ala Cys Pro

```
                20                  25                  30
Cys Glu Glu Lys Asp Gly Ile Leu Thr Val Ser Cys Glu Asn Arg Gly
             35                  40                  45
Ile Ile Ser Leu Ser Glu Ile Ser Pro Pro Arg Phe Pro Ile Tyr His
         50                  55                  60
Leu Leu Leu Ser Gly Asn Leu Leu Asn Arg Leu Tyr Pro Asn Glu Phe
 65                  70                  75                  80
Val Asn Tyr Thr Gly Ala Ser Ile Leu His Leu Gly Ser Asn Val Ile
                 85                  90                  95
Gln Asp Ile Glu Thr Gly Ala Phe His Gly Leu Arg Gly Leu Arg Arg
            100                 105                 110
Leu His Leu Asn Asn Asn Lys Leu Glu Leu Leu Arg Asp Asp Thr Phe
            115                 120                 125
Leu Gly Leu Glu Asn Leu Glu Tyr Leu Gln Val Asp Tyr Asn Tyr Ile
            130                 135                 140
Ser Val Ile Glu Pro Asn Ala Phe Gly Lys Leu His Leu Leu Gln Val
145                 150                 155                 160
Leu Ile Leu Asn Asp Asn Leu Leu Ser Ser Leu Pro Asn Asn Leu Phe
                165                 170                 175
Arg Phe Val Pro Leu Thr His Leu Asp Leu Arg Gly Asn Arg Leu Lys
            180                 185                 190
Leu Leu Pro Tyr Val Gly Leu Leu Gln His Met Asp Lys Val Val Glu
            195                 200                 205
Leu Gln Leu Glu Glu Asn Pro Trp Asn Cys Ser Cys Glu Leu Ile Ser
            210                 215                 220
Leu Lys Asp Trp Leu Asp Ser Ile Ser Tyr Ser Ala Leu Val Gly Asp
225                 230                 235                 240
Val Val Cys Glu Thr Pro Phe Arg Leu His Gly Arg Asp Leu Asp Glu
                245                 250                 255
Val Ser Lys Gln Glu Leu Cys Pro Arg Arg Leu Ile Ser Asp Tyr Glu
            260                 265                 270
Met Arg Pro Gln Thr Pro Leu Ser Thr Thr Gly Tyr Leu His Thr Thr
            275                 280                 285
Pro Ala Ser Val Asn Ser Val Ala Thr Ser Ser Ala Val Tyr Lys
            290                 295                 300
Pro Pro Leu Lys Pro Pro Lys Gly Thr Arg Gln Pro Asn Lys Pro Arg
305                 310                 315                 320
Val Arg Pro Thr Ser Arg Gln Pro Ser Lys Asp Leu Gly Tyr Ser Asn
                325                 330                 335
Tyr Gly Pro Ser Ile Ala Tyr Gln Thr Lys Ser Pro Val Pro Leu Glu
            340                 345                 350
Cys Pro Thr Ala Cys Ser Cys Asn Leu Gln Ile Ser Asp Leu Gly Leu
            355                 360                 365
Asn Val Asn Cys Gln Glu Arg Lys Ile Glu Ser Ile Ala Glu Leu Gln
            370                 375                 380
Pro Lys Pro Tyr Asn Pro Lys Lys Met Tyr Leu Thr Glu Asn Tyr Ile
385                 390                 395                 400
Ala Val Val Arg Arg Thr Asp Phe Leu Glu Ala Thr Gly Leu Asp Leu
                405                 410                 415
Leu His Leu Gly Asn Asn Arg Ile Ser Met Ile Gln Asp Arg Ala Phe
            420                 425                 430
Gly Asp Leu Thr Asn Leu Arg Arg Leu Tyr Leu Asn Gly Asn Arg Ile
            435                 440                 445
```

-continued

```
Glu Arg Leu Ser Pro Glu Leu Phe Tyr Gly Leu Gln Ser Leu Gln Tyr
    450                 455                 460
Leu Phe Leu Gln Tyr Asn Leu Ile Arg Glu Ile Gln Ser Gly Thr Phe
465                 470                 475                 480
Asp Pro Val Pro Asn Leu Gln Leu Leu Phe Leu Asn Asn Asn Leu Leu
                485                 490                 495
Gln Ala Met Pro Ser Gly Val Phe Ser Gly Leu Thr Leu Leu Arg Leu
            500                 505                 510
Asn Leu Arg Ser Asn His Phe Thr Ser Leu Pro Val Ser Gly Val Leu
        515                 520                 525
Asp Gln Leu Lys Ser Leu Ile Gln Ile Asp Leu His Asp Asn Pro Trp
    530                 535                 540
Asp Cys Thr Cys Asp Ile Val Gly Met Lys Leu Trp Val Glu Gln Leu
545                 550                 555                 560
Lys Val Gly Val Leu Val Asp Glu Val Ile Cys Lys Ala Pro Lys Lys
                565                 570                 575
Phe Ala Glu Thr Asp Met Arg Ser Ile Lys Ser Glu Leu Leu Cys Pro
            580                 585                 590
Asp Tyr Ser Asp Val Val Ser Thr Pro Thr Pro Ser Ser Ile Gln
        595                 600                 605
Val Pro Ala Arg Thr Ser Ala Val Thr Pro Ala Val Arg Leu Asn Ser
    610                 615                 620
Thr Gly Ala Pro Ala Ser Leu Gly Ala Gly Gly Ala Ser Ser Val
625                 630                 635                 640
Pro Leu Ser Val Leu Ile Leu Ser Leu Leu Leu Val Phe Ile Met Ser
                645                 650                 655
Val Phe Val Ala Ala Gly Leu Phe Val Leu Val Met Lys Arg Arg Lys
            660                 665                 670
Lys Asn Gln Ser Asp His Thr Ser Thr Asn Asn Ser Asp Val Ser Ser
        675                 680                 685
Phe Asn Met Gln Tyr Ser Val Tyr Gly Gly Gly Gly Thr Gly Gly
    690                 695                 700
His Pro His Ala His Val His His Arg Gly Pro Ala Leu Pro Lys Val
705                 710                 715                 720
Lys Thr Pro Ala Gly His Val Tyr Glu Tyr Ile Pro His Pro Leu Gly
                725                 730                 735
His Met Cys Lys Asn Pro Ile Tyr Arg Ser Arg Glu Gly Asn Ser Val
            740                 745                 750
Glu Asp Tyr Lys Asp Leu His Glu Leu Lys Val Thr Tyr Ser Ser Asn
        755                 760                 765
His His Leu Gln Gln Gln Gln Pro Pro Pro Pro Gln Gln Pro
    770                 775                 780
Gln Gln Gln Pro Pro Gln Leu Gln Leu Gln Pro Gly Glu Glu Glu
785                 790                 795                 800
Arg Arg Glu Ser His His Leu Arg Ser Pro Ala Tyr Ser Val Ser Thr
                805                 810                 815
Ile Glu Pro Arg Glu Asp Leu Leu Ser Pro Val Gln Asp Ala Asp Arg
            820                 825                 830
Phe Tyr Arg Gly Ile Leu Glu Pro Asp Lys His Cys Ser Thr Thr Pro
        835                 840                 845
Ala Gly Asn Ser Leu Pro Glu Tyr Pro Lys Phe Pro Cys Ser Pro Ala
    850                 855                 860
```

```
Ala Tyr Thr Phe Ser Pro Asn Tyr Asp Leu Arg Arg Pro His Gln Tyr
865                 870                 875                 880

Leu His Pro Gly Ala Gly Asp Ser Arg Leu Arg Glu Pro Val Leu Tyr
            885                 890                 895

Ser Pro Pro Ser Ala Val Phe Val Glu Pro Asn Arg Asn Glu Tyr Leu
                900                 905                 910

Glu Leu Lys Ala Lys Leu Asn Val Gly Pro Asp Tyr Leu Glu Val Leu
            915                 920                 925

Glu Lys Gln Thr Thr Phe Ser Gln Phe
        930                 935

<210> SEQ ID NO 20
<211> LENGTH: 406
<212> TYPE: DNA
<213> ORGANISM: Mus musculus

<400> SEQUENCE: 20
aagaacccca tctaccggtc tcgagaaggc aattccgtgg aggattacaa agacctgcac      60
gagctcaagg tcacttacag cagcaaccac cacctgcagc agcagccgcc gccgccgccg     120
caacagcccc agcagcagcc ccctccgcag atgcagatgc agcctgggga ggaggagagg     180
cgggaaagcc accatttgag gagccccgcc tacagcgtca gcaccatcga gccccgagag     240
gacctactgt cgccggtgca ggacgctgat cgcttttaca gggcatttt agagccagac     300 aaacactgct ccactacccc tgcgggcagc agcctcccag aatacccctaa attcccatgc     360 agcccggctg cttacacttt ctccccaaac tatgaccgtt cggccg                    406

<210> SEQ ID NO 21
<211> LENGTH: 135
<212> TYPE: PRT
<213> ORGANISM: Mus musculus

<400> SEQUENCE: 21

Lys Asn Pro Ile Tyr Arg Ser Arg Glu Gly Asn Ser Val Glu Asp Tyr
1               5                   10                  15

Lys Asp Leu His Glu Leu Lys Val Thr Tyr Ser Ser Asn His His Leu
            20                  25                  30

Gln Gln Gln Pro Pro Pro Pro Gln Gln Pro Gln Gln Gln Pro Pro
        35                  40                  45

Pro Gln Met Gln Met Gln Pro Gly Glu Glu Glu Arg Arg Glu Ser His
    50                  55                  60

His Leu Arg Ser Pro Ala Tyr Ser Val Ser Thr Ile Glu Pro Arg Glu
65                  70                  75                  80

Asp Leu Leu Ser Pro Val Gln Asp Ala Asp Arg Phe Tyr Arg Gly Ile
            85                  90                  95

Leu Glu Pro Asp Lys His Cys Ser Thr Thr Pro Ala Gly Ser Ser Leu
            100                 105                 110

Pro Glu Tyr Pro Lys Phe Pro Cys Ser Pro Ala Ala Tyr Thr Phe Ser
        115                 120                 125

Pro Asn Tyr Asp Arg Ser Ala
    130                 135

<210> SEQ ID NO 22
<211> LENGTH: 3545
<212> TYPE: DNA
<213> ORGANISM: Homo sapiens
<220> FEATURE:
<221> NAME/KEY: CDS
```

<222> LOCATION: (112)..(3042)
<223> OTHER INFORMATION:

<400> SEQUENCE: 22

| | | |
|---|---|---|
| ctgatggatt tgcattcagg ttccagccct gcgtttccta tattgactcc ttatacacga | | 60 |
| cctggcgctc cagtttagga ggagacgttg ttttgtaatc aaccacgaac g atg aaa<br>                                                                                                     Met Lys<br>                                                                                                      1 | | 117 |
| cct tcc ata gct gag atg ctt cac aga gga agg atg ttg tgg ata att<br>Pro Ser Ile Ala Glu Met Leu His Arg Gly Arg Met Leu Trp Ile Ile<br>     5                   10                    15 | | 165 |
| ctt cta agc aca att gct cta gga tgg act acc ccg att ccc cta ata<br>Leu Leu Ser Thr Ile Ala Leu Gly Trp Thr Thr Pro Ile Pro Leu Ile<br> 20                     25                    30 | | 213 |
| gag gac tca gag gaa ata gat gag ccc tgt ttt gat cca tgc tac tgt<br>Glu Asp Ser Glu Glu Ile Asp Glu Pro Cys Phe Asp Pro Cys Tyr Cys<br>35                   40                    45                    50 | | 261 |
| gaa gtt aaa gaa agc ctc ttt cat ata cat tgt gac agt aaa gga ttt<br>Glu Val Lys Glu Ser Leu Phe His Ile His Cys Asp Ser Lys Gly Phe<br>                   55                    60                    65 | | 309 |
| aca aat att agt cag att acc gag ttc tgg tca aga cct ttt aaa ctg<br>Thr Asn Ile Ser Gln Ile Thr Glu Phe Trp Ser Arg Pro Phe Lys Leu<br>             70                    75                    80 | | 357 |
| tat ctg cag agg aat tct atg agg aaa tta tat acc aac agt ttt ctt<br>Tyr Leu Gln Arg Asn Ser Met Arg Lys Leu Tyr Thr Asn Ser Phe Leu<br>         85                    90                    95 | | 405 |
| cat ttg aat aat gct gtg tct att aat ctt ggg aac aat gca ttg cag<br>His Leu Asn Asn Ala Val Ser Ile Asn Leu Gly Asn Asn Ala Leu Gln<br>100                    105                   110 | | 453 |
| gac att cag act gga gct ttc aat ggt ctt aag att tta aag aga cta<br>Asp Ile Gln Thr Gly Ala Phe Asn Gly Leu Lys Ile Leu Lys Arg Leu<br>115                    120                   125                   130 | | 501 |
| tat cta cat gaa aac aaa cta gat gtc ttc aga aat gac acc ttc ctt<br>Tyr Leu His Glu Asn Lys Leu Asp Val Phe Arg Asn Asp Thr Phe Leu<br>                  135                   140                 145 | | 549 |
| ggc ttg gaa agt cta gaa tat ctg cag gca gat tac aat gtc att aaa<br>Gly Leu Glu Ser Leu Glu Tyr Leu Gln Ala Asp Tyr Asn Val Ile Lys<br>            150                    155                    160 | | 597 |
| cgt att gag agt ggg gca ttt cgg aac cta agt aaa ttg agg gtt ctg<br>Arg Ile Glu Ser Gly Ala Phe Arg Asn Leu Ser Lys Leu Arg Val Leu<br>         165                   170                   175 | | 645 |
| att tta aat gat aat ctc atc ccc atg ctt cca acc aat tta ttt aag<br>Ile Leu Asn Asp Asn Leu Ile Pro Met Leu Pro Thr Asn Leu Phe Lys<br>180                    185                   190 | | 693 |
| gct gtc tct tta acc cat ttg gac cta cgt gga aat agg tta aag gtt<br>Ala Val Ser Leu Thr His Leu Asp Leu Arg Gly Asn Arg Leu Lys Val<br>195                    200                   205                   210 | | 741 |
| ctt ttt tac cga gga atg cta gat cac att ggc aga agc ctg atg gag<br>Leu Phe Tyr Arg Gly Met Leu Asp His Ile Gly Arg Ser Leu Met Glu<br>                  215                   220                 225 | | 789 |
| ctc cag ctg gaa gaa aac cct tgg aac tgt aca tgt gaa att gta caa<br>Leu Gln Leu Glu Glu Asn Pro Trp Asn Cys Thr Cys Glu Ile Val Gln<br>            230                    235                    240 | | 837 |
| ctg aag agt tgg ctg gaa cgc att cct tat act gcc ctg gtg gga gac<br>Leu Lys Ser Trp Leu Glu Arg Ile Pro Tyr Thr Ala Leu Val Gly Asp<br>         245                   250                   255 | | 885 |
| att acc tgt gag acc cct ttc cac ttc cat gga aag gac cta cga gaa<br>Ile Thr Cys Glu Thr Pro Phe His Phe His Gly Lys Asp Leu Arg Glu<br>260                    265                   270 | | 933 |

```
atc agg aag aca gaa ctc tgt ccc ttg ttg tct gac tct gag gta gag    981
Ile Arg Lys Thr Glu Leu Cys Pro Leu Leu Ser Asp Ser Glu Val Glu
275                 280                 285                 290 gct agt ttg gga att cca cat tcg tca agt aag gag aat gca tgg       1029
Ala Ser Leu Gly Ile Pro His Ser Ser Ser Lys Glu Asn Ala Trp
            295                 300                 305 cca act aag cct tcc tca atg cta tcc tct gtt cat ttt act gct tct   1077
Pro Thr Lys Pro Ser Ser Met Leu Ser Ser Val His Phe Thr Ala Ser
                310                 315                 320 tct gtc gaa tac aag tcc tca aat aaa cag cct aag ccc acc aaa cag   1125
Ser Val Glu Tyr Lys Ser Ser Asn Lys Gln Pro Lys Pro Thr Lys Gln
            325                 330                 335 cct cga aca cca agg cca ccc tcc acc tcc caa gct tta tat cct ggt   1173
Pro Arg Thr Pro Arg Pro Pro Ser Thr Ser Gln Ala Leu Tyr Pro Gly
340                 345                 350 cca aac cag cct ccc att gct cct tat cag acc aga cca cca atc ccc   1221
Pro Asn Gln Pro Pro Ile Ala Pro Tyr Gln Thr Arg Pro Pro Ile Pro
355                 360                 365                 370 att ata tgc ccc act ggg tgt acc tgt aat ttg cac atc aat gac ctt   1269
Ile Ile Cys Pro Thr Gly Cys Thr Cys Asn Leu His Ile Asn Asp Leu
                375                 380                 385 ggc ttg act gtc aac tgc aaa gag cga gga ttt aat aac att tct gaa   1317
Gly Leu Thr Val Asn Cys Lys Glu Arg Gly Phe Asn Asn Ile Ser Glu
            390                 395                 400 ctt ctt cca agg ccc ttg aat gcc aag aaa ctg tat ctg agt agc aat   1365
Leu Leu Pro Arg Pro Leu Asn Ala Lys Lys Leu Tyr Leu Ser Ser Asn
        405                 410                 415 ctg att cag aaa ata tac cgt tct gat ttt tgg aat ttt tct tcc ttg   1413
Leu Ile Gln Lys Ile Tyr Arg Ser Asp Phe Trp Asn Phe Ser Ser Leu
420                 425                 430 gat ctc ttg cat ctg ggg aac aat cgt att tcc tat gtc caa gat ggg   1461
Asp Leu Leu His Leu Gly Asn Asn Arg Ile Ser Tyr Val Gln Asp Gly
435                 440                 445                 450 gcc ttt atc aac ttg ccc aac tta aag agc ctc ttc ctt aat ggc aac   1509
Ala Phe Ile Asn Leu Pro Asn Leu Lys Ser Leu Phe Leu Asn Gly Asn
                455                 460                 465 gat ata gag aag ctg aca cca ggc atg ttc cga ggc cta cag agt ttg   1557
Asp Ile Glu Lys Leu Thr Pro Gly Met Phe Arg Gly Leu Gln Ser Leu
            470                 475                 480 cac tac ttg tac ttt gag ttc aat gtc atc cgg gaa atc cag cct gca   1605
His Tyr Leu Tyr Phe Glu Phe Asn Val Ile Arg Glu Ile Gln Pro Ala
        485                 490                 495 gcc ttc agc ctc atg ccc aac ttg aag ctg cta ttc ctc aat aat aac   1653
Ala Phe Ser Leu Met Pro Asn Leu Lys Leu Leu Phe Leu Asn Asn Asn
500                 505                 510 tta ctg agg act ctg cca aca gac gcc ttt gct ggc aca tcc ctg gcc   1701
Leu Leu Arg Thr Leu Pro Thr Asp Ala Phe Ala Gly Thr Ser Leu Ala
515                 520                 525                 530 cgg ctc aac ctg agg aag aac tac ttc ctc tat ctt ccc gtg gct ggt   1749
Arg Leu Asn Leu Arg Lys Asn Tyr Phe Leu Tyr Leu Pro Val Ala Gly
                535                 540                 545 gtc ctg gaa cac ttg aat gcc att gtc cag ata gac ctc aat gag aat   1797
Val Leu Glu His Leu Asn Ala Ile Val Gln Ile Asp Leu Asn Glu Asn
            550                 555                 560 cct tgg gac tgc acc tgt gac ctg gtc ccc ttt aaa cag tgg atc gaa   1845
Pro Trp Asp Cys Thr Cys Asp Leu Val Pro Phe Lys Gln Trp Ile Glu
        565                 570                 575 acc atc agc tca gtc agt gtg gtt ggt gat gtg ctt tgc agg agc cct   1893
Thr Ile Ser Ser Val Ser Val Val Gly Asp Val Leu Cys Arg Ser Pro
580                 585                 590
```

```
gag aac ctc acg cac cgt gat gtg cgc act att gag ctg gaa gtt ctt    1941
Glu Asn Leu Thr His Arg Asp Val Arg Thr Ile Glu Leu Glu Val Leu
595                 600                 605                 610 tgc cca gag atg ctg cac gtt gca cca gct gga gaa tcc cca gcc cag    1989
Cys Pro Glu Met Leu His Val Ala Pro Ala Gly Glu Ser Pro Ala Gln
                615                 620                 625 cct gga gat tct cac ctt att ggg gca cca acc agt gca tca cct tat    2037
Pro Gly Asp Ser His Leu Ile Gly Ala Pro Thr Ser Ala Ser Pro Tyr
            630                 635                 640 gag ttt tct cct cct ggg ggc cct gtg cca ctt tct gtg tta att ctc    2085
Glu Phe Ser Pro Pro Gly Gly Pro Val Pro Leu Ser Val Leu Ile Leu
        645                 650                 655 agc ctg ctg gtt ctg ttt ttc tca gca gtc ttt gtt gct gca ggc ctc    2133
Ser Leu Leu Val Leu Phe Phe Ser Ala Val Phe Val Ala Ala Gly Leu
    660                 665                 670 ttt gcc tac gtg ctc cga agg cgt cga aag aag ctg ccc ttc aga agc    2181
Phe Ala Tyr Val Leu Arg Arg Arg Lys Lys Leu Pro Phe Arg Ser
675                 680                 685                 690 aag cgg cag gaa ggt gtg gac ctt act ggc atc caa atg caa tgc cac    2229
Lys Arg Gln Glu Gly Val Asp Leu Thr Gly Ile Gln Met Gln Cys His
                695                 700                 705 agg ctg ttt gag gat ggt gga ggt ggt ggt ggc gga agt ggg ggt ggt    2277
Arg Leu Phe Glu Asp Gly Gly Gly Gly Gly Gly Gly Ser Gly Gly Gly
            710                 715                 720 ggt cga cca act ctt tcc tct cca gag aag gcc cct ccc gtg ggt cat    2325
Gly Arg Pro Thr Leu Ser Ser Pro Glu Lys Ala Pro Pro Val Gly His
        725                 730                 735 gtg tat gag tac atc ccc cac ccg gtt acc caa atg tgc aac aac ccc    2373
Val Tyr Glu Tyr Ile Pro His Pro Val Thr Gln Met Cys Asn Asn Pro
    740                 745                 750 atc tac aag cct cgt gag gag gag gag gtg gct gtt tca tca gcc caa    2421
Ile Tyr Lys Pro Arg Glu Glu Glu Glu Val Ala Val Ser Ser Ala Gln
755                 760                 765                 770 gaa gca ggg agt gca gaa cgt ggg ggt cca ggg aca caa cca ccg gga    2469
Glu Ala Gly Ser Ala Glu Arg Gly Gly Pro Gly Thr Gln Pro Pro Gly
                775                 780                 785 atg ggt gag gct ctc cta gga agt gag cag ttt gct gag aca ccc aag    2517
Met Gly Glu Ala Leu Leu Gly Ser Glu Gln Phe Ala Glu Thr Pro Lys
            790                 795                 800 gag aac cat agt aac tac cgg acc ttg ctg gaa aaa gag aag gag tgg    2565
Glu Asn His Ser Asn Tyr Arg Thr Leu Leu Glu Lys Glu Lys Glu Trp
        805                 810                 815 gcc cta gca gtg tcc agc tcc cag ctt aac acc ata gtg acg gtg aat    2613
Ala Leu Ala Val Ser Ser Ser Gln Leu Asn Thr Ile Val Thr Val Asn
    820                 825                 830 cac cat cac cct cac cac cca gca gtt ggt ggg gtt tca gga gta gtt    2661
His His His Pro His His Pro Ala Val Gly Gly Val Ser Gly Val Val
835                 840                 845                 850 ggg gga act ggg gga gac ttg gca ggg ttc cgc cac cat gag aaa aat    2709
Gly Gly Thr Gly Gly Asp Leu Ala Gly Phe Arg His His Glu Lys Asn
                855                 860                 865 ggt ggg gtg gtg ctg ttt cct cct ggg gga ggc tgt ggt agt ggc agt    2757
Gly Gly Val Val Leu Phe Pro Pro Gly Gly Gly Cys Gly Ser Gly Ser
            870                 875                 880 atg cta cta gat cga gag agg cca cag cct gcc ccc tgc aca gtg gga    2805
Met Leu Leu Asp Arg Glu Arg Pro Gln Pro Ala Pro Cys Thr Val Gly
        885                 890                 895 ttt gtg gac tgt ctc tat gga aca gtg ccc aaa tta aag gaa ctg cac    2853
Phe Val Asp Cys Leu Tyr Gly Thr Val Pro Lys Leu Lys Glu Leu His
```

```
                 900             905             910
gtg cac cct cct ggc atg caa tac cca gac tta cag cag gat gcc agg    2901
Val His Pro Pro Gly Met Gln Tyr Pro Asp Leu Gln Gln Asp Ala Arg
915             920             925             930 ctc aaa gaa acc ctt ctc ttc tcg gct gaa aag ggc ttc aca gac cac    2949
Leu Lys Glu Thr Leu Leu Phe Ser Ala Glu Lys Gly Phe Thr Asp His
            935             940             945 caa acc caa aaa agt gat tac ctc gag tta agg gcc aaa ctt caa acc    2997
Gln Thr Gln Lys Ser Asp Tyr Leu Glu Leu Arg Ala Lys Leu Gln Thr
        950             955             960 aag ccg gat tac ctc gaa gtc ctg gag aag aca aca tac agg ttc        3042
Lys Pro Asp Tyr Leu Glu Val Leu Glu Lys Thr Thr Tyr Arg Phe
    965             970             975 taacagagag aagaaaatat attagtgctt ttttttttc aaagaaaag gaaaataaaa    3102 gaaatatatc ccttgctccc tttacacttg tcccagtaac tccatcctca cgatctttcc  3162 tacccctgaac aaaactaaaa ccgcatgata actagagaat acagatgtat gctctcccct 3222 ctcagatgcg atttggagga agggccatac tcagatcatt aatcaatgaa agtgccttcg  3282 cagactttg ccagcaaatg ttatcattat tttttttatac tgaaacttga gactttgact  3342
gtgccatgta aagatatac tggggatcat tgtatggatc ctaattaagt aaaattcaat   3402
gtgtcttttt attttcagta actatttttt ttatagttgt agttttgatt taagggggg   3462 gaaacaagtt gacatttgtc atttgtggct ttctttctta tcatcatggc acagattctg  3522
tacatgtatt aacaatgcag ttt                                         3545

<210> SEQ ID NO 23
<211> LENGTH: 977
<212> TYPE: PRT
<213> ORGANISM: Homo sapiens

<400> SEQUENCE: 23

Met Lys Pro Ser Ile Ala Glu Met Leu His Arg Gly Arg Met Leu Trp
1               5                   10                  15

Ile Ile Leu Leu Ser Thr Ile Ala Leu Gly Trp Thr Thr Pro Ile Pro
            20                  25                  30

Leu Ile Glu Asp Ser Glu Glu Ile Asp Glu Pro Cys Phe Asp Pro Cys
        35                  40                  45

Tyr Cys Glu Val Lys Glu Ser Leu Phe His Ile His Cys Asp Ser Lys
    50                  55                  60

Gly Phe Thr Asn Ile Ser Gln Ile Thr Glu Phe Trp Ser Arg Pro Phe
65                  70                  75                  80

Lys Leu Tyr Leu Gln Arg Asn Ser Met Arg Lys Leu Tyr Thr Asn Ser
                85                  90                  95

Phe Leu His Leu Asn Asn Ala Val Ser Ile Asn Leu Gly Asn Asn Ala
            100                 105                 110

Leu Gln Asp Ile Gln Thr Gly Ala Phe Asn Gly Leu Lys Ile Leu Lys
        115                 120                 125

Arg Leu Tyr Leu His Glu Asn Lys Leu Asp Val Phe Arg Asn Asp Thr
    130                 135                 140

Phe Leu Gly Leu Glu Ser Leu Glu Tyr Leu Gln Ala Asp Tyr Asn Val
145                 150                 155                 160

Ile Lys Arg Ile Glu Ser Gly Ala Phe Arg Asn Leu Ser Lys Leu Arg
                165                 170                 175

Val Leu Ile Leu Asn Asp Asn Leu Ile Pro Met Leu Pro Thr Asn Leu
            180                 185                 190
```

```
Phe Lys Ala Val Ser Leu Thr His Leu Asp Leu Arg Gly Asn Arg Leu
            195                 200                 205

Lys Val Leu Phe Tyr Arg Gly Met Leu Asp His Ile Gly Arg Ser Leu
    210                 215                 220

Met Glu Leu Gln Leu Glu Glu Asn Pro Trp Asn Cys Thr Cys Glu Ile
225                 230                 235                 240

Val Gln Leu Lys Ser Trp Leu Glu Arg Ile Pro Tyr Thr Ala Leu Val
                245                 250                 255

Gly Asp Ile Thr Cys Glu Thr Pro Phe His Phe His Gly Lys Asp Leu
            260                 265                 270

Arg Glu Ile Arg Lys Thr Glu Leu Cys Pro Leu Leu Ser Asp Ser Glu
        275                 280                 285

Val Glu Ala Ser Leu Gly Ile Pro His Ser Ser Ser Lys Glu Asn
    290                 295                 300

Ala Trp Pro Thr Lys Pro Ser Ser Met Leu Ser Ser Val His Phe Thr
305                 310                 315                 320

Ala Ser Ser Val Glu Tyr Lys Ser Ser Asn Lys Gln Pro Lys Pro Thr
                325                 330                 335

Lys Gln Pro Arg Thr Pro Arg Pro Ser Thr Ser Gln Ala Leu Tyr
            340                 345                 350

Pro Gly Pro Asn Gln Pro Ile Ala Pro Tyr Gln Thr Arg Pro Pro
        355                 360                 365

Ile Pro Ile Ile Cys Pro Thr Gly Cys Thr Cys Asn Leu His Ile Asn
    370                 375                 380

Asp Leu Gly Leu Thr Val Asn Cys Lys Glu Arg Gly Phe Asn Asn Ile
385                 390                 395                 400

Ser Glu Leu Leu Pro Arg Pro Leu Asn Ala Lys Lys Leu Tyr Leu Ser
                405                 410                 415

Ser Asn Leu Ile Gln Lys Ile Tyr Arg Ser Asp Phe Trp Asn Phe Ser
            420                 425                 430

Ser Leu Asp Leu Leu His Leu Gly Asn Asn Arg Ile Ser Tyr Val Gln
        435                 440                 445

Asp Gly Ala Phe Ile Asn Leu Pro Asn Leu Lys Ser Leu Phe Leu Asn
450                 455                 460

Gly Asn Asp Ile Glu Lys Leu Thr Pro Gly Met Phe Arg Gly Leu Gln
465                 470                 475                 480

Ser Leu His Tyr Leu Tyr Phe Glu Phe Asn Val Ile Arg Glu Ile Gln
                485                 490                 495

Pro Ala Ala Phe Ser Leu Met Pro Asn Leu Lys Leu Leu Phe Leu Asn
            500                 505                 510

Asn Asn Leu Leu Arg Thr Leu Pro Thr Asp Ala Phe Ala Gly Thr Ser
        515                 520                 525

Leu Ala Arg Leu Asn Leu Arg Lys Asn Tyr Phe Leu Tyr Leu Pro Val
530                 535                 540

Ala Gly Val Leu Glu His Leu Asn Ala Ile Val Gln Ile Asp Leu Asn
545                 550                 555                 560

Glu Asn Pro Trp Asp Cys Thr Cys Asp Leu Val Pro Phe Lys Gln Trp
                565                 570                 575

Ile Glu Thr Ile Ser Ser Val Ser Val Gly Asp Val Leu Cys Arg
            580                 585                 590

Ser Pro Glu Asn Leu Thr His Arg Asp Val Arg Thr Ile Glu Leu Glu
        595                 600                 605
```

-continued

```
Val Leu Cys Pro Glu Met Leu His Val Ala Pro Ala Gly Glu Ser Pro
    610                 615                 620
Ala Gln Pro Gly Asp Ser His Leu Ile Gly Ala Pro Thr Ser Ala Ser
625                 630                 635                 640
Pro Tyr Glu Phe Ser Pro Pro Gly Gly Pro Val Pro Leu Ser Val Leu
                645                 650                 655
Ile Leu Ser Leu Leu Val Leu Phe Phe Ser Ala Val Phe Val Ala Ala
            660                 665                 670
Gly Leu Phe Ala Tyr Val Leu Arg Arg Arg Lys Lys Leu Pro Phe
        675                 680                 685
Arg Ser Lys Arg Gln Glu Gly Val Asp Leu Thr Gly Ile Gln Met Gln
    690                 695                 700
Cys His Arg Leu Phe Glu Asp Gly Gly Gly Gly Gly Gly Ser Gly
705                 710                 715                 720
Gly Gly Gly Arg Pro Thr Leu Ser Ser Pro Glu Lys Ala Pro Pro Val
                725                 730                 735
Gly His Val Tyr Glu Tyr Ile Pro His Pro Val Thr Gln Met Cys Asn
            740                 745                 750
Asn Pro Ile Tyr Lys Pro Arg Glu Glu Glu Val Ala Val Ser Ser
        755                 760                 765
Ala Gln Glu Ala Gly Ser Ala Glu Arg Gly Gly Pro Gly Thr Gln Pro
    770                 775                 780
Pro Gly Met Gly Glu Ala Leu Leu Gly Ser Glu Gln Phe Ala Glu Thr
785                 790                 795                 800
Pro Lys Glu Asn His Ser Asn Tyr Arg Thr Leu Leu Glu Lys Glu Lys
                805                 810                 815
Glu Trp Ala Leu Ala Val Ser Ser Gln Leu Asn Thr Ile Val Thr
            820                 825                 830
Val Asn His His His Pro His His Pro Ala Val Gly Gly Val Ser Gly
        835                 840                 845
Val Val Gly Gly Thr Gly Gly Asp Leu Ala Gly Phe Arg His His Glu
    850                 855                 860
Lys Asn Gly Gly Val Val Leu Phe Pro Pro Gly Gly Cys Gly Ser
865                 870                 875                 880
Gly Ser Met Leu Leu Asp Arg Glu Arg Pro Gln Pro Ala Pro Cys Thr
                885                 890                 895
Val Gly Phe Val Asp Cys Leu Tyr Gly Thr Val Pro Lys Leu Lys Glu
            900                 905                 910
Leu His Val His Pro Pro Gly Met Gln Tyr Pro Asp Leu Gln Gln Asp
        915                 920                 925
Ala Arg Leu Lys Glu Thr Leu Leu Phe Ser Ala Glu Lys Gly Phe Thr
    930                 935                 940
Asp His Gln Thr Gln Lys Ser Asp Tyr Leu Glu Leu Arg Ala Lys Leu
945                 950                 955                 960
Gln Thr Lys Pro Asp Tyr Leu Glu Val Leu Glu Lys Thr Thr Tyr Arg
                965                 970                 975
Phe

<210> SEQ ID NO 24
<211> LENGTH: 2631
<212> TYPE: DNA
<213> ORGANISM: Homo sapiens
<220> FEATURE:
<221> NAME/KEY: CDS
<222> LOCATION: (118)..(2628)
```

-continued

<223> OTHER INFORMATION:

<400> SEQUENCE: 24

| | | |
|---|---|---|
| atgatttaca tacaagtaat ttttcaagta atgaccattg aaaaaatgtt ttcttttttat | | 60 |
| tttttagatt atttctcttt attcagaagc atacagttgt ttgctgattg caagaag | | 117 |

| atg ttt ctg tgg ctg ttt ctg att ttg tca gcc ctg att tct tcg aca | | 165 |
| Met Phe Leu Trp Leu Phe Leu Ile Leu Ser Ala Leu Ile Ser Ser Thr | | |
| 1               5                   10                  15 | | |

| aat gca gat tct gac ata tcg gtg gaa att tgc aat gtg tgt tcc tgc | | 213 |
| Asn Ala Asp Ser Asp Ile Ser Val Glu Ile Cys Asn Val Cys Ser Cys | | |
|             20                  25                  30 | | |

| gtg tca gtt gag aat gtg ctc tat gtc aac tgt gag aag gtt tca gtc | | 261 |
| Val Ser Val Glu Asn Val Leu Tyr Val Asn Cys Glu Lys Val Ser Val | | |
|         35                  40                  45 | | |

| tac aga cca aat cag ctg aaa cca cct tgg tct aat ttt tat cac ctc | | 309 |
| Tyr Arg Pro Asn Gln Leu Lys Pro Pro Trp Ser Asn Phe Tyr His Leu | | |
|     50                  55                  60 | | |

| aat ttc caa aat aat ttt tta aat att ctg tat cca aat aca ttc ttg | | 357 |
| Asn Phe Gln Asn Asn Phe Leu Asn Ile Leu Tyr Pro Asn Thr Phe Leu | | |
| 65                  70                  75                  80 | | |

| aat ttt tca cat gca gtc tcc ctg cat ctg ggg aat aat aaa ctg cag | | 405 |
| Asn Phe Ser His Ala Val Ser Leu His Leu Gly Asn Asn Lys Leu Gln | | |
|                 85                  90                  95 | | |

| aac att gag gga gga gcc ttt ctt ggg ctc agt gca tta aag cag ttg | | 453 |
| Asn Ile Glu Gly Gly Ala Phe Leu Gly Leu Ser Ala Leu Lys Gln Leu | | |
|             100                 105                 110 | | |

| cac ttg aac aac aat gaa tta aag att ctc cga gct gac act ttc ctt | | 501 |
| His Leu Asn Asn Asn Glu Leu Lys Ile Leu Arg Ala Asp Thr Phe Leu | | |
|         115                 120                 125 | | |

| ggc ata gag aac ttg gag tat ctc cag gct gac tac aat tta atc aag | | 549 |
| Gly Ile Glu Asn Leu Glu Tyr Leu Gln Ala Asp Tyr Asn Leu Ile Lys | | |
|     130                 135                 140 | | |

| tat att gaa cga gga gcc ttc aat aag ctc cac aaa ctg aaa gtt ctc | | 597 |
| Tyr Ile Glu Arg Gly Ala Phe Asn Lys Leu His Lys Leu Lys Val Leu | | |
| 145                 150                 155                 160 | | |

| att ctt aat gac aat ctg att tca ttc ctt cct gat aat att ttc cga | | 645 |
| Ile Leu Asn Asp Asn Leu Ile Ser Phe Leu Pro Asp Asn Ile Phe Arg | | |
|                 165                 170                 175 | | |

| ttc gca tct ttg acc cat ctg gat ata cga ggg aac aga atc cag aag | | 693 |
| Phe Ala Ser Leu Thr His Leu Asp Ile Arg Gly Asn Arg Ile Gln Lys | | |
|             180                 185                 190 | | |

| ctc cct tat atc ggg gtt ctg gaa cac att ggc cgt gtc gtt gaa ttg | | 741 |
| Leu Pro Tyr Ile Gly Val Leu Glu His Ile Gly Arg Val Val Glu Leu | | |
|         195                 200                 205 | | |

| caa ctg gaa gat aac cct tgg aac tgt agc tgt gat tta ttg ccc tta | | 789 |
| Gln Leu Glu Asp Asn Pro Trp Asn Cys Ser Cys Asp Leu Leu Pro Leu | | |
|     210                 215                 220 | | |

| aaa gct tgg ctg gag aac atg cca tat aac att tac ata gga gaa gct | | 837 |
| Lys Ala Trp Leu Glu Asn Met Pro Tyr Asn Ile Tyr Ile Gly Glu Ala | | |
| 225                 230                 235                 240 | | |

| atc tgt gaa act ccc agt gac tta tat gga agg ctt tta aaa gaa acc | | 885 |
| Ile Cys Glu Thr Pro Ser Asp Leu Tyr Gly Arg Leu Leu Lys Glu Thr | | |
|                 245                 250                 255 | | |

| aac aaa caa gag cta tgt ccc atg ggc acc ggc agt gat ttt gac gtg | | 933 |
| Asn Lys Gln Glu Leu Cys Pro Met Gly Thr Gly Ser Asp Phe Asp Val | | |
|             260                 265                 270 | | |

| cgc atc ctg cct cca tct cag ctg gaa aat ggc tac acc act ccc aat | | 981 |
| Arg Ile Leu Pro Pro Ser Gln Leu Glu Asn Gly Tyr Thr Thr Pro Asn | | |
|         275                 280                 285 | | |

-continued

| | |
|---|---|
| ggt cac act acc caa aca tct tta cac aga tta gta act aaa cca cca<br>Gly His Thr Thr Gln Thr Ser Leu His Arg Leu Val Thr Lys Pro Pro<br>290                     295                    300 | 1029 |
| aaa aca aca aat cct tcc aag atc tct gga atc gtt gca ggc aaa gcc<br>Lys Thr Thr Asn Pro Ser Lys Ile Ser Gly Ile Val Ala Gly Lys Ala<br>305                     310                   315                 320 | 1077 |
| ctc tcc aac cgc aat ctc agt cag att gtg tct tac caa aca agg gtg<br>Leu Ser Asn Arg Asn Leu Ser Gln Ile Val Ser Tyr Gln Thr Arg Val<br>                    325                   330                   335 | 1125 |
| cct cct cta aca cct tgc ccg gca cct tgc ttc tgc aaa aca cac cct<br>Pro Pro Leu Thr Pro Cys Pro Ala Pro Cys Phe Cys Lys Thr His Pro<br>            340                   345                   350 | 1173 |
| tca gat ttg gga cta agt gtg aac tgc caa gag aaa aat ata cag tct<br>Ser Asp Leu Gly Leu Ser Val Asn Cys Gln Glu Lys Asn Ile Gln Ser<br>                   355                   360                   365 | 1221 |
| atg tct gaa ctg ata ccg aaa cct tta aat gcg aag aag ctg cac gtc<br>Met Ser Glu Leu Ile Pro Lys Pro Leu Asn Ala Lys Lys Leu His Val<br>370                     375                   380 | 1269 |
| aat ggc aat agc atc aag gat gtg gac gta tca gac ttc act gac ttt<br>Asn Gly Asn Ser Ile Lys Asp Val Asp Val Ser Asp Phe Thr Asp Phe<br>385                     390                   395                 400 | 1317 |
| gaa gga ctg gat ttg ctt cat tta ggc agc aat caa att aca gtg att<br>Glu Gly Leu Asp Leu Leu His Leu Gly Ser Asn Gln Ile Thr Val Ile<br>                         405                   410                   415 | 1365 |
| aag gga gac gta ttt cac aat ctc act aat tta cgc agg cta tat ctc<br>Lys Gly Asp Val Phe His Asn Leu Thr Asn Leu Arg Arg Leu Tyr Leu<br>            420                   425                   430 | 1413 |
| aat ggc aat caa att gag aga ctc tat cct gaa ata ttt tca ggt ctt<br>Asn Gly Asn Gln Ile Glu Arg Leu Tyr Pro Glu Ile Phe Ser Gly Leu<br>                   435                   440                   445 | 1461 |
| cat aac ctg cag tat ctg tat ttg gaa tac aat ttg att aag gaa atc<br>His Asn Leu Gln Tyr Leu Tyr Leu Glu Tyr Asn Leu Ile Lys Glu Ile<br>450                     455                   460 | 1509 |
| tca gca ggc acc ttt gac tcc atg cca aat ttg cag tta ctg tac tta<br>Ser Ala Gly Thr Phe Asp Ser Met Pro Asn Leu Gln Leu Leu Tyr Leu<br>465                     470                   475                 480 | 1557 |
| aac aat aat ctc cta aag agc ctg cct gtt tac atc ttt tcc gga gca<br>Asn Asn Asn Leu Leu Lys Ser Leu Pro Val Tyr Ile Phe Ser Gly Ala<br>                   485                   490                   495 | 1605 |
| ccc tta gct aga ctg aac ctg agg aac aac aaa ttc atg tac ctg cct<br>Pro Leu Ala Arg Leu Asn Leu Arg Asn Asn Lys Phe Met Tyr Leu Pro<br>            500                   505                   510 | 1653 |
| gtc agt ggg gtc ctt gat cag ttg caa tct ctt aca cag att gac ttg<br>Val Ser Gly Val Leu Asp Gln Leu Gln Ser Leu Thr Gln Ile Asp Leu<br>               515                   520                   525 | 1701 |
| gag ggc aac cca tgg gac tgt act tgt gac ttg gtg gca tta aag ctg<br>Glu Gly Asn Pro Trp Asp Cys Thr Cys Asp Leu Val Ala Leu Lys Leu<br>530                     535                   540 | 1749 |
| tgg gtg gag aag ttg agc gac ggg att gtt gtg aaa gaa ctg aaa tgt<br>Trp Val Glu Lys Leu Ser Asp Gly Ile Val Val Lys Glu Leu Lys Cys<br>545                     550                   555                 560 | 1797 |
| gag acg cct gtt cag ttt gcc aac att gaa ctg aag tcc ctc aaa aat<br>Glu Thr Pro Val Gln Phe Ala Asn Ile Glu Leu Lys Ser Leu Lys Asn<br>                   565                   570                   575 | 1845 |
| gaa atc tta tgt ccc aaa ctt tta aat aag ccg tct gca cca ttc aca<br>Glu Ile Leu Cys Pro Lys Leu Leu Asn Lys Pro Ser Ala Pro Phe Thr<br>            580                   585                   590 | 1893 |
| agc cct gca cct gcc att aca ttc acc act cct ttg ggt ccc att cga<br>Ser Pro Ala Pro Ala Ile Thr Phe Thr Thr Pro Leu Gly Pro Ile Arg | 1941 |

```
                    595                 600                 605
agt cct cct ggt ggg cca gtg cct ctg tct att tta atc tta agt atc          1989
Ser Pro Pro Gly Gly Pro Val Pro Leu Ser Ile Leu Ile Leu Ser Ile
        610                 615                 620 tta gtg gtc ctc att tta acg gtg ttt gtt gct ttt tgc ctt ctt gtt          2037
Leu Val Val Leu Ile Leu Thr Val Phe Val Ala Phe Cys Leu Leu Val
625                 630                 635                 640 ttt gtc ctg cga cgc aac aag aaa ccc aca gtg aag cac gaa ggc ctg          2085
Phe Val Leu Arg Arg Asn Lys Lys Pro Thr Val Lys His Glu Gly Leu
                645                 650                 655 ggg aat cct gac tgt ggc tcc atg cag ctg cag cta agg aag cat gac          2133
Gly Asn Pro Asp Cys Gly Ser Met Gln Leu Gln Leu Arg Lys His Asp
            660                 665                 670 cac aaa acc aat aaa aaa gat gga ctg agc aca gaa gct ttc att cca          2181
His Lys Thr Asn Lys Lys Asp Gly Leu Ser Thr Glu Ala Phe Ile Pro
        675                 680                 685 caa act ata gaa cag atg agc aag agc cac act tgt ggc ttg aaa gag          2229
Gln Thr Ile Glu Gln Met Ser Lys Ser His Thr Cys Gly Leu Lys Glu
    690                 695                 700 tca gaa act ggg ttc atg ttt tca gat cct cca gga cag aaa gtt gtt          2277
Ser Glu Thr Gly Phe Met Phe Ser Asp Pro Pro Gly Gln Lys Val Val
705                 710                 715                 720 atg aga aat gtg gcc gac aag gag aaa gat tta tta cat gta gat acc          2325
Met Arg Asn Val Ala Asp Lys Glu Lys Asp Leu Leu His Val Asp Thr
                725                 730                 735 agg aag aga ctg agc aca att gat gag ctg gat gaa tta ttc cct agc          2373
Arg Lys Arg Leu Ser Thr Ile Asp Glu Leu Asp Glu Leu Phe Pro Ser
            740                 745                 750 agg gat tcc aat gtg ttt att cag aat ttt ctt gaa agc aaa aag gag          2421
Arg Asp Ser Asn Val Phe Ile Gln Asn Phe Leu Glu Ser Lys Lys Glu
        755                 760                 765 tat aat agc ata ggt gtc agt ggc ttt gag atc cgc tat cca gaa aaa          2469
Tyr Asn Ser Ile Gly Val Ser Gly Phe Glu Ile Arg Tyr Pro Glu Lys
    770                 775                 780 caa cca gac aaa aaa agt aag aag tca ctg ata ggt ggc aac cac agt          2517
Gln Pro Asp Lys Lys Ser Lys Lys Ser Leu Ile Gly Gly Asn His Ser
785                 790                 795                 800 aaa att gtt gtg gaa caa agg aag agt gag tat ttt gaa ctg aag gcg          2565
Lys Ile Val Val Glu Gln Arg Lys Ser Glu Tyr Phe Glu Leu Lys Ala
                805                 810                 815 aaa ctg cag agt tcc cct gac tac cta cag gtc ctt gag gag caa aca          2613
Lys Leu Gln Ser Ser Pro Asp Tyr Leu Gln Val Leu Glu Glu Gln Thr
            820                 825                 830 gct ttg aac aag atc tag                                                  2631
Ala Leu Asn Lys Ile
        835

<210> SEQ ID NO 25
<211> LENGTH: 837
<212> TYPE: PRT
<213> ORGANISM: Homo sapiens

<400> SEQUENCE: 25

Met Phe Leu Trp Leu Phe Leu Ile Leu Ser Ala Leu Ile Ser Ser Thr
1               5                   10                  15

Asn Ala Asp Ser Asp Ile Ser Val Glu Ile Cys Asn Val Cys Ser Cys
            20                  25                  30

Val Ser Val Glu Asn Val Leu Tyr Val Asn Cys Glu Lys Val Ser Val
        35                  40                  45
```

-continued

```
Tyr Arg Pro Asn Gln Leu Lys Pro Pro Trp Ser Asn Phe Tyr His Leu
 50                  55                  60

Asn Phe Gln Asn Asn Phe Leu Asn Ile Leu Tyr Pro Asn Thr Phe Leu
 65                  70                  75                  80

Asn Phe Ser His Ala Val Ser Leu His Leu Gly Asn Asn Lys Leu Gln
                 85                  90                  95

Asn Ile Glu Gly Gly Ala Phe Leu Gly Leu Ser Ala Leu Lys Gln Leu
            100                 105                 110

His Leu Asn Asn Asn Glu Leu Lys Ile Leu Arg Ala Asp Thr Phe Leu
        115                 120                 125

Gly Ile Glu Asn Leu Glu Tyr Leu Gln Ala Asp Tyr Asn Leu Ile Lys
    130                 135                 140

Tyr Ile Glu Arg Gly Ala Phe Asn Lys Leu His Lys Leu Lys Val Leu
145                 150                 155                 160

Ile Leu Asn Asp Asn Leu Ile Ser Phe Leu Pro Asp Asn Ile Phe Arg
                165                 170                 175

Phe Ala Ser Leu Thr His Leu Asp Ile Arg Gly Asn Arg Ile Gln Lys
            180                 185                 190

Leu Pro Tyr Ile Gly Val Leu Glu His Ile Gly Arg Val Val Glu Leu
        195                 200                 205

Gln Leu Glu Asp Asn Pro Trp Asn Cys Ser Cys Asp Leu Leu Pro Leu
    210                 215                 220

Lys Ala Trp Leu Glu Asn Met Pro Tyr Asn Ile Tyr Ile Gly Glu Ala
225                 230                 235                 240

Ile Cys Glu Thr Pro Ser Asp Leu Tyr Gly Arg Leu Leu Lys Glu Thr
                245                 250                 255

Asn Lys Gln Glu Leu Cys Pro Met Gly Thr Gly Ser Asp Phe Asp Val
            260                 265                 270

Arg Ile Leu Pro Pro Ser Gln Leu Glu Asn Gly Tyr Thr Thr Pro Asn
        275                 280                 285

Gly His Thr Thr Gln Thr Ser Leu His Arg Leu Val Thr Lys Pro Pro
    290                 295                 300

Lys Thr Thr Asn Pro Ser Lys Ile Ser Gly Ile Val Ala Gly Lys Ala
305                 310                 315                 320

Leu Ser Asn Arg Asn Leu Ser Gln Ile Val Ser Tyr Gln Thr Arg Val
                325                 330                 335

Pro Pro Leu Thr Pro Cys Pro Ala Pro Cys Phe Cys Lys Thr His Pro
            340                 345                 350

Ser Asp Leu Gly Leu Ser Val Asn Cys Gln Glu Lys Asn Ile Gln Ser
        355                 360                 365

Met Ser Glu Leu Ile Pro Lys Pro Leu Asn Ala Lys Lys Leu His Val
    370                 375                 380

Asn Gly Asn Ser Ile Lys Asp Val Asp Val Ser Asp Phe Thr Asp Phe
385                 390                 395                 400

Glu Gly Leu Asp Leu Leu His Leu Gly Ser Asn Gln Ile Thr Val Ile
                405                 410                 415

Lys Gly Asp Val Phe His Asn Leu Thr Asn Leu Arg Arg Leu Tyr Leu
            420                 425                 430

Asn Gly Asn Gln Ile Glu Arg Leu Tyr Pro Glu Ile Phe Ser Gly Leu
        435                 440                 445

His Asn Leu Gln Tyr Leu Tyr Leu Glu Tyr Asn Leu Ile Lys Glu Ile
    450                 455                 460

Ser Ala Gly Thr Phe Asp Ser Met Pro Asn Leu Gln Leu Leu Tyr Leu
```

```
                465                 470                 475                 480
Asn Asn Asn Leu Leu Lys Ser Leu Pro Val Tyr Ile Phe Ser Gly Ala
            485                 490                 495

Pro Leu Ala Arg Leu Asn Leu Arg Asn Asn Lys Phe Met Tyr Leu Pro
            500                 505                 510

Val Ser Gly Val Leu Asp Gln Leu Gln Ser Leu Thr Gln Ile Asp Leu
            515                 520                 525

Glu Gly Asn Pro Trp Asp Cys Thr Cys Asp Leu Val Ala Leu Lys Leu
            530                 535                 540

Trp Val Glu Lys Leu Ser Asp Gly Ile Val Lys Glu Leu Lys Cys
545                 550                 555                 560

Glu Thr Pro Val Gln Phe Ala Asn Ile Glu Leu Lys Ser Leu Lys Asn
            565                 570                 575

Glu Ile Leu Cys Pro Lys Leu Leu Asn Lys Pro Ser Ala Pro Phe Thr
            580                 585                 590

Ser Pro Ala Pro Ala Ile Thr Phe Thr Thr Pro Leu Gly Pro Ile Arg
            595                 600                 605

Ser Pro Pro Gly Gly Pro Val Pro Leu Ser Ile Leu Ile Leu Ser Ile
            610                 615                 620

Leu Val Val Leu Ile Leu Thr Val Phe Val Ala Phe Cys Leu Leu Val
625                 630                 635                 640

Phe Val Leu Arg Arg Asn Lys Lys Pro Thr Val Lys His Glu Gly Leu
            645                 650                 655

Gly Asn Pro Asp Cys Gly Ser Met Gln Leu Gln Leu Arg Lys His Asp
            660                 665                 670

His Lys Thr Asn Lys Lys Asp Gly Leu Ser Thr Glu Ala Phe Ile Pro
            675                 680                 685

Gln Thr Ile Glu Gln Met Ser Lys Ser His Thr Cys Gly Leu Lys Glu
            690                 695                 700

Ser Glu Thr Gly Phe Met Phe Ser Asp Pro Pro Gly Gln Lys Val Val
705                 710                 715                 720

Met Arg Asn Val Ala Asp Lys Glu Lys Asp Leu Leu His Val Asp Thr
            725                 730                 735

Arg Lys Arg Leu Ser Thr Ile Asp Glu Leu Asp Glu Leu Phe Pro Ser
            740                 745                 750

Arg Asp Ser Asn Val Phe Ile Gln Asn Phe Leu Glu Ser Lys Lys Glu
            755                 760                 765

Tyr Asn Ser Ile Gly Val Ser Gly Phe Glu Ile Arg Tyr Pro Glu Lys
            770                 775                 780

Gln Pro Asp Lys Lys Ser Lys Lys Ser Leu Ile Gly Gly Asn His Ser
785                 790                 795                 800

Lys Ile Val Val Glu Gln Arg Lys Ser Glu Tyr Phe Glu Leu Lys Ala
            805                 810                 815

Lys Leu Gln Ser Ser Pro Asp Tyr Leu Gln Val Leu Glu Glu Gln Thr
            820                 825                 830

Ala Leu Asn Lys Ile
            835

<210> SEQ ID NO 26
<211> LENGTH: 1694
<212> TYPE: DNA
<213> ORGANISM: Homo sapiens

<400> SEQUENCE: 26
```

-continued

```
tcactctatg aacagcacat ggtgagcccc atggttcatg tctatagaag tccatccttt      60
ggtccaaagc atctggaaga ggaagaagag aggaatgaga agaaggaag tgatgcaaaa      120
catctccaaa gaagtctttt ggaacaggaa atcattcac cactcacagg gtcaaatatg      180
aaatacaaaa ccacgaacca atcaacagaa tttttatcct tccaagatgc cagctcattg      240
tacagaaaca ttttagaaaa agaaaggaa cttcagcaac tgggaatcac agaataccta      300
aggaaaaaca ttgctcagct ccagcctgat atggaggcac attatcctgg agcccacgaa      360
gagctgaagt taatggaaac attaatgtac tcacgtccaa ggaaggtatt agtggaacag      420
acaaaaaatg agtattttga acttaaagct aatttacatg ctgaacctga ctatttagaa      480
gtcctggagc agcaaacata gatggagagt ttgagggctt cgcagaaat gctgtgattc      540
tgttttaagt ccatacctg taaataagtg ccttacgtga gtgtgtcatc aatcagaacc      600
taagcacagc agtaaactat ggggaaaaaa aagaagaag aaagaaact cagggatcac      660
tgggagaagc catggcatta tcttcaggca atttagtctg tcccaaataa aataaatcct      720
tgcatgtaaa tcattcaagg gttatagtaa tatttcatat actgaaaagt gtctcatagg      780
agtcctcttg cacatctaaa aaggctgaac atttaagtat cccgcaattt tcttgaattg      840
ctttccctat agattaatta caattggatt tcatcattta aaaaccatac ttgtatatgt      900
agttataata tgtaaggaat acattgttta taaccagtag gtacttcaaa aatgtgtatt      960
gtcaaacata cctaactttc ttgcaataaa tgcaaaagaa actggaactt gacaattata     1020
aatagtaata gtgaagaaaa aatagaaagg ttgcaattat ataggccatg ggtggctcaa     1080
aactttgaac atttgagctt aaacaaatgc cactctcatg cattctaaat taaaaagtta     1140
aaatgattaa tagttcaggt ggaagaaata agcatacttt ttgggttttc tacacatttt     1200
gtgtagacaa ttttaatgtc agtgctgctg tgaactaaag tatgtcattt atgctcaaag     1260
tttaattctt cttcttggga tattttaaaa atgctactga gattctgctg taaatatgac     1320
tagagaatat attgggtttg ctttatttca taggcttaat tctttgtaaa tctgaatgac     1380
cataatagaa atacatttct tgtggcaagt aattcacagt tgtaaagtaa ataggaaaaa     1440
ttattttatt tttattgatg tacattgata gatgccataa atcagtagca aaggcactt     1500
ctaaaggtaa gtggtttaag ttgcctcaag agagggacaa tgtagcttta ttttacaaga     1560
aggcatagtt agatttctat gaaatattta ttctgtacag ttttatatag ttttggttca     1620
caaaagtaat tattcttggg tgcctttcaa gaaaattaaa aatactactc actacaataa     1680
aactaaaatg aaaa                                                      1694
```

<210> SEQ ID NO 27
<211> LENGTH: 841
<212> TYPE: PRT
<213> ORGANISM: Homo sapiens

<400> SEQUENCE: 27

Met Lys Leu Trp Ile His Leu Phe Tyr Ser Ser Leu Ala Cys Ile
1               5                   10                  15

Ser Leu His Ser Gln Thr Pro Val Leu Ser Ser Arg Gly Ser Cys Asp
                20                  25                  30

Ser Leu Cys Asn Cys Glu Glu Lys Asp Gly Thr Met Leu Ile Asn Cys
            35                  40                  45

Glu Ala Lys Gly Ile Lys Met Val Ser Glu Ile Ser Val Pro Pro Ser
        50                  55                  60

Arg Pro Phe Gln Leu Ser Leu Leu Asn Asn Gly Leu Thr Met Leu His

-continued

```
                65                  70                  75                  80
Thr Asn Asp Phe Ser Gly Leu Thr Asn Ala Ile Ser Ile His Leu Gly
                    85                  90                  95
Phe Asn Asn Ile Ala Asp Ile Glu Ile Gly Ala Phe Asn Gly Leu Gly
                100                 105                 110
Leu Leu Lys Gln Leu His Ile Asn His Asn Ser Leu Glu Ile Leu Lys
                115                 120                 125
Glu Asp Thr Phe His Gly Leu Glu Asn Leu Glu Phe Leu Gln Ala Asp
                130                 135                 140
Asn Asn Phe Ile Thr Val Ile Glu Pro Ser Ala Phe Ser Lys Leu Asn
145                 150                 155                 160
Arg Leu Lys Val Leu Ile Leu Asn Asp Asn Ala Ile Glu Ser Leu Pro
                165                 170                 175
Pro Asn Ile Phe Arg Phe Val Pro Leu Thr His Leu Asp Leu Arg Gly
                180                 185                 190
Asn Gln Leu Gln Thr Leu Pro Tyr Val Gly Phe Leu Glu His Ile Gly
                195                 200                 205
Arg Ile Leu Asp Leu Gln Leu Glu Asp Asn Lys Trp Ala Cys Asn Cys
                210                 215                 220
Asp Leu Leu Gln Leu Lys Thr Trp Leu Glu Asn Met Pro Pro Gln Ser
225                 230                 235                 240
Ile Ile Gly Asp Val Val Cys Asn Ser Pro Pro Phe Phe Lys Gly Ser
                245                 250                 255
Ile Leu Ser Arg Leu Lys Lys Glu Ser Ile Cys Pro Thr Pro Pro Val
                260                 265                 270
Tyr Glu Glu His Glu Asp Pro Ser Gly Ser Leu His Leu Ala Ala Thr
                275                 280                 285
Ser Ser Ile Asn Asp Ser Arg Met Ser Thr Lys Thr Thr Ser Ile Leu
                290                 295                 300
Lys Leu Pro Thr Lys Ala Pro Gly Leu Ile Pro Tyr Ile Thr Lys Pro
305                 310                 315                 320
Ser Thr Gln Leu Pro Gly Pro Tyr Cys Pro Ile Pro Cys Asn Cys Lys
                325                 330                 335
Val Leu Ser Pro Ser Gly Leu Leu Ile His Cys Gln Glu Arg Asn Ile
                340                 345                 350
Glu Ser Leu Ser Asp Leu Arg Pro Pro Gln Asn Pro Arg Lys Leu
                355                 360                 365
Ile Leu Ala Gly Asn Ile Ile His Ser Leu Met Lys Ser Asp Leu Val
                370                 375                 380
Glu Tyr Phe Thr Leu Glu Met Leu His Leu Gly Asn Asn Arg Ile Glu
385                 390                 395                 400
Val Leu Glu Glu Gly Ser Phe Met Asn Leu Thr Arg Leu Gln Lys Leu
                405                 410                 415
Tyr Leu Asn Gly Asn His Leu Thr Lys Leu Ser Lys Gly Met Phe Leu
                420                 425                 430
Gly Leu His Asn Leu Glu Tyr Leu Tyr Leu Glu Tyr Asn Ala Ile Lys
                435                 440                 445
Glu Ile Leu Pro Gly Thr Phe Asn Pro Met Pro Lys Leu Lys Val Leu
                450                 455                 460
Tyr Leu Asn Asn Asn Leu Leu Gln Val Leu Pro Pro His Ile Phe Ser
465                 470                 475                 480
Gly Val Pro Leu Thr Lys Val Asn Leu Lys Thr Asn Gln Phe Thr His
                485                 490                 495
```

Leu Pro Val Ser Asn Ile Leu Asp Asp Leu Asp Leu Leu Thr Gln Ile
            500                 505                 510

Asp Leu Glu Asp Asn Pro Trp Asp Cys Ser Cys Asp Leu Val Gly Leu
        515                 520                 525

Gln Gln Trp Ile Gln Lys Leu Ser Lys Asn Thr Val Thr Asp Asp Ile
    530                 535                 540

Leu Cys Thr Ser Pro Gly His Leu Asp Lys Lys Glu Leu Lys Ala Leu
545                 550                 555                 560

Asn Ser Glu Ile Leu Cys Pro Gly Leu Val Asn Asn Pro Ser Met Pro
                565                 570                 575

Thr Gln Thr Ser Tyr Leu Met Val Thr Thr Pro Ala Thr Thr Thr Asn
            580                 585                 590

Thr Ala Asp Thr Ile Leu Arg Ser Leu Thr Asp Ala Val Pro Leu Ser
        595                 600                 605

Val Leu Ile Leu Gly Leu Leu Ile Met Phe Ile Thr Ile Val Phe Cys
    610                 615                 620

Ala Ala Gly Ile Val Val Leu Val Leu His Arg Arg Arg Arg Tyr Lys
625                 630                 635                 640

Lys Lys Gln Val Asp Glu Gln Met Arg Asp Asn Ser Pro Val His Leu
                645                 650                 655

Gln Tyr Ser Met Tyr Gly His Lys Thr Thr His His Thr Thr Glu Arg
            660                 665                 670

Pro Ser Ala Ser Leu Tyr Glu Gln His Met Val Ser Pro Met Val His
        675                 680                 685

Val Tyr Arg Ser Pro Ser Phe Gly Pro Lys His Leu Glu Glu Glu Glu
    690                 695                 700

Glu Arg Asn Glu Lys Glu Gly Ser Asp Ala Lys His Leu Gln Arg Ser
705                 710                 715                 720

Leu Leu Glu Gln Glu Asn His Ser Pro Leu Thr Gly Ser Asn Met Lys
                725                 730                 735

Tyr Lys Thr Thr Asn Gln Ser Thr Glu Phe Leu Ser Phe Gln Asp Ala
            740                 745                 750

Ser Ser Leu Tyr Arg Asn Ile Leu Glu Lys Glu Arg Glu Leu Gln Gln
        755                 760                 765

Leu Gly Ile Thr Glu Tyr Leu Arg Lys Asn Ile Ala Gln Leu Gln Pro
    770                 775                 780

Asp Met Glu Ala His Tyr Pro Gly Ala His Glu Glu Leu Lys Leu Met
785                 790                 795                 800

Glu Thr Leu Met Tyr Ser Arg Pro Arg Lys Val Leu Val Glu Gln Thr
                805                 810                 815

Lys Asn Glu Tyr Phe Glu Leu Lys Ala Asn Leu His Ala Glu Pro Asp
            820                 825                 830

Tyr Leu Glu Val Leu Glu Gln Gln Thr
        835                 840

<210> SEQ ID NO 28
<211> LENGTH: 639
<212> TYPE: DNA
<213> ORGANISM: Homo sapiens
<220> FEATURE:
<221> NAME/KEY: CDS
<222> LOCATION: (1)..(636)
<223> OTHER INFORMATION:

<400> SEQUENCE: 28

| | | |
|---|---|---|
| atg gtt tta ccc tca tat tca aaa tca gag gga ggg tca tta ttg gat<br>Met Val Leu Pro Ser Tyr Ser Lys Ser Glu Gly Gly Ser Leu Leu Asp<br>1                    5                    10                 15 | | 48 |
| atc tac tgt tta ctc acg tat tgg atg gag gtg gtg ccc acc ctc ttg<br>Ile Tyr Cys Leu Leu Thr Tyr Trp Met Glu Val Val Pro Thr Leu Leu<br>                    20                    25                    30 | | 96 |
| gca gag aca aag att cca gcc act gat gtc gct gat gcc agc ctg aat<br>Ala Glu Thr Lys Ile Pro Ala Thr Asp Val Ala Asp Ala Ser Leu Asn<br>             35                    40                    45 | | 144 |
| gaa tgt tcc agt acc gaa agg aaa caa gac gta gtg ttg ctg ttc gtg<br>Glu Cys Ser Ser Thr Glu Arg Lys Gln Asp Val Val Leu Leu Phe Val<br>      50                    55                    60 | | 192 |
| acc ttg tcc cac aca cag cca cct ctg ttt cac ctg cct tat gtc cag<br>Thr Leu Ser His Thr Gln Pro Pro Leu Phe His Leu Pro Tyr Val Gln<br>65                    70                    75                    80 | | 240 |
| aaa ccc tta atc tct aat gtg gag cag ctg atc ctg ggg atc ccg ggc<br>Lys Pro Leu Ile Ser Asn Val Glu Gln Leu Ile Leu Gly Ile Pro Gly<br>                    85                    90                    95 | | 288 |
| cag aat cgc cgg gag ata ggc cat ggc cag gat atc ttt cca gca gag<br>Gln Asn Arg Arg Glu Ile Gly His Gly Gln Asp Ile Phe Pro Ala Glu<br>             100                    105                   110 | | 336 |
| aag ctc tgc cat ctg cag gat cgc aag gtg aac ctt cac aga gct gcc<br>Lys Leu Cys His Leu Gln Asp Arg Lys Val Asn Leu His Arg Ala Ala<br>             115                    120                   125 | | 384 |
| tgg ggc gag tgt att gtt gca ccc aag act ctc agc ttc tct tac tgt<br>Trp Gly Glu Cys Ile Val Ala Pro Lys Thr Leu Ser Phe Ser Tyr Cys<br>      130                    135                    140 | | 432 |
| cag ggg acc tgc ccg gcc ctc aac agt gag ctc cgt cat tcc agc ttt<br>Gln Gly Thr Cys Pro Ala Leu Asn Ser Glu Leu Arg His Ser Ser Phe<br>145                    150                    155                    160 | | 480 |
| gag tgc tat aag agg gca gta cct acc tgt ccc tgg ctc ttc cag acc<br>Glu Cys Tyr Lys Arg Ala Val Pro Thr Cys Pro Trp Leu Phe Gln Thr<br>             165                    170                   175 | | 528 |
| tgc cgt ccc acc atg gtc aga ctc ttc tcc ctg atg gtc cag gat gac<br>Cys Arg Pro Thr Met Val Arg Leu Phe Ser Leu Met Val Gln Asp Asp<br>             180                    185                   190 | | 576 |
| gaa cac aag atg agt gtg cac tat gtg aac act tcc ttg gtg gag aag<br>Glu His Lys Met Ser Val His Tyr Val Asn Thr Ser Leu Val Glu Lys<br>             195                    200                   205 | | 624 |
| tgt ggc tgc tct tga<br>Cys Gly Cys Ser<br>      210 | | 639 |

<210> SEQ ID NO 29
<211> LENGTH: 212
<212> TYPE: PRT
<213> ORGANISM: Homo sapiens

<400> SEQUENCE: 29

Met Val Leu Pro Ser Tyr Ser Lys Ser Glu Gly Gly Ser Leu Leu Asp
1                  5                  10               15

Ile Tyr Cys Leu Leu Thr Tyr Trp Met Glu Val Val Pro Thr Leu Leu
                  20                  25                  30

Ala Glu Thr Lys Ile Pro Ala Thr Asp Val Ala Asp Ala Ser Leu Asn
           35                    40                    45

Glu Cys Ser Ser Thr Glu Arg Lys Gln Asp Val Val Leu Leu Phe Val
     50                    55                    60

Thr Leu Ser His Thr Gln Pro Pro Leu Phe His Leu Pro Tyr Val Gln
65                  70                  75                  80

```
Lys Pro Leu Ile Ser Asn Val Glu Gln Leu Ile Leu Gly Ile Pro Gly
                85                  90                  95

Gln Asn Arg Arg Glu Ile Gly His Gly Gln Asp Ile Phe Pro Ala Glu
            100                 105                 110

Lys Leu Cys His Leu Gln Asp Arg Lys Val Asn Leu His Arg Ala Ala
        115                 120                 125

Trp Gly Glu Cys Ile Val Ala Pro Lys Thr Leu Ser Phe Ser Tyr Cys
    130                 135                 140

Gln Gly Thr Cys Pro Ala Leu Asn Ser Glu Leu Arg His Ser Ser Phe
145                 150                 155                 160

Glu Cys Tyr Lys Arg Ala Val Pro Thr Cys Pro Trp Leu Phe Gln Thr
                165                 170                 175

Cys Arg Pro Thr Met Val Arg Leu Phe Ser Leu Met Val Gln Asp Asp
            180                 185                 190

Glu His Lys Met Ser Val His Tyr Val Asn Thr Ser Leu Val Glu Lys
        195                 200                 205

Cys Gly Cys Ser
    210

<210> SEQ ID NO 30
<211> LENGTH: 1061
<212> TYPE: DNA
<213> ORGANISM: Homo sapiens
<220> FEATURE:
<221> NAME/KEY: CDS
<222> LOCATION: (204)..(860)
<223> OTHER INFORMATION:

<400> SEQUENCE: 30
tggccaggca gaggtctgtg gagtggagag gcgaggcctc acggtggaac tctcagatga        60
cagcatgcag gcaccaagag agtggacgca catacagaag acagccatgc actgagctgg      120
ggacatgcaa caataacagg tgagttccaa caaattggtt caaaagagg ggggataaac       180 acgctggccc atgctgggca agc atg gca cca cct tcc agg cac tgt ctt ctt      233
                           Met Ala Pro Pro Ser Arg His Cys Leu Leu
                             1               5                  10 ctg atc agc act ctg ggt gtc ttt gca ctt aac tgc ttc acc aaa ggt        281
Leu Ile Ser Thr Leu Gly Val Phe Ala Leu Asn Cys Phe Thr Lys Gly
            15                  20                  25 cag aag aac agc acg ctc atc ttc aca agg gaa aac acc att cgg aac        329
Gln Lys Asn Ser Thr Leu Ile Phe Thr Arg Glu Asn Thr Ile Arg Asn
        30                  35                  40 tgc agc tgt tct gcg gac atc cgg gat tgt gac tac agt ttg gcc aac        377
Cys Ser Cys Ser Ala Asp Ile Arg Asp Cys Asp Tyr Ser Leu Ala Asn
    45                  50                  55 ctg atg tgc aac tgt aaa acc gtc ctg ccc ctt gca gta gag cga acc        425
Leu Met Cys Asn Cys Lys Thr Val Leu Pro Leu Ala Val Glu Arg Thr
60                  65                  70 agc tac aat ggc cat ctg acc atc tgg ttc acg gac aca tct gcg ctg        473
Ser Tyr Asn Gly His Leu Thr Ile Trp Phe Thr Asp Thr Ser Ala Leu
            75                  80                  85                  90 ggc cac ctg ctg aac ttc acg ctg gtc caa gac ctg aag ctt tcc ctg        521
Gly His Leu Leu Asn Phe Thr Leu Val Gln Asp Leu Lys Leu Ser Leu
                95                 100                 105 tgc agc acc aac act ctc ccc act gaa tac ctg gct att tgt ggt ctg        569
Cys Ser Thr Asn Thr Leu Pro Thr Glu Tyr Leu Ala Ile Cys Gly Leu
            110                 115                 120 aag agg ctg cgc atc aac atg gag gcc aag cat ccc ttc cca gag cag        617
Lys Arg Leu Arg Ile Asn Met Glu Ala Lys His Pro Phe Pro Glu Gln
```

-continued

```
                125                 130                 135
agc tta ctc atc cat agc ggt ggg gac agt gac tcc aga gag aag ccc    665
Ser Leu Leu Ile His Ser Gly Gly Asp Ser Asp Ser Arg Glu Lys Pro
    140                 145                 150 atg tgg tta cac aaa ggc tgg cag cca tgt atg tat atc tca ttc tta    713
Met Trp Leu His Lys Gly Trp Gln Pro Cys Met Tyr Ile Ser Phe Leu
155                 160                 165                 170 gat atg gct ctt ttc aac agg gac tca gcc tta aaa tca tat agt att    761
Asp Met Ala Leu Phe Asn Arg Asp Ser Ala Leu Lys Ser Tyr Ser Ile
                175                 180                 185 gaa aac gtt acc agc att gcc aac aac ttt cct gac ttt tct tac ttt    809
Glu Asn Val Thr Ser Ile Ala Asn Asn Phe Pro Asp Phe Ser Tyr Phe
            190                 195                 200 aga acc ttc cca atg cca agc aac aaa agc tat gtt gtc aca ttt att    857
Arg Thr Phe Pro Met Pro Ser Asn Lys Ser Tyr Val Val Thr Phe Ile
        205                 210                 215 tac tagcataata actgtgtcca gctgcctgga actttggcaa atgatgaata         910
Tyr atttgcagaa ggaatctgga ataaggccg tgagataggt atccctaccc acaactgtgc    970
ctctctccgc aggctccatt tgcaacacag ccacacatac caataaccag ctctctgttc   1030
tgctctgtgc ccaactgcga gaacactttt g                                  1061
```

<210> SEQ ID NO 31
<211> LENGTH: 219
<212> TYPE: PRT
<213> ORGANISM: Homo sapiens

<400> SEQUENCE: 31

```
Met Ala Pro Pro Ser Arg His Cys Leu Leu Ile Ser Thr Leu Gly
1               5                   10                  15

Val Phe Ala Leu Asn Cys Phe Thr Lys Gly Gln Lys Asn Ser Thr Leu
            20                  25                  30

Ile Phe Thr Arg Glu Asn Thr Ile Arg Asn Cys Ser Cys Ser Ala Asp
        35                  40                  45

Ile Arg Asp Cys Asp Tyr Ser Leu Ala Asn Leu Met Cys Asn Cys Lys
    50                  55                  60

Thr Val Leu Pro Leu Ala Val Glu Arg Thr Ser Tyr Asn Gly His Leu
65                  70                  75                  80

Thr Ile Trp Phe Thr Asp Thr Ser Ala Leu Gly His Leu Leu Asn Phe
                85                  90                  95

Thr Leu Val Gln Asp Leu Lys Leu Ser Leu Cys Ser Thr Asn Thr Leu
            100                 105                 110

Pro Thr Glu Tyr Leu Ala Ile Cys Gly Leu Lys Arg Leu Arg Ile Asn
        115                 120                 125

Met Glu Ala Lys His Pro Phe Pro Glu Gln Ser Leu Leu Ile His Ser
    130                 135                 140

Gly Gly Asp Ser Asp Ser Arg Glu Lys Pro Met Trp Leu His Lys Gly
145                 150                 155                 160

Trp Gln Pro Cys Met Tyr Ile Ser Phe Leu Asp Met Ala Leu Phe Asn
                165                 170                 175

Arg Asp Ser Ala Leu Lys Ser Tyr Ser Ile Glu Asn Val Thr Ser Ile
            180                 185                 190

Ala Asn Asn Phe Pro Asp Phe Ser Tyr Phe Arg Thr Phe Pro Met Pro
        195                 200                 205

Ser Asn Lys Ser Tyr Val Val Thr Phe Ile Tyr
```

```
                      210               215

<210> SEQ ID NO 32
<211> LENGTH: 921
<212> TYPE: DNA
<213> ORGANISM: Mus musculus
<220> FEATURE:
<221> NAME/KEY: CDS
<222> LOCATION: (255)..(890)
<223> OTHER INFORMATION:

<400> SEQUENCE: 32
accagtggtg acctcatgat ctcctcgtca gttctgcctg tgaagggtcc caccatctct    60
aacatcacca cactggagcc tcagcttctg agacaggaac tcttacagat gagccacaga  120
ctagagcact tttatgcgca ccacgggagc acatgctatc agtgctggcg agagtttgg   180 gggtaaggag gtgacctaca atggactggc tcatgaggga gaaacaggaa cacaccagtc  240
catgctggac aaga atg aca tca cct tcc agc ttc tgc ctc ctt ctg ctc    290
              Met Thr Ser Pro Ser Ser Phe Cys Leu Leu Leu Leu
                1               5                   10 caa gcg cta ggc atc gtt gcc ctt ggc cac ttc aca aaa gct cag aac    338
Gln Ala Leu Gly Ile Val Ala Leu Gly His Phe Thr Lys Ala Gln Asn
         15                  20                  25 aac aca ctg att ttc aca aaa gga aat acc att cgc aac tgc agc tgc    386
Asn Thr Leu Ile Phe Thr Lys Gly Asn Thr Ile Arg Asn Cys Ser Cys
         30                  35                  40 cca gta gac atc agg gac tgt gac tac agt ttg gct aac ttg ata tgc    434
Pro Val Asp Ile Arg Asp Cys Asp Tyr Ser Leu Ala Asn Leu Ile Cys
 45                  50                  55                  60 agc tgt aag tct atc ctg cct tct gcc atg gag caa acc agc tat cat    482
Ser Cys Lys Ser Ile Leu Pro Ser Ala Met Glu Gln Thr Ser Tyr His
                 65                  70                  75 ggc cat ctg acc atc tgg ttc aca gat ata tcc aca ttg ggc cac gtg    530
Gly His Leu Thr Ile Trp Phe Thr Asp Ile Ser Thr Leu Gly His Val
             80                  85                  90 ctg aag ttc act ctg gtc caa gac ttg aag ctt tcc cta tgt ggt tcc    578
Leu Lys Phe Thr Leu Val Gln Asp Leu Lys Leu Ser Leu Cys Gly Ser
         95                 100                 105 agc acc ttc ccc acc aag tac ctg gct atc tgt ggg ctg cag agg ctt    626
Ser Thr Phe Pro Thr Lys Tyr Leu Ala Ile Cys Gly Leu Gln Arg Leu
110                 115                 120 cgc atc cat act aag gcc agg cat ccc tcc cgg ggg cag agt ttg ctc    674
Arg Ile His Thr Lys Ala Arg His Pro Ser Arg Gly Gln Ser Leu Leu
125                 130                 135                 140 atc cac agc aga agg gaa ggc agt tcc ttg tac aaa ggc tgg caa aca    722
Ile His Ser Arg Arg Glu Gly Ser Ser Leu Tyr Lys Gly Trp Gln Thr
                145                 150                 155 tgt atg ttc atc tca ttc tta gat gtg gct ctt ttc aac ggg gac tca    770
Cys Met Phe Ile Ser Phe Leu Asp Val Ala Leu Phe Asn Gly Asp Ser
            160                 165                 170 tct tta aag tca tac agt att gac aac att tct agc ctc gcc agt gac    818
Ser Leu Lys Ser Tyr Ser Ile Asp Asn Ile Ser Ser Leu Ala Ser Asp
        175                 180                 185 ttt cct gac ttt tct tac ttt aaa acg tcc cca atg cca agc aac aga    866
Phe Pro Asp Phe Ser Tyr Phe Lys Thr Ser Pro Met Pro Ser Asn Arg
    190                 195                 200 agc tat gtt gtc aca gtt att tac tagcatcctg tgtccctcca ccaggaactc   920
Ser Tyr Val Val Thr Val Ile Tyr
205                 210 t                                                                  921
```

<210> SEQ ID NO 33
<211> LENGTH: 212
<212> TYPE: PRT
<213> ORGANISM: Mus musculus

<400> SEQUENCE: 33

```
Met Thr Ser Pro Ser Ser Phe Cys Leu Leu Leu Gln Ala Leu Gly
1               5                   10                  15

Ile Val Ala Leu Gly His Phe Thr Lys Ala Gln Asn Asn Thr Leu Ile
            20                  25                  30

Phe Thr Lys Gly Asn Thr Ile Arg Asn Cys Ser Cys Pro Val Asp Ile
        35                  40                  45

Arg Asp Cys Asp Tyr Ser Leu Ala Asn Leu Ile Cys Ser Cys Lys Ser
    50                  55                  60

Ile Leu Pro Ser Ala Met Glu Gln Thr Ser Tyr His Gly His Leu Thr
65                  70                  75                  80

Ile Trp Phe Thr Asp Ile Ser Thr Leu Gly His Val Leu Lys Phe Thr
                85                  90                  95

Leu Val Gln Asp Leu Lys Leu Ser Leu Cys Gly Ser Ser Thr Phe Pro
            100                 105                 110

Thr Lys Tyr Leu Ala Ile Cys Gly Leu Gln Arg Leu Arg Ile His Thr
        115                 120                 125

Lys Ala Arg His Pro Ser Arg Gly Gln Ser Leu Leu Ile His Ser Arg
    130                 135                 140

Arg Glu Gly Ser Ser Leu Tyr Lys Gly Trp Gln Thr Cys Met Phe Ile
145                 150                 155                 160

Ser Phe Leu Asp Val Ala Leu Phe Asn Gly Asp Ser Ser Leu Lys Ser
                165                 170                 175

Tyr Ser Ile Asp Asn Ile Ser Ser Leu Ala Ser Asp Phe Pro Asp Phe
            180                 185                 190

Ser Tyr Phe Lys Thr Ser Pro Met Pro Ser Asn Arg Ser Tyr Val Val
        195                 200                 205

Thr Val Ile Tyr
    210
```

<210> SEQ ID NO 34
<211> LENGTH: 693
<212> TYPE: DNA
<213> ORGANISM: Homo sapiens
<220> FEATURE:
<221> NAME/KEY: CDS
<222> LOCATION: (1)..(690)
<223> OTHER INFORMATION:

<400> SEQUENCE: 34

```
atg gcc tct ctt ggc ctc caa ctt gtg ggc tac atc cta ggc ctt ctg      48
Met Ala Ser Leu Gly Leu Gln Leu Val Gly Tyr Ile Leu Gly Leu Leu
1               5                   10                  15 ggg ctt ttg ggc aca ctg gtt gcc atg ctg ctc ccc agc tgg aaa aca      96
Gly Leu Leu Gly Thr Leu Val Ala Met Leu Leu Pro Ser Trp Lys Thr
            20                  25                  30 agt tct tat gtc ggt gcc agc att gtg aca gca gtt ggc ttc tcc aag     144
Ser Ser Tyr Val Gly Ala Ser Ile Val Thr Ala Val Gly Phe Ser Lys
        35                  40                  45 ggc ctc tgg atg gaa tgt gcc aca cac agc aca ggc atc acc cag tgt     192
Gly Leu Trp Met Glu Cys Ala Thr His Ser Thr Gly Ile Thr Gln Cys
    50                  55                  60
```

```
gac atc tat agc acc ctt ctg ggc ctg ccc gct gac atc cag ggt gcc        240
Asp Ile Tyr Ser Thr Leu Leu Gly Leu Pro Ala Asp Ile Gln Gly Ala
 65                  70                  75                  80 cag gcc atg atg gtg aca tcc agt gca atc tcc tcc ctg gcc tgc att        288
Gln Ala Met Met Val Thr Ser Ser Ala Ile Ser Ser Leu Ala Cys Ile
                     85                  90                  95 atc tct gtg gtg ggc atg aga tgc aca gtc ttc tgc cag gaa tcc cga        336
Ile Ser Val Val Gly Met Arg Cys Thr Val Phe Cys Gln Glu Ser Arg
                100                 105                 110 gcc aaa gac aga gtg gcg gta gca ggt gga gtc ttt ttc atc ctt gga        384
Ala Lys Asp Arg Val Ala Val Ala Gly Gly Val Phe Phe Ile Leu Gly
            115                 120                 125 ggc ctc ctg gga ttc att cct gtt gcc tgg aat ctt cat ggg atc cta        432
Gly Leu Leu Gly Phe Ile Pro Val Ala Trp Asn Leu His Gly Ile Leu
130                 135                 140 cgg gac ttc tac tca cca ctg gtg cct gac agc atg aaa ttt gag att        480
Arg Asp Phe Tyr Ser Pro Leu Val Pro Asp Ser Met Lys Phe Glu Ile
145                 150                 155                 160 gga gag gct ctt tac ttg ggc att att tct tcc ctg ttc tcc ctg ata        528
Gly Glu Ala Leu Tyr Leu Gly Ile Ile Ser Ser Leu Phe Ser Leu Ile
                165                 170                 175 gct gga atc atc ctc tgc ttt tcc tgc tca tcc cag aga aat cgc tcc        576
Ala Gly Ile Ile Leu Cys Phe Ser Cys Ser Ser Gln Arg Asn Arg Ser
                180                 185                 190 aac tac tac gat gcc tac caa gcc caa cct ctt gcc aca agg agc tct        624
Asn Tyr Tyr Asp Ala Tyr Gln Ala Gln Pro Leu Ala Thr Arg Ser Ser
            195                 200                 205 cca agg gct ggt caa cct ccc aaa gtc aag agt gag ttc aat tcc tac        672
Pro Arg Ala Gly Gln Pro Pro Lys Val Lys Ser Glu Phe Asn Ser Tyr
210                 215                 220 agc ctg aca ggg tat gtg tga                                            693
Ser Leu Thr Gly Tyr Val
225                 230
```

<210> SEQ ID NO 35
<211> LENGTH: 230
<212> TYPE: PRT
<213> ORGANISM: Homo sapiens

<400> SEQUENCE: 35

```
Met Ala Ser Leu Gly Leu Gln Leu Val Gly Tyr Ile Leu Gly Leu Leu
 1               5                  10                  15

Gly Leu Leu Gly Thr Leu Val Ala Met Leu Leu Pro Ser Trp Lys Thr
                20                  25                  30

Ser Ser Tyr Val Gly Ala Ser Ile Val Thr Ala Val Gly Phe Ser Lys
            35                  40                  45

Gly Leu Trp Met Glu Cys Ala Thr His Ser Thr Gly Ile Thr Gln Cys
 50                 55                  60

Asp Ile Tyr Ser Thr Leu Leu Gly Leu Pro Ala Asp Ile Gln Gly Ala
 65                 70                  75                  80

Gln Ala Met Met Val Thr Ser Ser Ala Ile Ser Ser Leu Ala Cys Ile
                85                  90                  95

Ile Ser Val Val Gly Met Arg Cys Thr Val Phe Cys Gln Glu Ser Arg
                100                 105                 110

Ala Lys Asp Arg Val Ala Val Ala Gly Gly Val Phe Phe Ile Leu Gly
            115                 120                 125

Gly Leu Leu Gly Phe Ile Pro Val Ala Trp Asn Leu His Gly Ile Leu
130                 135                 140
```

```
Arg Asp Phe Tyr Ser Pro Leu Val Pro Asp Ser Met Lys Phe Glu Ile
145                 150                 155                 160

Gly Glu Ala Leu Tyr Leu Gly Ile Ile Ser Ser Leu Phe Ser Leu Ile
            165                 170                 175

Ala Gly Ile Ile Leu Cys Phe Ser Cys Ser Ser Gln Arg Asn Arg Ser
        180                 185                 190

Asn Tyr Tyr Asp Ala Tyr Gln Ala Gln Pro Leu Ala Thr Arg Ser Ser
    195                 200                 205

Pro Arg Ala Gly Gln Pro Pro Lys Val Lys Ser Glu Phe Asn Ser Tyr
    210                 215                 220

Ser Leu Thr Gly Tyr Val
225                 230

<210> SEQ ID NO 36
<211> LENGTH: 1002
<212> TYPE: DNA
<213> ORGANISM: Homo sapiens
<220> FEATURE:
<221> NAME/KEY: misc_feature
<222> LOCATION: (998)..(998)
<223> OTHER INFORMATION: unknown amino

<400> SEQUENCE: 36
tgggttccga gttcattact acaggaaaaa ctgttctctt ctgtggcaca gagaaccctg      60
cttcaaagca gaagtagcag ttccggagtc cagctggcta aaactcatcc cagaggataa    120
tggcaaccca tgccttagaa atcgctgggc tgtttcttgg tggtgttgga atggtgggca    180
cagtggctgt cactgtcatg cctcagtgga gagtgtcggc cttcattgaa acaacatcg    240 tggtttttga aaacttctgg aaggactgtg gatgaattgc gtgaggcag ctaacatca    300 ggatgcagtg caaaatctat gattccctgc tggctctttc tccggaccta caggcagcca    360
gaggactgat gtgtgctgct ccgtgatgt ccttcttggc tttcatgatg gccatccttg    420
gcatgaaatg caccaggtgc acgggggaca atgagaaggt gaaagctcac attctgctga    480
cggctggaat caatctcatc atcacgggca tggtgggggc caaccctgtg aacctggttt    540
ccaatgccat catcagagat ttttttaccc caatagtgaa tgttgcccaa aaacgtgagc    600
ttggagaagc tctctactta ggatggacca cggcactggt gctsattgtt ggaggagctc    660
tgttctgctg cgttttttgy tgcaacgaaa agagcagtag ctacagatac tcgataccct    720
cccatcgcac aacccaaaaa agttatcaca ccggaaagaa gtcaccgagc gtctactcca    780
gaagtcagta tgtgtagttg tgtatgtttt tttaacttta ctataaagcc atgcaaatga    840
caaaaatcta tattactttc tcaaaatgga ccccaaagaa actttgattt actgttctta    900
actgcctaat cttaattaca ggaactgtgc atcagctatt tatgattcta taagctattt    960
cagcagaatg agatattaaa tccaatgctt tgattgtnct ag                     1002

<210> SEQ ID NO 37
<211> LENGTH: 225
<212> TYPE: PRT
<213> ORGANISM: Homo sapiens

<400> SEQUENCE: 37

Met Ala Thr His Ala Leu Glu Ile Ala Gly Leu Phe Leu Gly Gly Val
1               5                   10                  15

Gly Met Val Gly Thr Val Ala Val Thr Val Met Pro Gln Trp Arg Val
            20                  25                  30

Ser Ala Phe Ile Glu Asn Asn Ile Val Val Phe Glu Asn Phe Trp Glu
```

```
                  35                  40                  45
Gly Leu Trp Met Asn Cys Val Arg Gln Ala Asn Ile Arg Met Gln Cys
     50                  55                  60
Lys Ile Tyr Asp Ser Leu Leu Ala Leu Ser Pro Asp Leu Gln Ala Ala
 65                  70                  75                  80
Arg Gly Leu Met Cys Ala Ala Ser Val Met Ser Phe Leu Ala Phe Met
                 85                  90                  95
Met Ala Ile Leu Gly Met Lys Cys Thr Arg Cys Thr Gly Asp Asn Glu
                100                 105                 110
Lys Val Lys Ala His Ile Leu Leu Thr Ala Gly Ile Asn Leu Ile Ile
            115                 120                 125
Thr Gly Met Val Gly Ala Asn Pro Val Asn Leu Val Ser Asn Ala Ile
        130                 135                 140
Ile Arg Asp Phe Phe Thr Pro Ile Val Asn Val Ala Gln Lys Arg Glu
145                 150                 155                 160
Leu Gly Glu Ala Leu Tyr Leu Gly Trp Thr Thr Ala Leu Val Leu Ile
                165                 170                 175
Val Gly Gly Ala Leu Phe Cys Cys Val Phe Cys Cys Asn Glu Lys Ser
            180                 185                 190
Ser Ser Tyr Arg Tyr Ser Ile Pro Ser His Arg Thr Thr Gln Lys Ser
        195                 200                 205
Tyr His Thr Gly Lys Lys Ser Pro Ser Val Tyr Ser Arg Ser Gln Tyr
    210                 215                 220
Val
225

<210> SEQ ID NO 38
<211> LENGTH: 833
<212> TYPE: DNA
<213> ORGANISM: Homo sapiens
<220> FEATURE:
<221> NAME/KEY: CDS
<222> LOCATION: (159)..(830)
<223> OTHER INFORMATION:

<400> SEQUENCE: 38
ccaagttcag tcacagctac tgatttggac taaaacgtta tgggcagcag ccaaggagaa    60
catcatcaaa gacttctcta gactcaaaag gcttccacgt tctacatctt gagcatcttc   120
taccactccg aattgaacca gtcttcaaag taaaggca atg gca ttt tat ccc ttg   176
                                         Met Ala Phe Tyr Pro Leu
                                          1               5 caa att gct ggg ctg gtt ctt ggg ttc ctt ggc atg gtg ggg act ctt    224
Gln Ile Ala Gly Leu Val Leu Gly Phe Leu Gly Met Val Gly Thr Leu
            10                  15                  20 gcc aca acc ctt ctg cct cag tgg aga gta tca gct ttt gtt ggc agc    272
Ala Thr Thr Leu Leu Pro Gln Trp Arg Val Ser Ala Phe Val Gly Ser
        25                  30                  35 aac att att gtc ttt gag agg ctc tgg gaa ggg ctc tgg atg aat tgc    320
Asn Ile Ile Val Phe Glu Arg Leu Trp Glu Gly Leu Trp Met Asn Cys
    40                  45                  50 atc cga caa gcc agg gtc cgg ttg caa tgc aag ttc tat agc tcc ttg    368
Ile Arg Gln Ala Arg Val Arg Leu Gln Cys Lys Phe Tyr Ser Ser Leu
55                  60                  65                  70 ttg gct ctc ccg cct gcc ctg gaa aca gcc cgg gcc ctc atg tgt gtg    416
Leu Ala Leu Pro Pro Ala Leu Glu Thr Ala Arg Ala Leu Met Cys Val
                75                  80                  85 gct gtt gct ctc tcc ttg atc gcc ctg ctt att ggc atc tgt ggc atg    464
```

```
                                                              -continued

Ala Val Ala Leu Ser Leu Ile Ala Leu Leu Ile Gly Ile Cys Gly Met
        90                  95                 100 aag cag gtc cag tgc aca ggc tct aac gag agg gcc aaa gca tac ctt      512
Lys Gln Val Gln Cys Thr Gly Ser Asn Glu Arg Ala Lys Ala Tyr Leu
            105                 110                 115 ctg gga act tca gga gtc ctc ttc atc ctg acg ggt atc ttc gtt ctg      560
Leu Gly Thr Ser Gly Val Leu Phe Ile Leu Thr Gly Ile Phe Val Leu
    120                 125                 130 att ccg gtg agc tgg aca gcc aat ata atc atc aga gat ttc tac aac      608
Ile Pro Val Ser Trp Thr Ala Asn Ile Ile Ile Arg Asp Phe Tyr Asn
135                 140                 145                 150 cca gcc atc cac ata ggt cag aaa cga gag ctg gga gca gca ctt ttc      656
Pro Ala Ile His Ile Gly Gln Lys Arg Glu Leu Gly Ala Ala Leu Phe
                155                 160                 165 ctt ggc tgg gca agc gct gct gtc ctc ttc att gga ggg ggt ctg ctt      704
Leu Gly Trp Ala Ser Ala Ala Val Leu Phe Ile Gly Gly Gly Leu Leu
            170                 175                 180 tgt gga ttt tgc tgc tgc aac aga aag aag caa ggg tac aga tat cca      752
Cys Gly Phe Cys Cys Cys Asn Arg Lys Lys Gln Gly Tyr Arg Tyr Pro
        185                 190                 195 gtg cct ggc tac cgt gtg cca cac aca gat aag cga aga aat acg aca      800
Val Pro Gly Tyr Arg Val Pro His Thr Asp Lys Arg Arg Asn Thr Thr
200                 205                 210 atg ctt agt aag acc tcc acc agt tat gtc taa                          833
Met Leu Ser Lys Thr Ser Thr Ser Tyr Val
215                 220

<210> SEQ ID NO 39
<211> LENGTH: 224
<212> TYPE: PRT
<213> ORGANISM: Homo sapiens

<400> SEQUENCE: 39

Met Ala Phe Tyr Pro Leu Gln Ile Ala Gly Leu Val Leu Gly Phe Leu
1               5                  10                  15

Gly Met Val Gly Thr Leu Ala Thr Thr Leu Leu Pro Gln Trp Arg Val
            20                  25                  30

Ser Ala Phe Val Gly Ser Asn Ile Ile Val Phe Glu Arg Leu Trp Glu
        35                  40                  45

Gly Leu Trp Met Asn Cys Ile Arg Gln Ala Arg Val Arg Leu Gln Cys
    50                  55                  60

Lys Phe Tyr Ser Ser Leu Leu Ala Leu Pro Pro Ala Leu Glu Thr Ala
65                  70                  75                  80

Arg Ala Leu Met Cys Val Ala Val Ala Leu Ser Leu Ile Ala Leu Leu
                85                  90                  95

Ile Gly Ile Cys Gly Met Lys Gln Val Gln Cys Thr Gly Ser Asn Glu
            100                 105                 110

Arg Ala Lys Ala Tyr Leu Leu Gly Thr Ser Gly Val Leu Phe Ile Leu
        115                 120                 125

Thr Gly Ile Phe Val Leu Ile Pro Val Ser Trp Thr Ala Asn Ile Ile
    130                 135                 140

Ile Arg Asp Phe Tyr Asn Pro Ala Ile His Ile Gly Gln Lys Arg Glu
145                 150                 155                 160

Leu Gly Ala Ala Leu Phe Leu Gly Trp Ala Ser Ala Ala Val Leu Phe
                165                 170                 175

Ile Gly Gly Gly Leu Leu Cys Gly Phe Cys Cys Cys Asn Arg Lys Lys
            180                 185                 190
```

```
Gln Gly Tyr Arg Tyr Pro Val Pro Gly Tyr Arg Val Pro His Thr Asp
        195                 200                 205

Lys Arg Arg Asn Thr Thr Met Leu Ser Lys Thr Ser Thr Ser Tyr Val
    210                 215                 220
```

<210> SEQ ID NO 40
<211> LENGTH: 393
<212> TYPE: DNA
<213> ORGANISM: Homo sapiens
<220> FEATURE:
<221> NAME/KEY: CDS
<222> LOCATION: (1)..(390)
<223> OTHER INFORMATION:

<400> SEQUENCE: 40

```
atg gcc gtg act gcc tgt cag ggc ttg ggg ttc gtg gtt tca ctg att    48
Met Ala Val Thr Ala Cys Gln Gly Leu Gly Phe Val Val Ser Leu Ile
1               5                   10                  15 ggg att gcg ggc atc att gct gcc acc tgc atg gcc cag tgg agc acc    96
Gly Ile Ala Gly Ile Ile Ala Ala Thr Cys Met Ala Gln Trp Ser Thr
            20                  25                  30 caa gac ttg tac aac aac ccc gta aca gct gtt ttc aac tac cag ggg   144
Gln Asp Leu Tyr Asn Asn Pro Val Thr Ala Val Phe Asn Tyr Gln Gly
        35                  40                  45 ctg tgg cgc tcc tgt gtc cga gag agc tct ggc ttc acc gag tgc cgg   192
Leu Trp Arg Ser Cys Val Arg Glu Ser Ser Gly Phe Thr Glu Cys Arg
    50                  55                  60 ggc tac ttc acc ctg ctg ggg ctg cca ggt aag ggc cag gtg tct ggc   240
Gly Tyr Phe Thr Leu Leu Gly Leu Pro Gly Lys Gly Gln Val Ser Gly
65                  70                  75                  80 tgg ctg gag gga gag att gga ggt gga gag gaa act gca ggc tct gtc   288
Trp Leu Glu Gly Glu Ile Gly Gly Gly Glu Glu Thr Ala Gly Ser Val
                85                  90                  95 tgg gca cca cga cag gga ctg ctg ggg agg gag gaa ctg cga ttc gtg   336
Trp Ala Pro Arg Gln Gly Leu Leu Gly Arg Glu Glu Leu Arg Phe Val
            100                 105                 110 ttt gac agg ggc aac agc cac ctg cac cag ggt gga ata gga gga cgg   384
Phe Asp Arg Gly Asn Ser His Leu His Gln Gly Gly Ile Gly Gly Arg
        115                 120                 125 gaa cct tag                                                       393
Glu Pro
    130
```

<210> SEQ ID NO 41
<211> LENGTH: 130
<212> TYPE: PRT
<213> ORGANISM: Homo sapiens

<400> SEQUENCE: 41

```
Met Ala Val Thr Ala Cys Gln Gly Leu Gly Phe Val Val Ser Leu Ile
1               5                   10                  15

Gly Ile Ala Gly Ile Ile Ala Ala Thr Cys Met Ala Gln Trp Ser Thr
            20                  25                  30

Gln Asp Leu Tyr Asn Asn Pro Val Thr Ala Val Phe Asn Tyr Gln Gly
        35                  40                  45

Leu Trp Arg Ser Cys Val Arg Glu Ser Ser Gly Phe Thr Glu Cys Arg
    50                  55                  60

Gly Tyr Phe Thr Leu Leu Gly Leu Pro Gly Lys Gly Gln Val Ser Gly
65                  70                  75                  80

Trp Leu Glu Gly Glu Ile Gly Gly Gly Glu Glu Thr Ala Gly Ser Val
                85                  90                  95
```

```
Trp Ala Pro Arg Gln Gly Leu Leu Gly Arg Glu Glu Leu Arg Phe Val
            100                 105                 110

Phe Asp Arg Gly Asn Ser His Leu His Gln Gly Gly Ile Gly Gly Arg
        115                 120                 125

Glu Pro
    130

<210> SEQ ID NO 42
<211> LENGTH: 2247
<212> TYPE: DNA
<213> ORGANISM: Homo sapiens
<220> FEATURE:
<221> NAME/KEY: misc_feature
<222> LOCATION: (742)..(742)
<223> OTHER INFORMATION: unknown amino
<221> NAME/KEY: misc_feature
<222> LOCATION: (747)..(747)
<223> OTHER INFORMATION: unknown amino
<221> NAME/KEY: misc_feature
<222> LOCATION: (793)..(793)
<223> OTHER INFORMATION: unknown amino
<221> NAME/KEY: misc_feature
<222> LOCATION: (814)..(814)
<223> OTHER INFORMATION: unknown amino
<221> NAME/KEY: misc_feature
<222> LOCATION: (828)..(828)
<223> OTHER INFORMATION: unknown amino
<221> NAME/KEY: misc_feature
<222> LOCATION: (850)..(850)
<223> OTHER INFORMATION: unknown amino
<221> NAME/KEY: misc_feature
<222> LOCATION: (906)..(906)
<223> OTHER INFORMATION: unknown amino
<221> NAME/KEY: CDS
<222> LOCATION: (1)..(2244)
<223> OTHER INFORMATION:

<400> SEQUENCE: 42 atg gag gca aat cag tgc ccc ctg gtt gtg gaa cca tct tac cca gac      48
Met Glu Ala Asn Gln Cys Pro Leu Val Val Glu Pro Ser Tyr Pro Asp
1               5                   10                  15 ctg gtc atc aat gta gga gaa gtg act ctt gga gaa gaa aac aga aaa      96
Leu Val Ile Asn Val Gly Glu Val Thr Leu Gly Glu Glu Asn Arg Lys
            20                  25                  30 aag ctg cag aaa att cag aga gac caa gag aag gag aga gtt atg cgg     144
Lys Leu Gln Lys Ile Gln Arg Asp Gln Glu Lys Glu Arg Val Met Arg
        35                  40                  45 gct gca tgt gct tta tta aac tca gga gga gga gtg att cga atg gcc     192
Ala Ala Cys Ala Leu Leu Asn Ser Gly Gly Gly Val Ile Arg Met Ala
    50                  55                  60 aag aag gtt gag cat ccc gtg gag atg gga ctg gat tta gaa cag tct     240
Lys Lys Val Glu His Pro Val Glu Met Gly Leu Asp Leu Glu Gln Ser
65                  70                  75                  80 ttg aga gag ctt att cag tct tca gat ctg cag gct ttc ttt gag acc     288
Leu Arg Glu Leu Ile Gln Ser Ser Asp Leu Gln Ala Phe Phe Glu Thr
                85                  90                  95 aag caa caa gga agg tgt ttt tac att ttt gtt aaa tct tgg agc agt     336
Lys Gln Gln Gly Arg Cys Phe Tyr Ile Phe Val Lys Ser Trp Ser Ser
            100                 105                 110 ggc cct ttc cct gaa gat cgc tct gtc aag ccc cgc ctt tgc agc ctc     384
Gly Pro Phe Pro Glu Asp Arg Ser Val Lys Pro Arg Leu Cys Ser Leu
        115                 120                 125 agt tct tca tta tac cgt aga tct gag acc tct gtg cgt tcc atg gac     432
Ser Ser Ser Leu Tyr Arg Arg Ser Glu Thr Ser Val Arg Ser Met Asp
    130                 135                 140
```

-continued

```
tca aga gag gca ttc tgt ttc ctg aag acc aaa agg aag cca aaa atc         480
Ser Arg Glu Ala Phe Cys Phe Leu Lys Thr Lys Arg Lys Pro Lys Ile
145                 150                 155                 160 ttg gaa gaa gga cct ttt cac aaa att cac aag ggt gta tac caa gag         528
Leu Glu Glu Gly Pro Phe His Lys Ile His Lys Gly Val Tyr Gln Glu
                165                 170                 175 ctc cct aac tcg gat cct gct gac cca aac tcg gat cct gct gac cta         576
Leu Pro Asn Ser Asp Pro Ala Asp Pro Asn Ser Asp Pro Ala Asp Leu
            180                 185                 190 att ttc caa aaa gac tat ctt gaa tat ggt gaa atc ctg cct ttt cct         624
Ile Phe Gln Lys Asp Tyr Leu Glu Tyr Gly Glu Ile Leu Pro Phe Pro
        195                 200                 205 gag tct cag tta gta gag ttt aaa cag ttc tct aca aaa cac ttc caa         672
Glu Ser Gln Leu Val Glu Phe Lys Gln Phe Ser Thr Lys His Phe Gln
210                 215                 220 gaa tat gta aaa agg aca att cca gaa tac gtc cct gca ttt gca aac         720
Glu Tyr Val Lys Arg Thr Ile Pro Glu Tyr Val Pro Ala Phe Ala Asn
225                 230                 235                 240 act gga gga ggc tat ctt ttt ntt ggn gtg gat gat aag agt agg gaa         768
Thr Gly Gly Gly Tyr Leu Phe Xaa Gly Val Asp Asp Lys Ser Arg Glu
                245                 250                 255 gtc ctg gga tgt gca aaa gaa aat ntt gac cct gac tct ttg aga ngg         816
Val Leu Gly Cys Ala Lys Glu Asn Xaa Asp Pro Asp Ser Leu Arg Xaa
            260                 265                 270 aaa ata gaa can gcc ata tac aaa cta cct tgt ntt cat ttt tgc caa         864
Lys Ile Glu Thr Ala Ile Tyr Lys Leu Pro Cys Xaa His Phe Cys Gln
        275                 280                 285 ccc caa cgc ccg ata acc ttc aca ctc aaa att gtg gat gtn tta aaa         912
Pro Gln Arg Pro Ile Thr Phe Thr Leu Lys Ile Val Asp Val Leu Lys
290                 295                 300 agg gga gag ctc tat ggc tat gct tgc atg atc aga gta aat ccc ttc         960
Arg Gly Glu Leu Tyr Gly Tyr Ala Cys Met Ile Arg Val Asn Pro Phe
305                 310                 315                 320 tgc tgt gca gtg ttc tca gaa gct ccc aat tca tgg ata gtg gag gac        1008
Cys Cys Ala Val Phe Ser Glu Ala Pro Asn Ser Trp Ile Val Glu Asp
                325                 330                 335 aag tac gtc tgc agc ctg aca acc gag aaa tgg gta ggc atg atg aca        1056
Lys Tyr Val Cys Ser Leu Thr Thr Glu Lys Trp Val Gly Met Met Thr
            340                 345                 350 gac aca gat cca gat ctt cta cag ttg tct gaa gat ttt gaa tgt cag        1104
Asp Thr Asp Pro Asp Leu Leu Gln Leu Ser Glu Asp Phe Glu Cys Gln
        355                 360                 365 ctg agt cta tct agt ggg cct ccc ctt agc aga cca gtg tac tcc aag        1152
Leu Ser Leu Ser Ser Gly Pro Pro Leu Ser Arg Pro Val Tyr Ser Lys
370                 375                 380 aaa ggc ctg gaa cat aaa aag gaa ctc cag caa ctt tta ttt tca gtc        1200
Lys Gly Leu Glu His Lys Lys Glu Leu Gln Gln Leu Leu Phe Ser Val
385                 390                 395                 400 cca cca gga tat ttg cga tat act cca gag tca ctc tgg agg gac ctg        1248
Pro Pro Gly Tyr Leu Arg Tyr Thr Pro Glu Ser Leu Trp Arg Asp Leu
                405                 410                 415 atc tca gag cac aga gga cta gag gag tta ata aat aag caa atg caa        1296
Ile Ser Glu His Arg Gly Leu Glu Glu Leu Ile Asn Lys Gln Met Gln
            420                 425                 430 cct ttc ttt cgg gga att gtg atc ctc tct aga agc tgg gct gtg gac        1344
Pro Phe Phe Arg Gly Ile Val Ile Leu Ser Arg Ser Trp Ala Val Asp
        435                 440                 445 ctg aac ttg cag gag aag cca gga gtc atc tgt gat gct ctg ctg ata        1392
Leu Asn Leu Gln Glu Lys Pro Gly Val Ile Cys Asp Ala Leu Leu Ile
450                 455                 460
```

```
gca cag aac agc acc ccc att ctc tac acc att ctc agg gag cag gat      1440
Ala Gln Asn Ser Thr Pro Ile Leu Tyr Thr Ile Leu Arg Glu Gln Asp
465                 470                 475                 480 gca gag ggc cag gac tac tgc act cgc acc gcc ttt act ttg aag cag      1488
Ala Glu Gly Gln Asp Tyr Cys Thr Arg Thr Ala Phe Thr Leu Lys Gln
                485                 490                 495 aag cta gtg aac atg ggg ggc tac acc ggg aag gtg tgt gtc agg gcc      1536
Lys Leu Val Asn Met Gly Gly Tyr Thr Gly Lys Val Cys Val Arg Ala
            500                 505                 510 aag gtc ctc tgc ctg agt cct gag agc agc gca gag gcc ttg gag gct      1584
Lys Val Leu Cys Leu Ser Pro Glu Ser Ser Ala Glu Ala Leu Glu Ala
        515                 520                 525 gca gtg tct ccg atg gat tac cct gcg tcc tat agc ctt gca ggc acc      1632
Ala Val Ser Pro Met Asp Tyr Pro Ala Ser Tyr Ser Leu Ala Gly Thr
    530                 535                 540 cag cac atg gaa gcc ctg ctg cag tcc ctc gtg att gtc tta ctc ggc      1680
Gln His Met Glu Ala Leu Leu Gln Ser Leu Val Ile Val Leu Leu Gly
545                 550                 555                 560 ttc agg tct ctc ttg agt gac cag ctc ggc tgt gag gtt tta aat ctg      1728
Phe Arg Ser Leu Leu Ser Asp Gln Leu Gly Cys Glu Val Leu Asn Leu
                565                 570                 575 ctc aca gcc cag cag tat gag ata ttc tcc aga agc ctc cgc aag aac      1776
Leu Thr Ala Gln Gln Tyr Glu Ile Phe Ser Arg Ser Leu Arg Lys Asn
            580                 585                 590 aga gag ttg ttt gtc cac ggc tta cct ggc tca ggg aag acc atc atg      1824
Arg Glu Leu Phe Val His Gly Leu Pro Gly Ser Gly Lys Thr Ile Met
        595                 600                 605 gcc atg aag atc atg gag aag atc agg aat gtg ttt cac tgt gag gca      1872
Ala Met Lys Ile Met Glu Lys Ile Arg Asn Val Phe His Cys Glu Ala
    610                 615                 620 cac aga att ctc tac gtt tgt gaa aac cag cct ctg agg aac ttt atc      1920
His Arg Ile Leu Tyr Val Cys Glu Asn Gln Pro Leu Arg Asn Phe Ile
625                 630                 635                 640 agt gat aga aat atc tgc cga gca gag acc cgg aaa act ttc cta aga      1968
Ser Asp Arg Asn Ile Cys Arg Ala Glu Thr Arg Lys Thr Phe Leu Arg
                645                 650                 655 gaa aac ttt gaa cac att caa cac atc gtc att gac gaa gct cag aat      2016
Glu Asn Phe Glu His Ile Gln His Ile Val Ile Asp Glu Ala Gln Asn
            660                 665                 670 ttc cgt act gaa gat ggg gac tgg tat ggg aag gca aaa agc atc act      2064
Phe Arg Thr Glu Asp Gly Asp Trp Tyr Gly Lys Ala Lys Ser Ile Thr
        675                 680                 685 cgg aga gca aag ggt ggc cca gga att ctc tgg atc ttt ctg gat tac      2112
Arg Arg Ala Lys Gly Gly Pro Gly Ile Leu Trp Ile Phe Leu Asp Tyr
    690                 695                 700 ttt cag acc agc cac ttg gat tgc agt ggc ctc cct cct ctc tca gac      2160
Phe Gln Thr Ser His Leu Asp Cys Ser Gly Leu Pro Pro Leu Ser Asp
705                 710                 715                 720 caa tat cca aga gaa gag ctc acc aga ata gtt cgc aat gca gat cca      2208
Gln Tyr Pro Arg Glu Glu Leu Thr Arg Ile Val Arg Asn Ala Asp Pro
                725                 730                 735 ata gcc aag tac tta caa aaa gaa aat gca agt aat tag                  2247
Ile Ala Lys Tyr Leu Gln Lys Glu Asn Ala Ser Asn
            740                 745

<210> SEQ ID NO 43
<211> LENGTH: 748
<212> TYPE: PRT
<213> ORGANISM: Homo sapiens
<220> FEATURE:
```

```
<221> NAME/KEY: misc_feature
<222> LOCATION: (248)..(248)
<223> OTHER INFORMATION: The 'Xaa' at location 248 stands for Ile, Val,
      Leu, or Phe.
<221> NAME/KEY: misc_feature
<222> LOCATION: (265)..(265)
<223> OTHER INFORMATION: The 'Xaa' at location 265 stands for Ile, Val,
      Leu, or Phe.
<221> NAME/KEY: misc_feature
<222> LOCATION: (272)..(272)
<223> OTHER INFORMATION: The 'Xaa' at location 272 stands for Arg, Gly,
      or Trp.
<221> NAME/KEY: misc_feature
<222> LOCATION: (284)..(284)
<223> OTHER INFORMATION: The 'Xaa' at location 284 stands for Ile, Val,
      Leu, or Phe.
<221> NAME/KEY: misc_feature
<222> LOCATION: (742)..(742)
<223> OTHER INFORMATION: unknown amino
<221> NAME/KEY: misc_feature
<222> LOCATION: (747)..(747)
<223> OTHER INFORMATION: unknown amino
<221> NAME/KEY: misc_feature
<222> LOCATION: (793)..(793)
<223> OTHER INFORMATION: unknown amino
<221> NAME/KEY: misc_feature
<222> LOCATION: (814)..(814)
<223> OTHER INFORMATION: unknown amino
<221> NAME/KEY: misc_feature
<222> LOCATION: (828)..(828)
<223> OTHER INFORMATION: unknown amino
<221> NAME/KEY: misc_feature
<222> LOCATION: (850)..(850)
<223> OTHER INFORMATION: unknown amino
<221> NAME/KEY: misc_feature
<222> LOCATION: (906)..(906)
<223> OTHER INFORMATION: unknown amino

<400> SEQUENCE: 43

Met Glu Ala Asn Gln Cys Pro Leu Val Val Glu Pro Ser Tyr Pro Asp
  1               5                  10                  15

Leu Val Ile Asn Val Gly Glu Val Thr Leu Gly Glu Glu Asn Arg Lys
                 20                  25                  30

Lys Leu Gln Lys Ile Gln Arg Asp Gln Glu Lys Glu Arg Val Met Arg
             35                  40                  45

Ala Ala Cys Ala Leu Leu Asn Ser Gly Gly Gly Val Ile Arg Met Ala
 50                  55                  60

Lys Lys Val Glu His Pro Val Glu Met Gly Leu Asp Leu Glu Gln Ser
 65                  70                  75                  80

Leu Arg Glu Leu Ile Gln Ser Ser Asp Leu Gln Ala Phe Phe Glu Thr
                 85                  90                  95

Lys Gln Gln Gly Arg Cys Phe Tyr Ile Phe Val Lys Ser Trp Ser Ser
            100                 105                 110

Gly Pro Phe Pro Glu Asp Arg Ser Val Lys Pro Arg Leu Cys Ser Leu
        115                 120                 125

Ser Ser Ser Leu Tyr Arg Arg Ser Glu Thr Ser Val Arg Ser Met Asp
130                 135                 140

Ser Arg Glu Ala Phe Cys Phe Leu Lys Thr Lys Arg Lys Pro Lys Ile
145                 150                 155                 160

Leu Glu Glu Gly Pro Phe His Lys Ile His Lys Gly Val Tyr Gln Glu
                165                 170                 175

Leu Pro Asn Ser Asp Pro Ala Asp Pro Asn Ser Asp Pro Ala Asp Leu
            180                 185                 190

Ile Phe Gln Lys Asp Tyr Leu Glu Tyr Gly Glu Ile Leu Pro Phe Pro
        195                 200                 205
```

```
Glu Ser Gln Leu Val Glu Phe Lys Gln Phe Ser Thr Lys His Phe Gln
    210                 215                 220
Glu Tyr Val Lys Arg Thr Ile Pro Glu Tyr Val Pro Ala Phe Ala Asn
225                 230                 235                 240
Thr Gly Gly Tyr Leu Phe Xaa Gly Val Asp Asp Lys Ser Arg Glu
            245                 250                 255
Val Leu Gly Cys Ala Lys Glu Asn Xaa Asp Pro Asp Ser Leu Arg Xaa
            260                 265                 270
Lys Ile Glu Thr Ala Ile Tyr Lys Leu Pro Cys Xaa His Phe Cys Gln
            275                 280                 285
Pro Gln Arg Pro Ile Thr Phe Thr Leu Lys Ile Val Asp Val Leu Lys
290                 295                 300
Arg Gly Glu Leu Tyr Gly Tyr Ala Cys Met Ile Arg Val Asn Pro Phe
305                 310                 315                 320
Cys Cys Ala Val Phe Ser Glu Ala Pro Asn Ser Trp Ile Val Glu Asp
            325                 330                 335
Lys Tyr Val Cys Ser Leu Thr Thr Glu Lys Trp Val Gly Met Met Thr
            340                 345                 350
Asp Thr Asp Pro Asp Leu Leu Gln Leu Ser Glu Asp Phe Glu Cys Gln
            355                 360                 365
Leu Ser Leu Ser Ser Gly Pro Pro Leu Ser Arg Pro Val Tyr Ser Lys
370                 375                 380
Lys Gly Leu Glu His Lys Lys Glu Leu Gln Gln Leu Leu Phe Ser Val
385                 390                 395                 400
Pro Pro Gly Tyr Leu Arg Tyr Thr Pro Glu Ser Leu Trp Arg Asp Leu
            405                 410                 415
Ile Ser Glu His Arg Gly Leu Glu Glu Leu Ile Asn Lys Gln Met Gln
            420                 425                 430
Pro Phe Phe Arg Gly Ile Val Ile Leu Ser Arg Ser Trp Ala Val Asp
            435                 440                 445
Leu Asn Leu Gln Glu Lys Pro Gly Val Ile Cys Asp Ala Leu Leu Ile
450                 455                 460
Ala Gln Asn Ser Thr Pro Ile Leu Tyr Thr Ile Leu Arg Glu Gln Asp
465                 470                 475                 480
Ala Glu Gly Gln Asp Tyr Cys Thr Arg Thr Ala Phe Thr Leu Lys Gln
            485                 490                 495
Lys Leu Val Asn Met Gly Gly Tyr Thr Gly Lys Val Cys Val Arg Ala
            500                 505                 510
Lys Val Leu Cys Leu Ser Pro Glu Ser Ser Ala Glu Ala Leu Glu Ala
            515                 520                 525
Ala Val Ser Pro Met Asp Tyr Pro Ala Ser Tyr Ser Leu Ala Gly Thr
530                 535                 540
Gln His Met Glu Ala Leu Leu Gln Ser Leu Val Ile Val Leu Leu Gly
545                 550                 555                 560
Phe Arg Ser Leu Leu Ser Asp Gln Leu Gly Cys Glu Val Leu Asn Leu
            565                 570                 575
Leu Thr Ala Gln Gln Tyr Glu Ile Phe Ser Arg Ser Leu Arg Lys Asn
            580                 585                 590
Arg Glu Leu Phe Val His Gly Leu Pro Gly Ser Gly Lys Thr Ile Met
            595                 600                 605
Ala Met Lys Ile Met Glu Lys Ile Arg Asn Val Phe His Cys Glu Ala
610                 615                 620
His Arg Ile Leu Tyr Val Cys Glu Asn Gln Pro Leu Arg Asn Phe Ile
```

```
                625                 630                 635                 640
Ser Asp Arg Asn Ile Cys Arg Ala Glu Thr Arg Lys Thr Phe Leu Arg
                    645                 650                 655

Glu Asn Phe Glu His Ile Gln His Ile Val Ile Asp Glu Ala Gln Asn
                660                 665                 670

Phe Arg Thr Glu Asp Gly Asp Trp Tyr Gly Lys Ala Lys Ser Ile Thr
            675                 680                 685

Arg Arg Ala Lys Gly Gly Pro Gly Ile Leu Trp Ile Phe Leu Asp Tyr
        690                 695                 700

Phe Gln Thr Ser His Leu Asp Cys Ser Gly Leu Pro Pro Leu Ser Asp
705                 710                 715                 720

Gln Tyr Pro Arg Glu Glu Leu Thr Arg Ile Val Arg Asn Ala Asp Pro
                    725                 730                 735

Ile Ala Lys Tyr Leu Gln Lys Glu Asn Ala Ser Asn
                740                 745

<210> SEQ ID NO 44
<211> LENGTH: 2676
<212> TYPE: DNA
<213> ORGANISM: Homo sapiens
<220> FEATURE:
<221> NAME/KEY: CDS
<222> LOCATION: (1)..(2673)
<223> OTHER INFORMATION:

<400> SEQUENCE: 44 atg agt ctt agg att gat gtg gat aca aac ttt cct gag tgt gtt gta      48
Met Ser Leu Arg Ile Asp Val Asp Thr Asn Phe Pro Glu Cys Val Val
1               5                   10                  15 gat gca gga aaa gtc acc ctt ggg act cag cag agg cag gag atg gac      96
Asp Ala Gly Lys Val Thr Leu Gly Thr Gln Gln Arg Gln Glu Met Asp
            20                  25                  30 cct cgc ctg cgg gag aaa cag aat gaa atc atc ctg cga gca gta tgt     144
Pro Arg Leu Arg Glu Lys Gln Asn Glu Ile Ile Leu Arg Ala Val Cys
        35                  40                  45 gct ctg ctg aat tct ggt ggg ggc ata atc aag gct gag att gag aac     192
Ala Leu Leu Asn Ser Gly Gly Gly Ile Ile Lys Ala Glu Ile Glu Asn
    50                  55                  60 aaa ggc tac aat tat gaa cgt cat gga gta gga ttg gat gtg cct cca     240
Lys Gly Tyr Asn Tyr Glu Arg His Gly Val Gly Leu Asp Val Pro Pro
65                  70                  75                  80 att ttc aga agc cat tta gat aag atg cag aag gaa aac cac ttt ttg     288
Ile Phe Arg Ser His Leu Asp Lys Met Gln Lys Glu Asn His Phe Leu
                85                  90                  95 att ttt gtg aaa tca tgg aac aca gag gct ggt gtg cca ctt gct acc     336
Ile Phe Val Lys Ser Trp Asn Thr Glu Ala Gly Val Pro Leu Ala Thr
            100                 105                 110 tta tgc tcc aat ttg tac cac aga gag aga aca tcc acc gat gtc atg     384
Leu Cys Ser Asn Leu Tyr His Arg Glu Arg Thr Ser Thr Asp Val Met
        115                 120                 125 gat tct cag gaa gct ctg gca ttc ctc aaa tgc agg act cag act cca     432
Asp Ser Gln Glu Ala Leu Ala Phe Leu Lys Cys Arg Thr Gln Thr Pro
    130                 135                 140 acg aat att aat gtt tcc aat tca tta ggt cca cag gca gct cag ggt     480
Thr Asn Ile Asn Val Ser Asn Ser Leu Gly Pro Gln Ala Ala Gln Gly
145                 150                 155                 160 agt gta caa tat gaa ggt aac ata aat gtg tca gct gct gct tta ttt     528
Ser Val Gln Tyr Glu Gly Asn Ile Asn Val Ser Ala Ala Ala Leu Phe
                165                 170                 175
```

```
gat aga aag cgg ctt cag tat ctg gaa aaa ctc aac ctt cct gag tcc      576
Asp Arg Lys Arg Leu Gln Tyr Leu Glu Lys Leu Asn Leu Pro Glu Ser
            180                 185                 190 aca cat gtt gaa ttt gta atg ttc tcg aca gac gtg tca cac tgt gtt      624
Thr His Val Glu Phe Val Met Phe Ser Thr Asp Val Ser His Cys Val
        195                 200                 205 aaa gac aga ctt ccg aag tgt gtt tct gca ttt gca aat act gaa gga      672
Lys Asp Arg Leu Pro Lys Cys Val Ser Ala Phe Ala Asn Thr Glu Gly
    210                 215                 220 gga tat gta ttt ttt ggt gtg cat gat gag act tgt caa gtg att gga      720
Gly Tyr Val Phe Phe Gly Val His Asp Glu Thr Cys Gln Val Ile Gly
225                 230                 235                 240 tgt gaa aaa gag aaa ata gac ctt acg agc ttg agg gct tct att gat      768
Cys Glu Lys Glu Lys Ile Asp Leu Thr Ser Leu Arg Ala Ser Ile Asp
                245                 250                 255 ggc tgt att aag aag cta cct gtc cat cat ttc tgc aca cag agg cct      816
Gly Cys Ile Lys Lys Leu Pro Val His His Phe Cys Thr Gln Arg Pro
            260                 265                 270 gag ata aaa tat gtc ctt aac ttc ctt gaa gtg cat gat aag ggg gcc      864
Glu Ile Lys Tyr Val Leu Asn Phe Leu Glu Val His Asp Lys Gly Ala
        275                 280                 285 ctc cgt gga tat gtc tgt gca atc aag gtg gag aaa ttc tgc tgt gcg      912
Leu Arg Gly Tyr Val Cys Ala Ile Lys Val Glu Lys Phe Cys Cys Ala
    290                 295                 300 gtg ttt gcc aaa gtg cct agt tcc tgg cag gtg aag gac aac cgt gtg      960
Val Phe Ala Lys Val Pro Ser Ser Trp Gln Val Lys Asp Asn Arg Val
305                 310                 315                 320 aga caa ttg ccc aca aga gaa tgg act gct tgg atg atg gaa gct gac     1008
Arg Gln Leu Pro Thr Arg Glu Trp Thr Ala Trp Met Met Glu Ala Asp
                325                 330                 335 cca gac ctt tcc agg tgt cct gag atg gtt ctc cag ttg agt ttg tca     1056
Pro Asp Leu Ser Arg Cys Pro Glu Met Val Leu Gln Leu Ser Leu Ser
            340                 345                 350 tct gcc acg ccc cgc agc aag cct gtg tgc att cat aag aat tcg gaa     1104
Ser Ala Thr Pro Arg Ser Lys Pro Val Cys Ile His Lys Asn Ser Glu
        355                 360                 365 tgt ctg aaa gag cag cag aaa cgc tac ttt cca gta ttt tca gac aga     1152
Cys Leu Lys Glu Gln Gln Lys Arg Tyr Phe Pro Val Phe Ser Asp Arg
    370                 375                 380 gtg gta tat act cca gaa agc ctc tac aag gaa ctc ttc tca caa cat     1200
Val Val Tyr Thr Pro Glu Ser Leu Tyr Lys Glu Leu Phe Ser Gln His
385                 390                 395                 400 aaa gga ctc aga gac tta ata aat aca gaa atg cgc cct ttc tct caa     1248
Lys Gly Leu Arg Asp Leu Ile Asn Thr Glu Met Arg Pro Phe Ser Gln
                405                 410                 415 gga ata ttg att ttt tct caa agc tgg gct gtg gat tta ggt ctg caa     1296
Gly Ile Leu Ile Phe Ser Gln Ser Trp Ala Val Asp Leu Gly Leu Gln
            420                 425                 430 gag aag cag gga gtc atc tgt gat gct ctt cta att tcc cag aac aac     1344
Glu Lys Gln Gly Val Ile Cys Asp Ala Leu Leu Ile Ser Gln Asn Asn
        435                 440                 445 acc cct att ctc tac acc atc ttc agc aag tgg gat gcg ggg tgc aag     1392
Thr Pro Ile Leu Tyr Thr Ile Phe Ser Lys Trp Asp Ala Gly Cys Lys
    450                 455                 460 ggc tat tct atg ata gtt gcc tat tct ttg aag cag aag ctg gtg aac     1440
Gly Tyr Ser Met Ile Val Ala Tyr Ser Leu Lys Gln Lys Leu Val Asn
465                 470                 475                 480 aaa ggc ggc tac act ggg agg tta tgc atc acc ccc ttg gtc tgt gtg     1488
Lys Gly Gly Tyr Thr Gly Arg Leu Cys Ile Thr Pro Leu Val Cys Val
                485                 490                 495
```

| | |
|---|---|
| ctg aat tct gat aga aaa gca cag agc gtt tac agt tcg tat tta caa<br>Leu Asn Ser Asp Arg Lys Ala Gln Ser Val Tyr Ser Ser Tyr Leu Gln<br>500 505 510 | 1536 |
| att tac cct gaa tcc tat aac ttc atg acc ccc cag cac atg gaa gcc<br>Ile Tyr Pro Glu Ser Tyr Asn Phe Met Thr Pro Gln His Met Glu Ala<br>515 520 525 | 1584 |
| ctg tta cag tcc ctc gtg ata gtc ttg ctt ggg ttc aaa tcc ttc tta<br>Leu Leu Gln Ser Leu Val Ile Val Leu Leu Gly Phe Lys Ser Phe Leu<br>530 535 540 | 1632 |
| agt gaa gag ctg ggc tct gag gtt ttg aac cta ctg aca aat aaa cag<br>Ser Glu Glu Leu Gly Ser Glu Val Leu Asn Leu Leu Thr Asn Lys Gln<br>545 550 555 560 | 1680 |
| tat gag ttg ctt tca aag aac ctt cgc aag acc aga gag ttg ttt gtt<br>Tyr Glu Leu Leu Ser Lys Asn Leu Arg Lys Thr Arg Glu Leu Phe Val<br>565 570 575 | 1728 |
| cat ggc tta cct gga tca ggg aag act atc ttg gct ctt agg atc atg<br>His Gly Leu Pro Gly Ser Gly Lys Thr Ile Leu Ala Leu Arg Ile Met<br>580 585 590 | 1776 |
| gag aag atc agg aat gtg ttt cac tgt gaa ccg gct aac att ctc tac<br>Glu Lys Ile Arg Asn Val Phe His Cys Glu Pro Ala Asn Ile Leu Tyr<br>595 600 605 | 1824 |
| atc tgt gaa aac cag ccc ctg aag aag ttg gtg agt ttc agc aag aaa<br>Ile Cys Glu Asn Gln Pro Leu Lys Lys Leu Val Ser Phe Ser Lys Lys<br>610 615 620 | 1872 |
| aac atc tgc cag cca gtg acc cgg aaa acc ttc atg aaa aac aac ttt<br>Asn Ile Cys Gln Pro Val Thr Arg Lys Thr Phe Met Lys Asn Asn Phe<br>625 630 635 640 | 1920 |
| gaa cac atc cag cac att atc att gat gac gct cag aat ttc cgt act<br>Glu His Ile Gln His Ile Ile Ile Asp Asp Ala Gln Asn Phe Arg Thr<br>645 650 655 | 1968 |
| gaa gat ggg gac tgg tat ggg aaa gca aag ttc atc act cga cag caa<br>Glu Asp Gly Asp Trp Tyr Gly Lys Ala Lys Phe Ile Thr Arg Gln Gln<br>660 665 670 | 2016 |
| agg gat ggc cca gga gtt ctc tgg atc ttt ctg gac tac ttt cag acc<br>Arg Asp Gly Pro Gly Val Leu Trp Ile Phe Leu Asp Tyr Phe Gln Thr<br>675 680 685 | 2064 |
| tat cac ttg agt tgc agt ggc ctc ccc cct ccc tca gac cag tat cca<br>Tyr His Leu Ser Cys Ser Gly Leu Pro Pro Pro Ser Asp Gln Tyr Pro<br>690 695 700 | 2112 |
| aga gaa gag atc aac aga gtg gtc cgc aat gca ggt cca ata gct aat<br>Arg Glu Glu Ile Asn Arg Val Val Arg Asn Ala Gly Pro Ile Ala Asn<br>705 710 715 720 | 2160 |
| tac cta caa caa gta atg cag gaa gcc cga caa aat cct cca cct aac<br>Tyr Leu Gln Gln Val Met Gln Glu Ala Arg Gln Asn Pro Pro Pro Asn<br>725 730 735 | 2208 |
| ctc ccc cct ggg tcc ctg gtg atg ctc tat gaa cct aaa tgg gct caa<br>Leu Pro Pro Gly Ser Leu Val Met Leu Tyr Glu Pro Lys Trp Ala Gln<br>740 745 750 | 2256 |
| ggt gtc cca ggc aac tta gag att att gaa gac ttg aac ttg gag gag<br>Gly Val Pro Gly Asn Leu Glu Ile Ile Glu Asp Leu Asn Leu Glu Glu<br>755 760 765 | 2304 |
| ata ctg atc tat gta gcg aat aaa tgc cgt ttt ctc ttg cgg aat ggt<br>Ile Leu Ile Tyr Val Ala Asn Lys Cys Arg Phe Leu Leu Arg Asn Gly<br>770 775 780 | 2352 |
| tat tct ccg aag gat att gct gtg ctt ttc acc aaa gca agt gaa gtg<br>Tyr Ser Pro Lys Asp Ile Ala Val Leu Phe Thr Lys Ala Ser Glu Val<br>785 790 795 800 | 2400 |
| gaa aaa tat aaa gac agg ctt cta aca gca atg agg aag aga aaa ctg<br>Glu Lys Tyr Lys Asp Arg Leu Leu Thr Ala Met Arg Lys Arg Lys Leu | 2448 |

-continued

```
                 805                 810                 815
tct cag ctc cat gag gag tct gat ctg tta cta cag atc ggt gat gcg    2496
Ser Gln Leu His Glu Glu Ser Asp Leu Leu Leu Gln Ile Gly Asp Ala
                820                 825                 830 tcg gat gtt cta acc gat cac att gtg ttg gac agt gtc tgt cga ttt    2544
Ser Asp Val Leu Thr Asp His Ile Val Leu Asp Ser Val Cys Arg Phe
                835                 840                 845 tca ggc ctg gaa aga aat atc gtg ttt gga atc aat cca gga gta gcc    2592
Ser Gly Leu Glu Arg Asn Ile Val Phe Gly Ile Asn Pro Gly Val Ala
            850                 855                 860 cca ccg gct ggg gcc tac aat ctt ctc tgt ttg gct tct agg gca        2640
Pro Pro Ala Gly Ala Tyr Asn Leu Leu Leu Cys Leu Ala Ser Arg Ala
865                 870                 875                 880 aaa aga cat ctg tat att ctg aag gct tct gtg tga                    2676
Lys Arg His Leu Tyr Ile Leu Lys Ala Ser Val
                885                 890
```

<210> SEQ ID NO 45
<211> LENGTH: 891
<212> TYPE: PRT
<213> ORGANISM: Homo sapiens

<400> SEQUENCE: 45

```
Met Ser Leu Arg Ile Asp Val Asp Thr Asn Phe Pro Glu Cys Val Val
1               5                   10                  15

Asp Ala Gly Lys Val Thr Leu Gly Thr Gln Gln Arg Gln Glu Met Asp
                20                  25                  30

Pro Arg Leu Arg Glu Lys Gln Asn Glu Ile Ile Leu Arg Ala Val Cys
            35                  40                  45

Ala Leu Leu Asn Ser Gly Gly Ile Ile Lys Ala Glu Ile Glu Asn
        50                  55                  60

Lys Gly Tyr Asn Tyr Glu Arg His Gly Val Gly Leu Asp Val Pro Pro
65                  70                  75                  80

Ile Phe Arg Ser His Leu Asp Lys Met Gln Lys Glu Asn His Phe Leu
                85                  90                  95

Ile Phe Val Lys Ser Trp Asn Thr Glu Ala Gly Val Pro Leu Ala Thr
                100                 105                 110

Leu Cys Ser Asn Leu Tyr His Arg Glu Arg Thr Ser Thr Asp Val Met
            115                 120                 125

Asp Ser Gln Glu Ala Leu Ala Phe Leu Lys Cys Arg Thr Gln Thr Pro
130                 135                 140

Thr Asn Ile Asn Val Ser Asn Ser Leu Gly Pro Gln Ala Ala Gln Gly
145                 150                 155                 160

Ser Val Gln Tyr Glu Gly Asn Ile Asn Val Ser Ala Ala Leu Phe
                165                 170                 175

Asp Arg Lys Arg Leu Gln Tyr Leu Glu Lys Leu Asn Leu Pro Glu Ser
            180                 185                 190

Thr His Val Glu Phe Val Met Phe Ser Thr Asp Val Ser His Cys Val
        195                 200                 205

Lys Asp Arg Leu Pro Lys Cys Val Ser Ala Phe Ala Asn Thr Glu Gly
210                 215                 220

Gly Tyr Val Phe Phe Gly Val His Asp Glu Thr Cys Gln Val Ile Gly
225                 230                 235                 240

Cys Glu Lys Glu Lys Ile Asp Leu Thr Ser Leu Arg Ala Ser Ile Asp
                245                 250                 255

Gly Cys Ile Lys Lys Leu Pro Val His His Phe Cys Thr Gln Arg Pro
```

-continued

```
                260                 265                 270
Glu Ile Lys Tyr Val Leu Asn Phe Leu Glu Val His Asp Lys Gly Ala
            275                 280                 285
Leu Arg Gly Tyr Val Cys Ala Ile Lys Val Glu Lys Phe Cys Cys Ala
        290                 295                 300
Val Phe Ala Lys Val Pro Ser Ser Trp Gln Val Lys Asp Asn Arg Val
305                 310                 315                 320
Arg Gln Leu Pro Thr Arg Glu Trp Thr Ala Trp Met Met Glu Ala Asp
                325                 330                 335
Pro Asp Leu Ser Arg Cys Pro Glu Met Val Leu Gln Leu Ser Leu Ser
            340                 345                 350
Ser Ala Thr Pro Arg Ser Lys Pro Val Cys Ile His Lys Asn Ser Glu
        355                 360                 365
Cys Leu Lys Glu Gln Gln Lys Arg Tyr Phe Pro Val Phe Ser Asp Arg
    370                 375                 380
Val Val Tyr Thr Pro Glu Ser Leu Tyr Lys Glu Leu Phe Ser Gln His
385                 390                 395                 400
Lys Gly Leu Arg Asp Leu Ile Asn Thr Glu Met Arg Pro Phe Ser Gln
                405                 410                 415
Gly Ile Leu Ile Phe Ser Gln Ser Trp Ala Val Asp Leu Gly Leu Gln
            420                 425                 430
Glu Lys Gln Gly Val Ile Cys Asp Ala Leu Leu Ile Ser Gln Asn Asn
        435                 440                 445
Thr Pro Ile Leu Tyr Thr Ile Phe Ser Lys Trp Asp Ala Gly Cys Lys
    450                 455                 460
Gly Tyr Ser Met Ile Val Ala Tyr Ser Leu Lys Gln Lys Leu Val Asn
465                 470                 475                 480
Lys Gly Gly Tyr Thr Gly Arg Leu Cys Ile Thr Pro Leu Val Cys Val
                485                 490                 495
Leu Asn Ser Asp Arg Lys Ala Gln Ser Val Tyr Ser Ser Tyr Leu Gln
            500                 505                 510
Ile Tyr Pro Glu Ser Tyr Asn Phe Met Thr Pro Gln His Met Glu Ala
        515                 520                 525
Leu Leu Gln Ser Leu Val Ile Val Leu Leu Gly Phe Lys Ser Phe Leu
    530                 535                 540
Ser Glu Glu Leu Gly Ser Glu Val Leu Asn Leu Leu Thr Asn Lys Gln
545                 550                 555                 560
Tyr Glu Leu Leu Ser Lys Asn Leu Arg Lys Thr Arg Glu Leu Phe Val
                565                 570                 575
His Gly Leu Pro Gly Ser Gly Lys Thr Ile Leu Ala Leu Arg Ile Met
            580                 585                 590
Glu Lys Ile Arg Asn Val Phe His Cys Glu Pro Ala Asn Ile Leu Tyr
        595                 600                 605
Ile Cys Glu Asn Gln Pro Leu Lys Lys Leu Val Ser Phe Ser Lys Lys
    610                 615                 620
Asn Ile Cys Gln Pro Val Thr Arg Lys Thr Phe Met Lys Asn Asn Phe
625                 630                 635                 640
Glu His Ile Gln His Ile Ile Ile Asp Asp Ala Gln Asn Phe Arg Thr
                645                 650                 655
Glu Asp Gly Asp Trp Tyr Gly Lys Ala Lys Phe Ile Thr Arg Gln Gln
            660                 665                 670
Arg Asp Gly Pro Gly Val Leu Trp Ile Phe Leu Asp Tyr Phe Gln Thr
        675                 680                 685
```

```
Tyr His Leu Ser Cys Ser Gly Leu Pro Pro Ser Asp Gln Tyr Pro
    690                 695                 700

Arg Glu Glu Ile Asn Arg Val Val Arg Asn Ala Gly Pro Ile Ala Asn
705                 710                 715                 720

Tyr Leu Gln Gln Val Met Gln Glu Ala Arg Gln Asn Pro Pro Pro Asn
                725                 730                 735

Leu Pro Pro Gly Ser Leu Val Met Leu Tyr Glu Pro Lys Trp Ala Gln
                740                 745                 750

Gly Val Pro Gly Asn Leu Glu Ile Ile Glu Asp Leu Asn Leu Glu Glu
                755                 760                 765

Ile Leu Ile Tyr Val Ala Asn Lys Cys Arg Phe Leu Leu Arg Asn Gly
    770                 775                 780

Tyr Ser Pro Lys Asp Ile Ala Val Leu Phe Thr Lys Ala Ser Glu Val
785                 790                 795                 800

Glu Lys Tyr Lys Asp Arg Leu Leu Thr Ala Met Arg Lys Arg Lys Leu
                805                 810                 815

Ser Gln Leu His Glu Glu Ser Asp Leu Leu Gln Ile Gly Asp Ala
                820                 825                 830

Ser Asp Val Leu Thr Asp His Ile Val Leu Asp Ser Val Cys Arg Phe
    835                 840                 845

Ser Gly Leu Glu Arg Asn Ile Val Phe Gly Ile Asn Pro Gly Val Ala
    850                 855                 860

Pro Pro Ala Gly Ala Tyr Asn Leu Leu Leu Cys Leu Ala Ser Arg Ala
865                 870                 875                 880

Lys Arg His Leu Tyr Ile Leu Lys Ala Ser Val
                885                 890

<210> SEQ ID NO 46
<211> LENGTH: 1737
<212> TYPE: DNA
<213> ORGANISM: Homo sapiens
<220> FEATURE:
<221> NAME/KEY: CDS
<222> LOCATION: (1)..(1734)
<223> OTHER INFORMATION:

<400> SEQUENCE: 46 atg aac atc agt gtt gat ttg gaa acg aat tat gcc gag ttg gtt cta        48
Met Asn Ile Ser Val Asp Leu Glu Thr Asn Tyr Ala Glu Leu Val Leu
1               5                   10                  15 gat gtg gga aga gtc act ctt gga gag aac agt agg aaa aaa atg aag        96
Asp Val Gly Arg Val Thr Leu Gly Glu Asn Ser Arg Lys Lys Met Lys
            20                  25                  30 gat tgt aaa ctg aga aaa aag cag aat gaa agg gtc tca cga gct atg       144
Asp Cys Lys Leu Arg Lys Lys Gln Asn Glu Arg Val Ser Arg Ala Met
        35                  40                  45 tgt gct ctg ctc aat tct gga ggg gga gtg atc aag gct gaa att gag       192
Cys Ala Leu Leu Asn Ser Gly Gly Gly Val Ile Lys Ala Glu Ile Glu
    50                  55                  60 aat gaa gac tat agt tat aca aaa gat gga ata gga cta gat ttg gaa       240
Asn Glu Asp Tyr Ser Tyr Thr Lys Asp Gly Ile Gly Leu Asp Leu Glu
65                  70                  75                  80 aat tct ttt agt aac att ctg tta ttt gtt cct gag tac tta gac ttc       288
Asn Ser Phe Ser Asn Ile Leu Leu Phe Val Pro Glu Tyr Leu Asp Phe
                85                  90                  95 atg cag aat ggt aac tac ttt ctg att ttt gtg aag tca tgg agc ttg       336
Met Gln Asn Gly Asn Tyr Phe Leu Ile Phe Val Lys Ser Trp Ser Leu
            100                 105                 110
```

```
aac acc tct ggt ctg cgg att acc acc ttg agc tcc aat ttg tac aaa    384
Asn Thr Ser Gly Leu Arg Ile Thr Thr Leu Ser Ser Asn Leu Tyr Lys
            115                 120                 125 aga gat ata aca tct gca aaa gtc atg aat gcc act gct gca ctg gag    432
Arg Asp Ile Thr Ser Ala Lys Val Met Asn Ala Thr Ala Ala Leu Glu
130                 135                 140 ttc ctc aaa gac atg aaa aag act aga ggg aga ttg tat tta aga cca    480
Phe Leu Lys Asp Met Lys Lys Thr Arg Gly Arg Leu Tyr Leu Arg Pro
145                 150                 155                 160 gaa ttg ctg gca aag agg ccc tgt gtt gat ata caa gaa gaa aat aac    528
Glu Leu Leu Ala Lys Arg Pro Cys Val Asp Ile Gln Glu Glu Asn Asn
                165                 170                 175 atg aag gcc ttg gcc ggg gtt ttt ttt gat aga aca gaa ctt gat cgg    576
Met Lys Ala Leu Ala Gly Val Phe Phe Asp Arg Thr Glu Leu Asp Arg
            180                 185                 190 aaa gaa aaa ttg acc ttt act gaa tcc aca cat gtt gaa att aaa aac    624
Lys Glu Lys Leu Thr Phe Thr Glu Ser Thr His Val Glu Ile Lys Asn
            195                 200                 205 ttc tcg aca gaa aag ttg tta caa cga att aaa gag att ctc cct caa    672
Phe Ser Thr Glu Lys Leu Leu Gln Arg Ile Lys Glu Ile Leu Pro Gln
210                 215                 220 tat gtt tct gca ttt gca aat act gat gga gga tat ttg ttc att ggt    720
Tyr Val Ser Ala Phe Ala Asn Thr Asp Gly Gly Tyr Leu Phe Ile Gly
225                 230                 235                 240 tta aat gaa gat aaa gaa ata att ggc ttt aaa gca gag atg agt gac    768
Leu Asn Glu Asp Lys Glu Ile Ile Gly Phe Lys Ala Glu Met Ser Asp
                245                 250                 255 ctc gat gac tta gaa aga gaa atc gaa aag tcc att agg aag atg cct    816
Leu Asp Asp Leu Glu Arg Glu Ile Glu Lys Ser Ile Arg Lys Met Pro
            260                 265                 270 gtg cat cac ttc tgt atg gag aag aag aag ata aat tat tca tgc aaa    864
Val His His Phe Cys Met Glu Lys Lys Lys Ile Asn Tyr Ser Cys Lys
            275                 280                 285 ttc ctt gga gta tat gat aaa gga agt ctt tgt gga tat gtc tgt gca    912
Phe Leu Gly Val Tyr Asp Lys Gly Ser Leu Cys Gly Tyr Val Cys Ala
290                 295                 300 ctc aga gtg gag cgc ttc tgc tgt gca gtg ttt gct aaa gag cct gat    960
Leu Arg Val Glu Arg Phe Cys Cys Ala Val Phe Ala Lys Glu Pro Asp
305                 310                 315                 320 tcc tgg cat gtg aaa gat aac cgt gtg atg cag ttg acc agg aag gaa   1008
Ser Trp His Val Lys Asp Asn Arg Val Met Gln Leu Thr Arg Lys Glu
                325                 330                 335 tgg atc cag ttc atg gtg gag gct gaa cca aaa ttt tcc agt tca tat   1056
Trp Ile Gln Phe Met Val Glu Ala Glu Pro Lys Phe Ser Ser Ser Tyr
            340                 345                 350 gaa gag gtg atc tct caa ata aat acg tca tta cct gct ccc cac agt   1104
Glu Glu Val Ile Ser Gln Ile Asn Thr Ser Leu Pro Ala Pro His Ser
            355                 360                 365 tgg cct ctt ttg gaa tgg caa cgg cag aga cat cac tgt cca ggg cta   1152
Trp Pro Leu Leu Glu Trp Gln Arg Gln Arg His His Cys Pro Gly Leu
370                 375                 380 tca gga agg ata acg tat act cca gaa aac ctt tgc aga aaa ctg ttc   1200
Ser Gly Arg Ile Thr Tyr Thr Pro Glu Asn Leu Cys Arg Lys Leu Phe
385                 390                 395                 400 tta caa cat gaa gga ctt aag caa tta ata tgt gaa gaa atg gac tct   1248
Leu Gln His Glu Gly Leu Lys Gln Leu Ile Cys Glu Glu Met Asp Ser
                405                 410                 415 gtc aga aag ggc tca ctg atc ttc tct agg agc tgg tct gtg gat ctg   1296
Val Arg Lys Gly Ser Leu Ile Phe Ser Arg Ser Trp Ser Val Asp Leu
```

-continued

```
                   420                 425                 430
ggc ttg caa gag aac cac aaa gtc ctc tgt gat gct ctt ctg att tcc    1344
Gly Leu Gln Glu Asn His Lys Val Leu Cys Asp Ala Leu Leu Ile Ser
            435                 440                 445 cag gac agt cct cca gtc cta tac acc ttc cac atg gta cag gat gag    1392
Gln Asp Ser Pro Pro Val Leu Tyr Thr Phe His Met Val Gln Asp Glu
        450                 455                 460 gag ttt aaa ggc tat tct aca caa act gcc cta acc tta aag cag aag    1440
Glu Phe Lys Gly Tyr Ser Thr Gln Thr Ala Leu Thr Leu Lys Gln Lys
465                 470                 475                 480 ctg gca aaa att ggt ggt tac act aaa aaa gtg tgt gtc atg aca aag    1488
Leu Ala Lys Ile Gly Gly Tyr Thr Lys Lys Val Cys Val Met Thr Lys
                485                 490                 495 atc ttc tac ttg agc cct gaa ggc atg aca agc tgc cag tat gat tta    1536
Ile Phe Tyr Leu Ser Pro Glu Gly Met Thr Ser Cys Gln Tyr Asp Leu
            500                 505                 510 agg tcg caa gta att tac cct gaa tcc tac tat ttt aca aga agg aaa    1584
Arg Ser Gln Val Ile Tyr Pro Glu Ser Tyr Tyr Phe Thr Arg Arg Lys
        515                 520                 525 tac ttg ctg aaa gcc ctt ttt aaa gcc tta aag aga ctc aag tct ctg    1632
Tyr Leu Leu Lys Ala Leu Phe Lys Ala Leu Lys Arg Leu Lys Ser Leu
530                 535                 540 aga gac cag ttt tcc ttt gca gaa aat cta tac cag ata atc ggt ata    1680
Arg Asp Gln Phe Ser Phe Ala Glu Asn Leu Tyr Gln Ile Ile Gly Ile
545                 550                 555                 560 gat tgc ttt cag aag aat gat aaa aag atg ttt aaa tct tgt cga agg    1728
Asp Cys Phe Gln Lys Asn Asp Lys Lys Met Phe Lys Ser Cys Arg Arg
                565                 570                 575 ctc acc tga                                                        1737
Leu Thr
```

<210> SEQ ID NO 47
<211> LENGTH: 578
<212> TYPE: PRT
<213> ORGANISM: Homo sapiens

<400> SEQUENCE: 47

```
Met Asn Ile Ser Val Asp Leu Glu Thr Asn Tyr Ala Glu Leu Val Leu
1               5                   10                  15

Asp Val Gly Arg Val Thr Leu Gly Glu Asn Ser Arg Lys Lys Met Lys
                20                  25                  30

Asp Cys Lys Leu Arg Lys Lys Gln Asn Glu Arg Val Ser Arg Ala Met
            35                  40                  45

Cys Ala Leu Leu Asn Ser Gly Gly Val Ile Lys Ala Glu Ile Glu
        50                  55                  60

Asn Glu Asp Tyr Ser Tyr Thr Lys Asp Gly Ile Gly Leu Asp Leu Glu
65                  70                  75                  80

Asn Ser Phe Ser Asn Ile Leu Leu Phe Val Pro Glu Tyr Leu Asp Phe
                85                  90                  95

Met Gln Asn Gly Asn Tyr Phe Leu Ile Phe Val Lys Ser Trp Ser Leu
            100                 105                 110

Asn Thr Ser Gly Leu Arg Ile Thr Thr Leu Ser Ser Asn Leu Tyr Lys
        115                 120                 125

Arg Asp Ile Thr Ser Ala Lys Val Met Asn Ala Thr Ala Ala Leu Glu
    130                 135                 140

Phe Leu Lys Asp Met Lys Lys Thr Arg Gly Arg Leu Tyr Leu Arg Pro
145                 150                 155                 160
```

-continued

```
Glu Leu Leu Ala Lys Arg Pro Cys Val Asp Ile Gln Glu Glu Asn Asn
                165                 170                 175

Met Lys Ala Leu Ala Gly Val Phe Phe Asp Arg Thr Glu Leu Asp Arg
            180                 185                 190

Lys Glu Lys Leu Thr Phe Thr Glu Ser Thr His Val Glu Ile Lys Asn
        195                 200                 205

Phe Ser Thr Glu Lys Leu Leu Gln Arg Ile Lys Glu Ile Leu Pro Gln
    210                 215                 220

Tyr Val Ser Ala Phe Ala Asn Thr Asp Gly Gly Tyr Leu Phe Ile Gly
225                 230                 235                 240

Leu Asn Glu Asp Lys Glu Ile Ile Gly Phe Lys Ala Glu Met Ser Asp
                245                 250                 255

Leu Asp Asp Leu Glu Arg Glu Ile Glu Lys Ser Ile Arg Lys Met Pro
            260                 265                 270

Val His His Phe Cys Met Glu Lys Lys Ile Asn Tyr Ser Cys Lys
        275                 280                 285

Phe Leu Gly Val Tyr Asp Lys Gly Ser Leu Cys Gly Tyr Val Cys Ala
    290                 295                 300

Leu Arg Val Glu Arg Phe Cys Cys Ala Val Phe Ala Lys Glu Pro Asp
305                 310                 315                 320

Ser Trp His Val Lys Asp Asn Arg Val Met Gln Leu Thr Arg Lys Glu
                325                 330                 335

Trp Ile Gln Phe Met Val Glu Ala Glu Pro Lys Phe Ser Ser Ser Tyr
            340                 345                 350

Glu Glu Val Ile Ser Gln Ile Asn Thr Ser Leu Pro Ala Pro His Ser
        355                 360                 365

Trp Pro Leu Leu Glu Trp Gln Arg Gln Arg His Cys Pro Gly Leu
    370                 375                 380

Ser Gly Arg Ile Thr Tyr Thr Pro Glu Asn Leu Cys Arg Lys Leu Phe
385                 390                 395                 400

Leu Gln His Glu Gly Leu Lys Gln Leu Ile Cys Glu Glu Met Asp Ser
                405                 410                 415

Val Arg Lys Gly Ser Leu Ile Phe Ser Arg Ser Trp Ser Val Asp Leu
            420                 425                 430

Gly Leu Gln Glu Asn His Lys Val Leu Cys Asp Ala Leu Leu Ile Ser
        435                 440                 445

Gln Asp Ser Pro Pro Val Leu Tyr Thr Phe His Met Val Gln Asp Glu
    450                 455                 460

Glu Phe Lys Gly Tyr Ser Thr Gln Thr Ala Leu Thr Leu Lys Gln Lys
465                 470                 475                 480

Leu Ala Lys Ile Gly Gly Tyr Thr Lys Lys Val Cys Val Met Thr Lys
                485                 490                 495

Ile Phe Tyr Leu Ser Pro Glu Gly Met Thr Ser Cys Gln Tyr Asp Leu
            500                 505                 510

Arg Ser Gln Val Ile Tyr Pro Glu Ser Tyr Phe Thr Arg Arg Lys
        515                 520                 525

Tyr Leu Leu Lys Ala Leu Phe Lys Ala Leu Lys Arg Leu Lys Ser Leu
    530                 535                 540

Arg Asp Gln Phe Ser Phe Ala Glu Asn Leu Tyr Gln Ile Ile Gly Ile
545                 550                 555                 560

Asp Cys Phe Gln Lys Asn Asp Lys Lys Met Phe Lys Ser Cys Arg Arg
                565                 570                 575

Leu Thr
```

```
<210> SEQ ID NO 48
<211> LENGTH: 2694
<212> TYPE: DNA
<213> ORGANISM: Homo sapiens
<220> FEATURE:
<221> NAME/KEY: CDS
<222> LOCATION: (1)..(2691)
<223> OTHER INFORMATION:

<400> SEQUENCE: 48
```

| | | | | | | | | | | | | | | | | |
|---|---|---|---|---|---|---|---|---|---|---|---|---|---|---|---|---|
| atg | gag | gca | aat | cac | tgc | tcc | ctg | ggt | gtg | tat | cca | tct | tac | cca | gac | 48 |
| Met | Glu | Ala | Asn | His | Cys | Ser | Leu | Gly | Val | Tyr | Pro | Ser | Tyr | Pro | Asp | |
| 1 | | | | 5 | | | | | 10 | | | | | 15 | | |
| ctg | gtc | atc | gat | gtc | gga | gaa | gtg | act | ctg | gga | gaa | gaa | aac | aga | aaa | 96 |
| Leu | Val | Ile | Asp | Val | Gly | Glu | Val | Thr | Leu | Gly | Glu | Glu | Asn | Arg | Lys | |
| | | | 20 | | | | | 25 | | | | | 30 | | | |
| aag | cta | cag | aaa | act | cag | aga | gac | caa | gag | agg | gcg | aga | gtt | ata | cgg | 144 |
| Lys | Leu | Gln | Lys | Thr | Gln | Arg | Asp | Gln | Glu | Arg | Ala | Arg | Val | Ile | Arg | |
| | | 35 | | | | | 40 | | | | | 45 | | | | |
| gcc | gcg | tgt | gct | tta | tta | aac | tca | gga | gga | gga | gtg | att | cag | atg | gaa | 192 |
| Ala | Ala | Cys | Ala | Leu | Leu | Asn | Ser | Gly | Gly | Gly | Val | Ile | Gln | Met | Glu | |
| 50 | | | | | 55 | | | | | 60 | | | | | | |
| atg | gcc | aac | agg | gat | gag | cgt | ccc | aca | gag | atg | gga | ctg | gat | tta | gaa | 240 |
| Met | Ala | Asn | Arg | Asp | Glu | Arg | Pro | Thr | Glu | Met | Gly | Leu | Asp | Leu | Glu | |
| 65 | | | | | 70 | | | | | 75 | | | | | 80 | |
| gaa | tcc | ttg | aga | aag | ctt | att | cag | tat | cca | tat | ttg | cag | gct | ttc | ttt | 288 |
| Glu | Ser | Leu | Arg | Lys | Leu | Ile | Gln | Tyr | Pro | Tyr | Leu | Gln | Ala | Phe | Phe | |
| | | | | 85 | | | | | 90 | | | | | 95 | | |
| gag | act | aag | caa | cac | gga | agg | tgt | ttt | tat | att | ttt | gtt | aaa | tct | tgg | 336 |
| Glu | Thr | Lys | Gln | His | Gly | Arg | Cys | Phe | Tyr | Ile | Phe | Val | Lys | Ser | Trp | |
| | | | 100 | | | | | 105 | | | | | 110 | | | |
| agt | ggt | gat | cct | ttc | ctt | aaa | gat | ggt | tct | ttc | aat | tcc | cgc | att | tgc | 384 |
| Ser | Gly | Asp | Pro | Phe | Leu | Lys | Asp | Gly | Ser | Phe | Asn | Ser | Arg | Ile | Cys | |
| | | 115 | | | | | 120 | | | | | 125 | | | | |
| agc | ctt | agt | tct | tca | tta | tac | tgt | aga | tct | ggc | acc | tct | gtg | ctt | cac | 432 |
| Ser | Leu | Ser | Ser | Ser | Leu | Tyr | Cys | Arg | Ser | Gly | Thr | Ser | Val | Leu | His | |
| 130 | | | | | 135 | | | | | 140 | | | | | | |
| atg | aat | tca | aga | cag | gca | ttc | gat | ttc | ctg | aag | acc | aag | gaa | aga | cag | 480 |
| Met | Asn | Ser | Arg | Gln | Ala | Phe | Asp | Phe | Leu | Lys | Thr | Lys | Glu | Arg | Gln | |
| 145 | | | | | 150 | | | | | 155 | | | | | 160 | |
| tcc | aaa | tat | aat | ctg | att | aat | gaa | ggg | tct | cca | cct | agt | aaa | att | atg | 528 |
| Ser | Lys | Tyr | Asn | Leu | Ile | Asn | Glu | Gly | Ser | Pro | Pro | Ser | Lys | Ile | Met | |
| | | | | 165 | | | | | 170 | | | | | 175 | | |
| aaa | gct | gta | tac | cag | aac | ata | tct | gag | tca | aat | cct | gca | tat | gaa | gtt | 576 |
| Lys | Ala | Val | Tyr | Gln | Asn | Ile | Ser | Glu | Ser | Asn | Pro | Ala | Tyr | Glu | Val | |
| | | | 180 | | | | | 185 | | | | | 190 | | | |
| ttc | caa | act | gac | act | att | gaa | tat | ggt | gaa | atc | cta | tct | ttt | cct | gag | 624 |
| Phe | Gln | Thr | Asp | Thr | Ile | Glu | Tyr | Gly | Glu | Ile | Leu | Ser | Phe | Pro | Glu | |
| | | 195 | | | | | 200 | | | | | 205 | | | | |
| tct | cca | tcc | ata | gag | ttt | aaa | cag | ttc | tct | aca | aaa | cat | atc | caa | caa | 672 |
| Ser | Pro | Ser | Ile | Glu | Phe | Lys | Gln | Phe | Ser | Thr | Lys | His | Ile | Gln | Gln | |
| 210 | | | | | 215 | | | | | 220 | | | | | | |
| tat | gta | gaa | aat | ata | att | cca | gag | tac | atc | tct | gca | ttt | gca | aac | act | 720 |
| Tyr | Val | Glu | Asn | Ile | Ile | Pro | Glu | Tyr | Ile | Ser | Ala | Phe | Ala | Asn | Thr | |
| 225 | | | | | 230 | | | | | 235 | | | | | 240 | |
| gag | gga | ggc | tat | ctt | ttt | att | gga | gtg | gat | gat | aag | agt | agg | aaa | gtc | 768 |
| Glu | Gly | Gly | Tyr | Leu | Phe | Ile | Gly | Val | Asp | Asp | Lys | Ser | Arg | Lys | Val | |
| | | | | 245 | | | | | 250 | | | | | 255 | | |
| ctg | gga | tgt | gcc | aaa | gaa | cag | gtt | gac | cct | gac | tct | ttg | aaa | aat | gta | 816 |
| Leu | Gly | Cys | Ala | Lys | Glu | Gln | Val | Asp | Pro | Asp | Ser | Leu | Lys | Asn | Val | |

```
                    260              265              270
att gca aga gca att tct aag ttg ccc att gtt cat ttt tgc tct tca        864
Ile Ala Arg Ala Ile Ser Lys Leu Pro Ile Val His Phe Cys Ser Ser
        275              280              285 aaa cct cgg gta gag tac agc acc aaa atc gta gaa gtg ttt tgt ggg        912
Lys Pro Arg Val Glu Tyr Ser Thr Lys Ile Val Glu Val Phe Cys Gly
    290              295              300 aaa gag ttg tat ggc tat ctc tgt gtg att aaa gtg aag gca ttc tgt        960
Lys Glu Leu Tyr Gly Tyr Leu Cys Val Ile Lys Val Lys Ala Phe Cys
305              310              315              320 tgt gtg gtg ttc tcg gaa gct ccc aag tca tgg atg gtg agg gag aag       1008
Cys Val Val Phe Ser Glu Ala Pro Lys Ser Trp Met Val Arg Glu Lys
                325              330              335 tac atc cgc ccc ttg aca act gag gaa tgg gta gag aaa atg atg gac       1056
Tyr Ile Arg Pro Leu Thr Thr Glu Glu Trp Val Glu Lys Met Met Asp
            340              345              350 gca gat cca gag ttt cct cca gac ttt gct gag gcc ttt gag tct cag       1104
Ala Asp Pro Glu Phe Pro Pro Asp Phe Ala Glu Ala Phe Glu Ser Gln
        355              360              365 ttg agt cta tct gac agt cct tca ctt tgc aga cca gtg tat tct aag       1152
Leu Ser Leu Ser Asp Ser Pro Ser Leu Cys Arg Pro Val Tyr Ser Lys
    370              375              380 aaa ggt ctg gaa cac aaa gct gat cta caa caa cat tta ttt cca gtt       1200
Lys Gly Leu Glu His Lys Ala Asp Leu Gln Gln His Leu Phe Pro Val
385              390              395              400 cca cca gga cat ttg gaa tgt act cca gag tcc ctc tgg aag gag ctg       1248
Pro Pro Gly His Leu Glu Cys Thr Pro Glu Ser Leu Trp Lys Glu Leu
                405              410              415 tct tta cag cat gaa gga cta aag gag tta ata cac aag caa atg cga       1296
Ser Leu Gln His Glu Gly Leu Lys Glu Leu Ile His Lys Gln Met Arg
            420              425              430 cct ttc tcc cag gga att gtg atc ctc tct aga agc tgg gct gtg gac       1344
Pro Phe Ser Gln Gly Ile Val Ile Leu Ser Arg Ser Trp Ala Val Asp
        435              440              445 ctg aac ttg cag gag aag cca gga gtc atc tgt gat gct ctg ctg ata       1392
Leu Asn Leu Gln Glu Lys Pro Gly Val Ile Cys Asp Ala Leu Leu Ile
    450              455              460 gca cag aac agc acc ccc att ctc tac acc att ctc agg gag cag gat       1440
Ala Gln Asn Ser Thr Pro Ile Leu Tyr Thr Ile Leu Arg Glu Gln Asp
465              470              475              480 gca gag ggc cag gac tac tgc act cgc acc gcc ttt act ttg aag cag       1488
Ala Glu Gly Gln Asp Tyr Cys Thr Arg Thr Ala Phe Thr Leu Lys Gln
                485              490              495 aag cta gtg aac atg ggg ggc tac acc ggg aag gtg tgt gtc agg gcc       1536
Lys Leu Val Asn Met Gly Gly Tyr Thr Gly Lys Val Cys Val Arg Ala
            500              505              510 aag gtc ctc tgc ctg agt cct gag agc agc gca gag gcc ttg gag gct       1584
Lys Val Leu Cys Leu Ser Pro Glu Ser Ser Ala Glu Ala Leu Glu Ala
        515              520              525 gca gtg tct ccg atg gat tac cct gcg tcc tat agc ctt gca ggc acc       1632
Ala Val Ser Pro Met Asp Tyr Pro Ala Ser Tyr Ser Leu Ala Gly Thr
    530              535              540 cag cac atg gaa gcc ctg ctg cag tcc ctc gtg att gtc tta ctc ggc       1680
Gln His Met Glu Ala Leu Leu Gln Ser Leu Val Ile Val Leu Leu Gly
545              550              555              560 ttc agg tct ctc ttg agt gac cag ctc ggc tgt gag gtt tta aat ctg       1728
Phe Arg Ser Leu Leu Ser Asp Gln Leu Gly Cys Glu Val Leu Asn Leu
                565              570              575 ctc aca gcc cag cag tat gag ata ttc tcc aga agc ctc cgc aag aac       1776
```

```
Leu Thr Ala Gln Gln Tyr Glu Ile Phe Ser Arg Ser Leu Arg Lys Asn
            580                 585                 590 aga gag ttg ttt gtc cac ggc tta cct ggc tca ggg aag acc atc atg     1824
Arg Glu Leu Phe Val His Gly Leu Pro Gly Ser Gly Lys Thr Ile Met
            595                 600                 605 gcc atg aag atc atg gag aag atc agg aat gtg ttt cac tgt gag gca     1872
Ala Met Lys Ile Met Glu Lys Ile Arg Asn Val Phe His Cys Glu Ala
610                 615                 620 cac aga att ctc tac gtt tgt gaa aac cag cct ctg agg aac ttt atc     1920
His Arg Ile Leu Tyr Val Cys Glu Asn Gln Pro Leu Arg Asn Phe Ile
625                 630                 635                 640 agt gat aga aat atc tgc cga gca gag acc cgg gaa act ttc cta aga     1968
Ser Asp Arg Asn Ile Cys Arg Ala Glu Thr Arg Glu Thr Phe Leu Arg
                645                 650                 655 gaa aaa ttt gaa cac att caa cac atc gtc att gac gaa gct cag aat     2016
Glu Lys Phe Glu His Ile Gln His Ile Val Ile Asp Glu Ala Gln Asn
            660                 665                 670 ttc cgt act gaa gat ggg gac tgg tat agg aag gca aaa acc atc act     2064
Phe Arg Thr Glu Asp Gly Asp Trp Tyr Arg Lys Ala Lys Thr Ile Thr
            675                 680                 685 cag aga gaa aag gat tgt cca gga gtt ctc tgg atc ttt ctg gac tac     2112
Gln Arg Glu Lys Asp Cys Pro Gly Val Leu Trp Ile Phe Leu Asp Tyr
690                 695                 700 ttt cag acc agt cac ttg ggt cac agt ggc ctt ccc cct ctc tca gca     2160
Phe Gln Thr Ser His Leu Gly His Ser Gly Leu Pro Pro Leu Ser Ala
705                 710                 715                 720 cag tat cca aga gaa gag ctc acc aga gta gtt cgc aat gca gat gaa     2208
Gln Tyr Pro Arg Glu Glu Leu Thr Arg Val Val Arg Asn Ala Asp Glu
                725                 730                 735 ata gcc gag tac ata caa caa gaa atg caa cta att ata gaa aat cct     2256
Ile Ala Glu Tyr Ile Gln Gln Glu Met Gln Leu Ile Ile Glu Asn Pro
            740                 745                 750 cca att aat atc ccc cat ggg tat ctg gca att ctc agt gaa gct aaa     2304
Pro Ile Asn Ile Pro His Gly Tyr Leu Ala Ile Leu Ser Glu Ala Lys
            755                 760                 765 tgg gtt cca ggt gtt cca ggc aac aca aag att att aaa aac ttt act     2352
Trp Val Pro Gly Val Pro Gly Asn Thr Lys Ile Ile Lys Asn Phe Thr
770                 775                 780 ttg gag caa ata gtg acc tat gtg gca gac acc tgc agg tgc ttc ttt     2400
Leu Glu Gln Ile Val Thr Tyr Val Ala Asp Thr Cys Arg Cys Phe Phe
785                 790                 795                 800 gaa agg ggc tat tct cca aag gat gtt gct gtg ctt gtc agc acc gtg     2448
Glu Arg Gly Tyr Ser Pro Lys Asp Val Ala Val Leu Val Ser Thr Val
                805                 810                 815 aca gaa gtg gag cag tat cag tct aag ctc ttg aaa gca atg agg aag     2496
Thr Glu Val Glu Gln Tyr Gln Ser Lys Leu Leu Lys Ala Met Arg Lys
            820                 825                 830 aaa atg gtg gtg cag ctc agt gat gca tgt gat atg ttg ggt gtg cac     2544
Lys Met Val Val Gln Leu Ser Asp Ala Cys Asp Met Leu Gly Val His
            835                 840                 845 att gtg ttg gac agt gtc cgg cga ttc tca ggc ctg gaa agg agc ata     2592
Ile Val Leu Asp Ser Val Arg Arg Phe Ser Gly Leu Glu Arg Ser Ile
850                 855                 860 gtg ttt ggg atc cat cca agg aca gct gac cca gct atc tta ccc aat     2640
Val Phe Gly Ile His Pro Arg Thr Ala Asp Pro Ala Ile Leu Pro Asn
865                 870                 875                 880 att ctg atc tgt ctg gct tcc agg gca aaa cag cac cta tat att ttt     2688
Ile Leu Ile Cys Leu Ala Ser Arg Ala Lys Gln His Leu Tyr Ile Phe
                885                 890                 895
```

```
ctg tga                                                                    2694
Leu <210> SEQ ID NO 49
<211> LENGTH: 897
<212> TYPE: PRT
<213> ORGANISM: Homo sapiens

<400> SEQUENCE: 49

Met Glu Ala Asn His Cys Ser Leu Gly Val Tyr Pro Ser Tyr Pro Asp
 1               5                  10                  15

Leu Val Ile Asp Val Gly Glu Val Thr Leu Gly Glu Glu Asn Arg Lys
            20                  25                  30

Lys Leu Gln Lys Thr Gln Arg Asp Gln Glu Arg Ala Arg Val Ile Arg
        35                  40                  45

Ala Ala Cys Ala Leu Leu Asn Ser Gly Gly Gly Val Ile Gln Met Glu
    50                  55                  60

Met Ala Asn Arg Asp Glu Arg Pro Thr Glu Met Gly Leu Asp Leu Glu
65                  70                  75                  80

Glu Ser Leu Arg Lys Leu Ile Gln Tyr Pro Tyr Leu Gln Ala Phe Phe
                85                  90                  95

Glu Thr Lys Gln His Gly Arg Cys Phe Tyr Ile Phe Val Lys Ser Trp
            100                 105                 110

Ser Gly Asp Pro Phe Leu Lys Asp Gly Ser Phe Asn Ser Arg Ile Cys
        115                 120                 125

Ser Leu Ser Ser Ser Leu Tyr Cys Arg Ser Gly Thr Ser Val Leu His
    130                 135                 140

Met Asn Ser Arg Gln Ala Phe Asp Phe Leu Lys Thr Lys Glu Arg Gln
145                 150                 155                 160

Ser Lys Tyr Asn Leu Ile Asn Glu Gly Ser Pro Ser Lys Ile Met
                165                 170                 175

Lys Ala Val Tyr Gln Asn Ile Ser Glu Ser Asn Pro Ala Tyr Glu Val
            180                 185                 190

Phe Gln Thr Asp Thr Ile Glu Tyr Gly Glu Ile Leu Ser Phe Pro Glu
        195                 200                 205

Ser Pro Ser Ile Glu Phe Lys Gln Phe Ser Thr Lys His Ile Gln Gln
    210                 215                 220

Tyr Val Glu Asn Ile Ile Pro Glu Tyr Ile Ser Ala Phe Ala Asn Thr
225                 230                 235                 240

Glu Gly Gly Tyr Leu Phe Ile Gly Val Asp Asp Lys Ser Arg Lys Val
                245                 250                 255

Leu Gly Cys Ala Lys Glu Gln Val Asp Pro Asp Ser Leu Lys Asn Val
            260                 265                 270

Ile Ala Arg Ala Ile Ser Lys Leu Pro Ile Val His Phe Cys Ser Ser
        275                 280                 285

Lys Pro Arg Val Glu Tyr Ser Thr Lys Ile Val Glu Val Phe Cys Gly
    290                 295                 300

Lys Glu Leu Tyr Gly Tyr Leu Cys Val Ile Lys Val Lys Ala Phe Cys
305                 310                 315                 320

Cys Val Val Phe Ser Glu Ala Pro Lys Ser Trp Met Val Arg Glu Lys
                325                 330                 335

Tyr Ile Arg Pro Leu Thr Thr Glu Glu Trp Val Glu Lys Met Met Asp
            340                 345                 350

Ala Asp Pro Glu Phe Pro Pro Asp Phe Ala Glu Ala Phe Glu Ser Gln
        355                 360                 365
```

-continued

```
Leu Ser Leu Ser Asp Ser Pro Ser Leu Cys Arg Pro Val Tyr Ser Lys
    370                 375                 380

Lys Gly Leu Glu His Lys Ala Asp Leu Gln Gln His Leu Phe Pro Val
385                 390                 395                 400

Pro Pro Gly His Leu Glu Cys Thr Pro Glu Ser Leu Trp Lys Glu Leu
                405                 410                 415

Ser Leu Gln His Glu Gly Leu Lys Glu Leu Ile His Lys Gln Met Arg
            420                 425                 430

Pro Phe Ser Gln Gly Ile Val Ile Leu Ser Arg Ser Trp Ala Val Asp
        435                 440                 445

Leu Asn Leu Gln Glu Lys Pro Gly Val Ile Cys Asp Ala Leu Leu Ile
450                 455                 460

Ala Gln Asn Ser Thr Pro Ile Leu Tyr Thr Ile Leu Arg Glu Gln Asp
465                 470                 475                 480

Ala Glu Gly Gln Asp Tyr Cys Thr Arg Thr Ala Phe Thr Leu Lys Gln
                485                 490                 495

Lys Leu Val Asn Met Gly Gly Tyr Thr Gly Lys Val Cys Val Arg Ala
            500                 505                 510

Lys Val Leu Cys Leu Ser Pro Glu Ser Ser Ala Glu Ala Leu Glu Ala
        515                 520                 525

Ala Val Ser Pro Met Asp Tyr Pro Ala Ser Tyr Ser Leu Ala Gly Thr
530                 535                 540

Gln His Met Glu Ala Leu Leu Gln Ser Leu Val Ile Val Leu Leu Gly
545                 550                 555                 560

Phe Arg Ser Leu Leu Ser Asp Gln Leu Gly Cys Glu Val Leu Asn Leu
                565                 570                 575

Leu Thr Ala Gln Gln Tyr Glu Ile Phe Ser Arg Ser Leu Arg Lys Asn
            580                 585                 590

Arg Glu Leu Phe Val His Gly Leu Pro Gly Ser Gly Lys Thr Ile Met
        595                 600                 605

Ala Met Lys Ile Met Glu Lys Ile Arg Asn Val Phe His Cys Glu Ala
610                 615                 620

His Arg Ile Leu Tyr Val Cys Glu Asn Gln Pro Leu Arg Asn Phe Ile
625                 630                 635                 640

Ser Asp Arg Asn Ile Cys Arg Ala Glu Thr Arg Glu Thr Phe Leu Arg
                645                 650                 655

Glu Lys Phe Glu His Ile Gln His Ile Val Ile Asp Glu Ala Gln Asn
            660                 665                 670

Phe Arg Thr Glu Asp Gly Asp Trp Tyr Arg Lys Ala Lys Thr Ile Thr
        675                 680                 685

Gln Arg Glu Lys Asp Cys Pro Gly Val Leu Trp Ile Phe Leu Asp Tyr
690                 695                 700

Phe Gln Thr Ser His Leu Gly His Ser Gly Leu Pro Pro Leu Ser Ala
705                 710                 715                 720

Gln Tyr Pro Arg Glu Glu Leu Thr Arg Val Val Arg Asn Ala Asp Glu
                725                 730                 735

Ile Ala Glu Tyr Ile Gln Gln Glu Met Gln Leu Ile Ile Glu Asn Pro
            740                 745                 750

Pro Ile Asn Ile Pro His Gly Tyr Leu Ala Ile Leu Ser Glu Ala Lys
        755                 760                 765

Trp Val Pro Gly Val Pro Gly Asn Thr Lys Ile Ile Lys Asn Phe Thr
770                 775                 780
```

-continued

```
Leu Glu Gln Ile Val Thr Tyr Val Ala Asp Thr Cys Arg Cys Phe Phe
785                 790                 795                 800

Glu Arg Gly Tyr Ser Pro Lys Asp Val Ala Val Leu Val Ser Thr Val
            805                 810                 815

Thr Glu Val Glu Gln Tyr Gln Ser Lys Leu Leu Lys Ala Met Arg Lys
        820                 825                 830

Lys Met Val Val Gln Leu Ser Asp Ala Cys Asp Met Leu Gly Val His
            835                 840                 845

Ile Val Leu Asp Ser Val Arg Arg Phe Ser Gly Leu Glu Arg Ser Ile
    850                 855                 860

Val Phe Gly Ile His Pro Arg Thr Ala Asp Pro Ala Ile Leu Pro Asn
865                 870                 875                 880

Ile Leu Ile Cys Leu Ala Ser Arg Ala Lys Gln His Leu Tyr Ile Phe
                885                 890                 895

Leu
```

<210> SEQ ID NO 50
<211> LENGTH: 1074
<212> TYPE: DNA
<213> ORGANISM: Homo sapiens
<220> FEATURE:
<221> NAME/KEY: CDS
<222> LOCATION: (1)..(1071)
<223> OTHER INFORMATION:

<400> SEQUENCE: 50

```
atg gag agt ctc aag act gat act gaa atg ccg tat cct gag gta ata       48
Met Glu Ser Leu Lys Thr Asp Thr Glu Met Pro Tyr Pro Glu Val Ile
1               5                   10                  15 gta gat gtg ggc aga gtg att ttt gga gaa gaa aac agg aag aag atg       96
Val Asp Val Gly Arg Val Ile Phe Gly Glu Glu Asn Arg Lys Lys Met
                20                  25                  30 acc aac agc tgt ttg aaa aga tct gag aat tct aga att atc cgg gct      144
Thr Asn Ser Cys Leu Lys Arg Ser Glu Asn Ser Arg Ile Ile Arg Ala
            35                  40                  45 ata tgt gca ctg tta aat tct gga ggt ggt gtg atc aaa gca gag att      192
Ile Cys Ala Leu Leu Asn Ser Gly Gly Gly Val Ile Lys Ala Glu Ile
        50                  55                  60 gat gat aaa acc tat agt tac caa tgc cat ggg ctg gga cag gat ttg      240
Asp Asp Lys Thr Tyr Ser Tyr Gln Cys His Gly Leu Gly Gln Asp Leu
65                  70                  75                  80 gaa act tct ttt caa aag ctc ctt cct tca ggt tca cag aaa tac ctt      288
Glu Thr Ser Phe Gln Lys Leu Leu Pro Ser Gly Ser Gln Lys Tyr Leu
                85                  90                  95 gac tac atg cag cag ggg cac aat ctc ctg att ttt gtg aag tca tgg      336
Asp Tyr Met Gln Gln Gly His Asn Leu Leu Ile Phe Val Lys Ser Trp
            100                 105                 110 agc cca gat gtt ttc agc ctt cca cta agg att tgc agc ttg cgc tcc      384
Ser Pro Asp Val Phe Ser Leu Pro Leu Arg Ile Cys Ser Leu Arg Ser
        115                 120                 125 aat ttg tat cgg aga gat gtg act tct gct atc aac ttg agt gct agc      432
Asn Leu Tyr Arg Arg Asp Val Thr Ser Ala Ile Asn Leu Ser Ala Ser
    130                 135                 140 agt gcc ctg gag ctt ctc aga gag aag ggg ttt aga gcc caa aga gga      480
Ser Ala Leu Glu Leu Leu Arg Glu Lys Gly Phe Arg Ala Gln Arg Gly
145                 150                 155                 160 aga cca agg gtg aag aag ttg cat cct cag cag gtt ctc aat aga tgc      528
Arg Pro Arg Val Lys Lys Leu His Pro Gln Gln Val Leu Asn Arg Cys
                165                 170                 175
```

```
att cag gaa gag gaa gat atg agg ata ttg gcc tca gaa ttt ttt aaa       576
Ile Gln Glu Glu Glu Asp Met Arg Ile Leu Ala Ser Glu Phe Phe Lys
        180                 185                 190 aag gac aaa ctc atg tat aag gag aaa ctc aac ttt act gag tca aca       624
Lys Asp Lys Leu Met Tyr Lys Glu Lys Leu Asn Phe Thr Glu Ser Thr
    195                 200                 205 cat gtt gaa ttt aaa agg ttc acc acc aaa aaa gtc ata cct cgg att       672
His Val Glu Phe Lys Arg Phe Thr Thr Lys Lys Val Ile Pro Arg Ile
210                 215                 220 aag gaa atg ctg cct cat tat gtt tct gca ttt gcc aac act caa ggg       720
Lys Glu Met Leu Pro His Tyr Val Ser Ala Phe Ala Asn Thr Gln Gly
225                 230                 235                 240 gga tat gtc ctc att ggg gtg gat gat aag agc aaa gaa gtg gtt gga       768
Gly Tyr Val Leu Ile Gly Val Asp Asp Lys Ser Lys Glu Val Val Gly
            245                 250                 255 tgt aag tgg gaa aaa gtg aat cct gac tta cta aaa aaa gaa atc gaa       816
Cys Lys Trp Glu Lys Val Asn Pro Asp Leu Leu Lys Lys Glu Ile Glu
        260                 265                 270 aac tgc ata gaa aaa ttg cct aca ttc cac ttc tgc tgt gag aag cca       864
Asn Cys Ile Glu Lys Leu Pro Thr Phe His Phe Cys Cys Glu Lys Pro
    275                 280                 285 aag gta aat ttc act aca aaa atc ctg aat gtg tac caa aaa gat gtc       912
Lys Val Asn Phe Thr Thr Lys Ile Leu Asn Val Tyr Gln Lys Asp Val
290                 295                 300 ctg gat ggt tat gtc tgt gtg att caa gtg gag ccc ttc tgt tgc gtg       960
Leu Asp Gly Tyr Val Cys Val Ile Gln Val Glu Pro Phe Cys Cys Val
305                 310                 315                 320 gtg ttt gca gag gcc cca gat tcc tgg atc atg aaa gac aat tct gtc      1008
Val Phe Ala Glu Ala Pro Asp Ser Trp Ile Met Lys Asp Asn Ser Val
            325                 330                 335 aca cgg ctg aca gct gag cag tgg gtg gtc atg atg ctg gat act cag      1056
Thr Arg Leu Thr Ala Glu Gln Trp Val Val Met Met Leu Asp Thr Gln
        340                 345                 350 tca ggt aaa ggg aag tga                                              1074
Ser Gly Lys Gly Lys
        355
```

<210> SEQ ID NO 51
<211> LENGTH: 357
<212> TYPE: PRT
<213> ORGANISM: Homo sapiens

<400> SEQUENCE: 51

```
Met Glu Ser Leu Lys Thr Asp Thr Glu Met Pro Tyr Pro Glu Val Ile
1               5                   10                  15

Val Asp Val Gly Arg Val Ile Phe Gly Glu Glu Asn Arg Lys Lys Met
            20                  25                  30

Thr Asn Ser Cys Leu Lys Arg Ser Glu Asn Ser Arg Ile Ile Arg Ala
        35                  40                  45

Ile Cys Ala Leu Leu Asn Ser Gly Gly Val Ile Lys Ala Glu Ile
    50                  55                  60

Asp Asp Lys Thr Tyr Ser Tyr Gln Cys His Gly Leu Gly Gln Asp Leu
65                  70                  75                  80

Glu Thr Ser Phe Gln Lys Leu Leu Pro Ser Gly Ser Gln Lys Tyr Leu
                85                  90                  95

Asp Tyr Met Gln Gln Gly His Asn Leu Leu Ile Phe Val Lys Ser Trp
            100                 105                 110

Ser Pro Asp Val Phe Ser Leu Pro Leu Arg Ile Cys Ser Leu Arg Ser
        115                 120                 125
```

```
Asn Leu Tyr Arg Arg Asp Val Thr Ser Ala Ile Asn Leu Ser Ala Ser
    130                 135                 140

Ser Ala Leu Glu Leu Leu Arg Glu Lys Gly Phe Arg Ala Gln Arg Gly
145                 150                 155                 160

Arg Pro Arg Val Lys Lys Leu His Pro Gln Gln Val Leu Asn Arg Cys
                165                 170                 175

Ile Gln Glu Glu Glu Asp Met Arg Ile Leu Ala Ser Glu Phe Phe Lys
            180                 185                 190

Lys Asp Lys Leu Met Tyr Lys Glu Lys Leu Asn Phe Thr Glu Ser Thr
        195                 200                 205

His Val Glu Phe Lys Arg Phe Thr Thr Lys Val Ile Pro Arg Ile
    210                 215                 220

Lys Glu Met Leu Pro His Tyr Val Ser Ala Phe Ala Asn Thr Gln Gly
225                 230                 235                 240

Gly Tyr Val Leu Ile Gly Val Asp Asp Lys Ser Lys Glu Val Val Gly
                245                 250                 255

Cys Lys Trp Glu Lys Val Asn Pro Asp Leu Leu Lys Lys Glu Ile Glu
            260                 265                 270

Asn Cys Ile Glu Lys Leu Pro Thr Phe His Phe Cys Cys Glu Lys Pro
        275                 280                 285

Lys Val Asn Phe Thr Thr Lys Ile Leu Asn Val Tyr Gln Lys Asp Val
    290                 295                 300

Leu Asp Gly Tyr Val Cys Val Ile Gln Val Glu Pro Phe Cys Cys Val
305                 310                 315                 320

Val Phe Ala Glu Ala Pro Asp Ser Trp Ile Met Lys Asp Asn Ser Val
                325                 330                 335

Thr Arg Leu Thr Ala Glu Gln Trp Val Met Met Leu Asp Thr Gln
            340                 345                 350

Ser Gly Lys Gly Lys
        355

<210> SEQ ID NO 52
<211> LENGTH: 807
<212> TYPE: DNA
<213> ORGANISM: Mus musculus
<220> FEATURE:
<221> NAME/KEY: CDS
<222> LOCATION: (1)..(804)
<223> OTHER INFORMATION:

<400> SEQUENCE: 52 atg ctg ttc gtc aag cag agt gac aag ggg atc aac agt aag agg agg      48
Met Leu Phe Val Lys Gln Ser Asp Lys Gly Ile Asn Ser Lys Arg Arg
1               5                   10                  15 agc aaa gcc agg agg ctg aag ctt ggc ctg cca gga ccc cca ggg cca      96
Ser Lys Ala Arg Arg Leu Lys Leu Gly Leu Pro Gly Pro Pro Gly Pro
            20                  25                  30 cca ggt cct cag ggc ccc cca ggc ccc ttt atc cca tct gag gtt ctg     144
Pro Gly Pro Gln Gly Pro Pro Gly Pro Phe Ile Pro Ser Glu Val Leu
        35                  40                  45 ctg aag gag ttc cag ctg ttg ctg aaa ggc gca gta cgg cag cga gag     192
Leu Lys Glu Phe Gln Leu Leu Leu Lys Gly Ala Val Arg Gln Arg Glu
    50                  55                  60 agc cat ctg gag cac tgc acc agg gat ctc act aca cca gcc tcg ggt     240
Ser His Leu Glu His Cys Thr Arg Asp Leu Thr Thr Pro Ala Ser Gly
65                  70                  75                  80 agc cct tcc cgt gtc cca gcc gcc cag gag ctt gat agc cag gac cca     288
```

```
                                                                              -continued Ser Pro Ser Arg Val Pro Ala Ala Gln Glu Leu Asp Ser Gln Asp Pro
                85                  90                  95 ggg gca ttg tta gct ctg ctg gct gcg acc ttg gcc cag ggc ccg cgg     336
Gly Ala Leu Leu Ala Leu Leu Ala Ala Thr Leu Ala Gln Gly Pro Arg
            100                 105                 110 gca cca cgt gtg gag gcc gca ttc cac tgt cgc ttg cgc cgg gat gtg     384
Ala Pro Arg Val Glu Ala Ala Phe His Cys Arg Leu Arg Arg Asp Val
        115                 120                 125 cag gtg gat cgg cgt gcg ttg cac gag ctt ggg atc tac tac ctg ccc     432
Gln Val Asp Arg Arg Ala Leu His Glu Leu Gly Ile Tyr Tyr Leu Pro
    130                 135                 140 gaa gtt gag gga gcc ttc cac cgg ggc cca ggc ttg aat ctg acc agc     480
Glu Val Glu Gly Ala Phe His Arg Gly Pro Gly Leu Asn Leu Thr Ser
145                 150                 155                 160 ggc cag tac acc gca cct gtg gct ggc ttc tat gcg ctt gct gcc act     528
Gly Gln Tyr Thr Ala Pro Val Ala Gly Phe Tyr Ala Leu Ala Ala Thr
                165                 170                 175 ctg cac gtg gca ctc acc gag cag cca aga aag gga cca aca cga ccc     576
Leu His Val Ala Leu Thr Glu Gln Pro Arg Lys Gly Pro Thr Arg Pro
            180                 185                 190 cgg gat cgt ctg cgc ctg ctg atc tgc atc cag tct ctc tgt cag cac     624
Arg Asp Arg Leu Arg Leu Leu Ile Cys Ile Gln Ser Leu Cys Gln His
        195                 200                 205 aat gcc tcc ctg gag act gtg atg ggg ctg gag aac agc agc gag ctc     672
Asn Ala Ser Leu Glu Thr Val Met Gly Leu Glu Asn Ser Ser Glu Leu
    210                 215                 220 ttc acc atc tca gta aat ggt gtc ctc tat cta cag gca gga cac tac     720
Phe Thr Ile Ser Val Asn Gly Val Leu Tyr Leu Gln Ala Gly His Tyr
225                 230                 235                 240 act tct gtc ttc ttg gac aat gcc agc ggc tcc tcc ctc acg gta cgc     768
Thr Ser Val Phe Leu Asp Asn Ala Ser Gly Ser Ser Leu Thr Val Arg
                245                 250                 255 agt ggc tct cac ttc agt gct atc ctc ctg ggc ctg tga                 807
Ser Gly Ser His Phe Ser Ala Ile Leu Leu Gly Leu
            260                 265

<210> SEQ ID NO 53
<211> LENGTH: 268
<212> TYPE: PRT
<213> ORGANISM: Mus musculus

<400> SEQUENCE: 53

Met Leu Phe Val Lys Gln Ser Asp Lys Gly Ile Asn Ser Lys Arg Arg
1               5                   10                  15

Ser Lys Ala Arg Arg Leu Lys Leu Gly Leu Pro Gly Pro Pro Gly Pro
                20                  25                  30

Pro Gly Pro Gln Gly Pro Pro Gly Pro Phe Ile Pro Ser Glu Val Leu
            35                  40                  45

Leu Lys Glu Phe Gln Leu Leu Lys Gly Ala Val Arg Gln Arg Glu
        50                  55                  60

Ser His Leu Glu His Cys Thr Arg Asp Leu Thr Thr Pro Ala Ser Gly
65                  70                  75                  80

Ser Pro Ser Arg Val Pro Ala Ala Gln Glu Leu Asp Ser Gln Asp Pro
                85                  90                  95

Gly Ala Leu Leu Ala Leu Leu Ala Ala Thr Leu Ala Gln Gly Pro Arg
            100                 105                 110

Ala Pro Arg Val Glu Ala Ala Phe His Cys Arg Leu Arg Arg Asp Val
        115                 120                 125
```

-continued

```
Gln Val Asp Arg Arg Ala Leu His Glu Leu Gly Ile Tyr Tyr Leu Pro
    130                 135                 140

Glu Val Glu Gly Ala Phe His Arg Gly Pro Gly Leu Asn Leu Thr Ser
145                 150                 155                 160

Gly Gln Tyr Thr Ala Pro Val Ala Gly Phe Tyr Ala Leu Ala Ala Thr
                165                 170                 175

Leu His Val Ala Leu Thr Glu Gln Pro Arg Lys Gly Pro Thr Arg Pro
                180                 185                 190

Arg Asp Arg Leu Arg Leu Leu Ile Cys Ile Gln Ser Leu Cys Gln His
            195                 200                 205

Asn Ala Ser Leu Glu Thr Val Met Gly Leu Glu Asn Ser Ser Glu Leu
    210                 215                 220

Phe Thr Ile Ser Val Asn Gly Val Leu Tyr Leu Gln Ala Gly His Tyr
225                 230                 235                 240

Thr Ser Val Phe Leu Asp Asn Ala Ser Gly Ser Ser Leu Thr Val Arg
                245                 250                 255

Ser Gly Ser His Phe Ser Ala Ile Leu Leu Gly Leu
                260                 265
```